(12) United States Patent
Yamashita et al.

(10) Patent No.: US 7,981,419 B2
(45) Date of Patent: Jul. 19, 2011

(54) METHOD FOR TREATING HYPOPHOSPHATEMIC BONE DISEASES USING FGF-23 ANTIBODY

(75) Inventors: Takeyoshi Yamashita, Tokyo (JP); Takashi Shimada, Brookline, MA (US); Satoru Mizutani, Yokohama (JP); Seiji Fukumoto, Tokyo (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 173 days.

(21) Appl. No.: 12/325,551

(22) Filed: Dec. 1, 2008

(65) Prior Publication Data

US 2009/0110677 A1 Apr. 30, 2009

Related U.S. Application Data

(63) Continuation of application No. 10/344,339, filed as application No. PCT/JP01/06944 on Aug. 10, 2001, now abandoned.

(30) Foreign Application Priority Data

| Aug. 11, 2000 | (JP) | 2000-245144 |
| Sep. 21, 2000 | (JP) | 2000-287684 |
| Dec. 22, 2000 | (JP) | 2000-391077 |
| Apr. 19, 2001 | (JP) | 2001-121527 |

(51) Int. Cl.
*A61K 39/395* (2006.01)
*C07K 16/22* (2006.01)

(52) U.S. Cl. .................. 424/139.1; 530/387.9
(58) Field of Classification Search .......... None
See application file for complete search history.

(56) References Cited

U.S. PATENT DOCUMENTS

| 5,585,089 | A | 12/1996 | Queen et al. |
| 5,958,879 | A | 9/1999 | Kopchick et al. |
| 6,001,358 | A | 12/1999 | Black et al. |
| 6,617,118 | B2 | 9/2003 | Roffler et al. |
| 7,094,551 | B2 | 8/2006 | Zahradnik et al. |
| 7,223,563 | B2 | 5/2007 | Econs et al. |
| 7,314,618 | B2 | 1/2008 | Econs et al. |
| 2002/0156001 | A1 | 10/2002 | Econs et al. |
| 2004/0082506 | A1 | 4/2004 | Yamashita et al. |
| 2004/0171825 | A1 | 9/2004 | Bougueleret et al. |
| 2005/0048058 | A1 | 3/2005 | Yamazaki et al. |
| 2006/0160181 | A1 | 7/2006 | Luethy et al. |
| 2009/0110677 | A1 | 4/2009 | Yamashita et al. |
| 2009/0148461 | A1 | 6/2009 | Yamazaki et al. |

FOREIGN PATENT DOCUMENTS

| CA | 2418215 | | 1/2002 |
| CN | 1446227 | A | 10/2003 |
| EP | 120694 | | 10/1984 |
| EP | 125023 | | 11/1984 |
| EP | 0314161 | A1 | 10/1988 |
| EP | 1466925 | A1 | 10/2004 |
| GB | 2188638 | A | 10/1987 |
| JP | S-61-178926 | | 11/1986 |
| JP | H-02-117920 | | 2/1990 |
| WO | WO 99/60017 | | 11/1999 |
| WO | WO 00/10383 | | 3/2000 |
| WO | WO 00/60085 | A1 | 10/2000 |
| WO | WO 00/73454 | A1 | 12/2000 |
| WO | WO 01/40466 | A2 | 6/2001 |
| WO | WO 01/42451 | A2 | 6/2001 |
| WO | WO 01/49740 | A1 | 7/2001 |
| WO | WO 01/60850 | A1 | 8/2001 |
| WO | WO 01/61007 | A2 | 8/2001 |
| WO | WO 01/66595 | A2 | 9/2001 |
| WO | WO 01/66596 | A2 | 9/2001 |
| WO | WO 02/08271 | A1 | 1/2002 |
| WO | WO 02/14504 | A1 | 2/2002 |
| WO | WO 02/76467 | A1 | 3/2002 |
| WO | WO 02/088358 | A2 | 11/2002 |
| WO | WO 03/057733 | A1 | 1/2003 |
| WO | WO 02/43478 | | 5/2004 |
| WO | WO 2006/078072 | A1 | 7/2006 |
| WO | WO-2008/057683 | A2 | 5/2008 |
| WO | WO 2008/092019 | A1 | 7/2008 |

OTHER PUBLICATIONS

Notice of Allowance for Korean Patent Application 10-2003-7001931 Dated Nov. 26, 2008.
Kenneth E. White et al., "Molecular cloning of a novel human UDP-GaINAc:polypeptide N-acetylgalactosaminyltransferase, GaINAc-T8, and analysis as a candidate autosomal dominant hypophophatemic rickets (ADHR) gene", Gene 246 (2000), 347-356.
NCBI GenBank Accession No. NP_065689 (Mar. 25, 2007).
NCBI GenBank Accession No. NM_020638 (Mar. 25, 2007).
NCBI GenBank Accession No. AY566236 (Mar. 16, 2004).
Non-Final Office Action dated Dec. 29,2009, issued in related U.S. Appl. No. 10/500,296.
International Search Report of PCT Patent Application No. PCT/JP03/00017 dated Feb. 5, 2003—international, counterpart to related U.S. Appl. No. 10/500,296.
International Search Report of PCT Patent Application No. PCT/JP2008/052918 dated Mar. 13, 2008—international, counterpart to related U.S. Appl. No. 12/030,593.
Preissner et al., "Evaluation of the Immutopics Human FGF-23 (C-term) ELISA Kit", Clinical Chemistry, vol. 52, No. 6, Suppl. S, Jun. 2006, p. A174.
Supplementary European Search Report EP 08 71 1707 dated Feb. 9, 2010.
Japanese Office Action Application No. JP 2003-558047 dated Jan. 26, 2010.
Takashi Shimada et al., "Possible Roles of Fibroblast Growth Factor 23 in Developing X-Linked Hypophosphatemia", Clin. Pediatr. Endocrinol. 2005; 14(Supp123) 33-37.

(Continued)

*Primary Examiner* — Christine J Saoud
(74) *Attorney, Agent, or Firm* — Stephen A. Bent; Foley & Lardner LLP

(57) ABSTRACT

A method for treating a hypophosphatemic bone disease, such as X-linked hypophosphatemia (XLH). The method entails administering to a subject a pharmaceutical composition, which contains an antibody that binds to an FGF-23 polypeptide and a pharmaceutically acceptable carrier.

1 Claim, 37 Drawing Sheets

OTHER PUBLICATIONS

Satoshi Toyoshima, "Experiment Techniques II", Hirokawa Publishing Co., 1995, first edition, pp. 110-113.
Non-Final Office Action U.S. Appl. No. 12/030,593 dated Apr. 6, 2010.
Marc Drezner, Reviews in Endocrine & Metabolic Disorders 2001;2: 175-186.
Razzaque et al., Nephrol Dial Transplant, Oct. 2005; 20(10):2032-2035.
Inaba et al., Osteoporos Int. Oct. 2006; 17(10):1506-1513.
Vajdos et al., J. Mol. Biol. Jul. 5, 2002; 320(2):415-428.
Webster's New World Dictionary, Third College Edition, 1988, pp. 1067-1068.
Kobayashi et al., Eur J. Endocrinol. Jan. 2006;154(1)93-99.
Canadian Patent Office Action for 2,418,802 dated Feb. 13, 2009.
First Office Action Chinese Application No. 200810086683.1 dated Mar. 8, 2010.
Human Fibroblast Growth Factor-23 (FGF-23) Elisa Kit 96-Well Plate, EZHFG23-32K, Millipore, Feb. 3, 2009 (17 pgs.).
Human Intact FGF-23 Elisa Kit, Enzyme-Linked ImmunoSorbent Assay (ELISA) for the Determination of Human Fibroblas Growth Factor 23 Levels in Plasma or Cell Culture, 96 Test Kit, Cat. No. 60-6500, Immotopics, Inc., Oct. 2008 (4 pgs.).
Monoclonal Anti-human FGF-23 Antibody, R&D Systems. Cat. No. MAB2604, Apr. 18, 2005.
Monoclanal Anti-human/mouse FGF-23 Antibody, R&D Systems, Cat. No. MAB2629, Sep. 13, 2007.
Monoclonal Anti-mouse FGF-23 Antibody, R&D Systems, Cat. No. MAB26291, Mar. 20, 2007.
Final Office Action for U.S. Appl. No. 10/500,296 dated Apr. 10, 2009.
Non-Final Office Action for U.S. Appl. No. 10/500,296 dated Jul. 24, 2008.
Advisory Action for U.S. Appl. No. 10/500,296 dated Mar. 28, 2008.
Final Office Action for U.S. Appl. No. 10/500,296 dated Oct. 19, 2007.
Non-Final Office Action for U.S. Appl. No. 10/500,296 dated Jan. 30, 2007.
Non-Final Office Action for U.S. Appl. No. 10/500,296 dated Jan. 13, 2006.
Aono et al., "The improving effect of anti FGF23 neutralizing antibody on hypophosphatemia and rickets of Hyp mice", *The Japanese Society for Bone and Mineral Research (JSBMR)*, Annual Meeting of the JSBMR, 22$^{nd}$ Program, Aug. 2004, vol. 22, pp. 137. (English translation provided).
Ando, et al., *Tan-Clone-Kotai-Jikken-Manual* ("Experimental Manual for Monoclonal Antibody") (written by and published by Kodansha Scientific, Ltd., Tokyo, Japan (1991).
Antibody Engineering, A Practical Approach, IRL Press, 1996.
Antibody Engineering, A Practical Guide, W.H. Freeman and Company, 1992.
Baker and Worthley, "The Essentials of Calcium, Magnesium and Phosphate Metabolism: Part II. Disorders," *Critical Care & Resuscitation.*, 2000, vol. 4, pp. 307-315.
Better et al., "*Escherichia coli* Secretion of an Active Chimeric Antibody Fragment," *Science*, May 20, 1998 (nti), vol. 240, pp. 1041-1043.
Bost, et al., "Antibodies Against a Peptide Sequence within the HIV Envelope Protein Crossreacts with Human Interleukin-2", *Immunol. Invest.*, 1988, vol. 17, Nos. 577-586pp. 577-586.
Bruggemann, et al., "The Immunogenicity of Chimeric Antibodies", *J. Exp. Med.*, Dec. 1989, vol. 170, No. 6, pp. 2153-2157.
Campbell, A.M., *Monoclonal Antibody Technology*, Elsevier Science Publishers, Inc., 1984, pp. 1-32.
Carter, et al., "High Level *Escherichia coli* Expression and Production of a Bivalent Humanized Antibody Fragment," *Bio/Technology*, 1992, vol. 10, pp. 163-167.
Delves, P. J., "Antibody Production Essential Techniques", *Monoclonal Antibodies*, Ed. Shepherd and Dean, Oxford University Press, 2000.
Fishwild, et al., "High-avidity Human IgGκ Monoclonal Antibodies from a Novel Strain of Minilocus Transgenic Mice," *Nat Biotechnol.*, Jul. 1996, vol. 14, No. 7, pp. 845-851.
Fukagawa, et al., "FGF23: its Role in Renal Bone Disease", *Pediat. Nephrol*, 2006, vol. 21, pp. 1802-1806.
Goding, J. W., *Monoclonal Antibodies: Principles and Practice*, Academic Press, 1993 and 1995.
Gupta, et al., "FGF-23 is Elevated by Chronic Hyperphosphatemia," *J. Clin. Endocrinol.& Metab.*, 2004. vol. 89, No. 9, pp. 4489-4492.
Imel, et al., "FGF23 Concentrations Vary with Disease Status in Autosomal Dominant Hypophosphatemic Rickets," *J.of Bone and Mineral Research*, 2007, vol. 22, pp. 520-526.
Ishida & Lonberg, IBC's 11th Antibody Engineering, Abstract 2000.
Jonsson, et al., "Fibroblast Growth Factor 23 in Oncogenic Osteomalacia and X-Linked Hypophosphatemia," *N. Engl. J. Med.*, Apr. 24, 2003, vol. 348, No. 17, pp. 1656-1663.
Karlsson, et al., "Kinetic Analysis of Monoclonal Antibody-Antigen Interactions with a New Biosensor Based Analytical System," *Journal of Immunological Methods*, 1991, vol. 145, pp. 229-240.
Kearney, et al., "A New Mouce Myeloma Cell Line that has Lost Immunoglobulin Expression but Permits the Construction of Antibody-Secreting Hybrid Cell Lines", *J Immunology*, Sep. 1979, vol. 123, No. 3, pp. 1548-1550.
King, D.J., *Applications and Engineering of Monoclonal Antibodies*, T. J. International Ltd, 1998.
Kitamura, et al., "A B Cell-deficient Mouse by Targeted Distribution of the Membrane Exon of the Immunoglobulin μ Chain Gene," *Nature*, 1991, vol. 350, No. 4, pp. 423-426.
Kohler, et al., "Derivation of Specific Antibody-producing Tissue Culture and Tumor Lines by Cell Fusion", *European J. Immunology*, 1966, vol. 6, pp. 511-519.
Lah, et al., "Phage Surface Presentation and Secretion of Antibody Fragments using an Adaptable Phagemid Vector," *Human Antibodies & Hybridomas*, 1994, vol. 5, Nos. 1 and 2, pp. 48-56.
Larsson, et al., "Circulating Concentration of FGF-23 Increases as Renal Function Declines in Patients with Chronic Kidney Disease, but does not Change in Response to Variation in Phosphate Intake in Healthy Voluneers," *Kidney International*, 2003, vol. 64, pp. 2272-2279.
Lorenz-Depiereux, et al., The Autosomal Dominant Hypophosphatemic Rickets (ADHR) Gene is a Secreted Fibroblast Growth Factor (FGF23), *Eur. J. Human Genetics*, 2001, vol. 9, Supplement 1, P0772, 10$^{th}$ International Congress of Human Genetics, Vienna Austria, May 15-19, 2001.
Lorenz-Depiereux, et al., "DMP1 Mutations in Autosomal Recessive Hypophosphatemia Implicate a Bone Matrix Protein in the Regulation of Phosphate Homeostasis," *Nature Genetics*, Nov. 2006, vol. 38, No. 11, pp. 1248-1250.
Mark, et al., "Site-specific Mutagenesis of the Human Fibroblast Interferon Gene", *Proc Natl Acad Sci U.S.A.*, Sep. 1984, vol. 81, No. 18, pp. 5662-5666.
Mohammadi, et al., "Structual Basis for Fibroblast Growth Factor Receptor Activation," *Cytokine & Growth Factor Reviews*, Apr. 2005, vol. 16, No. 2, pp. 107-137.
Ornitz, et al., "Fibroblast Growth Factors," *Genome Biology*, 2001, vol. 2, No. 3, pp. 3005.1-3005.12.
Reiter, et al., "Engineering Interchain Disulfide Bonds into Conserved Framework Regions of Fv Fragments: Improved Biochemical Characteristics of Recombinant Immunotoxins Containing Disulfide-stabilized Fv", *Protein Engineering*, 1994, vol. 7, No. 5, pp. 697-704.
Riechmann, et al., "Reshaping Human Antibodies for Therapy", *Nature*, Mar. 1988, vol. 332, No. 6162, pp. 323-327.
Riminucci, et al., "FGF-23 in Fibrous Dysplasia of Bone and its Relationship to Renal Phosphate Wasting," *J. Clin. Invest.*, 2003, vol. 112, No. 5, pp. 683-692.
Shibata et al., "Monoclonal Antibodies Against Recombinant Human FGF-23", J. Am. Soc. Nephrol., Sep., 2002, vol. 13, p. 499A (SU-P0151).
Shimada et al., "Mutant FGF-23 responsible for autosomal dominant hypophosphatemic rickets is resistant to proteolytic cleavage and causes hypophosphatemia in vivo", Endocrinology, Aug. 2002, vol. 143, No. 8 pp. 3179-3182.

Shimada et al, "FGF-23 Is a Novel Humoral Factor Regulating Vitamin D Metabolism", Journal of the American Society of Nephrology, Sep. 2002, vol. 13, (Program & Abstract Issue), p. 28A.

Shimada, T. "Targeted Ablation of FGF23 Demonstrates an Essential Physiological Role of FGF23 in Phosphate and Vitamin D Metabolism ", *J. Clin. Invest.*, Feb. 2004, vol. 113, No. 4, pp. 561-568.

Shimada, T. "FGF23 and Phosphorus metabolism", *The Japanese Society for Bone and Mineral Research (JSBMR)*, Annual Meeting of the JSBMR, 23rd Program, Jun. 20, 2005, vol. 23, pp. 121. (English translation provided).

Shinichi Aizawa, "Biotechnology Manual Series 8, Gene Targeting," Yodosha, 1995.

Shulman, et al., "A Better Cell Line for Making Hybridomas Secreting Specific Antibodies", *Nature*, Nov. 1978, vol. 276, No. 5685, pp. 269-270.

Sunaga, et al., "Efficient Removal of loxP-Flanked DNA Sequences in a Gene-Targeted Locus by Transient Expression of Cre Recombinanse in Fertilized Eggs," *Molecular Reproduction and Development*, 1997, vol. 46, pp. 109-113.

Superti-Furga, et al., *American Journal of Medical Genetics*, Siminar Medical Genetics, 2001, vol. 106, pp. 282-293.

Tomizuka, et al., "Double Trans-Chromosomic Mice: Maintenance of Two Individual Human Chromosome Fragments Containing Ig Heavy And Antibodies", *Proc Natl Acad Sci U.S.A.*, 2000, vol. 97, No. 2, pp. 722-727.

Urakawa, et al., "Klotho Converts Canonical FGF Receptor into a Specific Receptor for FGF23," *Nature*, Dec. 2006, vol. 444, pp. 770-774.

Van Kroonenbergh, et al., "Human Immunological Response to Mouse Monoclonal Antibodies in the Treatment or Diagnosis of Malignant Diseases," *Nuclear Medicine Communications.*, 1988, vol. 9, pp. 919-930.

White, et al., "Autosomal-dominant Hypophosphatemic Rickets (ADHR) Mutations Stabalize FGF-23", *Kidney International*, 2001, vol. 60, pp. 2079-2086.

Wright, et al., "High Level Expression of Active Human Alpha-1-Antitrypsin in the Milk of Transgenic Sheep", *Bio/Technology*, Sep. 1991, vol. 9, No. 9, pp. 830-834.

Yamamoto, et al., "The Role of Fibroblast Growth Factor 23 in Hypophosphatemia and Abnormal Regulation of Vitamin D Metabolism in Patients with McCune-Albright Syndrome," *J. Bone Miner. Metab.*, 2005, vol. 23, pp. 231-237.

Yamazaki, et al., "Increased Circulatory Level of Biologically Active Full Length FGF-23 in Patients with Hypophosphatemic Rickets/Osteomalacia," *J. Clin. Endocrinol. Metab.*, 2002, vol. 87, pp. 4957-4960.

Yamazaki et al, "Development of the ELISA System Using Monoclonal Antibodies against FGF-23 and Demonstration of Increased Plasma Concentration of FGF-23 in Tumor-Induced Osteomalacia", ENDO, 2002, The Endocrine Society's 84th Annual Meeting, Program & Abstract, p. 66.

Yamazaki et al., "FGF-23 Protein is Present in Normal Plasma and Is increased in Patients with Tumor-Induced Osteomalacia", (Sep. 2002), The Journal of Bone and Mineral Research, vol. 17, suppl. 1, p. 159.

Yamazaki, et al., "Detection of Circulating FGF-23 by Monoclonal Antibodies Against Recombinant Human FGF-23", *Journal of the American Society of Nephrology*, vol. 13 (Program and Abstracts Issue), Sep. 2002, p. 499A.

Yamazaki, et al., "Anti-FGF23 neutralizing antibodies show the physiological role and structural features of FGF23", *Journal of Bone and Mineral Research*, vol. 23, No. 9, Sep. 2008, pp. 1509-1518.

Yelton, et al., "Fusion of Mouse Myeloma and Spleen Cells", *Current Topics in Microbiology and Immunology*, 1978, vol. 81, pp. 1-7.

Yu, et al., "Analysis of the Biochemical Mechanisms for the Endocrine Actions of Fibroblast Growth Factor-23", *Endocrinology*, Nov. 2005, vol. 146, No. 11, pp. 4647-4656.

Japanese Office Action 2003-5580417 dated Aug. 20, 2009.

Yukihiro Hasegawa et al., "Vitamin D-Resistant Hypophosphatemic Rickets", The Bone, vol. 15, No. 6, Nov. 2001, pp. 1-9.

Ann E. Bowe et al., "FGF-23 Inhibits Renal Tubular Phosphate Transport and Is a PHEX Substrate", Biochemical and Biophysical Research Communications 284, 977-981 (2001).

Aschinberg et al., "Vitamin D-resistant rickets associated with epidermal nevus syndrome: Demonstration of a phosphaturic substance in the dermal lesions", *The Journal of Pediatrics*, Jul. 1997, pp. 56-60, vol. 91, No. 1, The C.V. Mosby Company, St. Louis, Mo.

Benjannet et al., "α1-Antitrypsin Portland Inhibits Processing of Precursors Mediated by Proprotein Convertases Primarily within the constitutive Secretory Pathway", *The Journal of Biological Chemistry*, Oct. 17, 1997, pp. 2610-2618, vol. 272, No. 42, The American Society for Biochemistry and Molecular Biology, Inc.

Briand et al., "Application and limitations of the multiple antigen peptide (MAP) system in the production and evaluation of anti-peptide and anti-protein antibodies", *Journal of Immunnological Methods*, 1992, pp. 255-265, vol. 156, No. 2, Elsevier Science Publishers B.V.

Cai et al., "Brief Report: Inhibition of Renal Phosphate Transport by a Tumor Product in a Patient with Oncogenic Osteomalcia", *The New England Journal of Medicine*, Jun. 9, 1994, pp. 1645-1649, vol. 330, No. 23, The Massachusetts Medical Society.

Drezner, "PHEX gene and hypophosphatemia", *Kidney International*, Jan. 2000, pp. 9-18, vol. 57, No. 1, The International Society of Nephrology.

Ecarot et al., "Defective Bone Formation by Hyp Mouse Bone cells Transplanted into Normal Mice: Evidence in Favor of an Intrinsic Osteoblast Defect", *Journal of Bone and Mineral Research*, Feb. 1992, pp. 215-20, vol. 7, No. 2, Mary Ann Liebert, Inc.

Econs et al., "Autosomal Dominant Hypophosphatemic Rickets Is Linked to Chromosome 12p13" *The Journal of Clinical Investigation*, Dec. 1, 1997, pp. 2653-2657, vol. 100, No. 11, The Rockefeller University Press.

Econs et al., "Tumor-Induced Osteomalacia—Unveiling a New Hormone", *The New England Journal of Medicine*, Jun. 9, 1994, pp. 1679-1681, vol. 330, No. 23, The Massachusetts Medical Society.

Econs, "New Insights Into the Pathogenesis of Inherited Phosphate Wasting Disorders" *Bone*, Pergamon Press, Oxford, GB, vol. 25, No. 1, Jul. 1999 pp. 131-135.

Fukumoto et al., "Diagnostic Utility of Magnetic Resonance Imaging Skeletal Survey in a Patient With Oncogenic Osteomalacia", *Bone*, Sep. 1999, pp. 375-377, vol. 25, No. 3, Elsevier.

Han et al., "Epinephrine translocates GLUT-4 but inhibits insulin-stimulated glucose transport in rat muscle", *American Journal of Physiology*, Apr. 1998, pp. E700-7, vol. 274, No. 4, The American Physiological Society.

Kessler et al., "A Modified Procedure for the Rapid Preparrtion of Efficiently Transporin Vesicles From Small Intestinal Brush Border Membranes" *Biochimica et Biophysica Acta*, Jan. 4, 1978, pp. 136-155, vol. 506, No. 1, Elsevier/North-Holland Biomedical Press.

Lajeunesse et al., "Direct demonstration of a humorally-mediated inhibition of renal phosphate transport in the *Hyp* mouse", *Kidney International*, Nov. 1996, pp. 1531-1538, vol. 50, No. 5, The International Society of Nephrology.

Lau et al., "Evidence for a Humoral Phosphaturic Factor in Oncogenic Hypophospatemic Osteomalacia", *Clinical Research*, Apr. 1979, p. 421A, vol. 27, No. 2.

Lorenz-Depiereux et al., *European Journal of Human Genetics*, 2001, 9(Supplement 1): P0772.

Lorenz-Depiereux et al., "Autosomal Dominant Hypophosphatemic Rickets (ADHR) Is Caused by Mutations in a Gene Encoding a Novel Member of the Fibroblast Growth Factor Family(FGF-21)" *American Journal of Human Genetics*, vol. 67, No. 4, suppl. 2, Oct. 2000, p. 12.

Lu et al., "Chemically Unambiguous Peptide Immunogen: Preparation, Orientation and Antigenicity of Purified Peptide Conjugated to the Multiple Antigen Peptide System", *Molecular Immunology*, Jun. 1991, pp. 623-630, vol. 28, No. 6, Pergamon Press, Great Britain.

Meyer et al., "Parabiosis Suggests a Humoral Factor Is Involved in *X*-Linked Hypophosphatemia in Mice", *Journal of Bone and Mineral Research*, Aug. 1989, pp. 493-500, vol. 4, No. 4, Mary Ann Leibert, Inc.

Miyauchi et al, Hemangiopericytoma-Induced Osteomalacia: Tumor Transplantation in Nude Mice Causes Hypophosphatemia and Tumor Extracts Inhibit Renal 25-Hydroxyvitamin D 1-Hydroxylase Activity, *Journal of Clinical Endocrinology and Metabolism*, Jul. 1988, pp. 46-53, vol. 67, No. 1, The Endocrine Society.

Nelson et al., "Oncogenic osteomalacia: is there a new phoshate regulating hormone?", *Clinical Endocrinology*, Dec. 1997, pp. 635-642, vol. 47, No. 6, Blackwell Science Ltd.

Nykjaer et al., "An Endocytic Pathway Essential for Renal Uptake and Activation of the Steroid 25-(OH) Vitamin $D_3$", Feb. 19, 1999, pp. 507-515, vol. 96, No. 4, Cell Press.

Popovtzer et al., "Tumor-Induced Hypophosphatemic Osteomalacia (TUO): Evidence for a Phosphaturic Cyclic AMP-Independent Action of Tumor Extract", *Clinical Research*, Apr. 1981, p. 418A, vol. 29, No. 2.

Posnett et al., "A Novel Method for Producing Anti-peptide Antibodies", *The Journal of Biological Chemistry*, Feb. 5, 1988, pp. 1719-1725, vol. 263, No. 4, The American Society for Biochemistry and Molecular Biology, Inc.

Rowe et al., "Candidate 56 and 58 kDa Protein(s) Responsible for Mediating the Renal Defects in Oncogenic Hypophosphatemic Osteomalacia", *Bone*, Feb. 1996, pp. 159-169, vol. 18, No. 2, Elsevier.

Rowe et al., "MEPE, a New Gene Expressed in Bone Marrow and Tumors Causing Osteomalacia", *Genomics*, Jul. 1, 2000, pp. 54-68, vol. 67, No. 1, Academic Press.

Shimada et al., "Cloning and characterization of FGF23 as a causative factor of tumor-induced osteomalacia", *Proc. Nalt. Acad. Sci.*, May 2, 2001, pp. 6500-6505, vol. 98, No. 11.

Shirahata et al., "E1A and *ras* Oncogenes Synergistically Enhance Recombinant Protei Production under Control of the Cytomegalovirus Promoter in BHK-21 Cells", *Biosci. Biotech. Biochem.*, Feb. 1995, pp. 345-347, vol. 59, No. 2, Japan Society For Bioscience, Biotechnology, and Agrochemistry.

Strom et al., "*Pex* gene deletions in Gy and Hyp mice provide mouse models for X-linked hypophosphatemia", *Human Molecular Genetics*, Feb. 1997, pp. 165-171, vol. 6, No. 2, The Oxford University Press.

Tatsumi et al., "Identification of Three Isoforms for the $NA^+$-dependent Phosphate Cotransporter (NaPi-2) in Rat Kidney", *The Journal of Biological Chemistry*, Oct. 30, 1998, pp. 28568-28575, vol. 273, No. 44, The Society for Biochemistry and Molecular Biology, Inc.

Wen et al., "PTEN controls tumor-induced angiogenesis", *Proceedings of the National Academy of Sciences*, Apr. 14, 2001, pp. 4622-4627, vol. 98, No. 6.

White et al., "Autosomal dominant hypophosphataemic rickets is associated with mutations in *FGF23*", *Nature Genetics*, Nov. 2000, pp. 345-348, vol. 26.

White et al., "Molecular cloning of a novel human UDP-GaINAc: polypeptide N-acetylgalactosaminyltransferase, GaINAc-T8, and analysis as a candidate autosomal dominant hypophosphatemic rickets (ADHR) gene", Gene, Elsevier Biomedical Press, Amsterdam NL, vol. 246, No. 1-2, Apr. 2000, pp. 347-356.

Wilkins et al., "Oncogenic Osteomalacia: Evidence for a Humoral Phosphaturic Factor", *Journal of Clinical Endocrinology and Metabolism*, Oct. 22, 2000, pp. 1628-1634, vol. 80, No. 5, The Endocrine Society.

Yamasita et al., "Identification of a Novel Fibroblast Growth Factor, FGF-23, Preferentially Expressed in the Ventrolateral Thalamic Nucleus of the Brain", *Biochemical and Biophysical Research Communications*, Oct. 22, 2000, pp. 494-498, vol. 277, No. 2, Academic Press.

Advisory Action dated Dec. 7, 2007 for U.S. Appl. No. 10/344,339.

Final Office Action dated Jun. 22, 2007 for U.S. Appl. No. 10/344,339.

Kohler et al, Continuous cultures of fused cells secreting antibody of predefined specificity, Nature, 1975, 256:495-497.

Non-Final Office Action for U.S. Appl. No. 10/344,339 dated Jan. 18, 2008.

Non-Final Office Action for U.S. Appl. No. 10/344,339 dated Sep. 27, 2006.

Office Action dated Aug. 20, 2009 for JP Application No. 2003-558047.

Office Action on dated Jul. 24, 2008 for U.S. Appl. No. 10/500,296.

Search Report dated 04/26/04 for EP Application No. 04001555.4.

Supplementary European Search Report of European Patent Application No. EP 01 95 8379 dated May 27, 2005—international, counterpart to U.S. Appl. No. 10/344,339.

US Notice of Allowance dated Jun. 22, 2010 for U.S. Appl. No. 10/500,296.

US Notice of Allowance dated Sep. 17, 2010 for U.S. Appl. No. 12/030,593.

US Office Action dated Dec. 29, 2009 for U.S. Appl. No. 10/500,296.

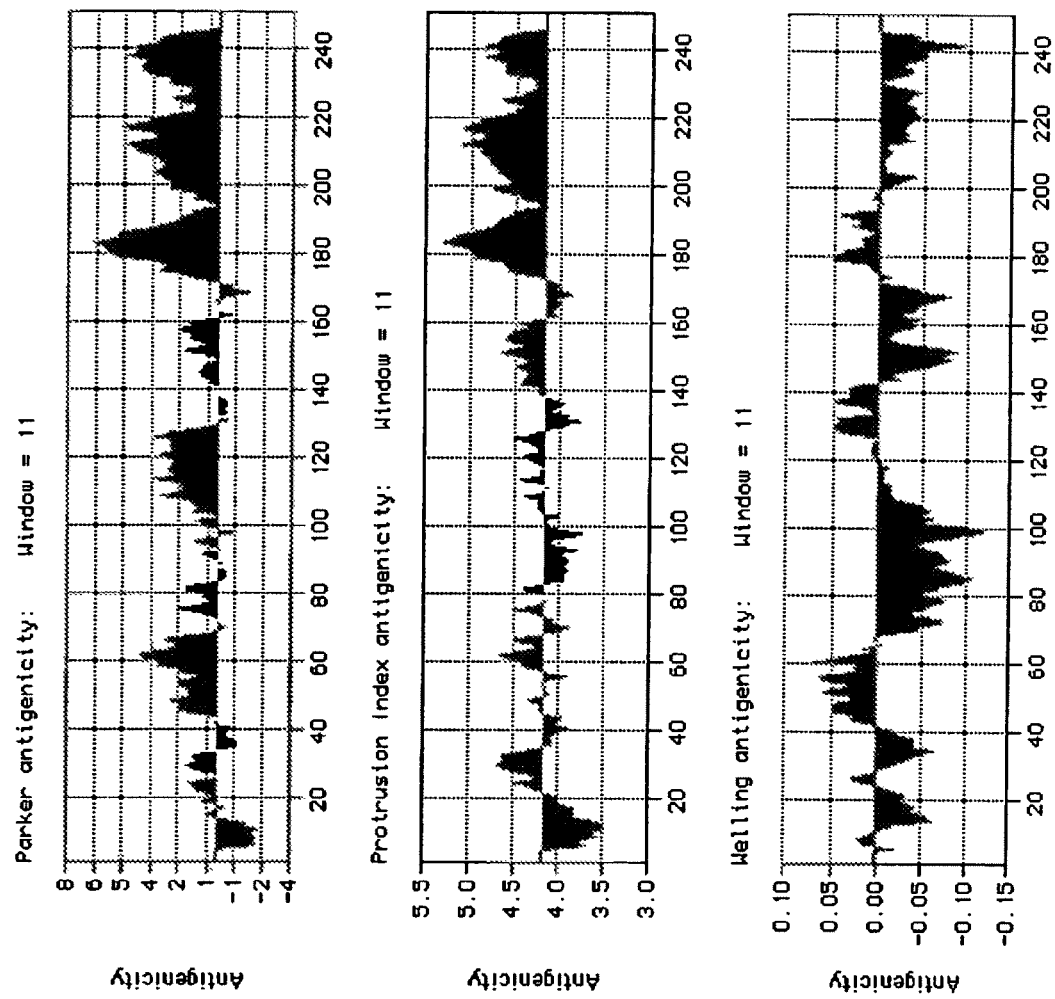

FIG. 6

Residue Nos. 72 to 251 of the amino acid sequence of SEQ ID NO: 2 (hOST311) and SEQ ID NO: 10 (mOST311)

Match% 69.4

```
              -----80--------90-------100-------110-------120-
hOST311:  ALMIRSEDAGFVVITGVMSRRYLCMDFRGNIFGSHYFDPENCRFQHQTLE
          :::::::::::: ::::.:::::::::::::: ::::: :::::.::::
mOST311:  ALMITSEDAGSVVITGAMTRRFLCMDLHGNIFGSLHFSPENCKFRQWTLE
          1---------10--------20--------30--------40--------50

-----130-------140-------150-------160-------170-
hOST311:  NGYDVYHSPQYHFLVSLGRAKRAFLPGMNPPPYSQFLSRRNEIPLIHFNT
          ::::::: ::::::::::::::::::  ::: :: ::::::::   ::
mOST311:  NGYDVYLSQKHHYLVSLGRAKRIFQPGTNPPPFSQFLARRNEVPLLRFYT
          ----------60--------70--------80--------90-------100

-----180-------190-------200-------210-------220-
hOST311:  PIPRRHTRSAEDDSERDPLNVLKPRARMTPAPASCSQELPSAEDNSPMAS
          : :::::::::: ::::::::::::::: ::  :. :. :: ::
mOST311:  VRPRRHTRSAEDPPERDPLNVLKPRPRATPVPVSCSRELPSAEGGPAAS
          ---------110-------120-------130-------140-------150

-----230-------240-------250-
hOST311:  DPLGVVRGGRVNTHAGGTGPEGCRPFAKFI
          :::::: ::: :    ::  ::::::: :
mOST311:  DPLGVLRRGRGDARGGAGGADRCRPFPREV
          ---------160-------170-------180
```

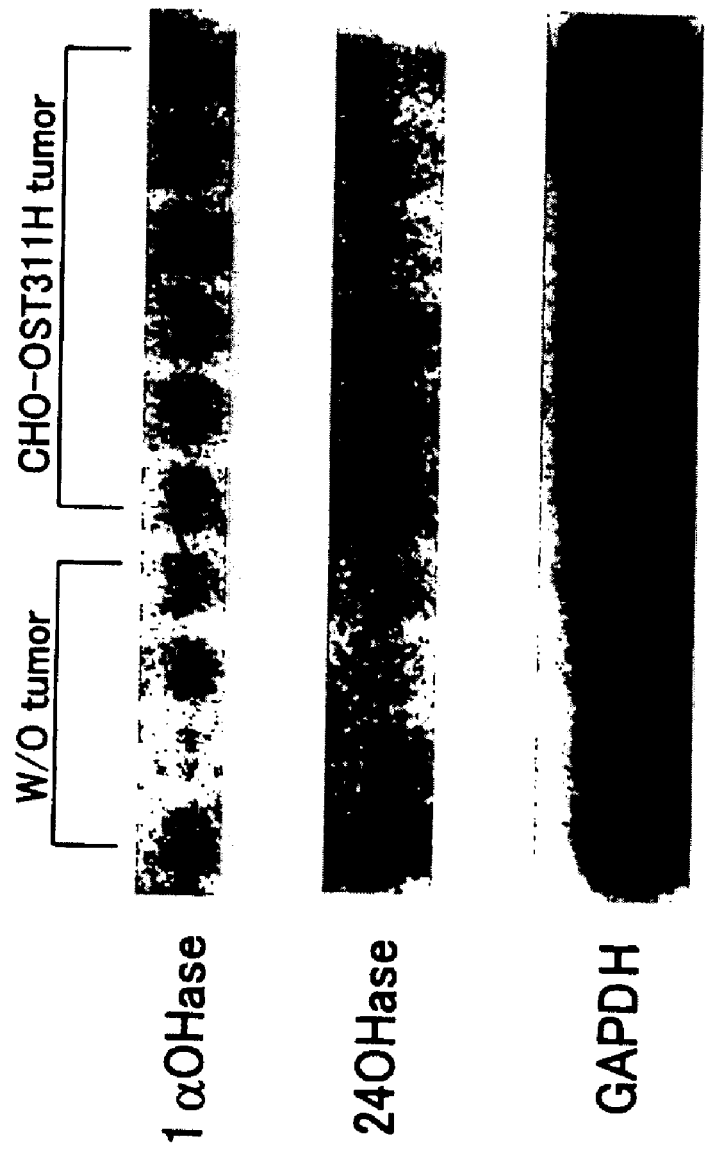

FIG.19
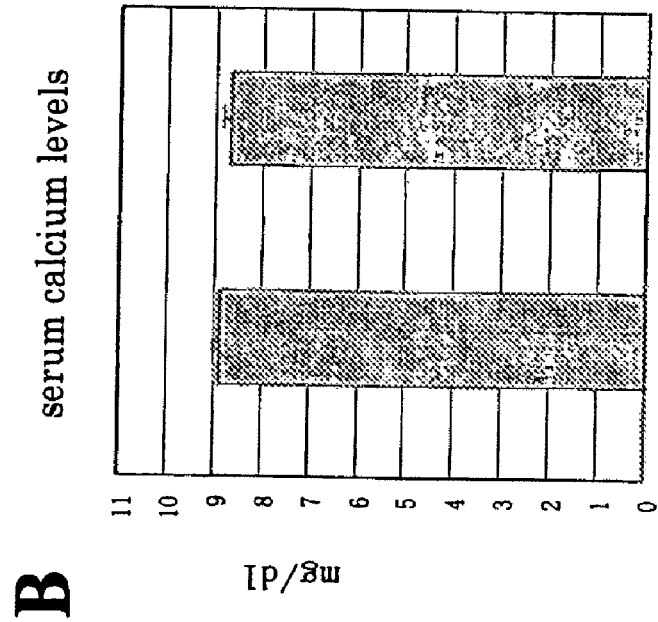
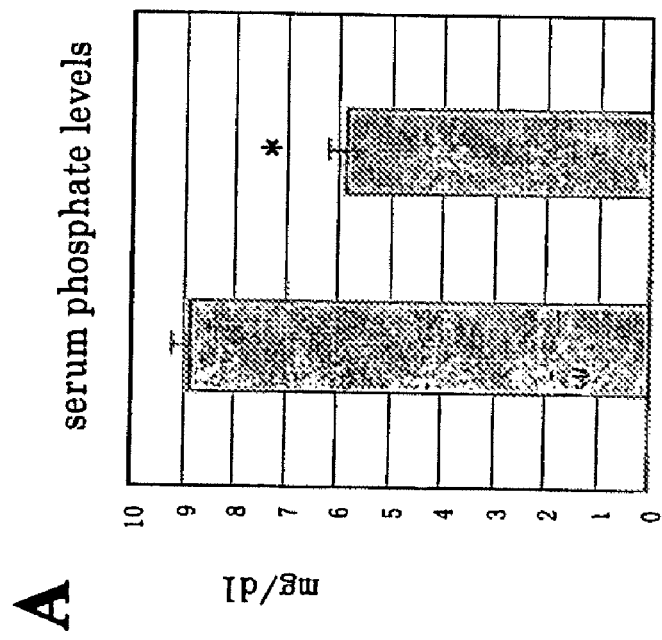

FIG.26

SEQUENCE LISTING

```
<160> NUMBER OF SEQ ID NOS: 94

<210> SEQ ID NO 1
<211> LENGTH: 2770
<212> TYPE: DNA
<213> ORGANISM: Homo sapiens
<220> FEATURE:
<221> NAME/KEY: CDS
<222> LOCATION: (133)..(885)

<400> SEQUENCE: 1
gaatccagtc taggatcctc acaccagcta cttgcaaggg agaaggaaaa ggccagtaag      60
gcctgggcca ggagagtccc gacaggagtg tcaggtttca atctcagcac cagccactca     120
gagcagggca cg atg ttg ggg gcc cgc ctc agg ctc tgg gtc tgt gcc ttg    171
              Met Leu Gly Ala Arg Leu Arg Leu Trp Val Cys Ala Leu
                1               5                  10 tgc agc gtc tgc agc atg agc gtc ctc aga gcc tat ccc aat gcc tcc      219
Cys Ser Val Cys Ser Met Ser Val Leu Arg Ala Tyr Pro Asn Ala Ser
 15                  20                  25 cca ctg ctc ggc tcc agc tgg ggt ggc ctg atc cac ctg tac aca gcc      267
Pro Leu Leu Gly Ser Ser Trp Gly Gly Leu Ile His Leu Tyr Thr Ala
 30                  35                  40                  45 aca gcc agg aac agc tac cac ctg cag atc cac aag aat ggc cat gtg      315
Thr Ala Arg Asn Ser Tyr His Leu Gln Ile His Lys Asn Gly His Val
                 50                  55                  60 gat ggc gca ccc cat cag acc atc tac agt gcc ctg atg atc aga tca      363
Asp Gly Ala Pro His Gln Thr Ile Tyr Ser Ala Leu Met Ile Arg Ser
             65                  70                  75 gag gat gct ggc ttt gtg gtg att aca ggt gtg atg agc aga aga tac      411
Glu Asp Ala Gly Phe Val Val Ile Thr Gly Val Met Ser Arg Arg Tyr
         80                  85                  90 ctc tgc atg gat ttc aga ggc aac att ttt gga tca cac tat ttc gac      459
Leu Cys Met Asp Phe Arg Gly Asn Ile Phe Gly Ser His Tyr Phe Asp
     95                 100                 105 ccg gag aac tgc agg ttc caa cac cag acg ctg gaa aac ggg tac gac      507
Pro Glu Asn Cys Arg Phe Gln His Gln Thr Leu Glu Asn Gly Tyr Asp
110                 115                 120                 125 gtc tac cac tct cct cag tat cac ttc ctg gtc agt ctg ggc cgg gcg      555
Val Tyr His Ser Pro Gln Tyr His Phe Leu Val Ser Leu Gly Arg Ala
                130                 135                 140 aag aga gcc ttc ctg cca ggc atg aac cca ccc cg tac tcc cag ttc       603
Lys Arg Ala Phe Leu Pro Gly Met Asn Pro Pro Pro Tyr Ser Gln Phe
            145                 150                 155 ctg tcc cgg agg aac gag atc ccc cta att cac ttc aac acc ccc ata      651
Leu Ser Arg Arg Asn Glu Ile Pro Leu Ile His Phe Asn Thr Pro Ile
        160                 165                 170 cca cgg cgg cac acc cgg agc gcc gag gac gac tcg gag cgg gac ccc      699
Pro Arg Arg His Thr Arg Ser Ala Glu Asp Asp Ser Glu Arg Asp Pro
    175                 180                 185 ctg aac gtg ctg aag ccc cgg gcc cgg atg acc ccg gcc ccg gcc tcc      747
Leu Asn Val Leu Lys Pro Arg Ala Arg Met Thr Pro Ala Pro Ala Ser
190                 195                 200                 205
```

| | | | | | | | | | | | | | |
|---|---|---|---|---|---|---|---|---|---|---|---|---|---|
| tgt | tca | cag | gag | ctc | ccg | agc | gcc | gag | gac | aac | agc | ccg | atg | gcc | agt | 795 |
| Cys | Ser | Gln | Glu | Leu | Pro | Ser | Ala | Glu | Asp | Asn | Ser | Pro | Met | Ala | Ser | |
| | | | 210 | | | | | 215 | | | | | 220 | | | |

```
tgt tca cag gag ctc ccg agc gcc gag gac aac agc ccg atg gcc agt       795
Cys Ser Gln Glu Leu Pro Ser Ala Glu Asp Asn Ser Pro Met Ala Ser
            210                 215                 220 gac cca tta ggg gtg gtc agg ggc ggt cga gtg aac acg cac gct ggg       843
Asp Pro Leu Gly Val Val Arg Gly Gly Arg Val Asn Thr His Ala Gly
            225                 230                 235 gga acg ggc ccg gaa ggc tgc cgc ccc ttc gcc aag ttc atc               885
Gly Thr Gly Pro Glu Gly Cys Arg Pro Phe Ala Lys Phe Ile
            240                 245                 250 tagggtcgct ggaagggcac cctctttaac ccatccctca gcaaacgcag ctcttcccaa     945
ggaccaggtc ccttgacgtt ccgaggatgg gaaaggtgac aggggcatgt atggaatttg    1005
ctgcttctct ggggtccctt ccacaggagg tcctgtgaga accaaccttt gaggcccaag    1065
tcatggggtt tcaccgcctt cctcactcca tatagaacac ctttcccaat aggaaacccc    1125
aacaggtaaa ctagaaattt ccccttcatg aaggtagaga aaggggtct ctcccaacat     1185 atttctcttc cttgtgcctc tcctctttat cacttttaag cataaaaaaa aaaaaaaaaa    1245
aaaaaaaaaa aaaagcagt gggttcctga gctcaagact ttgaaggtgt agggaagagg     1305
aaatcggaga tcccagaagc ttctccactg ccctatgcat ttatgttaga tgccccgatc    1365
ccactggcat ttgagtgtgc aaaccttgac attaacagct gaatggggca agttgatgaa    1425
aacactactt tcaagccttc gttcttcctt gagcatctct ggggaagagc tgtcaaagaa   1485
ctggtggtag gctggtgaaa acttgacagc tagacttgat gcttgctgaa atgaggcagg    1545
aatcataata gaaaactcag cctccctaca gggtgagcac cttctgtctc gctgtctccc    1605
tctgtgcagc cacagccaga gggcccagaa tggccccact ctgttcccaa gcagttcatg    1665
atacagcctc accttttggc cccatctctg gttttttgaaa atttggtcta aggaataaat   1725
agcttttaca ctggctcacg aaaatctgcc ctgctagaat ttgcttttca aaatggaaat    1785
aaattccaac tctcctaaga ggcatttaat taaggctcta cttccaggtt gagtaggaat    1845
ccattctgaa caaactacaa aaatgtgact ggggaaggggg ctttgagaga ctgggactgc   1905
tctgggttag gttttctgtg gactgaaaaa tcgtgtcctt ttctctaaat gaagtggcat    1965
caaggactca gggggaaaga aatcagggga catgttatag aagttatgaa aagacaacca    2025
catggtcagg ctcttgtctg tggtctctag ggctctgcag cagcagtggc tcttcgatta    2085
gttaaaactc tcctaggctg acacatctgg gtctcaatcc ccttggaaat tcttggtgca    2145
ttaaatgaag ccttaccccca ttactgcggt tcttcctgta aggggctcc attttcctcc    2205 ctctctttaa atgaccacct aaaggacagt atattaacaa gcaaagtcga ttcaacaaca    2265
gcttcttccc agtcactttt ttttttctca ctgccatcac atactaacct tatactttga    2325
tctattcttt ttggttatga gagaaatgtt gggcaactgt ttttacctga tggttttaag    2385
ctgaacttga aggactggtt cctattctga aacagtaaaa ctatgtataa tagtatatag    2445
ccatgcatgg caaatatttt aatatttctg ttttcatttc ctgttggaaa tattatcctg    2505
cataatagct attggaggct cctcagtgaa agatcccaaa aggattttgg tggaaaacta    2565
gttgtaatct cacaaactca acactaccat caggggtttt ctttatggca aagccaaaat    2625
agctcctaca atttcttata tccctcgtca tgtggcagta tttatttatt tatttggaag    2685
tttgcctatc cttctatatt tatagatatt tataaaaatg taacccccttt ttcctttctt    2745 ctgtttaaaa taaaaataaa attta                                         2770
```

<210> SEQ ID NO 2
<211> LENGTH: 251

```
<212> TYPE: PRT
<213> ORGANISM: Homo sapiens

<400> SEQUENCE: 2

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

Asp Phe Arg Gly Asn Ile Phe Gly Ser His Tyr Phe Asp Pro Glu Asn
            100                 105                 110

Cys Arg Phe Gln His Gln Thr Leu Glu Asn Gly Tyr Asp Val Tyr His
        115                 120                 125

Ser Pro Gln Tyr His Phe Leu Val Ser Leu Gly Arg Ala Lys Arg Ala
    130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Arg Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
    210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile
                245                 250

<210> SEQ ID NO 3
<211> LENGTH: 684
<212> TYPE: DNA
<213> ORGANISM: Homo sapiens
<220> FEATURE:
<221> NAME/KEY: CDS
<222> LOCATION: (1)..(681)

<400> SEQUENCE: 3 tat ccc aat gcc tcc cca ctg ctc ggc tcc agc tgg ggt ggc ctg atc      48
Tyr Pro Asn Ala Ser Pro Leu Leu Gly Ser Ser Trp Gly Gly Leu Ile
 1               5                  10                  15 cac ctg tac aca gcc aca gcc agg aac agc tac cac ctg cag atc cac      96
His Leu Tyr Thr Ala Thr Ala Arg Asn Ser Tyr His Leu Gln Ile His
            20                  25                  30 aag aat ggc cat gtg gat ggc gca ccc cat cag acc atc tac agt gcc     144
Lys Asn Gly His Val Asp Gly Ala Pro His Gln Thr Ile Tyr Ser Ala
        35                  40                  45 ctg atg atc aga tca gag gat gct ggc ttt gtg gtg att aca ggt gtg     192
Leu Met Ile Arg Ser Glu Asp Ala Gly Phe Val Val Ile Thr Gly Val
    50                  55                  60
```

```
atg agc aga aga tac ctc tgc atg gat ttc aga ggc aac att ttt gga     240
Met Ser Arg Arg Tyr Leu Cys Met Asp Phe Arg Gly Asn Ile Phe Gly
65                  70                  75                  80 tca cac tat ttc gac ccg gag aac tgc agg ttc caa cac cag acg ctg     288
Ser His Tyr Phe Asp Pro Glu Asn Cys Arg Phe Gln His Gln Thr Leu
                85                  90                  95 gaa aac ggg tac gac gtc tac cac tct cct cag tat cac ttc ctg gtc     336
Glu Asn Gly Tyr Asp Val Tyr His Ser Pro Gln Tyr His Phe Leu Val
            100                 105                 110 agt ctg ggc cgg gcg aag aga gcc ttc ctg cca ggc atg aac cca ccc     384
Ser Leu Gly Arg Ala Lys Arg Ala Phe Leu Pro Gly Met Asn Pro Pro
        115                 120                 125 ccg tac tcc cag ttc ctg tcc cgg agg aac gag atc ccc cta att cac     432
Pro Tyr Ser Gln Phe Leu Ser Arg Arg Asn Glu Ile Pro Leu Ile His
    130                 135                 140 ttc aac acc ccc ata cca cgg cgg cac acc cgg agc gcc gag gac gac     480
Phe Asn Thr Pro Ile Pro Arg Arg His Thr Arg Ser Ala Glu Asp Asp
145                 150                 155                 160 tcg gag cgg gac ccc ctg aac gtg ctg aag ccc cgg gcc cgg atg acc     528
Ser Glu Arg Asp Pro Leu Asn Val Leu Lys Pro Arg Ala Arg Met Thr
                165                 170                 175 ccg gcc ccg gcc tcc tgt tca cag gag ctc ccg agc gcc gag gac aac     576
Pro Ala Pro Ala Ser Cys Ser Gln Glu Leu Pro Ser Ala Glu Asp Asn
            180                 185                 190 agc ccg atg gcc agt gac cca tta ggg gtg gtc agg ggc ggt cga gtg     624
Ser Pro Met Ala Ser Asp Pro Leu Gly Val Val Arg Gly Gly Arg Val
        195                 200                 205 aac acg cac gct ggg gga acg ggc ccg gaa ggc tgc cgc ccc ttc gcc     672
Asn Thr His Ala Gly Gly Thr Gly Pro Glu Gly Cys Arg Pro Phe Ala
    210                 215                 220 aag ttc atc tag                                                     684
Lys Phe Ile
225

<210> SEQ ID NO 4
<211> LENGTH: 227
<212> TYPE: PRT
<213> ORGANISM: Homo sapiens

<400> SEQUENCE: 4

Tyr Pro Asn Ala Ser Pro Leu Leu Gly Ser Ser Trp Gly Gly Leu Ile
1               5                   10                  15

His Leu Tyr Thr Ala Thr Ala Arg Asn Ser Tyr His Leu Gln Ile His
            20                  25                  30

Lys Asn Gly His Val Asp Gly Ala Pro His Gln Thr Ile Tyr Ser Ala
        35                  40                  45

Leu Met Ile Arg Ser Glu Asp Ala Gly Phe Val Val Ile Thr Gly Val
    50                  55                  60

Met Ser Arg Arg Tyr Leu Cys Met Asp Phe Arg Gly Asn Ile Phe Gly
65                  70                  75                  80

Ser His Tyr Phe Asp Pro Glu Asn Cys Arg Phe Gln His Gln Thr Leu
                85                  90                  95

Glu Asn Gly Tyr Asp Val Tyr His Ser Pro Gln Tyr His Phe Leu Val
            100                 105                 110

Ser Leu Gly Arg Ala Lys Arg Ala Phe Leu Pro Gly Met Asn Pro Pro
        115                 120                 125

Pro Tyr Ser Gln Phe Leu Ser Arg Arg Asn Glu Ile Pro Leu Ile His
    130                 135                 140

Phe Asn Thr Pro Ile Pro Arg Arg His Thr Arg Ser Ala Glu Asp Asp
```

```
                145                 150                 155                 160
Ser Glu Arg Asp Pro Leu Asn Val Leu Lys Pro Arg Ala Arg Met Thr
                    165                 170                 175

Pro Ala Pro Ala Ser Cys Ser Gln Glu Leu Pro Ser Ala Glu Asp Asn
                180                 185                 190

Ser Pro Met Ala Ser Asp Pro Leu Gly Val Val Arg Gly Gly Arg Val
            195                 200                 205

Asn Thr His Ala Gly Gly Thr Gly Pro Glu Gly Cys Arg Pro Phe Ala
        210                 215                 220

Lys Phe Ile
225

<210> SEQ ID NO 5
<211> LENGTH: 465
<212> TYPE: DNA
<213> ORGANISM: Homo sapiens
<220> FEATURE:
<221> NAME/KEY: CDS
<222> LOCATION: (1)..(465)

<400> SEQUENCE: 5 tat ccc aat gcc tcc cca ctg ctc ggc tcc agc tgg ggt ggc ctg atc        48
Tyr Pro Asn Ala Ser Pro Leu Leu Gly Ser Ser Trp Gly Gly Leu Ile
1               5                   10                  15 cac ctg tac aca gcc aca gcc agg aac agc tac cac ctg cag atc cac        96
His Leu Tyr Thr Ala Thr Ala Arg Asn Ser Tyr His Leu Gln Ile His
                20                  25                  30 aag aat ggc cat gtg gat ggc gca ccc cat cag acc atc tac agt gcc       144
Lys Asn Gly His Val Asp Gly Ala Pro His Gln Thr Ile Tyr Ser Ala
            35                  40                  45 ctg atg atc aga tca gag gat gct ggc ttt gtg gtg att aca ggt gtg       192
Leu Met Ile Arg Ser Glu Asp Ala Gly Phe Val Val Ile Thr Gly Val
        50                  55                  60 atg agc aga aga tac ctc tgc atg gat ttc aga ggc aac att ttt gga       240
Met Ser Arg Arg Tyr Leu Cys Met Asp Phe Arg Gly Asn Ile Phe Gly
65                  70                  75                  80 tca cac tat ttc gac ccg gag aac tgc agg ttc caa cac cag acg ctg       288
Ser His Tyr Phe Asp Pro Glu Asn Cys Arg Phe Gln His Gln Thr Leu
                85                  90                  95 gaa aac ggg tac gac gtc tac cac tct cct cag tat cac ttc ctg gtc       336
Glu Asn Gly Tyr Asp Val Tyr His Ser Pro Gln Tyr His Phe Leu Val
            100                 105                 110 agt ctg ggc cgg gcg aag aga gcc ttc ctg cca ggc atg aac cca ccc       384
Ser Leu Gly Arg Ala Lys Arg Ala Phe Leu Pro Gly Met Asn Pro Pro
        115                 120                 125 ccg tac tcc cag ttc ctg tcc cgg agg aac gag atc ccc cta att cac       432
Pro Tyr Ser Gln Phe Leu Ser Arg Arg Asn Glu Ile Pro Leu Ile His
    130                 135                 140 ttc aac acc ccc ata cca cgg cgg cac acc cgg                           465
Phe Asn Thr Pro Ile Pro Arg Arg His Thr Arg
145                 150                 155

<210> SEQ ID NO 6
<211> LENGTH: 155
<212> TYPE: PRT
<213> ORGANISM: Homo sapiens

<400> SEQUENCE: 6

Tyr Pro Asn Ala Ser Pro Leu Leu Gly Ser Ser Trp Gly Gly Leu Ile
1               5                   10                  15

His Leu Tyr Thr Ala Thr Ala Arg Asn Ser Tyr His Leu Gln Ile His
```

```
                    20                  25                  30
Lys Asn Gly His Val Asp Gly Ala Pro His Gln Thr Ile Tyr Ser Ala
                35                  40                  45
Leu Met Ile Arg Ser Glu Asp Ala Gly Phe Val Val Ile Thr Gly Val
        50                  55                  60
Met Ser Arg Arg Tyr Leu Cys Met Asp Phe Arg Gly Asn Ile Phe Gly
65                  70                  75                  80
Ser His Tyr Phe Asp Pro Glu Asn Cys Arg Phe Gln His Gln Thr Leu
                85                  90                  95
Glu Asn Gly Tyr Asp Val Tyr His Ser Pro Gln Tyr His Phe Leu Val
                100                 105                 110
Ser Leu Gly Arg Ala Lys Arg Ala Phe Leu Pro Gly Met Asn Pro Pro
            115                 120                 125
Pro Tyr Ser Gln Phe Leu Ser Arg Arg Asn Glu Ile Pro Leu Ile His
        130                 135                 140
Phe Asn Thr Pro Ile Pro Arg Arg His Thr Arg
145                 150                 155

<210> SEQ ID NO 7
<211> LENGTH: 219
<212> TYPE: DNA
<213> ORGANISM: Homo sapiens
<220> FEATURE:
<221> NAME/KEY: CDS
<222> LOCATION: (1)..(216)

<400> SEQUENCE: 7 agc gcc gag gac gac tcg gag cgg gac ccc ctg aac gtg ctg aag ccc        48
Ser Ala Glu Asp Asp Ser Glu Arg Asp Pro Leu Asn Val Leu Lys Pro
1               5                   10                  15 cgg gcc cgg atg acc ccg gcc ccg gcc tcc tgt tca cag gag ctc ccg        96
Arg Ala Arg Met Thr Pro Ala Pro Ala Ser Cys Ser Gln Glu Leu Pro
            20                  25                  30 agc gcc gag gac aac agc ccg atg gcc agt gac cca tta ggg gtg gtc       144
Ser Ala Glu Asp Asn Ser Pro Met Ala Ser Asp Pro Leu Gly Val Val
        35                  40                  45 agg ggc ggt cga gtg aac acg cac gct ggg gga acg ggc ccg gaa ggc       192
Arg Gly Gly Arg Val Asn Thr His Ala Gly Gly Thr Gly Pro Glu Gly
    50                  55                  60 tgc cgc ccc ttc gcc aag ttc atc tag                                   219
Cys Arg Pro Phe Ala Lys Phe Ile
65                  70

<210> SEQ ID NO 8
<211> LENGTH: 72
<212> TYPE: PRT
<213> ORGANISM: Homo sapiens

<400> SEQUENCE: 8

Ser Ala Glu Asp Asp Ser Glu Arg Asp Pro Leu Asn Val Leu Lys Pro
1               5                   10                  15

Arg Ala Arg Met Thr Pro Ala Pro Ala Ser Cys Ser Gln Glu Leu Pro
            20                  25                  30

Ser Ala Glu Asp Asn Ser Pro Met Ala Ser Asp Pro Leu Gly Val Val
        35                  40                  45

Arg Gly Gly Arg Val Asn Thr His Ala Gly Gly Thr Gly Pro Glu Gly
    50                  55                  60

Cys Arg Pro Phe Ala Lys Phe Ile
65                  70
```

```
<210> SEQ ID NO 9
<211> LENGTH: 543
<212> TYPE: DNA
<213> ORGANISM: Mus sp.
<220> FEATURE:
<221> NAME/KEY: CDS
<222> LOCATION: (1)..(540)

<400> SEQUENCE: 9 gcc ctg atg att aca tca gag gac gcc ggc tct gtg gtg ata aca gga    48
Ala Leu Met Ile Thr Ser Glu Asp Ala Gly Ser Val Val Ile Thr Gly
1               5                   10                  15 gcc atg act cga agg ttc ctt tgt atg gat ctc cac ggc aac att ttt    96
Ala Met Thr Arg Arg Phe Leu Cys Met Asp Leu His Gly Asn Ile Phe
            20                  25                  30 gga tcg ctt cac ttc agc cca gag aat tgc aag ttc cgc cag tgg acg   144
Gly Ser Leu His Phe Ser Pro Glu Asn Cys Lys Phe Arg Gln Trp Thr
        35                  40                  45 ctg gag aat ggc tat gac gtc tac ttg tcg cag aag cat cac tac ctg   192
Leu Glu Asn Gly Tyr Asp Val Tyr Leu Ser Gln Lys His His Tyr Leu
    50                  55                  60 gtg agc ctg ggc cgc gcc aag cgc atc ttc cag ccg ggc acc aac ccg   240
Val Ser Leu Gly Arg Ala Lys Arg Ile Phe Gln Pro Gly Thr Asn Pro
65                  70                  75                  80 ccg ccc ttc tcc cag ttc ctg gct cgc agg aac gag gtc ccg ctg ctg   288
Pro Pro Phe Ser Gln Phe Leu Ala Arg Arg Asn Glu Val Pro Leu Leu
                85                  90                  95 cat ttc tac act gtt cgc cca cgg cgc cac acg cgc agc gcc gag gac   336
His Phe Tyr Thr Val Arg Pro Arg Arg His Thr Arg Ser Ala Glu Asp
            100                 105                 110 cca ccg gag cgc gac cca ctg aac gtg ctc aag ccg cgg ccc cgc gcc   384
Pro Pro Glu Arg Asp Pro Leu Asn Val Leu Lys Pro Arg Pro Arg Ala
        115                 120                 125 acg cct gtg cct gta tcc tgc tct cgc gag ctg ccg agc gca gag gaa   432
Thr Pro Val Pro Val Ser Cys Ser Arg Glu Leu Pro Ser Ala Glu Glu
    130                 135                 140 ggt ggc ccc gca gcc agc gat cct ctg ggg gtg ctg cgc aga ggc cgt   480
Gly Gly Pro Ala Ala Ser Asp Pro Leu Gly Val Leu Arg Arg Gly Arg
145                 150                 155                 160 gga gat gct cgc ggg ggc gcg gga ggc gcg gat agg tgt cgc ccc ttt   528
Gly Asp Ala Arg Gly Gly Ala Gly Ala Asp Arg Cys Arg Pro Phe
                165                 170                 175 ccc agg ttc gtc tag                                                543
Pro Arg Phe Val
            180

<210> SEQ ID NO 10
<211> LENGTH: 180
<212> TYPE: PRT
<213> ORGANISM: Mus sp.

<400> SEQUENCE: 10

Ala Leu Met Ile Thr Ser Glu Asp Ala Gly Ser Val Val Ile Thr Gly
1               5                   10                  15

Ala Met Thr Arg Arg Phe Leu Cys Met Asp Leu His Gly Asn Ile Phe
            20                  25                  30

Gly Ser Leu His Phe Ser Pro Glu Asn Cys Lys Phe Arg Gln Trp Thr
        35                  40                  45

Leu Glu Asn Gly Tyr Asp Val Tyr Leu Ser Gln Lys His His Tyr Leu
    50                  55                  60

Val Ser Leu Gly Arg Ala Lys Arg Ile Phe Gln Pro Gly Thr Asn Pro
```

```
                65                  70                  75                  80
Pro Pro Phe Ser Gln Phe Leu Ala Arg Arg Asn Glu Val Pro Leu Leu
                    85                  90                  95

His Phe Tyr Thr Val Arg Pro Arg Arg His Thr Arg Ser Ala Glu Asp
                100                 105                 110

Pro Pro Glu Arg Asp Pro Leu Asn Val Leu Lys Pro Arg Pro Arg Ala
                115                 120                 125

Thr Pro Val Pro Val Ser Cys Ser Arg Glu Leu Pro Ser Ala Glu Glu
        130                 135                 140

Gly Gly Pro Ala Ala Ser Asp Pro Leu Gly Val Leu Arg Arg Gly Arg
145                 150                 155                 160

Gly Asp Ala Arg Gly Gly Ala Gly Gly Ala Asp Arg Cys Arg Pro Phe
                165                 170                 175

Pro Arg Phe Val
            180

<210> SEQ ID NO 11
<211> LENGTH: 13200
<212> TYPE: DNA
<213> ORGANISM: Homo sapiens

<400> SEQUENCE: 11
ggctctcatg gctttagctc taacatgttg tatgggtttg gacaccttga aaagtgctta     60
ggaggtcttg gggccagacc tggattcaaa tccaacctct tccacatgtt acctttctat    120
ctctaggcaa gttacttaaa ctgtgtgcat agatcagttt cctgatctat ataaagaaaa    180
taacagcatc tcctcaaaga gttattctga agatgaaatg ggttactaca gtaaagcac    240 ttagagcagt aagtggaaca gtaagctctc catgagcgtt agttcttgct gtgattcttt    300
ggagaagcag cctagggaag gagaagacct tgtcctggct ctaccattta tttgctttgt    360
gcctttggac atggaaacac taagatttcc atttcttcat gtaaagtatt aaaatcttga    420
taatgcatgg agtgcctatc tcacagagtg gcagtgaggt tcaaataagc taatagatgt    480
gaaaatgctt tgtaaactat aaaaaaaaac tgtacaaatg tagggtaaca aatgccatct    540
cttctgtcct atacctgtaa gcttgcactc attttgtatt atagttactt attttatct    600 gcctcctgca ttagatttga gctcctcaag ataggaatca catcttgctg tctcctatat    660
caacctgtac atgagtctag cttgatgcct gtacatggca tatactcagt acagggaaac    720
tggaagaata gcaaactcct tgtgtgtttt tcgggtgtg tgttccagta gcttgctccc    780
ctttagactg tatgtgccag gactattcca cccgacatca ggtgtagctt cccagagggc    840
tcactgtgaa cagcatctgc aggcaggcat ccaacaccaa gctgagcact catgtacaga    900
cactaaatgt ggggacaccc tgtcctgagg ctcggatccc cagtgctcag ccagcagctg    960
ttccaatccc catgaggtct ctgaatgagt ctccttacta ctggagagac tactagttta   1020
gttgccctcg atagtccaaa ctagggaaat tgagaaattg aaccttggca tattcagtga   1080
agtccagact aaggaagctg agaaactgaa ccttggcatg ttcactgacc tcaaggcctt   1140
acttcttttt cttccatttc aaaatcttcc caaaatggca actttggctt ttgtgccct   1200 gctcctagct cccatctttc atgaagtggg tgttcttaga ggatgccatc tgcctgatgg   1260
tgtcatgtat ctctatatcc tgcaagctac ccaccaaatc tgctcacag attaagcact   1320 ggatacatac ttgctgattg gaatttaaag aaaaccaaaa taagtaaact cgacaggaga   1380
ttaattgcct aggagtcggt tgactgcttg actgaagctg gatttttttt gggaaccgct   1440
ggctgccttc acatttcctg atggaagtgg gacaggtcaa cagacagccc agagtggcag   1500
```

```
ataacttttg cccacacgtc attcattttt tggagcgttg gcttgaaatt gagggtgtg    1560 tgtgtctgga accgacgtgc cttccgtgcg cctccggggt ctttgcactt tctttcaatg   1620
ggctgattac aacacagagg atgtggacag tggagttttt cctgtttgat gtcacactgc   1680 tacccttaa aagtctgacg gcaaaaagga gggaatccag tctaggatcc tcacaccagc    1740
tacttgcaag ggagaaggaa aaggccagta aggcctgggc caggagagtc ccgacaggag   1800
tgtcaggttt caatctcagc accagccact cagagcaggg cacgatgttg ggggcccgcc   1860
tcaggctctg ggtctgtgcc ttgtgcagcg tctgcagcat gagcgtcctc agagcctatc   1920
ccaatgcctc cccactgctc ggctccagct ggggtggcct gatccacctg tacacagcca   1980
cagccaggaa cagctaccac ctgcagatcc acaagaatgg ccatgtggat ggcgcacccc   2040
atcagaccat ctacagtgag tagggcttca ggctgggaag aagggagca cccttgttgt     2100 ccatctacag gaggcttggg gaggttgggg actagactgg agggctaatc caaccctcct   2160
agctttctgc ccaggaacca cttattgtct ttgtgtgtgt gtgtgtttgt gtgtgtgtgt   2220
gtgtgcgtgt gtatttaaaa cttaggggaa gattctgtca ctctcctaat tagcatttgc   2280
tggtttttct caatatgaat aatttttatt tcaactaaaa cccttcccac agtaggagcc   2340
atgttccctt tgccccgtca aaagattgaa aaaatgtaca gaaagaaagg caaggagtct   2400
aagagaaaaa gaagccaggc agatcaacag acactaagtt tcagctcatg gactttggac   2460
tgggttaact agggaggttg taaagattcc tgggtcatac ccagattgtt atagataaat   2520 ctggggctc tttccaactc tggccttata aaaattcttg gaaaaatgta ttaaagacag     2580
actgtccatg tatgttgtct tggtgagaat ggccaagtat acaacccatc cacccattca   2640
tttgtccatg catccatcca tccatccatc catccatcca tccatccatc catccatcca   2700
tccaacaggt ttaatgggtg tttcagacac ccaggtaccc aggtacccag tatgagttgg   2760
tgattcttct ctgtggaact gaaaggtgtc cagtcagtag caagtcaagc tagttagaaa   2820
cttattggca acatgagaca actggaatgt ttttaaagat caggtttgtg gagaattgga   2880
tcacaatcca caataatcaa tccattagca atgattcaaa tgagggtccc tttgtgtgca   2940
cctatataag gggtaatgtg gtgaaagcag ggatagatat tgaaaaagac tggatcttct   3000
attttaagaa aacgtgagaa aacacctcaa agcatacaga aaaatgcaaa ctgatccaat   3060
atagctcaaa ttaaaggaaa gaaaaattag ttagacaatc tctaactaaa gaaaacatag   3120
gaattatgat ttgcccttta ttgttgtaat aaataaatta attatttttg ctgtgacctt   3180
gctgtgtgtg aggcatttat tcttctaggc tccaaggtc cttaaacctg gttgcaagat     3240
atacaacatg caaattaag ttgcaagata tataacatgc gaaattgaca gtttaacctc     3300
ttcaagtact aaatgcatat tgacaggaga taaaggaga gaggaaagtt ctctccgaat     3360
accaaacagg ttccagaact ccagagaata tagtaagact caggagtcaa catcttggaa   3420
accaagtttg agtctcatgg caaaaatttc aattaaatct ggatacactt gatgcacccg   3480
aagtgttgtt catttattc aatgatatt taataggatc taccatgtgc ctggcattct      3540
accaagcgct gtggctgaaa actaagacac aaccttcaa ggacctcatg gtctgtcgtc     3600
ctaccttgtc agccagctca ctaccagact ttcaggaaat gcaattttgc atgtctcatg   3660
gaggggacac ccttactcta attcaagact atatgtgggc caggtgtggt ggctcacgcc   3720
tgtaatccca gcactctggg aggccgaggc aggcagatca cgaggtcagg agattgagac   3780
catcctggct aacacagtga aaccccatct ctactaaaaa tacaaaaaat tagccaggcg   3840
tggtggcagg cgcctgtagt cccagctact tgggaggctg aggcaggaga atggcgtgaa   3900
```

```
cccgggaggc agagcttgca gtgagccgag attgcgccac tgcactccag cctgggtgac   3960
agagcgagac tccatctcaa aaaaaaaaaa aaaaaaaaa aaaagactat atgtgattta    4020
aaatgcagaa tagtagatta tggtaaatta ttttgattct cttagatgga aagggctgca   4080
tccaactaga gaatgtttat acaacttgtc tcgaatcctg gaatcccgtt gctgaaagga   4140
actccttaaa gacgtttctt cctgaacaag aattagggta gaacagaaca ggccggctac   4200
ggtggggagt gagtgtgaag agtcaacctc ctgggctggc agtctgaact tagaccttt    4260 ccttgaaagc ccacctcgta tcaggcccca agggatcact gagtgctagt tagagtgaat   4320
taaaatgact gagaagcagc aaaataaatt gaactgactt cagattttta aaaatagaaa   4380
tgtgattttg tttccttaga cataggcact agctaaacat tgcatcttta aagagttaaa   4440
catgaatgcg gggaggggaa cttcgggtca gggtagtggg agggagatct acttttccta   4500
gtctatgtag ataactttt gtactgttca atgagttgtc atgtgtatta tgggaaaaaa    4560
aaagtgcagg aaaaaattac acactacaat taaaagttac ccaaaagagg ccagatgcgg   4620
tggctcacgc gtataatctc agcactttgg gaggccgagg tgggaggatc acttgaagtc   4680
aggggttcga gaccagtctg gccaacatgg ggaaaccctg tctctactaa aaatacaaaa   4740
attagtgggg tgtggtgcct gcctgtagtc acagctactt gggaggctga ggcagaagaa   4800
tcgcttgtac cccagaggtg gagcttgcag tgagctgaga tcgcaccact gtgctccagc   4860
ctgggtgaca gagtgagact ccgtctcaaa aaaaaacgt tacccaaaag aaagaggaaa    4920
gattaatgca tgtagataag aagcacaact aattaaatgt ctggtgaagg atttgtaatg   4980
acctcatcag tgactgttaa gcaatgtttt tacactgatg gaaacctaaa atgtgagggg   5040 tatttttcc cctcctaatt atccatttct attgaattct ggtttatctt attactttgc    5100
tgtaagaaat tcttaagagt tgagtgcaca acccatcttt gggtcactgg acttgacaaa   5160
atgaagttat ctcctgccta ccagattctt caagctccct taggactcac aagcgctgct   5220
gccaggtacc cctctggtgt ccttatcacc cgttccatga acaaggccat cctctgactc   5280 cccttatcc ttattatatg gaaacagcaa gagagagatg cttattgtcc ctggtaatat    5340
catttcctag atcctgctat tttcacttcc tccatcttcc ccataggaac tatctttatt   5400
gaagctgaat taccgctgag ctccttcagc ctttttcata cgttttctt ttgaggtgct    5460 caaagcactt cactgctatc atcttattta tcacttactg gccacaagag tagaatggag   5520
tagataattt tctacttcta taagcagagg ttgaagcaaa gtggtaatag taaaaattac   5580
tagcacttag gaagtgcttt ctaaaggata aaaacattat ctcattatgt cttcaagatg   5640
accaaatgag gtaaatgttt ctgctgtcct cattttatat gtgaaaaaac aagagttaaa   5700
gaacttaaat aactggctga aggtcagaca ggtagtaaaa gacctagagg acaccttgac   5760
cccaaatccc aagctgttcc aaggtcacac gcacggagac acctccgtca ttgaaggcaa   5820
agtccattaa gcctgctcag ctccaacagg cggggctggt tgctccggca gtccatggtt   5880
tgttccttcc ttctgcaaaa ttctcccttg aatctgtgca gactgcgaaa agatgccttt   5940
tgaaagcaca aaggaaagaa actctgactc tctcacattt tctaaacttt cacattggct   6000
cacactgttt gatggaagag tctgtgtgcc ctccgtagca gcttctcaca gttcctcaac   6060
caccgccgga tgttttctag ggggactggc tctggaaacc aggagcgtgt gtgccataca   6120
cactgcccac actgacccca agcatcaagc cagcacacct gtcaaggcat gggcccggca   6180
taaacagcag gtcagaacac gccacgtgat gtcctctgtt tgctcgacac tttcgagtca   6240
cttttaccac cattatcccc ttcgatcatc accctatgaa gtaggcagga cagccattgt   6300
```

```
tctatttcac agctgaggaa actgaggcta gtgcaaggtc agcaagtggc acaattggga    6360
ccaaaatcca agtccctgg ttcttggcac ctggctcagt gcccttccc cgagcccta     6420 gtgctgctgt gactccttgt cctcactgcc tgcagcatgt attttagcat ttgatattgt    6480
cttctcagac tcttagtgat ttctgctgga ggcttgttac cgggtggtgg aagatgtct    6540 ctgacctgag tttcaatcct gtcttagttt ccttatcact taaattagga tattgctgct    6600
actactacta ctaataataa taataatcag tactaacaat ataaaatttg ttttgagaat    6660
ttaaaatatg taaagtgctt agagtgcaac cgctcaaaga ccattactaa atgtaatttt    6720
ttcccaatta gactgaaaag tcaccagaac agaaaccatt tctttttttt tttttttgag    6780
acggagtctc gctctgtcgc ccaggctgga gtgcagtggt gcaatctcgg cttactgcta    6840
gctccgcctc ccaggttcat gccattctcc tgcctcagcc tcccgagtag ctgggactac    6900
aggtgcccac caacacacct ggctaatttt ttttgtattt tagtagagaa gaggtttcac    6960
cgtgttagcc aggatggtct tgatctcctg acctcatgat ccacccgcct cagcctccca    7020
gagtgctggg attacaggca tgagccaccg cacccagtcg aaaccatttc ttacacgttc    7080
cttatatttc tccaaaggtt taccacaaaa ctagccatac atttgagaca cataggcaga    7140
caccactgtg gaggaattta agcatccttt gcgcctgtca taccccagtc cactttctgg    7200
gaagctttcc tcaaggttcc cctcagccaa actttgaaac aaattaactt ctctctttgg    7260
ccctcttcct ttctcacctt tctggggctt gtctccaccc tcattccctc tgttccgcgt    7320
cagtccaatt tcagtcccta tcatgatttc tactcagcta gtacctaatt attgctgctt    7380
attttcctca aggtccttg tattgagcct gcatgggata ggagaagagc tttggccttt    7440
aaatcacccc cacaaggctc catcacttgc taggcacaaa cattgggcat ttacaacctc    7500
tccaagctac agttgcagaa gaggaattag aatccctgca tgggattcta gctgcctccc    7560
tggaggctat gaggtcagat gagatgcacc tagaaattct gtgataggca actggaagta    7620
gccccaaaga cctaaagtaa tgattttta cagaaaatgt caggtaatta aataacatgt    7680
ggggaagaaa tctcgctgaa ttatcacgca tgttacacca gtatatgatc taattgtgcc    7740
tttgccacaa aacagtaatt taaagccatt atcaattact taagaggtag gtcgtgtgaa    7800
tgggtttcag gcccttgtcg gagactagtt tttgagaggg gacactgaaa gtccatgagg    7860
ggctgcacct ggagaggtca ccaccaagtg agaaaatgac aaagaaccaa cccaagaaga    7920
gccaagaaga aaattccatc cgtcacttat attgattcaa cataaacagt tataccctct    7980
gctcctaagc agctcactct aaggaacgca ctggataggt aaactcagct aaagcaagtt    8040
aaatggaata catgctgtaa tagaggtgaa ggcattgtcc tgaggagctg agaaggaaga    8100
acaactgatt ttgaatggaa agatgaggaa agtcttcata gagatggtga cgcctgagcc    8160
tggtcttgaa gagtgagtga cttcaataag tagagaagga agaggagat caactctact    8220 accattctgt acacatactg ggtgttgact gatgtattag acaattacac agacatccag    8280
gaggagaatc agactctatg gcaagctgga tccttgaaag acatctcagc atagatttaa    8340
aaatcacaaa gtagaaggca tggaagaatg tgactatcac cacaaacatt caaaggtatt    8400
agtaaggcaa aagggaaaat aaagacggtc caggtagaga gagagaaaca tgtgttcagc    8460
acaggtagaa gaattccagg agctcagagt gccccataca ggcaacaaga tgaagcagga    8520
ggtgaatgac tgtatgtgtg ttgggggcaa gagaggatgt cagaagaaac gctgaatatg    8580
cagaaatgag gctgaattta agagtgctga agttatcacc acccctaaaa tcaatccagg    8640
gaggtttcat gaaggtaggt tttcaggagg tgcttgaagg tgggaattgg atggcaatga    8700
```

```
gtctttgccc tgcctgtttt tctccatagg tgccctgatg atcagatcag aggatgctgg    8760
ctttgtggtg attacaggtg tgatgagcag aagatacctc tgcatggatt tcagaggcaa    8820
cattttggga tcagtgagtt tcttttttgt gttggtcacc atttgcaaac aattaaccta    8880
atttctttga cacgacatag acttttctag cttaacaatt ccatttgcag tgtaccctgg    8940
tgacctgttt ccactgatac ttcatgcagt ctaagtatga attaaacgtg aatgctcacg    9000
tttaatagct ggggtttgaa ctcaggcaat ctggctccag atcccaggct ctcagcccct    9060
agtctgcact gcccattgga acccactttt ttttttatt attatacttt aagttttagg    9120
gtacatgtgc acattgtgca ggttagttac atacgtatac atgtgccatg ctggtgtgct    9180
gcacccacta actcatcatc tagcattagg tatatctccc aatgctatcc ctcccccctc    9240
cccccacccc acaacagtcc ccagagtgtg atgttcccct tcctgtgtcc atgtgatctc    9300
attgttcaat tcccacctac gagtgagaat atgcggtgtt tggttttttg ttcttgcgat    9360
agtttactga gaatgatggt ttccaatttc atccatgtcc ctacaaagga catgaactca    9420
tcatttttta tggctgcata gtattccatg gtgtatatgt gccacatttt cttaatccag    9480
tctatcattg ttggacattt gggttgtgga acccactttt gaatctagca caggccctgg    9540
tatgtagtcg taggtcctca agtcatgtca attcacgttg taaagtacat tagaaagggt    9600
gaaaagccat tggtgtcttc ttgattctgg gactagctgt gactttgggt aaatctcctc    9660
acttctccaa acttcagcat tttcacttgg aaaaagcgaa gtggaataga ccacgtgacc    9720
tgtggagctc cctccagtta aagatttta attaataacc cctgcccaa ttgtgatagc     9780 tattcattcg gattggtaag caaaggattt cccaaactaa aggctgctgg cctcttttgg    9840
aggattttga gatagtaaaa tagtaggact gcttatctca ggagtctctg accaccacac    9900
atgcccacta gaaactccac aagaacagag actttctgtt ttgctttctg ctgcatccca    9960
gcccctacaa tagtgtctgg ctagagtagg taaacaaaca aacaaaaaat ctgttgaacc    10020
actattgaaa tatagataac taactaaaca tccgttaacc cctctaggca tgtagatagt    10080
cctgatctgt aaactgctta cttttgtggag cttgaggatt aaaagaaata acaggcaaag    10140
gccttcgtgg ggcactcagt aaaacccagt actagtggta gaggattcaa acccagctca    10200
tctgtcagca aagttcatgt ctccaatccc gtcagtgctc tcattcatgt ttgaccctat    10260
aaactccatc ccctctcctt tctccagtaa agagacaaac ccaagccaat tttcagccag    10320
cagaggcttg gaaaagatag agggcaggaa ggacaaggtg gtgcctactc caggaaaacc    10380
acaggccagg ccagcccggg cctccaggca gtaagcggag gccccagtag tcgtagtctc    10440
tgaaagggcg aactatatag tcagggcttg agcattaatc aaaaccactc taccccagca    10500
gggaacaaag gggtgaaggc tcaacgccct aagaactgca gagcttcagg ccggctggca    10560
caagcatgtg gccccaggag gagctgggga gtgggtgggg ccccactgc cagccttcac     10620 gtggttcgct cttgtccttc cagcactatt tcgacccgga gaactgcagg ttccaacacc    10680
agacgctgga aaacgggtac gacgtctacc actctcctca gtatcacttc ctggtcagtc    10740
tgggccgggc gaagagagcc ttcctgccag gcatgaaccc acccccgtac tcccagttcc    10800
tgtcccggag gaacgagatc cccctaattc acttcaacac ccccatacca cggcggcaca    10860
cccggagcgc cgaggacgac tcggagcggg acccctgaa cgtgctgaag cccgggccc     10920 ggatgacccc ggccccggcc tcctgttcac aggagctccc gagcgccgag acaacagcc     10980 cgatggccag tgacccatta ggggtggtca ggggcggtcg agtgaacacg cacgctgggg    11040
gaacgggccc ggaaggctgc cgccccttcg ccaagttcat ctagggtcgc tggaagggca    11100
```

```
ccctctttaa cccatccctc agcaaacgca gctcttccca aggaccaggt cccttgacgt   11160
tccgaggatg ggaaaggtga caggggcatg tatggaattt gctgcttctc tggggtccct   11220
tccacaggag gtcctgtgag aaccaacctt tgaggcccaa gtcatggggt ttcaccgcct   11280
tcctcactcc atatagaaca cctttcccaa taggaaaccc caacaggtaa actagaaatt   11340
tccccttcat gaaggtagag agaagggtc tctcccaaca tatttctctt ccttgtgcct   11400
ctcctcttta tcacttttaa gcataaaaaa aaaaaaaaa aaaaaaaaa aaaaagcag    11460 tgggttcctg agctcaagac tttgaaggtg tagggaagag gaaatcggag atcccagaag   11520
cttctccact gccctatgca tttatgttag atgccccgat cccactggca tttgagtgtg   11580
caaaccttga cattaacagc tgaatggggc aagttgatga aaacactact ttcaagcctt   11640
cgttcttcct tgagcatctc tggggaagag ctgtcaaaag actggtggta ggctggtgaa   11700
aacttgacag ctagacttga tgcttgctga aatgaggcag gaatcataat agaaaactca   11760
gcctccctac agggtgagca ccttctgtct cgctgtctcc ctctgtgcag ccacagccag   11820
agggcccaga atggccccac tctgttccca agcagttcat gatacagcct cacctttggg   11880
ccccatctct ggttttgaa aatttggtct aaggaataaa tagcttttac actggctcac   11940
gaaaatctgc cctgctagaa tttgcttttc aaaatggaaa taaattccaa ctctcctaag   12000
aggcatttaa ttaaggctct acttccaggt tgagtaggaa tccattctga acaaactaca   12060
aaaatgtgac tgggaagggg gctttgagag actgggactg ctctgggtta ggttttctgt   12120
ggactgaaaa atcgtgtcct tttctctaaa tgaagtggca tcaaggactc aggggggaaag   12180 aaatcagggg acatgttata gaagttatga aaagacaacc acatggtcag gctcttgtct   12240
gtggtctcta gggctctgca gcagcagtgg ctcttcgatt agttaaaact ctcctaggct   12300
gacacatctg ggtctcaatc cccttggaaa ttcttggtgc attaaatgaa gccttacccc   12360
attactgcgg ttcttcctgt aagggggctc cattttcctc cctctcttta aatgaccacc   12420
taaaggacag tatattaaca agcaaagtcg attcaacaac agcttcttcc cagtcacttt   12480 ttttttctc actgccatca catactaacc ttatactttg atctattctt tttggttatg    12540
agagaaatgt tgggcaactg ttttttacctg atggttttaa gctgaacttg aaggactggt   12600
tcctattctg aaacagtaaa actatgtata atagtatata gccatgcatg gcaaatattt   12660
taatatttct gttttcattt cctgttggaa atattatcct gcataatagc tattggaggc   12720
tcctcagtga aagatcccaa aaggattttg gtggaaaact agttgtaatc tcacaaactc   12780
aacactacca tcagggtttt tctttatggc aaagccaaaa tagctcctac aatttcttat   12840
atccctcgtc atgtggcagt atttatttat ttatttggaa gtttgcctat ccttctatat   12900
ttatagatat ttataaaaat gtaacccctt tttcctttct tctgtttaaa ataaaaataa   12960
aatttatctc agcttctgtt agcttatcct ctttgtagta ctacttaaaa gcatgtcgga   13020
atataagaat aaaaaggatt atgggagggg aacattaggg aaatccagag aaggcaaaat   13080 tgaaaaaag attttagaat tttaaaattt tcaaagattt cttccattca taaggagact   13140
caatgatttt aattgatcta gacagaatta tttaagtttt atcaatattg gatttctggt   13200
```

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic primer -continued

<400> SEQUENCE: 12
ttctgtctcg ctgtctccc                                              19

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ccccttccca gtcacattt                                              19

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggggcatcta acataaatgc                                             20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
agccactcag agcagggcac                                             20

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggtggcggcc gtctagaact a                                           21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tcagtctggg ccgggcgaag a                                           21

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18

-continued cacgttcaag gggtcccgct                                              20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tctgaaatcc atgcagaggt                                              20

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gggaggcatt gggataggct c                                            21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ctagatgaac ttggcgaagg g                                            21

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ccggaattca gccactcaga gcagggcacg                                   30

<210> SEQ ID NO 23
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ataagaatgc ggccgctcaa tggtgatggt gatgatggat gaacttggcg aa          52

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
taatacgact cactataggg                                              20

```
<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
attaaccctc actaaaggga                                                   20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
accacagtcc atgccatcac                                                   20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tccaccaccc tgttgctgta                                                   20

<210> SEQ ID NO 28
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Asn Ser Tyr His Leu Gln Ile His Lys Asn Gly His Val Asp Gly
1               5                   10                  15

Ala Pro His Gln Cys
            20

<210> SEQ ID NO 29
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Phe Gln His Gln Thr Leu Glu Asn Gly Tyr Asp Val Tyr His Ser
1               5                   10                  15

Pro Gln Tyr His Cys
            20

<210> SEQ ID NO 30
<211> LENGTH: 26
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 30
tgaaggtcgg tgtgaacgga tttggc                                          26

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
catgtaggcc atgaggtcca ccac                                            24

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gtaaagaacc ctgtgtattc c                                               21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ctgccttaag aaatccataa t                                               21

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gaggaatcac agtctcattc                                                 20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cttggggagg tgcccgggac                                                 20

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 36
tccctcttag aagacaatac a                                                 21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gtgtttaaag gcagtattac a                                                 21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cagacagaga catccgtgta g                                                 21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ccacatggtc caggttcagt c                                                 21

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gacggtgaga ctcggaacgt                                                   20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tccggaaaat ctggccatac                                                   20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42

-continued taatacgact cactataggg                        20

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gatttaggtg acactatag                         19

<210> SEQ ID NO 44
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ataagaatgc ggccgctcag atgaacttgg cgaa        34

<210> SEQ ID NO 45
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
atgaattcca ccatgttggg ggcccgcctc agg         33

<210> SEQ ID NO 46
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
atgcggccgc ctaatgatga tgatgatgat ggatgaactt ggcgaaggg    49

<210> SEQ ID NO 47
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ataccacggc agcacaccca gagcgccgag             30

<210> SEQ ID NO 48
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ctcggcgctc tgggtgtgct gccgtggtat             30

<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Met Asn Pro Pro Tyr Ser Gln Phe Leu Ser Arg Arg Asn Glu
1               5                   10                  15

Cys

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Cys Asn Thr Pro Ile Pro Arg Arg His Thr Arg
1               5                   10

<210> SEQ ID NO 51
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ser Ala Glu Asp Asp Ser Glu Arg Asp Pro Leu Asn Val Leu Lys Cys
1               5                   10                  15

<210> SEQ ID NO 52
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Leu Pro Ser Ala Glu Asp Asn Ser Pro Met Ala Ser Asp Cys
1               5                   10

<210> SEQ ID NO 53
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
atgcggccgc tatcgaccgc ccctgaccac ccc                               33

<210> SEQ ID NO 54
<211> LENGTH: 33
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 54
atgcggccgc tacgggagct cctgtgaaca gga                                33

<210> SEQ ID NO 55
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
atgcggccgc tcaacaggag gccggggccg gggt                               34

<210> SEQ ID NO 56
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
atgcggccgc tcacggggtc atccgggccc gggg                               34

<210> SEQ ID NO 57
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
aattccacca tgttgggggc ccgcctcagg ctctgggtct gtgcttgtgc agcgtctgca   60
gcatgagcgt cctgcatgc                                               79

<210> SEQ ID NO 58
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
aattgcatgc aggacgctca tgctgcagac gctgcacaag gcacagaccc agagcctgag   60
gcgggccccc aacatggtgg                                              80

<210> SEQ ID NO 59
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
atatgcatgc ctccagctgg ggtggcctga tccac                              35

<210> SEQ ID NO 60
<211> LENGTH: 23
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 60
tgtatcccaa tgcctcccca ctg                                           23

<210> SEQ ID NO 61
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
atggatccct agatgaactt ggcgaaggg                                     29

<210> SEQ ID NO 62
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
atcatatgta tcccaatgcc tccccactg                                     29

<210> SEQ ID NO 63
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
atgcggccgc ctagatgaac ttggcgaagg g                                  31

<210> SEQ ID NO 64
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gaattcatat gaaatacccg aacgcttccc cgctgctggg ctccagctg               49

<210> SEQ ID NO 65
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
cccaagcttg cggccgccta gatgaacttg gc                                 32

<210> SEQ ID NO 66
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 66
aacaccccca tagcacggcg gcaca                                          25

<210> SEQ ID NO 67
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
tgtgccgccg tgctatgggg gtgtt                                          25

<210> SEQ ID NO 68
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
acccccatac cagcgcggca cacccg                                         26

<210> SEQ ID NO 69
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
cgggtgtgcc gcgctggtat gggggt                                         26

<210> SEQ ID NO 70
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
cccataccac gggcgcacac ccggag                                         26

<210> SEQ ID NO 71
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
ctccgggtgt gcgcccgtgg tatggg                                         26

<210> SEQ ID NO 72
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
```
ataccacggc gggccacccg gagcgc            26

<210> SEQ ID NO 73
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gcgctccggg tgcccgccg tggtat            26

<210> SEQ ID NO 74
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
ccacggcggc acgcccggag cgccg            25

<210> SEQ ID NO 75
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
cggcgctccg ggcgtgccgc cgtgg            25

<210> SEQ ID NO 76
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
cggcggcaca ccgcgagcgc cgagga            26

<210> SEQ ID NO 77
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
tcctcggcgc tcgcggtgtg ccgccg            26

<210> SEQ ID NO 78
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
cggcacaccc gggccgccga ggacga            26

```
<210> SEQ ID NO 79
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
tcgtcctcgg cggcccgggt gtgccg                                       26

<210> SEQ ID NO 80
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80 accccatac cacagcggca cacccg                                        26

<210> SEQ ID NO 81
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
cgggtgtgcc gctgtggtat gggggt                                       26

<210> SEQ ID NO 82
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
cccataccac ggcagcacac ccggag                                       26

<210> SEQ ID NO 83
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
ctccgggtgt gctgccgtgg tatggg                                       26

<210> SEQ ID NO 84
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
cggcggcaca cccagagcgc cgagga                                       26

<210> SEQ ID NO 85
```

```
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
tcctcggcgc tctgggtgtg ccgccg                                            26

<210> SEQ ID NO 86
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
cggcggcaca cctggagcgc cgagg                                             25

<210> SEQ ID NO 87
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
cctcggcgct ccaggtgtgc cgccg                                             25

<210> SEQ ID NO 88
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 88

His His His His His His
1               5

<210> SEQ ID NO 89
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Leu Ala Leu Pro Ala His His Asn Ala Thr Arg Leu
1               5                   10

<210> SEQ ID NO 90
<211> LENGTH: 747
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(744)

<400> SEQUENCE: 90 atg ggc agc agc cat cat cat cat cat cac agc agc ggc ctg gtg ccg     48
```

```
Met Gly Ser Ser His His His His His Ser Ser Gly Leu Val Pro
1               5                   10                  15 cgc ggc agc cat atg tat ccc aat gcc tcc cca ctg ctc ggc tcc agc      96
Arg Gly Ser His Met Tyr Pro Asn Ala Ser Pro Leu Leu Gly Ser Ser
            20              25                  30 tgg ggt ggc ctg atc cac ctg tac aca gcc aca gcc agg aac agc tac     144
Trp Gly Gly Leu Ile His Leu Tyr Thr Ala Thr Ala Arg Asn Ser Tyr
        35              40                  45 cac ctg cag atc cac aag aat ggc cat gtg gat ggc gca ccc cat cag     192
His Leu Gln Ile His Lys Asn Gly His Val Asp Gly Ala Pro His Gln
    50              55                  60 acc atc tac agt gcc ctg atg atc aga tca gag gat gct ggc ttt gtg     240
Thr Ile Tyr Ser Ala Leu Met Ile Arg Ser Glu Asp Ala Gly Phe Val
65              70                  75                  80 gtg att aca ggt gtg atg agc aga aga tac ctc tgc atg gat ttc aga     288
Val Ile Thr Gly Val Met Ser Arg Arg Tyr Leu Cys Met Asp Phe Arg
            85                  90                  95 ggc aac att ttt gga tca cac tat ttc gac ccg gag aac tgc agg ttc     336
Gly Asn Ile Phe Gly Ser His Tyr Phe Asp Pro Glu Asn Cys Arg Phe
        100                 105                 110 caa cac cag acg ctg gaa aac ggg tac gac gtc tac cac tct cct cag     384
Gln His Gln Thr Leu Glu Asn Gly Tyr Asp Val Tyr His Ser Pro Gln
    115                 120                 125 tat cac ttc ctg gtc agt ctg ggc cgg gcg aag aga gcc ttc ctg cca     432
Tyr His Phe Leu Val Ser Leu Gly Arg Ala Lys Arg Ala Phe Leu Pro
130                 135                 140 ggc atg aac cca ccc ccg tac tcc cag ttc ctg tcc cgg agg aac gag     480
Gly Met Asn Pro Pro Pro Tyr Ser Gln Phe Leu Ser Arg Arg Asn Glu
145             150                 155                 160 atc ccc cta att cac ttc aac acc ccc ata cca cgg cgg cac acc cgg     528
Ile Pro Leu Ile His Phe Asn Thr Pro Ile Pro Arg Arg His Thr Arg
            165                 170                 175 agc gcc gag gac gac tcg gag cgg gac ccc ctg aac gtg ctg aag ccc     576
Ser Ala Glu Asp Asp Ser Glu Arg Asp Pro Leu Asn Val Leu Lys Pro
        180                 185                 190 cgg gcc cgg atg acc ccg gcc ccg gcc tcc tgt tca cag gag ctc ccg     624
Arg Ala Arg Met Thr Pro Ala Pro Ala Ser Cys Ser Gln Glu Leu Pro
    195                 200                 205 agc gcc gag gac aac agc ccg atg gcc agt gac cca tta ggg gtg gtc     672
Ser Ala Glu Asp Asn Ser Pro Met Ala Ser Asp Pro Leu Gly Val Val
210                 215                 220 agg ggc ggt cga gtg aac acg cac gct ggg gga acg ggc ccg gaa ggc     720
Arg Gly Gly Arg Val Asn Thr His Ala Gly Gly Thr Gly Pro Glu Gly
225                 230                 235                 240 tgc cgc ccc ttc gcc aag ttc atc tag                                  747
Cys Arg Pro Phe Ala Lys Phe Ile
                245
```

<210> SEQ ID NO 91
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

```
Met Gly Ser Ser His His His His His His Ser Ser Gly Leu Val Pro
1               5                   10                  15

Arg Gly Ser His Met Tyr Pro Asn Ala Ser Pro Leu Leu Gly Ser Ser
            20                  25                  30
```

```
Trp Gly Gly Leu Ile His Leu Tyr Thr Ala Thr Ala Arg Asn Ser Tyr
            35                  40                  45

His Leu Gln Ile His Lys Asn Gly His Val Asp Gly Ala Pro His Gln
 50                  55                  60

Thr Ile Tyr Ser Ala Leu Met Ile Arg Ser Glu Asp Ala Gly Phe Val
 65                  70                  75                  80

Val Ile Thr Gly Val Met Ser Arg Arg Tyr Leu Cys Met Asp Phe Arg
                 85                  90                  95

Gly Asn Ile Phe Gly Ser His Tyr Phe Asp Pro Glu Asn Cys Arg Phe
                100                 105                 110

Gln His Gln Thr Leu Glu Asn Gly Tyr Asp Val Tyr His Ser Pro Gln
            115                 120                 125

Tyr His Phe Leu Val Ser Leu Gly Arg Ala Lys Arg Ala Phe Leu Pro
        130                 135                 140

Gly Met Asn Pro Pro Tyr Ser Gln Phe Leu Ser Arg Arg Asn Glu
145                 150                 155                 160

Ile Pro Leu Ile His Phe Asn Thr Pro Ile Pro Arg Arg His Thr Arg
                165                 170                 175

Ser Ala Glu Asp Asp Ser Glu Arg Asp Pro Leu Asn Val Leu Lys Pro
                180                 185                 190

Arg Ala Arg Met Thr Pro Ala Pro Ala Ser Cys Ser Gln Glu Leu Pro
            195                 200                 205

Ser Ala Glu Asp Asn Ser Pro Met Ala Ser Asp Pro Leu Gly Val Val
        210                 215                 220

Arg Gly Gly Arg Val Asn Thr His Ala Gly Gly Thr Gly Pro Glu Gly
225                 230                 235                 240

Cys Arg Pro Phe Ala Lys Phe Ile
                245
```

<210> SEQ ID NO 92
<211> LENGTH: 690
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(687)

<400> SEQUENCE: 92

```
atg aaa tac ccg aac gct tcc ccg ctg ctg ggc tcc agc tgg ggt ggc      48
Met Lys Tyr Pro Asn Ala Ser Pro Leu Leu Gly Ser Ser Trp Gly Gly
 1               5                  10                  15 ctg atc cac ctg tac aca gcc aca gcc agg aac agc tac cac ctg cag      96
Leu Ile His Leu Tyr Thr Ala Thr Ala Arg Asn Ser Tyr His Leu Gln
                 20                  25                  30 atc cac aag aat ggc cat gtg gat ggc gca ccc cat cag acc atc tac     144
Ile His Lys Asn Gly His Val Asp Gly Ala Pro His Gln Thr Ile Tyr
             35                  40                  45 agt gcc ctg atg atc aga tca gag gat gct ggc ttt gtg gtg att aca     192
Ser Ala Leu Met Ile Arg Ser Glu Asp Ala Gly Phe Val Val Ile Thr
         50                  55                  60 ggt gtg atg agc aga aga tac ctc tgc atg gat ttc aga ggc aac att     240
Gly Val Met Ser Arg Arg Tyr Leu Cys Met Asp Phe Arg Gly Asn Ile
 65                  70                  75                  80 ttt gga tca cac tat ttc gac ccg gag aac tgc agg ttc caa cac cag     288
Phe Gly Ser His Tyr Phe Asp Pro Glu Asn Cys Arg Phe Gln His Gln
                 85                  90                  95
```

```
acg ctg gaa aac ggg tac gac gtc tac cac tct cct cag tat cac ttc    336
Thr Leu Glu Asn Gly Tyr Asp Val Tyr His Ser Pro Gln Tyr His Phe
        100                 105                 110 ctg gtc agt ctg ggc cgg gcg aag aga gcc ttc ctg cca ggc atg aac    384
Leu Val Ser Leu Gly Arg Ala Lys Arg Ala Phe Leu Pro Gly Met Asn
    115                 120                 125 cca ccc ccg tac tcc cag ttc ctg tcc cgg agg aac gag atc ccc cta    432
Pro Pro Pro Tyr Ser Gln Phe Leu Ser Arg Arg Asn Glu Ile Pro Leu
130                 135                 140 att cac ttc aac acc ccc ata cca cgg cgg cac acc cgg agc gcc gag    480
Ile His Phe Asn Thr Pro Ile Pro Arg Arg His Thr Arg Ser Ala Glu
145                 150                 155                 160 gac gac tcg gag cgg gac ccc ctg aac gtg ctg aag ccc cgg gcc cgg    528
Asp Asp Ser Glu Arg Asp Pro Leu Asn Val Leu Lys Pro Arg Ala Arg
                165                 170                 175 atg acc ccg gcc ccg gcc tcc tgt tca cag gag ctc ccg agc gcc gag    576
Met Thr Pro Ala Pro Ala Ser Cys Ser Gln Glu Leu Pro Ser Ala Glu
            180                 185                 190 gac aac agc ccg atg gcc agt gac cca tta ggg gtg gtc agg ggc ggt    624
Asp Asn Ser Pro Met Ala Ser Asp Pro Leu Gly Val Val Arg Gly Gly
        195                 200                 205 cga gtg aac acg cac gct ggg gga acg ggc ccg gaa ggc tgc cgc ccc    672
Arg Val Asn Thr His Ala Gly Gly Thr Gly Pro Glu Gly Cys Arg Pro
    210                 215                 220 ttc gcc aag ttc atc tag                                            690
Phe Ala Lys Phe Ile
225

<210> SEQ ID NO 93
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Met Lys Tyr Pro Asn Ala Ser Pro Leu Leu Gly Ser Ser Trp Gly Gly
1               5                   10                  15

Leu Ile His Leu Tyr Thr Ala Thr Ala Arg Asn Ser Tyr His Leu Gln
            20                  25                  30

Ile His Lys Asn Gly His Val Asp Gly Ala Pro His Gln Thr Ile Tyr
        35                  40                  45

Ser Ala Leu Met Ile Arg Ser Glu Asp Ala Gly Phe Val Val Ile Thr
    50                  55                  60

Gly Val Met Ser Arg Arg Tyr Leu Cys Met Asp Phe Arg Gly Asn Ile
65                  70                  75                  80

Phe Gly Ser His Tyr Phe Asp Pro Glu Asn Cys Arg Phe Gln His Gln
                85                  90                  95

Thr Leu Glu Asn Gly Tyr Asp Val Tyr His Ser Pro Gln Tyr His Phe
            100                 105                 110

Leu Val Ser Leu Gly Arg Ala Lys Arg Ala Phe Leu Pro Gly Met Asn
        115                 120                 125

Pro Pro Pro Tyr Ser Gln Phe Leu Ser Arg Arg Asn Glu Ile Pro Leu
    130                 135                 140

Ile His Phe Asn Thr Pro Ile Pro Arg Arg His Thr Arg Ser Ala Glu
145                 150                 155                 160

Asp Asp Ser Glu Arg Asp Pro Leu Asn Val Leu Lys Pro Arg Ala Arg
                165                 170                 175
```

```
Met Thr Pro Ala Pro Ala Ser Cys Ser Gln Glu Leu Pro Ser Ala Glu
            180                 185                 190

Asp Asn Ser Pro Met Ala Ser Asp Pro Leu Gly Val Val Arg Gly Gly
        195                 200                 205

Arg Val Asn Thr His Ala Gly Gly Thr Gly Pro Glu Gly Cys Arg Pro
    210                 215                 220

Phe Ala Lys Phe Ile
225

<210> SEQ ID NO 94
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
tttttttttt tttttttt                                               18
```

METHOD FOR TREATING HYPOPHOSPHATEMIC BONE DISEASES USING FGF-23 ANTIBODY

This application is a continuation of U.S. patent application Ser. No. 10/344,339, filed Jul. 21, 2003, which is a national phase entry of PCT Application No. PCT/JP01/06944, filed Aug. 10, 2001, which claims priority to Japanese Patent Application Nos. 2000-245144, filed Aug. 11, 2000, 2000-287684, filed Sep. 21, 2000, 2000-391077, filed Dec. 22, 2000, and 2001-121527, filed Apr. 19, 2001, the contents of which are incorporated by reference in their entireties.

SEQUENCE LISTING

The instant application contains a Sequence Listing which has been submitted in ASCII format via EFS-Web and is hereby incorporated by reference in its entirety. Said ASCII copy, created on Feb. 22, 2011, is named 81356318.txt and is 72,592 bytes in size.

TECHNICAL FIELD

The present invention relates to a polypeptide that regulates phosphate metabolism, calcium metabolism, calcification and/or vitamin D metabolism, a DNA encoding the polypeptide, and a pharmaceutical composition containing the polypeptide as an active ingredient, and an antibody recognizing the polypeptide, a pharmaceutical composition containing the antibody as an active ingredient, a diagnostic method using the antibody, and a diagnostic composition.

BACKGROUND ART

Inorganic phosphates (hereinafter, may be referred to as "phosphate") are essential in energy metabolism in vivo and maintenance of cellular functions, and play an important role in tissue calcification in cooperation with calcium. Supply of phosphate to an organism depends mainly on absorption in the intestinal tract, and phosphate excretion depends on urinary excretion in the kidney and fecal excretion in the intestinal tract. In living organisms, phosphate is distributed in body fluid, intracellular fractions and calcified tissues. The level of excretion of inorganic phosphate in an adult is maintained at almost the same level of absorption of inorganic phosphate, suggesting the presence of a regulatory mechanism which maintains homeostasis of the phosphate metabolism. It is known that the metabolism of calcium, which shares similarity with the phosphate metabolism in terms of a distribution and homeostatic control of blood level, is controlled in a co-operative manner in mammals by regulatory factors, such as, at least parathyroid hormone, calcitonin and 1α,25-dihydroxyvitamin D3.

In the regulation of phosphate metabolism it is known that parathyroid hormone promotes phosphate excretion, and that 1α,25-dihydroxyvitamin D3 promotes phosphate absorption in the intestinal tract. This clearly suggests close association between phosphate metabolism and calcium metabolism. However, a substance primarily controlling phosphate has not yet been elucidated.

Now, examples of a disease which is associated with the loss of the homeostasis of phosphate metabolism and lower inorganic phosphate levels in the blood include primary hyperparathyroidism, hereditary hypophosphatemic rickets, and tumor-induced osteomalacia.

Primary hyperparathyroidism is a disease characterized by an overproduction of parathyroid hormone in the parathyroid glands, and is known to develop hypophosphatemia with increased phosphate excretion because overproduced parathyroid hormone suppresses reabsorption of inorganic phosphate in the kidney.

Further, known examples of hypophosphatemia resulting from hereditary diseases include type I vitamin D-dependent rickets, type II vitamin D-dependent rickets and vitamin D-resistant rickets. Type I vitamin D-dependent rickets is a disease caused by hereditary dysfunction of the synthase to produce active vitamin D metabolites, and type II vitamin D-dependent rickets is a disease caused by hereditary dysfunction of vitamin D receptor. Both diseases develop hypophosphatemia together with hypocalcemia due to attenuated action of vitamin D3 metabolites. In contrast, for vitamin D-resistant rickets, at least 2 types of clinical conditions, X-linked chromosomal and autosomal hypophosphatemic rickets resulting from different causes are known to exist.

Both of the above-mentioned clinical conditions of vitamin D-resistant rickets lead to hypophosphatemia characterized by renal phosphate. Recently, it has been shown in patients with X-linked hypophosphatemic rickets (hereinafter, also referred to as "XLH") that the disease is induced by mutations in the gene encoding an endopeptidase-like protein, named PHEX, on X chromosome. However, a mechanism how dysfunction of PHEX protein induces hypophosphatemia has not been elucidated. Interestingly, gene analysis of a naturally occurring mutant mouse (Hyp) which developed hypophosphatemia has revealed the partial deletion of the gene encoding PHEX in this mouse. Experiments using these mice have revealed that PHEX deficient mice have normal renal function, and a humoral factor, which is different from parathyroid hormone, but induces hypophosphatemia, is present in the body fluid of Hyp mice. Concerning autosomal dominant hypophosphatemic rickets/osteomalacia (hereinafter also referred to as ADHR), a gene responsible for this disease has been pursued, and the presence of such a gene in 12p13 region has been indicated by linkage analysis. However, the region that has been narrowed down so far is still wide and contains many genes, so that no candidate gene has been specified yet.

Tumor-induced osteomalacia is a disease which develops hypophosphatemia with increased renal phosphate in association with tumorigenesis, and is characterized in that the hypophosphatemia is eliminated by irradiation to tumor or removal of tumor. In this disease, it is thought that tumor produces a factor which induces hypophosphatemia due to suppressed reabsorption of phosphate in the kidneys.

It has not been confirmed whether a putative causative molecule for vitamin D-resistant rickets is identical to that for tumor-induced osteomalacia. However, the two factors are identical in that they clearly are unknown phosphate metabolism factors which promote urinary phosphate excretion. The putative phosphate metabolism regulatory factor is often referred to as, the name Phosphatonin. The relationship of this unknown phosphate metabolism regulatory factor and vitamin D-resistant rickets or tumor-induced osteomalacia has been summarized as general remarks (Neison, A. E., Clinical Endocrinology, 47:635-642, 1997; Drezner, M. K., Kidney Int., 57:9-18, 2000).

Another characteristic of vitamin D-resistant rickets or tumor-induced osteomalacia is impairment of bone calcification. This impaired bone calcification could be thought to be secondarily developed by hypophosphatemia. However, since abnormal bone calcification in experiments using Hyp mice, the model mice for vitamin D-resistant rickets is shown to develop independently from phosphate levels (Ecarot, B., J. Bone Miner. Res., 7:215-220, 1992; Xiao, Z. S., Am. J. Physiol., E700-E708, 1998), it is conceivable that the above unknown regulatory factor for phosphate metabolism can directly regulate calcification in bone tissue.

As described above, research data have strongly been suggesting the presence of an unknown factor which regulates phosphate metabolism, but there has been no case that can elucidate at a molecular level, an entity which exhibits the putative activity. While WO99/60017 discloses a novel polypeptide sequence as a novel polypeptide hormone, Phosphatonin, however, it does not disclose the characteristic activity of phosphatonin which concerns induction of hypophosphatemia. Thus, it is conceivable that an unidentified intrinsic factor regulating phosphate metabolism may exist in organisms.

Vitamin D2 and vitamin D3 ingested from foods, or vitamin D3 synthesized in the skin is hydrolyzed by vitamin D-25-hydroxylase existing mainly in the liver to produce 25-hydroxyvitamin D. Then, 25-hydroxyvitamin D is hydrolyzed by 25-hydroxyvitamin D-1α-hydroxylase existing in renal epithelial cells of proximal tubules in the kidney to produce 1α25-dihydroxyvitamin D. This 1α,25-dihydroxyvitamin D is a mineral regulatory hormone having physiological activities that increase serum calcium and phosphate levels, and is known to be responsible for inhibiting the secretion of parathyroid hormone and to be involved in the promotion of bone resorption. 1α,25-dihydroxyvitamin D is then converted into metabolites in vivo which has not the above physiological activities by 24-hydroxylase existing mainly in the kidney or small intestine. In this regard, 24-hydroxylase is thought to be an enzyme which is responsible for the inactivation of 1α,25-dihydroxyvitamin D. On the other hand, 24-hydroxylase is known to also act on 25-hydroxy vitamin D and convert it into 24,25-dihydroxyvitamin D. The 24,25-dihydroxyvitamin D has been reported to have physiological effects that increase bone mass or promote differentiation of cartilage, suggesting that this enzyme has an aspect for generating biological active vitamin D metabolites.

Known factors that regulate the expression level of 1α-hydroxylase, which has an important role in the activation of vitamin D, include parathyroid hormone (PTH), calcitonin, 1α,25-dihydroxyvitamin D and the like. PTH whose secretion is promoted by decreases in blood calcium levels acts on PTH receptors existing in epithelial cells of the renal proximal tubules to promote transcription of 1α-hydroxylase gene through an elevated intracellular cAMP level, so as to increase blood 1α,25-dihydroxyvitamin D concentration. 1α,25-dihydroxyvitamin D promotes absorption of calcium from the intestinal tract and calcium reabsorption in the kidney, thereby increasing the blood calcium level. Further, it has been reported that the binding of 1α,25-dihydroxyvitamin D to vitamin D receptor (VDR) acts on a promoter region of 1α-hydroxylase gene or PTH gene to suppress the transcription of such genes. Specifically, 1α,25-dihydroxyvitamin D has a feedback control mechanism for its activation factor, PTH and 1α-hydroxylase. This mechanism plays an important role in maintaining homeostasis of calcium metabolism.

Recently, it has been reported that a decrease in serum phosphate level enhances the expression of 1α-hydroxylase gene. In phosphate metabolism, the presence of a mechanism is also assumed that enhancement in the expression of 1α-hydroxylase gene association with decreased serum phosphate level elevates serum 1α,25-dihydroxyvitamin D level and, consequently, corrects the serum phosphate level by promoting absorption of phosphate from the small intestine.

Examples of a factor responsible for regulating the expression of 24-hydroxylase gene include 1α,25-dihydroxyvitamin D and PTH. It has been shown that 1α,25-dihydroxyvitamin D interact with the vitamin D receptor (VDR) and the complex binds to a vitamin D receptor response sequence existing in the promoter region of 24-hydroxylase gene so as to promote transcription. 1α,25-dihydroxyvitamin D is thought to activate 24-hydroxylase, and then to induce a decrease in the 1α,25-dihydroxyvitamin D level due to the activated catabolic pathway. It is known that the expression of 24-hydroxylase gene is suppressed by PTH, but its detailed molecular mechanism is unknown.

DISCLOSURE OF THE INVENTION

The purpose of the present invention is to provide a novel tumor-derived factor which is capable of inducing decreases in blood phosphate levels.

It is conceivable that a tumor identified in tumor-induced osteomalacia secretes a soluble factor having physiological activity, so that the blood phosphate levels decrease. The tumor-derived factor causes the homeostasis of phosphate metabolism to fail. Therefore, the factor may be characterized by any one of (1) the factor which is not originally produced in vivo is produced tumor-specifically, (2) the factor is overproduced in tumor, though it is also produced in normal tissue, and (3) the factor is produced in tumor without being physiologically controlled.

Based on an assumption that a tumor-derived hypophosphatemia-inducing factor is characteristically produced in a tumor-induced osteomalacia-derived tumor as described above, we have anticipated enhanced transcription of a gene encoding the hypophosphatemia-inducing factor or enhanced stability of mRNA of the factor in a tumor. Hence, after extraction of RNA from a part of the tumor tissues that were excised from a patient with tumor-induced osteomalacia for therapeutic purposes, we prepared cDNA library using phage vectors and plasmid vectors, and then screened for gene fragments that were specifically expressed in the tumor. Methods performed for screening were a method which selects cDNA fragments determined to be specifically expressed in the tumor, and a method which selects cDNA fragments in a tumor-derived cDNA library which do not cross-react with cDNA probes derived from a cell line of epithelial cells of the renal proximal tubules. We further narrowed down the selected cDNA fragments by confirming for novelty in sequences and characteristic expression in the tumor, thereby obtaining a plurality of cDNA fragments expected to encode the hypophosphatemia-inducing factor. From the sequence information, we attempted to clone cDNAs containing ORF to which each fragment belongs and successfully obtained DNAs encoding novel polypeptides. We further thoroughly studied to find biological activities of the novel polypeptides, so that we have completed the present invention by elucidating that the novel polypeptide has activities to suppress phosphate transport, to induce hypophosphatemia and to suppress calcification of bone tissue in animals.

Specifically, the present invention is as follows.
(1) A DNA, which encodes the following polypeptide (a), (b), (c) or (d):
  (a) a polypeptide consisting of an amino acid sequence represented by SEQ ID NO: 2 or 4,
  (b) a polypeptide consisting of an amino acid sequence derived from the amino acid sequence represented by SEQ ID NO: 2 or 4 by deletion, substitution or addition of one or several amino acids, and having hypophosphatemia-inducing activity, phosphate transport-suppressing activity, calcification-suppressing activity or in vivo vitamin D metabolism-regulating activity,
  (c) a polypeptide consisting of a partial sequence of the amino acid sequence represented by SEQ ID NO: 2, wherein the above partial sequence contains an amino acid sequence at least ranging from the 34$^{th}$ to 201$^{st}$ amino acids in the above amino acid sequence, or
(d) a polypeptide consisting of a partial sequence of the amino acid sequence represented by SEQ ID NO: 2, wherein the partial sequence:
(i) contains an amino acid sequence at least ranging from the 34$^{th}$ to 201$^{st}$ amino acids in the above amino acid sequence,
(ii) consists of an amino acid sequence derived from the partial sequence by deletion, substitution or addition of one or several amino acids, and
(iii) has hypophosphatemia-inducing activity, phosphate transport-suppressing activity, calcification-suppressing activity or in vivo vitamin D metabolism-regulating activity.
(2) A DNA, which contains the following DNA (e) or (f):
(e) a DNA consisting of a nucleotide sequence ranging from the 133rd to 885th nucleotides in the nucleotide sequence represented by SEQ ID NO: 1 or a nucleotide sequence ranging from the 1$^{st}$ to 681$^{st}$ nucleotides in the nucleotide sequence represented by SEQ ID NO: 3, or
(f) a DNA hybridizing under stringent conditions to a probe prepared from a DNA consisting of the whole or a part of the nucleotide sequence represented by SEQ ID NO: 1 or 3, and encoding a polypeptide having hypophosphatemia-inducing activity, phosphate transport-suppressing activity, calcification-suppressing activity or in vivo vitamin D metabolism-regulating activity.

Here, the term "stringent conditions" satisfies conditions of a sodium concentration of 750 mM or more, preferably 900 mM or more, a temperature of 40° C. or more, preferably, 42° C. Specifically, stringent conditions consist of 6×SSC, 5× Denhardt, 0.5% SDS, 50% Formamide and 42° C.
(3) A recombinant vector, which contains the above DNA.
(4) A transformant, which contains the above recombinant vector.
(5) A polypeptide, which is the following polypeptide (a), (b), (c) or (d):
(a) a polypeptide consisting of an amino acid sequence represented by SEQ ID NO: 2 or 4,
(b) a polypeptide consisting of an amino acid sequence derived from the amino acid sequence represented by SEQ ID NO: 2 or 4 by deletion, substitution or addition of one or several amino acids, and having hypophosphatemia-inducing activity, phosphate transport-suppressing activity, calcification-suppressing activity or in vivo vitamin D metabolism-regulating activity,
(c) a polypeptide consisting of a partial sequence of the amino acid sequence represented by SEQ ID NO: 2, wherein the above partial sequence contains at least an amino acid sequence ranging from the 34$^{th}$ to 201$^{st}$ amino acids in the above amino acid sequence, or
(d) a polypeptide consisting of a partial sequence of the amino acid sequence represented by SEQ ID NO: 2 wherein the partial sequence:
(i) contains an amino acid sequence ranging from at least the 34$^{th}$ to 201$^{st}$ amino acids in the above amino acid sequence,
(ii) consists of an amino acid sequence derived from the partial sequence by deletion, substitution, or addition of one or several amino acids, and
(iii) has hypophosphatemia-inducing activity, phosphate transport-suppressing activity, calcification-suppressing activity or in vivo vitamin D metabolism-regulating activity.

The above polypeptide also includes a polypeptide modified by at least one substance selected from the group consisting of polyethylene glycol, dextran, poly (N-vinyl-pyrrolidone), polypropylene glycol homopolymer, copolymer of polypropylene oxide and polyethylene oxide, polyoxyethylated polyol and polyvinyl alcohol.
(6) A pharmaceutical composition which contains the above polypeptide as an active ingredient.

The above pharmaceutical composition can be used to enable in vivo regulation of calcium metabolism, phosphate metabolism, calcification or vitamin D metabolism. Further, the above pharmaceutical composition is effective against at least one condition selected from the group consisting of hyperphosphatemia, hyperparathyroidism, renal osteodystrophy, ectopic calcification, osteoporosis and hypervitaminosis D.
(7) An antibody, which reacts with the above polypeptide or partial fragments thereof.

The above antibody can be obtained by a method comprising the steps of immunizing an animal with the polypeptide of the present invention or partial fragments thereof, as an antigen.
(8) A pharmaceutical composition, which contains the above antibody as an active ingredient.

The above pharmaceutical composition can regulate in vivo calcium metabolism, phosphate metabolism, calcification or vitamin D metabolism, or be effective against bone diseases. Here, the bone disease is at least one disease selected from the group consisting of osteoporosis, vitamin D-resistant rickets, renal osteodystrophy, dialysis-associated bone diseases, osteopathy with hypocalcification, Paget's disease and tumor-induced osteomalacia.
(9) A diagnostic agent, which contains the above antibody and is for a disease which develops at least one abnormality of abnormal calcium metabolism, abnormal phosphate metabolism, abnormal calcification and abnormal vitamin D metabolism (for example, a disease selected from the group consisting of renal failure, renal phosphate leak, renal tubular acidosis and Fanconi's syndrome).
(10) A diagnostic agent for a bone disease, which contains the above antibody, wherein the bone disease is at least a disease selected from the group consisting of osteoporosis, vitamin D-resistant rickets, renal osteodystrophy, dialysis-associated bone diseases, osteopathy with hypocalcification, Paget's disease and tumor-induced osteomalacia.
(11) A diagnostic agent, which contains a DNA having a nucleotide sequence represented by SEQ ID NO: 11 or partial fragments thereof, and is for a disease which develops at least one abnormality of abnormal calcium metabolism, abnormal phosphate metabolism, abnormal calcification and abnormal vitamin D metabolism.

An example of the partial sequence has a sequence ranging from the 498$^{th}$ to 12966$^{th}$ nucleotides of the nucleotide sequence represented by SEQ ID NO: 11. An example of the disease is autosomal dominant hypophosphatemic rickets/osteomalacia.

The present invention is explained in detail as follows. This specification includes part or all of the contents disclosed in the specification and/or drawings of Japanese Patent Application Nos. 2000-245144, 2000-287684, 2000-391077 and 2001-121527, which are priority documents of the present application.

The terms used in the present specification are defined as follows.

The term "activity to decrease blood 1,25-dihydroxyvitamin D3 levels" indicates an activity which acts to decrease blood levels of 1,25-dihydroxyvitamin D3.

The term "hypophosphatemia-inducing activity" indicates an activity which acts to decrease blood phosphate levels. Blood phosphate level is defined by the balance between (i) absorption from the intestinal tract and excretion into urine and feces, and (ii) in vivo distribution of phosphate to cells or calcified tissues as represented by bone tissues. Therefore, the term "hypophosphatemia-inducing activity" used in the present specification means an activity to lower blood phosphate levels in a healthy living organism, and does not necessarily mean an activity to cause pathologic hypophosphatemia. The hypophosphatemia-inducing activity may be equivalent, on a tissue level, to phosphate absorption-suppressing activity in the intestinal tract, phosphate excretion-promoting activity in the kidney or the intestinal tract, or activity which promotes transfer of phosphate into cells.

Further, the term "phosphate transport-suppressing activity" in the present invention means an activity which acts on a target cell so as to suppress activity of a phosphate transport carrier existing on the cell membrane. Possible target cells are mainly epithelial cells of the renal tubules, epithelial cells of the intestines or osteoblasts.

Furthermore, the term "calcification-suppressing activity" in the present invention means an activity which suppresses the process to generate or accumulate crystal substances containing calcium and phosphate as compositions in bone tissues and soft tissues.

Furthermore, the term "in vivo vitamin D metabolism-regulating activity" indicates a potency to regulate changes in the absolute amounts or in the abundance ratio of vitamin D existing in vivo or of the metabolites synthesized in vivo therefrom. In vivo regulation of the vitamin D and of the metabolite thereof is ruled by mainly (i) absorption or excretion in the intestinal tract and (ii) reabsorption or excretion in the kidney, followed by (iii) in vivo synthesis of vitamin D, and (iv) metabolic conversion mainly led by hydroxylation reaction. Known, main metabolites resulting from the metabolic conversion (iv) are as follows: 25-hydroxyvitamin D which is produced by hydroxylation at position 25 of vitamin D by vitamin D-25-hydroxylase; 1α,25-dihydroxyvitamin D which is produced by hydroxylation at position 1α of hydroxyvitamin D by 25-hydroxyvitamin D-1α-hydroxylase; or 24,25-dihydroxyvitamin D or 1α 24,25-trihydroxyvitamin D which is produced by introduction of a hydroxyl group at position 24 of the metabolite by 24-hydroxylase. Vitamin D metabolism-regulating activity can be represented as an activity to regulate an enzymatic activity, gene expression or changes in expressed protein levels of enzymes involved in the generation of such vitamin D metabolites.

1. DNA Encoding Polypeptide which Regulates Phosphate Metabolism, Calcium Metabolism, Calcification and Vitamin D Metabolism (1) DNA Cloning A DNA represented by SEQ ID NO: 1, which is one of DNAs of the present invention, is obtained by screening a cDNA library prepared using a part of a tumor excised from a patient suspected of having tumor-induced osteomalacia.

Tumor-induced osteomalacia is a disease which develops hypophosphatemia and osteomalacia due to insufficient calcification of bone tissues in association with the presence of tumors, and is characterized in that the removal of the tumor causes these symptoms to disappear. There have been reports that tumor extracts promote urinary phosphate excretion in rats (Popvtzer, M. M. et al., Clinical Research 29: 418A, 1981), and that hypophosphatemia was induced in an experiment of transplanting excised tumors into mice (Miyauchi, A. et al., J. Clin. Endocrinol. Metab. 67:46-53, 1988). Thus, it has been considered that tumors produce and secrete a systemic unknown factor.

We used a case relating to the tumor described in Fukumoto, S. et al., Bone 25: 375-377, 1999. In this case, a significant recovery from hypophosphatemia was achieved by operative excision of the tumor. Further, the tumor size in this case was as small as about 1 cm in diameter. Based on an inference that such a small tissue produces and secretes an active substance which induces hypophosphatemia and systemic osteomalacia, we have anticipated that the tumor-derived cDNA library that we have prepared contains, at a higher frequency compared to another tissue-derived cDNA library, at least a partial fragment of the gene encoding the active substance involved in the induction of such clinical conditions. Accordingly, to identify a sequence of the fragment of the gene encoding the tumor-derived active substance, cDNA fragments that are specifically abundant in cDNA library of the tumor were extracted by a differential screening method.

Next, the nucleotide sequences of the obtained cDNA fragments were identified, and compared to each other. Then based on overlap of the nucleotide sequences, contigs were prepared to classify each sequence thought to be derived from the same gene. Homology searches were performed for the thus obtained nucleotide sequences with the nucleotide sequences registered at Genbank which is the database provided by National Center for Biotechnology Information (USA) (hereinafter, may also referred to as "NCBI"). In this way, the nucleotide sequence that is specifically abundant in the tumor cDNA library, that is, a sequence ranging from nucleotide Nos. 1522 to 2770 of the nucleotide sequence represented by SEQ ID NO: 1 was obtained. This sequence was identical to a part of the human sequence, 12p13 BAC RPCI11-388F6 registered at Genbank under Accession No. AC008012. This registered sequence is thought to represent a partial sequence of 12p13 region of a human chromosome sequence. While the locations of estimated genes within the registered sequence were shown with the nucleotide sequence information, the sequence ranging from nucleotide Nos. 1522 to 2770 of the nucleotide sequence represented by SEQ ID NO: 1, and the nucleotide sequence represented by SEQ ID NO: 1 of the present invention were not included in the any of specified regions of estimated genes.

Probes and PCR primers were then designed based on the nucleotide sequence ranging from nucleotide Nos. 1522 to 2770 of the nucleotide sequence represented by SEQ ID NO: 1, and then a continuous nucleotide sequence contained in the tumor cDNA library was isolated and identified, thereby obtaining the nucleotide sequence represented by SEQ ID NO: 1 of the present invention. The nucleotide sequence of SEQ ID NO: 1 had an open reading frame (hereinafter, may also be referred to as "ORF") encoding a polypeptide consisting of an amino acid sequence represented by SEQ ID NO: 2 of the present invention that is inferred to have a secretion signal. We have considered that this is a polypeptide having a novel sequence, because the amino acid sequence of the polypeptide has not been registered at Genbank amino acid sequence database. After a search using the nucleotide sequence represented by SEQ ID NO: 1 and the amino acid sequence represented by SEQ ID NO: 2, we have identified a nucleotide sequence represented by SEQ ID NO: 9 and an amino acid sequence represented by SEQ ID NO: 10, which are thought to be murine orthologs of the molecule. As described later, a recombinant protein prepared according to a human amino acid sequence shows activity in mice. Thus, the amino acid sequence represented by SEQ ID NO: 2 was compared with the amino acid sequence represented by SEQ ID NO: 10 or murine full-length sequence (Biochem. Biophys. Res. Commun. 2000, 277(2), 494-498), so that the present invention makes it possible to easily assess whether proteins, wherein an amino acid, other than amino acids conserved between the two has been substituted, has biological activity equivalent to, or similar to that of the polypeptide of the present invention.

(2) Determination of Nucleotide Sequence

The nucleotide sequence of DNA obtained as described in (1) above is determined. The nucleotide sequence can be determined by known techniques, such as the Maxam-Gilbert's chemical modification method or a dideoxynucleotide chain termination method using M13 phage. Normally, sequencing is performed using an automatic sequencer (for example, 373A DNA sequencer manufactured by PERKIN-ELMER).

The nucleotide sequence of the DNA of the present invention is exemplified in SEQ ID NO: 1, and the amino acid sequence of the polypeptide of the present invention is exemplified in SEQ ID NO: 2. As long as the polypeptide consisting of the amino acid sequence has hypophosphatemia-inducing activity, phosphate transport-suppressing activity, calcification-suppressing activity or vitamin D metabolite-regulating activity, the amino acid sequence may contain a mutation, such as deletion, substitution or addition of one or several amino acids.

For example, 1 or several, preferably 1 to 10, more preferably 1 to 5 amino acids may be deleted from the amino acid sequence represented by SEQ ID NO: 2; 1 or several, preferably 1 to 10, more preferably 1 to 5 amino acids may be added to the amino acid sequence represented by SEQ ID NO: 2; or 1 or several, preferably 1 to 10, more preferably 1 to 5 amino acids may be substituted with (an)other amino acids in the amino acid sequence represented by SEQ ID NO: 2.

Further, as a method of substitution, conservative substitution may be performed within a family which retains the characteristics of the amino acids to some extent. Examples of families generally classified according to the characteristics of amino acid side chains are as follows.
(i) Acidic amino acid family: aspartic acid, glutamic acid
(ii) Basic amino acid family: lysine, arginine, histidine
(iii) Nonpolar amino acid family: alanine, valine, leucine, isoleucine, proline, phenylalanine, methionine, tryptophan
(iv) Non-charged polar amino acid family: glycin, asparagine, glutamine, cysteine, serine, threonine, tyrosine
(v) Aliphatic hydroxyamino acid family: serine, threonine
(vi) Amide-containing amino acid family: asparagine, glutamine
(vii) Aliphatic amino acid: alanine, valine, leucine, isoleucine
(viii) Aromatic amino acid family: phenylalanine, tryptophan, tyrosine
(ix) Hydrophobic amino acid family: leucine, isoleucine, valine
(x) Small amino acid family: alanine, serine, threonine, methionine, glycin Examples of substitution are sequences which are derived from the amino acid sequence represented by SEQ ID NO: 2 by substitution of the $176^{th}$ Arg and/or $179^{th}$ Arg with (an) other amino acids, preferably, Ala, Gln or Trp, so that cleavage is inhibited or suppressed therein. Further, the polypeptide of the present invention also encompasses a polypeptide consisting of an amino acid sequence derived from the amino acid sequence represented by SEQ ID NO: 2 by deletion of 10 or more amino acids on the N-terminal side, C-terminal side or both sides (terminal-deleted type). Examples of such terminus-deleted forms include a sequence derived from the amino acid sequence represented by SEQ ID NO: 2 by deletion of 20, 40, 45 or 50 amino acids on the C-terminal side, and/or 24 or 33 amino acids on the N-terminal side. Embodiments of the terminal-deleted types are as shown below.

| Number of amino acids deleted on the N-terminal side | Number of amino acids deleted on the C-terminal side | Position in the amino acid sequence represented by SEQ ID NO: 2 (Nucleotide No. in SEQ ID NO: 1) |
|---|---|---|
| 33 on the N-terminal side | No deletion | 34-251(232-885) |
| 33 on the N-terminal side | 20 on the C-terminal side | 34-231(232-825) |
| 33 on the N-terminal side | 40 on the C-terminal side | 34-211(232-765) |
| 33 on the N-terminal side | 45 on the C-terminal side | 34-206(232-750) |
| 33 on the N-terminal side | 50 on the C-terminal side | 34-201(232-735) |
| 24 on the N-terminal side | No deletion | 25-251(205-885) (corresponding to the $1^{st}$ to the $681^{st}$ in SEQ ID NO: 3, and SEQ ID NO: 4) |
| 24 on the N-terminal side | 20 on the C-terminal side | 25-231(205-825) |
| 24 on the N-terminal side | 40 on the C-terminal side | 25-211(205-765) |
| 24 on the N-terminal side | 45 on the C-terminal side | 25-206(205-750) |
| 24 on the N-terminal side | 50 on the C-terminal side | 25-201(205-735) |
| No deletion | 20 on the C-terminal side | 1-231(133-825) |
| No deletion | 40 on the C-terminal side | 1-211(133-765) |
| No deletion | 45 on the C-terminal side | 1-206(133-750) |
| No deletion | 50 on the C-terminal side | 1-201(133-735) |

In addition to partial fragments (terminal-deleted type partial fragments) of the amino acid sequence represented by SEQ ID NO: 2 above, the polypeptide of the present invention encompasses mutated fragments that are derived from these terminal-deleted type polypeptides by deletion, substitution or addition of one or several amino acids. Figures in parentheses following the position numbers of amino acids shown in SEQ ID NO: 2 in the above list indicate the position numbers of nucleotides in the nucleotide sequence represented by SEQ ID NO: 1. Hence, the present invention also encompasses DNAs consisting of the nucleotide sequences shown by these positions, or DNAs hybridizing under stringent conditions to these DNAs.

In the present invention, to introduce a mutation into at least a part of the amino acid sequence of the polypeptide of the present invention, a technique which introduces a mutation into the nucleotide sequence of a DNA encoding the amino acid is employed.

Mutations can be introduced into DNA by a known technique, such as the Kunkel method or the Gapped duplex method, or a method according thereto. For example, a mutation is introduced based on the site-directed mutagenesis method using a mutant oligonucleotide as a primer. Further, a mutation can also be introduced using a kit for introducing mutations, such as Mutan-K (TAKARA), Mutan-G (TAKARA), LA PCR in vitro Mutagenesis series kit (TAKARA) or the like.

Furthermore, the DNA of the present invention also encompasses a DNA hybridizing under stringent conditions to a probe prepared from the above DNA of the present invention (SEQ ID NO: 1, 3, 5, 7 and 9) and encoding a polypeptide having hypophosphatemia-inducing activity, phosphate transport-suppressing activity, calcification-suppressing activity or vitamin D metabolism-regulating activity. The probe used herein has a sequence which is complementary to the entire sequence of or a sequence (partial sequence) of continuous 17 nucleotides or more of the sequence represented by SEQ ID NO: 1, 3, 5, 7 or 9.

Here, the term "stringent conditions" satisfies conditions of sodium concentration of 750 mM or more, preferably, 900 mM or more, and temperature of 40° C. or more, preferably 42° C. Specifically, the stringent conditions used herein indicate the conditions consisting of 6×SSC, 5× Denhardt, 0.5% SDS, 50% Formamide and 42° C. In addition, 6×SSC means 900 mM NaCl and 90 mM sodium citrate. Denhardt's solution (Denhardt) contains BSA (bovine serum albumin), polyvinylpyrrolidone and Ficoll 400. 50× Denhardt consists of a composition of 1% BSA, 1% polyvinylpyrrolidone and 1% Ficoll 400 (5× Denhardt means a one-tenth concentration of 50× Denhardt).

Once the nucleotide sequence of the DNA of the present invention is determined, the DNA of the present invention can be obtained by chemical synthesis or PCR using primers synthesized from the determined nucleotide sequence.

2. Recombinant Vector Containing the DNA of the Present Invention and Preparation of Transformant (1) Preparation of Recombinant Vector The recombinant vector of the present invention can be obtained by ligating (inserting) the DNA of the present invention into an appropriate vector. A vector for inserting the DNA of the present invention is not specifically limited, as long as it can be replicated in a host. Examples of such a vector include plasmid DNA and phage DNA.

Examples of plasmid DNAs include plasmids derived from *Escherichia coli* (for example, pBR322, pBR325, pUC118 and pUC119), plasmids derived from *Bacillus subtilis* (for example, pUB110 and pTP5), plasmids derived from yeast (for example, YEp13, YEp24 and YCp50). An example of a phage DNA is λ phage. Further, animal virus vectors such as a retrovirus, adenovirus or vaccinia virus, or insect virus vectors such as baculovirus can be used. Furthermore, a fusion plasmid to which GST, His-tag and the like are ligated can be used.

In order to insert the DNA of the present invention into a vector, a method can be employed, which comprises cleaving the purified DNA using an appropriate restriction enzyme at first, and ligating to the obtained cleaved DNA to the vector by inserting the cleaved DNA into a restriction enzyme site or multi-cloning site of an appropriate vector DNA.

The DNA of the present invention is required to be incorporated into a vector so that the DNA can exert its function. To the vector of the present invention, in addition to a promoter and the DNA of the present invention, cis element such as an enhancer, splicing signal, poly A addition signal, a selection marker and ribosome binding sequence (SD sequence) may be ligated, if necessary. In addition, examples of a selection marker include a dihydrofolate reductase gene, ampicillin resistance gene and neomycin-resistance gene.

(2) Preparation of Transformant

The transformant of the present invention can be obtained by introducing the recombinant vector of the present invention into a host, such that the target gene can be expressed. A host to be used herein is not specifically limited, as long as it can express the DNA of the present invention. Examples of such a host include bacteria of: the genus *Escherichia*, such as *Escherichia coli*; the genus *Bacillus*, such as *Bacillus subtilis*; the genus *Pseudomonas*, such as *Pseudomonas putida*; or yeast such as *Saccharomyces cerevisiae* or *Schizosaccharomyces pombe*. Further, animal cells, such as COS cells, CHO cells or HEK293 cells, and insect cells, such as Sf9 or Sf21 can also be used.

When bacteria, such as *Escherichia coli* is used as a host, it is preferable that the recombinant vector of the present invention can autonomously replicate in the bacteria, and comprises a promoter, ribosome binding sequence, the DNA of the present invention and transcription termination sequence. In addition, a gene regulating a promoter may also be contained. Examples of *Escherichia coli* include JM109 and HB 101, and an example of *Bacillus subtilis* is *Bacillus subtilis*. Any promoter may be used, as long as it can be expressed in a host, such as *Escherichia coli*. For example, promoters derived from *Escherichia coli*, such as a trp promoter, lac promoter, PL promoter or PR promoter or a phage-derived T7 promoter or the like may be used. An artificially designed and modified promoter, such as a tac promoter may be used. A method to be employed herein for introducing a recombinant vector into bacteria is not specifically limited, as long as it is a method for introducing DNA into bacteria. Examples of such a method include a method which uses calcium ion, and electroporation method.

When yeast is used as a host, for example, *Saccharomyces cerevisiae*, *Schizosaccharomyces pombe* and *Pichia pastoris* are used. A promoter to be used in this case is not specifically limited, as long as it can be expressed in yeast. Examples of such a promoter include a gall promoter, gal10 promoter, heat-shock protein promoter, MFα 1 promoter, PHO5 promoter, PGK promoter, GAP promoter, ADH promoter and AOX1 promoter. A method for introducing a recombinant vector into yeast is not specifically limited, as long as it is a method for introducing DNA into yeast. Examples of such a method include an electroporation method, spheroplast method and lithium acetate method.

When an animal cell is used as a host, monkey cells COS-7, Vero, Chinese hamster ovary cells (CHO cells), mouse L cells, rat GH3 cells, human FL, HEK293, HeLa, Jurkat cells or the like are used. As a promoter, SRα promoter, SV 40 promoter, LTR promoter, β-actin promoter or the like is used. In addition, an early gene promoter of human cytomegalovirus or the like may also be used. Examples of a method for introducing a recombinant vector into animal cells include an electroporation method, calcium phosphate method and lipofection method.

When an insect cell is used as a host, Sf9 cells, Sf21 cells or the like are used. As a method for introducing a recombinant vector to an insect cell, a calcium phosphate method, lipofection method, electroporation method or the like is used.

3. Polypeptide Having Hypophosphatemia-inducing Activity

Several attempts have been made to isolate and identify a tumor-derived factor having hypophosphatemia-inducing activity in tumor-induced osteomalacia. Thus, the polypeptide of the present invention has been shown to have characteristics of being a novel secretion factor which is produced by tumor-induced osteomalacia tumors. The predicted biological activities of the hypophosphatemia-inducing factor have been reported as follows.

Effect on the promotion of phosphate excretion into urine:
Aschinberg, L. C. et al., Journal of Pediatrics 91:56-60, 1977, Lau, K. et al., Clinical Research 27:421A, 1979, Miyauchi, A. et al., J. Clin. Endocrinol. Metab. 67:46-53, 1988

Suppression of phosphate transport activity of epithelial cells of the renal tubules:

Cai, Q. et al., N. Engl. J. Med. 330: 1645-1649, 1994, Wilkins, G. E. et al., J. Clin. Endocrinol. Metab. 80:1628-1634, 1995, Rowe, P. S. N. et al., Bone 18:159-169, 1996

Suppression of 25-hydroxyvitamin D-1α-hydroxylase activity:

Miyauchi, A. et al., J. Clin. Endocrinol. Metab. 67:46-53, 1988

In particular, it has been proposed that an unknown molecule directly having activity to suppress reabsorption of phosphate in the kidney has been referred to as "Phosphatonin" (Econs, M. J. & Drezner, M. K., N. Engl. J. Med 330: 1679-1681, 1994). It has also been suggested that an unknown molecule having such a biological activity is also present in XLH. Clinical findings for XLH patients are characterized by hypophosphatemia with enhanced urinary phosphate excretion, which is the same as tumor-induced osteomalacia patients, and XLH develops osteomalacia or rickets due to calcification insufficiency in bone tissues. A gene responsible for XLH has been shown to be a gene encoding an endopeptidase-like protein, called PHEX. Recently, Hyp mice, the natural mutant mice, known to express a phenotypic trait similar to that of XLH, have been shown to have a partial deletion in the gene encoding PHEX, thereby suggesting that determining Hyp mice to be XLH model mice is valid (Strom, T. M. et al. Human Molecular Genetics 6:165-171, 1997). That the hypophosphatemia-inducing factor in Hyp mice is a humoral factor has been shown by a parabiosis experiment using Hyp mice and normal mice (Meyer, R. A. et al., J. Bone Miner. Res. 4: 493-500, 1989). In this experiment, blood phosphate levels of normal mice decreased, and urinary phosphate excretion increased. Hence, it has been considered that the humoral hypophosphatemia-inducing factor existing in the Hyp mice acted on the normal mice. So far the relationship between PHEX expected to have a peptide cleavage activity and this unknown hypophosphatemia-inducing factor has not been clear. However, some hypotheses concerning a relationship that PHEX may regulate an activity of an unknown hypophosphatemia-inducing factor and a possibility that a hypophosphatemia-inducing factor found in tumor-induced osteomalacia may be identical to that found in XLH each other have been proposed (Drezner, M. K. Kidney Int 57:9-18, 2000). According to this hypothesis, PHEX and a hypophosphatemia-inducing factor are both normally expressed in the same cell, and PHEX acts suppressively on the hypophosphatemia-inducing factor. The functions of PHEX decrease or disappear in XLH patient, so that activity of hypophosphatemia-inducing factor is strongly expressed. It is presumed that in tumor-induced osteomalacia, both PHEX and hypophosphatemia-inducing factor are elevated, and finally active hypophosphatemia-inducing factor quantitatively exceeds the normal level. It is also presumed that this hypophosphatemia-inducing factor acts suppressively on the phosphate transport activity of NPT2 which is one of phosphate transporters in the kidney. Many attempts to search for such an unknown hypophosphatemia-inducing factor have been made, but none were able to identify the molecule. According to a study by Cai et al, it has been presumed that the molecular weight of a hypophosphatemia-inducing factor is between 8 kDa to 25 kDa (Cai, Q. et al., N. Engl. J. Med. 330: 1645-1649, 1994), while Rowe et al have proposed 56 kDa and 58 kDa proteins as candidate molecules. Recently, Rowe et al have filed a patent application (WO99/60017) for a polypeptide consisting of 430 amino acid residues as a tumor-derived phosphate metabolism-regulating factor for tumor-induced osteomalacia. However, the polypeptide disclosed in this application was a partial sequence of a protein which was originally present, and no biological activity relating to hypophosphatemia-inducing activity was disclosed. Recently, a polypeptide corresponding to the full-length molecule as disclosed by the name of MEPE in this patent has been reported, but no activity to induce hypophosphatemia was also disclosed (Rowe, P. S. N. et al, Genomics 67:54-68, 2000). In addition, no sequence or structural similarity between this molecule and the polypeptide of the present invention has been recognized.

As described above, the presence of a physiologically active factor having an activity to induce hypophosphatemia is inferred, but the entity thereof has not been shown so far. In the present invention, we have clarified the entity of the polypeptide, and a gene sequence encoding the polypeptide. Further, as described later, we have produced the polypeptide of the present invention, showed that the product acts as a regulatory factor for phosphate metabolism, calcium metabolism and vitamin D metabolism or calcification and osteogenesis, and the product is useful as a pharmaceutical composition. Furthermore, we have shown that the antibody of the present invention is useful not only for therapy, but also for clinical examination and diagnosis. Moreover, we have shown that the DNA encoding the polypeptide of the present invention is useful for the diagnosis of hereditary diseases, and for polymorphic diagnosis of phosphate metabolism, calcium metabolism and bone metabolism.

The polypeptide having a hypophosphatemia-inducing activity of the present invention can be produced by introducing, for example, a sequence containing nucleotide Nos. $133^{rd}$ to $885^{th}$ of the nucleotide sequence represented by SEQ ID NO: 1 into an appropriate host cell in a form capable of being expressed to prepare a transformant cell, and then allowing the DNA introduced into the transformant cell to be expressed. In addition, the polypeptide chain that is produced in this manner may be modified by a protein modification mechanism of the host, such as cleavage or addition of sugar chains.

The polypeptide of the present invention can be obtained by culturing the above transformants, and then collecting from the culture product. The term "culture product" means, in addition to culture supernatant, any cultured cells or cultured microorganisms, or disrupted cells or disrupted microorganisms.

The transformant of the present invention may be cultured by any ordinary method for culturing a host.

Either natural or synthetic medium can be used for culturing the transformant that is obtained using a microorganism, such as *Escherichia coli* or yeast as a host, as long as it contains a carbon source, a nitrogen source, inorganic salts and the like that are assimilable by microorganisms and allows efficient culturing of transformants. Examples of a carbon source include carbohydrates such as glucose, fructose, sucrose or starch, organic acid such as acetic acid or propionic acid, and alcohols such as ethanol or propanol. Examples of a nitrogen source include ammonia, ammonium salts of organic or inorganic acid such as ammonium chloride, ammonium sulfate, ammonium acetate or ammonium phosphate, or other nitrogen-containing compounds, and peptone, meat extract, and corn steep liquor. Examples of minerals include potassium primary phosphate, potassium secondary phosphate, magnesium phosphate, magnesium sulfate, sodium chloride, ferrous sulfate, manganese sulfate, copper sulfate and calcium carbonate.

Culturing is normally performed under aerobic conditions, such as shake culture or aeration-agitation culture, at 37° C. for 4 to 48 hours. During a culturing period, pH is maintained within 6.0 to 8.0. pH is adjusted using inorganic or organic acid, alkali solution or the like. While culturing, antibiotics, such as ampicillin or tetracycline, may be added to media, if necessary.

When a microorganism transformed with an expression vector using an inducible promoter is cultured, an inducer may be added to a medium, if necessary. For example, when a microorganism transformed with an expression vector having T7 promoter which can be induced with isopropyl-β-D-thiogalactopyranoside (IPTG) is cultured, IPTG or the like may be added to the medium. In addition, when a microorganism transformed with an expression vector using trp promoter which can be induced with indoleacetic acid (IAA) is cultured, IAA or the like can be added to a medium.

Examples of a medium for culturing a transformant that is obtained using an animal cell as a host include a generally employed RPMI1640 medium, DMEM medium or a medium supplemented with fetal calf serum or the like. Culturing is performed normally under 5% $CO_2$ at 37° C. for 1 to 10 days. While culturing, antibiotics, such as kanamycin or penicillin, may be added to media, if necessary. After culturing, when the polypeptide of the present invention is produced within microorganisms or cells, the target polypeptide is collected by ultrasonication, repetitive of freeze-thawing, homogenizing treatment or the like to disrupt the microorganisms or cells. Further, when the polypeptide of the present invention is produced outside bacteria or cells, the culture solution is used intact, or centrifugation or the like is performed to remove the bacteria or cells. Then, the polypeptide of the present invention can be isolated and purified from the above culture product by a singular or a combined use of general biochemical methods for isolation and purification of protein, such as ammonium sulfate precipitation, gel chromatography, ion exchange chromatography and affinity chromatography.

As described above about XLH, PHEX which is thought to be an endopeptidase, has an important meaning in regulation of the hypophosphatemia-inducing factor. Hence, it is possible that the polypeptide having the amino acid sequence of SEQ ID NO: 2 of the present invention may have varied activities as a result of further modification and cleavage. In the present invention, using CHO ras-clone 1 cells as a host, a cloned cell line producing a recombinant polypeptide conferred with six continuous His (SEQ ID NO: 88) at the C-terminus of the polypeptide chain of the present invention was prepared. This cell line was deposited at the National Institute of Advanced Industrial Science and Technology, International Patent Organism Depositary (Chuo 6, 1-1-1, Higashi, Tsukuba-shi, Ibaraki, Japan) (Accession number FERM BP-7273, original deposit date: Aug. 11, 2000).

When the polypeptide of the present invention produced by the cell line and secreted into the culture solution was examined, gene products having different sizes were detected by Western blotting using an antibody recognizing His-tag sequence, as shown in FIG. 2. Proteins corresponding to respective bands were isolated and the determination of N-terminal amino acid sequences was performed. Thus, the N-terminal amino acid sequences were identical to the N-terminal amino acid sequence represented by SEQ ID NO: 4 and that represented by SEQ ID NO: 8, respectively. It is considered that the protein having the former sequence corresponds to a protein of which signal sequence is removed, and the protein having the latter sequence corresponds to a protein cleaved with an enzyme, such as an endopeptidase.

Now, furin is known as one of proteolytic enzymes which recognize RXXR. Actually, when the polypeptide of the present invention was expressed in a furin-deficient cell line, no fragment was detected. Further, when a recombinant protein α1-PDX having furin inhibition activity was co-expressed with the polypeptide of the present invention, cleaved products in the supernatant decreased significantly.

Hence, the present invention also encompasses a method for producing the polypeptide of the present invention which comprises the step of using furin-deficient cells upon culturing, or allowing co-existence with a substance which suppresses furin activity.

Cai et al have suggested that phosphatetransport-suppressing activity in the culture supernatant obtained by culturing tumor-derived cells of tumor-induced osteomalacia exhibited within the molecular weight range of 8 kDa to 25 kDa when measured by a fractionation method with dialysis membranes. It is also conceivable that the activity may be varied by converting the polypeptide having the amino acid sequence of SEQ ID NO: 4 of the present invention into polypeptides resulting from cleavage between residue No. 179, Arg, and residue No. 180, Ser, of SEQ ID NO: 2.

The polypeptide of the present invention has an activity to suppress the phosphate transport activity of epithelial cells of the renal proximal tubules, which is a form of the effect of hypophosphatemia-inducing activity, as shown in Table 2 (Example 7). Most free inorganic phosphate existing in the blood is filtered in the glomeruli of the kidneys, wherein approximately 80 to 90% of the inorganic phosphate is reabsorbed in the renal proximal tubule.

This reabsorption is performed by phosphate transport by type II Na-dependent phosphate transporter existing on the lumen side of the proximal tubule. The polypeptide of the present invention has an activity to suppress phosphate transport activity. This means that the polypeptide of the present invention promotes urinary excretion of phosphate in vivo. Thus, it can be considered that the polypeptide of the present invention induces hypophosphatemia by exerting its activity to suppress phosphate reabsorption in the kidney, in particular, phosphate transport in renal cells of proximal tubules, so that the polypeptide of the present invention is expected to be the same substance as the above Phosphatonin.

Recently, Na-dependent phosphate transporter in the intestinal tract has been identified. The transporter is named type IIb, because it has a high homology with that of type II Na-dependent phosphate transporter existing in the kidney. It is conceivable that the polypeptide of the present invention may also be responsible for suppressing type IIb Na-dependent phosphate transporter existing on the lumen side of the intestinal tract, similarly for type II Na-dependent phosphate transporter in the kidney. This can be regarded as a form of the effect of the hypophosphatemia-inducing activity.

The in vivo activity of the polypeptide of the present invention was evaluated by an experiment wherein the above recombinant cells expressing the polypeptide of the present invention had been transplanted subcutaneously to nude mice.

The transplanted cells in this experiment were grown in subcutaneous space of nude mice, and then allowed to form tumors. The polypeptide of the present invention produced and secreted by the cell with the tumor formation is characterized by being released into the body fluid of the mice, so that releasing of tumor-derived humoral factor in tumor-induced osteomalacia can be reproduced in this animal model. In this model experiment, as shown in Table 4 (Example 11), mice transplanted with cells expressing the polypeptide of the present invention developed evident hypophosphatemia, compared to control individual mice allowed to generate tumors by transplantation with CHO cells into which no DNA of the present invention had been introduced, or individual mice that have generated no tumor. Accordingly, the polypeptide of the present invention was shown to have the hypophosphatemia-inducing activity. In addition, it was also shown that the phosphate reabsorption rate also decreased, and that phosphate reabsorption in the kidneys was suppressed. Therefore, it was concluded that the polypeptide of the present invention is the hypophosphatemia-inducing factor in tumor-induced osteomalacia.

On the other hand, in the above model experiment, hypocalcemia was found in the mice transplanted with the recombinant cells producing the polypeptide of the present invention. Thus, it was also shown that the polypeptide of the present invention is also an hypocalcemia-inducing factor. In the experiment described in Example 16, wherein CHO cells expressing the polypeptide of the present invention were transplanted into nude mice, it was shown that serum 1α,25-dihydroxyvitamin D levels continuously decreased. As described in Examples 19 and 20, it was shown that when a mutation-introduced polypeptide of the present invention or a wild type full-length polypeptide of the present invention was administered three times to normal mice, serum 1α,25-dihydroxyvitamin D levels decreased in both cases. Further, as described in Example 24, after a single administration of the polypeptide of the present invention, decreased serum 1α,25-dihydroxyvitamin D levels were observed within several hours. Hence, it is conceivable that this activity which causes such a decrease of 1α,25-dihydroxyvitamin D level is a major biological or physiological effect of the polypeptide of the present invention.

As described above, serum 1α,25-dihydroxyvitamin D levels are ruled by 1α-hydroxylase and 24-hydroxylase. As described in Example 16, it was shown that the effect of the polypeptide of the present invention to decrease serum 1α,25-dihydroxyvitamin D levels is accompanied by fluctuations in expression of these metabolic enzymes. Further, as described in Example 24, at 1 hour after administration of the polypeptide of the present invention, decreased gene transcription products of 1α-hydroxylase which is responsible for production of active vitamin D metabolites, and increased gene transcription products of 24-hydroxylase which catabolizes active vitamin D metabolites were observed. The serum 1α,25-dihydroxyvitamin D levels gradually decreased after these fluctuations in expression, suggesting that the effect of the polypeptide of the present invention to decrease serum 1α,25-dihydroxyvitamin D levels is at least due to suppressed expression of 1α-hydroxylase gene and enhanced expression of 24-hydroxylase gene.

In contrast, in a long-term transplantation experiment (from 44 to 46 days after transplantation) wherein CHO cells expressing the polypeptide of the present invention was transplanted into nude mice as described in Example 11, expression of the 1α-hydroxylase gene was elevated. The mouse serum PTH levels at this time point was proved to be significantly elevated compared to a control group. Thus, it can be presumed that enhanced expression of 1α-hydroxylase gene was caused by a PTH effect at a high level. However, interestingly, even in the presence of high PTH level, expression of 24-hydroxylase gene was kept elevated, it can be understood that the high PTH level failed to interfere with the regulation by the polypeptide of the present invention of expression of 24-hydroxylase gene. As described in Example 11, serum 1α,25-dihydroxyvitamin D3 levels was not increased although the mice expressed severe hypophosphatemia- or rickets-like clinical findings. This suggests the affect of continuous enhancement of expression of 24-hydroxylase gene by the polypeptide of the present invention.

A. Nykjaer et al have revealed that 25-hydroxyvitamin D is reabsorbed in the renal proximal tubule (Cell, Vol. 96, p507-515, 1999). While the present specification does not describe it, but in an experiment wherein CHO cells expressing the polypeptide of the present invention had been transplanted into nude mice, no significant change was found in the serum 25-hydroxyvitamin D level. In addition, it was not recognized that the action of the polypeptide of the present invention affected the fractional excretion (calculated with urinary level/serum level/GFR) of main electrolytes, such as sodium, potassium or chloride, main amino acids or glucose, supporting the fact that the reabsorption function of the renal tubule was undamaged (T. Shimada et al., Proc. Natl. Acad. Sci, in press). Therefore, it was suggested that the polypeptide of the present invention does not decrease serum 1α,25-dihydroxyvitamin D levels by inhibiting reabsorption of 25-hydroxyvitamin D in the renal tubule, but by specifically acting on the synthetic pathway of 1α,25-dihydroxyvitamin D.

It is known that the serum 1α,25-dihydroxyvitamin D level is significantly decreased in tumor-induced osteomalacia. Further, in hypophosphatemic vitamin D-resistant rickets (XLH) or Hyp, the model mice expressing the clinical conditions of XLH, serum 1α,25-dihydroxyvitamin D levels are within the normal range or within a range somewhat below the lower limit of the normal range, regardless of severely decreased serum phosphate levels. It is also known that the expression of 24-hydroxylase gene is elevated in Hyp mice. In these clinical conditions developing hypophosphatemia, normally, as serum phosphate level decreases, 1α-hydroxylase gene expression rises, thereby increasing serum 1α,25-dihydroxyvitamin D levels. Thus, it is thought that a failure in any of regulatory systems disabling such normal physiological response is at least one of the causes of the clinical conditions. These phenomena are analogous to the physiological responses observed in the mice described in Example 11, 19 or 20, strongly suggesting that the polypeptide of the present invention functions to decrease serum 1α,25-dihydroxyvitamin D3 levels in the above clinical conditions.

It is clear from the X-ray images shown in FIG. 5 that the degree of calcification in bone tissues of the mice transplanted with the recombinant cells expressing the polypeptide of the present invention was significantly decreased when compared to that in the control group. Thorax deformation or the like was also observed, suggesting that the polypeptide of the present invention had an effect on skeletal formation.

In other words, it is conceivable that the polypeptide of the present invention has an effect on suppressing calcification of bone tissues, or effect on promoting recruitment of calcium and phosphate from bone tissues. It is also conceivable that significant decreases in both blood phosphate and calcium levels caused secondary suppression of bone tissue calcification.

In Hyp mice, it is thought that bone-derived cells produce a factor which suppresses phosphate transport activity in the renal proximal tubule (Lajeunesse, D. et al., Kidney Int. 50: 1531-1538, 1996). Further, it has been reported that osteoblasts of Hyp mice release calcification-suppressing factors (Xiao, Z. S., Am. J. Physiol., E700-E708, 1998). As described above, in XLH and tumor-induced osteomalacia, clinical findings such as hypophosphatemia and insufficient calcification in bone tissues closely resembles from each other, and these clinical findings would likely be induced by a single humoral factor. Taken together these facts suggest the possibility that the renal phosphate transport-suppressing activity and the bone calcification-suppressing activity reported in these studies of Hyp mice can be caused by the same factor. In addition, it has also been reported that the osteoblasts of Hyp mice exhibit abnormal osteogenesis even in the state wherein calcium and phosphate levels are in the normal range (Ecarot, B. et al., J. Bone Miner. Res. 7: 215-220, 1992). The polypeptide of the present invention has activities that is similar to those of a putative factor of the above Hyp mice. Thus, it is conceivable that the polypeptide of the present invention has, in addition to the hypophosphatemia-inducing activity, an effect of directly regulating calcification of bone tissues not mediated by the abnormalities in calcium or phosphate metabolism.

In the course of completing the present invention, in addition to a gene encoding the polypeptide of the present invention, dentin matrix protein-1 (DMP-1) was also obtained as shown in Table 1 of Example 3. This gene is abundantly expressed in the dentin of teeth, and a protein encoded by this gene is thought to have an important role, as an extracellular matrix protein of dentin, in the formation of calcified matrix of dentin. Similarly, a gene encoding a matrix extracellular phosphorylation protein (MEPE) was obtained as OST190. Detailed functions of the molecule are unknown. Further similarly, a gene encoding osteopontin was also obtained. MEPE, DMP-1 and osteopontin have common characteristics in that they are phosphorylation proteins having RGD motif sequence, are rich in serine and threonine that can be phosphorylated, have high contents of glutamic acid and aspartic acid that are acidic amino acids, and show intense acidic protein characteristics. A characteristic acidic region, named ASARM sequence, is conserved between MEPE and DMP-1 (Rowe, P. S. N. et al, Genomics 67: 54-68, 2000), suggesting similarity in their physiological or functional significance. Interaction with inorganic calcium and/or phosphate upon the start of calcification is thought to be one of the functions of such a characteristic protein. Expression of osteopontin gene in a variety of cells has been reported, such as in macrophages, in addition to osteoblasts and osteoclasts. On the other hand, expression of DMP-1 in bone tissues, particularly in osteocytes has been reported recently. The gene expression of MEPE in the myeloid tissue or in osteosarcoma cells such as SaOS-2 are known. The fact that such an acidic matrix protein found in the calcified tissue has been found together with the polypeptide of the present invention in the course of the present invention represents an aspect of a type of effect of the polypeptide of the present invention. Specifically, there are possibilities that the polypeptide of the present invention induces expression of calcified tissue-specific molecules which are represented by the above molecules, so that the polypeptide regulates calcification, calcium metabolism and phosphate metabolism in a cooperative manner, or the induced molecule secondarily regulates calcification, calcium metabolism, and metabolism. It is also conceivable that the polypeptide of the present invention can regulate bone metabolism by directly acting on osteoblasts, osteocytes and osteoclasts. Hence, the polypeptide of the present invention may be effective in the therapy for metabolic bone diseases as represented by osteoporosis.

Recently, cells having osteoblast-like phenotype have been shown to appear at ectopic calcification sites, suggesting that calcification may occur by the mechanism similar to that of the process of calcification in bone tissue. Therefore, it is also conceivable that the polypeptide of the present invention is effective in the therapy of ectopic calcification by suppressing the appearance or function of such cells in charge of calcification.

In the present invention, the above polypeptide can be modified. For example, polyethylene glycol, dextran, poly (N-vinyl-pyrrolidone), polypropylene glycol homopolymer, copolymer of polypropylene oxide/ethylene oxide, polyoxyethylated polyol, polyvinyl alcohol and the like are appropriately selected for use. As a modification method, any known technique can be employed. For example, one such technique is disclosed in detail in JP Patent Publication (PCT translation) No. 10-510980.

4. Antibody Against Polypeptide of the Present Invention

An antibody of the present invention specifically reacts with the above polypeptide of the present invention. In the present invention, the term "antibody" means the entire antibody molecule or the fragment thereof (for example, Fab or F(ab')$_2$ fragment) which are capable of binding to the antigenic polypeptide or fragments thereof, and may be a polyclonal or a monoclonal antibody.

The antibody of the present invention can be prepared according to a standard method. For example, the antibody can be prepared by either an in vivo method, which involves immunization of animals once or several times (booster immunization) at an interval of several weeks using an antigen together with an adjuvant, or an in vitro method, which involves isolating immunocytes and allowing the immunocytes to be sensitized using an appropriate culture system. Examples of immunocytes capable of producing the antibody of the present invention include spleen cells, tonsil cells and lymphoid cells.

A polypeptide to be used as an antigen does not have to be the above entire polypeptide of the present invention. A part of the polypeptide may be used as an antigen. To use a short peptide as an antigen, particularly, a peptide having as short as approximately 20 amino acid residues, such a peptide is bound by chemical modification or the like to a carrier protein with high antigenicity, such as keyhole limpet hemocyanin or bovine serum albumin, or covalently bound to a peptide having the branched skeleton, such as a lysine core MAP peptide, instead of a carrier protein (Posnett et al., J. Biol. Chem. 263, 1719-1725, 1988; Lu et al., Mol. Immunol. 28, 623-630, 1991; Briand et al., J. Immunol. Methods 156, 255-265, 1992).

As an adjuvant, for example, Freund's complete or incomplete adjuvant, aluminum hydroxide gel or the like is used. As animals to be administered with an antigen, for example, a mouse, rat, rabbit, sheep, goat, chicken, cattle, horse, guinea pig and hamster are used.

Polyclonal antibodies can be obtained by collecting blood from these immunized animals, separating the serum, and purifying immunoglobulins using one of or an appropriate combination of ammonium sulfate precipitation, anion exchange chromatography, and protein A or G chromatography. When the above animal is a chicken, antibodies can be purified from the eggs.

Monoclonal antibodies can be prepared by purification from the culture supernatant of hybridomas prepared by allowing immunocytes, which have been sensitized in vitro or of the above animals, to fuse with parent cells that can be cultured, or from ascites obtained by intraperitoneal inoculation of the hybridomas into the animals. As parent cells, a generally available established cell line of an animal, such as a mouse, can be used. A preferred cell line to be used herein has drug selectivity, and has a characteristic such that it cannot survive in HAT selection medium (hypoxanthine, aminopterin and thymidine are contained) when it is in unfused state, but can survive only in its fused state with antibody-producing cells. Examples of such a cell line include X63, NS-1, P3U1, X63.653, SP2/0, Y3, SKO-007, GM1500, UC729-6, HM2.0 and NP4-1 cells.

Specific techniques to prepare monoclonal antibodies are as follows.

The polypeptide or the fragment thereof prepared as described above is administered as an antigen to the above animal. Antigen dosage per animal is 1 to 100 μg when an adjuvant is used. Immunization is performed mainly by intravenous, subcutaneous or intraperitoneal injection. In addition, the immunization interval is not specifically limited. At an interval of several days to several weeks, preferably 1 to 3 weeks, immunization is performed 1 to 10 times, preferably 2 to 5 times. 1 to 10 days later, preferably 1 to 4 days later the final immunization date, antibody-producing cells are collected.

To obtain hybridomas, cell fusion of antibody-producing cells and parent cells (myeloma cells) is performed. Cell fusion is performed in a serum-free medium for culturing animal cells, such as DMEM or RPMI-1640 medium, by mixing $5 \times 10^6$ to $1 \times 10^8$ cells/ml antibody-producing cells with $1 \times 10^6$ to $2 \times 10^7$ cells/ml myeloma cells (a preferred ratio of antibody-producing cells to myeloma cells is 5:1), and performing fusion reaction under the presence of a cell fusion-promoting agent. As a fusion-promoting agent, polyethylene glycol or the like having a mean molecular weight of 1000 to 6000 daltons can be used. In addition, antibody-producing cells and myeloma cells can also be fused with a commercial cell fusion device using electric stimulation (for example, electroporation).

Following the treatment to accomplish cell fusion, hybridomas of interest are selected from the cells. The cell suspension is appropriately diluted in, for example, RPMI-1640 medium containing fetal calf serum, inoculated on a microtiter plate at a concentration of approximately $5 \times 10^5$ cells/well. The selection medium is added to each well, and then culturing is performed while properly exchanging the selection medium. As a result, cells that have proliferated at around 14 days after the start of culturing in the selection medium can be obtained as hybridomas. The culture supernatant of the hybridomas that have proliferated is screened for the presence of antibodies which react with the polypeptide of the present invention. Screening for hybridomas may be performed according to an ordinary method, and the screening method is not specifically limited. For example, a part of the culture supernatant contained in wells in which hybridomas are grown is collected, and then screened by enzyme immunoassay, radioimmunoassay or the like.

Alternatively, monoclonal antibodies can be prepared by culturing immortalized antibody-producing cells which are obtained by allowing an appropriate virus, such as EB virus, to infect immunocytes sensitized in vitro or of the above immunized animal.

Aside from these cell engineering techniques, monoclonal antibodies can also be obtained by gene engineering techniques. For example, such antibody genes can also be amplified and obtained by PCR (polymerase chain reaction) from immunocytes sensitized in vitro or of the above animal. The gene is introduced into a microorganism, such as *Escherichia coli*, so as to allow it to produce antibodies, or used to allow a phage to express the antibody as a fusion protein on the surface.

Quantitative determination of the amount of the polypeptide of the present invention in vivo using the antibody of the present invention makes it possible to elucidate the relationship between the polypeptide of the present invention and clinical conditions of various diseases. Moreover, the antibody can be applied to diagnosis or therapy and subjected to perform efficient affinity purification of the polypeptide of the present invention.

It is assumed that there are some diseases of which cause resides in a decreased of serum 1α,25-dihydroxyvitamin D levels induced by the excessive action of the polypeptide of the present invention. For example, although hypophosphatemic vitamin D-resistant rickets (XLH) develops severe hypophosphatemia, no increase is found in serum 1α,25-dihydroxyvitamin D3 levels. The reason is thought to be abnormality in groups of vitamin D metabolizing enzyme genes. In this disease, excessive action of the polypeptide of the present invention may be involved. In Hyp, which is a mouse model of XLH, enhanced expression of 24-hydroxylase gene has been reported. This agrees with the effect of the polypeptide of the present invention to induce enhanced 24-hydroxylase gene expression. Therefore, it is expected that this disease can be treated by administering the antibody against the polypeptide of the present invention to normalize vitamin D metabolism and then to correct the serum 1α,25-dihydroxyvitamin D3 levels. An example of a disease that presents clinical findings similar to that of XLH is autosomal dominant hypophosphatemic rickets (ADHR). Upon cloning of the polypeptide of the present invention, we have inferred that a gene encoding the polypeptide is a gene responsible for ADHR, based on its location on the chromosome. Recently, a gene responsible for ADHR has been analyzed and reported that the disease is caused by a missense mutation in the gene encoding the polypeptide. We have further clarified that this mutation confers resistance against enzymatic cleavage, and showed that excessive effect of this molecule is a cause of the disease. It is conceivable that the antibody against the polypeptide of the present invention is effective in treating this disease through its suppressing effect. ADHR develops osteomalacia, disordered mineral metabolism and disordered vitamin D metabolism. Thus, among metabolic bone disease which closely relate to such metabolic pathway, there may be diseases on which the polypeptide of the present invention acts as a cause of the disease. It can be expected that the antibody against the polypeptide of the present invention is effective for such a disease. As one effect of 1α,25-dihydroxyvitamin D, suppression of differentiation into adipocytes is known. It is known that adipocytes in the bone marrow increases with age. In this case, there may be enhanced differentiation into adipocytes from common precursor cells of osteoblasts, adipocytes and stromal cells supporting hematopoiesis existing in the bone marrow. It is conceivable that in this process, the polypeptide of the present invention may excessively act to decrease local 1α,25-dihydroxyvitamin D levels. Therefore, it can be expected that the use of the antibody against the polypeptide of the present invention enables to increase blood or local 1α,25-dihydroxyvitamin D levels, suppress differentiation into adipocytes, and improve decreased ability of bone formation or hematopoiesis. In addition, the antibody is also expected to be effective against obesity. It is conceivable that there are other such diseases in which the polypeptide of the present invention is involved. Such a disease can be screened by an immunological quantitative determination method as represented by ELISA combined with the use of the antibody against the polypeptide of the present invention. Accordingly, the physiological normal range of the polypeptide of the present invention can be established, and disease groups deviated from the range can be clarified. It can be expected that the antibody against the polypeptide of the present invention is used for therapeutic purposes against diseases showing abnormally high blood levels of the polypeptide of the present invention as measured by the above method.

5. Pharmaceutical Composition (1) Pharmaceutical Composition Comprising the Polypeptide of the Present Invention The polypeptide of the present invention can be used as a pharmaceutical composition for diseases with unfavorably elevated blood phosphate levels. In chronic renal failure, decreased levels of phosphate excretion from the kidney result in elevated blood phosphate levels. Hyperphosphatemia further aggravates renal functions, and promotes secretion of parathyroid hormone from the parathyroid gland, thereby inducing secondary hyperparathyroidism. This disease causes itching of the skin, as well as decreased Ca absorption from the intestinal tract due to disordered synthesis of 1α,25-dihydroxyvitamin D3 in the kidney. In addition, the state of oversecretion of parathyroid hormone due to the retention of blood phosphate promotes Ca mobilization from bone tissues. When this state continues, osteitis fibrosa or hyperplasia of the parathyroid glands that is one of the clinical conditions of renal osteodystrophy. One preferred method to evade this state is to improve the above-mentioned hyperphosphatemia, but current medical treatment cannot sufficiently control hyperphosphatemia. In chronic renal failure at a stage wherein the urination function is retained, the polypeptide of the present invention has an activity to correct blood phosphate levels by suppressing type II Na-dependent phosphate transporter existing in epithelial cells of the renal proximal tubules to promote phosphate excretion into urine (phosphate transport-suppressing activity). In addition, the polypeptide of the present invention can correct blood phosphate levels by acting on the intestinal tract in a way similar to that in the kidneys to suppress type IIb Na-dependent phosphate transporter and thus reduce phosphate absorption into the body.

The polypeptide of the present invention can also be used as a pharmaceutical composition for diseases resulting from abnormal calcium metabolism and phosphate metabolism. The term "abnormal calcium metabolism" indicates a state at which serum calcium levels deviate from clinically defined normal range, or a state at which serum calcium levels are within the normal range, but the functions of the kidney, intestinal tract, bone tissue and parathyroid glands are abnormally increased or decreased to maintain serum calcium levels, or a state at which hormones regulating the serum calcium, such as parathyroid hormone, 1α,25-dihydroxyvitamin D3 or calcitonin exhibit abnormal values. In addition, the term "abnormal phosphate metabolism" indicates a state at which serum phosphate levels deviate from the clinically-defined normal range, or a state in which serum phosphate levels are within the normal range, but phosphate-balancing functions are abnormally increased or decreased in the kidney, intestinal tract and bone tissue.

Renal osteodystrophy along with the above secondary hyperparathyroidism takes various clinical forms, such as adynamic bone disease, osteitis fibrosa or the mixed type thereof. Against secondary hyperparathyroidism, 1α,25-dihydroxyvitamin D3, 1α-hydroxyvitamin D3 or the like is generally used to suppress parathyroid hormone. When the value of parathyroid hormone is not sufficiently suppressed, a pulse therapy (hereinafter, may also be referred to as "vitamin D pulse therapy") which involves administering over dose of 1α,25-dihydroxyvitamin D3 or 1α-hydroxyvitamin D3 may be performed. The normal serum parathyroid hormone level is 65 pg/ml or less. When parathyroid hormone levels are at the normal levels in this disease condition, adynamic bone disease, which is a form of renal osteodystrophy, is caused. Moreover, when parathyroid hormone levels increase, osteitis fibrosa, which is contrary to the above clinical condition, occurs. As a recent medical guideline for such diseases, it has been proposed that parathyroid hormone levels be maintained at approximately 130 to 260 pg/ml. However, fundamental causes of abnormal metabolism remain unknown. It is known that parathyroid hormone is induced by elevated blood phosphate levels, and is suppressed by elevated serum calcium levels. Since the polypeptide of the present invention lowers blood phosphate levels and blood calcium levels, it can be inferred that the polypeptide can modify the functions of parathyroid hormone. Further, there has been reported that in tumor-induced osteomalacia patients, 1α,25-dihydroxyvitamin D3 falls to the detection limit or below. Thus, it can also be inferred that the polypeptide of the present invention may be involved in regulating the activity of 1α,25-dihydroxyvitamin D3. It is conceivable that in renal osteodystrophy with the above abnormal regulation or impaired activity of parathyroid hormone, the polypeptide of the present invention can be used as a clinically useful pharmaceutical composition for either adynamic bone disease or osteitis fibrosa. Therefore, it is conceivable that administration of the polypeptide of the present invention provides a useful therapy for either osteitis fibrosa or adynamic bone disease, which are contrary to each other, in renal osteodystrophy.

Furthermore, the polypeptide of the present invention can be used as a pharmaceutical composition for ectopic calcification. Calcification of tissues other than bone tissues damages biofunctions. In particular, dysfunction due to calcification of the heart or blood vessel threatens life. A risk factor of this ectopic calcification is an increase in the product of blood calcium ion and phosphate ion levels (hereinafter, may also be referred to as "the calcium-phosphate product"). In the above therapy for secondary hyperparathyroidism, when the vitamin D pulse therapy is performed against clinical conditions of hyperphosphatemia, the calcium-phosphate product can increase to cause ectopic calcification. Calcification of the cardiovascular system in hemodialysis patients is a serious problem. The polypeptide of the present invention has an activity to significantly decrease serum calcium levels and phosphate levels as shown in Table 4, so that it can be expected to be effective against ectopic calcification along with various diseases.

Furthermore, the polypeptide of the present invention can be used as a pharmaceutical composition against metabolic bone diseases. The polypeptide of the present invention has a strong regulatory activity for calcium metabolism, phosphate metabolism, calcification or vitamin D metabolism. Examples of hormones involved in calcium metabolism and phosphate metabolism include calcitonin, parathyroid hormone and 1α,25-dihydroxyvitamin D3. Calcitonin has an activity to decrease serum calcium, and parathyroid hormone and 1α,25-dihydroxyvitamin D3 have an activity to increase serum calcium. Parathyroid hormone has been reported to have an effect on phosphate excretion to urine, and calcitonin has also been reported to have similar activity. 1α,25-dihydroxyvitamin D3 has an activity to promote phosphate absorption from the intestinal tract. As described above, each hormone has a different activity for maintaining the balance between blood calcium and phosphate levels, but calcitonin and 1α,25-dihydroxyvitamin D3 are used as therapeutic agents for osteoporosis. In addition, parathyroid hormone is being developed as a therapeutic drug for osteoporosis.

Bone metabolism is characterized in that catabolism and anabolism of bone tissues, that is, bone resorption and bone formation, are coupling. Continuous administration with parathyroid hormone causes bone mass to decrease. However, when allowed to act intermittently, parathyroid hormone is known to promote bone formation. Since the polypeptide of the present invention has an effect of regulating calcium metabolism and phosphate metabolism, it can be expected that the polypeptide can be effective against metabolic bone diseases including osteoporosis, when an appropriate method for using the polypeptide is selected.

Furthermore, the polypeptide of the present invention can be used as a pharmaceutical composition for diseases or clinical conditions with unfavorably elevated serum 1α,25-dihydroxyvitamin D levels, or for clinical conditions with unfavorable physiological responses induced by serum 1α,25-dihydroxyvitamin D.

1α,25-dihydroxyvitamin D is known to act on the parathyroid glands to suppress secretion of parathyroid hormone (PTH). Therefore, a therapy, which has been clinically established for secondary hyperparathyroidism in chronic renal failure, particularly for cases with high serum PTH levels, involves intermittent administration of a high concentration of 1α,25-dihydroxyvitamin D. A disadvantage of this therapy is that it easily induces ectopic calcification. In chronic renal failure patients with high serum phosphate levels, unfavorable calcification due to administration of 1α,25-dihydroxyvitamin D is often observed in tissues other than bone tissues. Since the polypeptide of the present invention has an effect to promote a quick decrease in serum 1α,25-dihydroxyvitamin D within several hours after administration of the polypeptide, the polypeptide is useful in therapy and in preventing ectopic calcification that is caused by excessive 1α,25-dihydroxyvitamin D levels.

Moreover, intermittent administration of high concentrations of 1α,25-dihydroxyvitamin D causes excessively suppressed PTH secretion, so that it can induce adynamic bone disease developing clinical conditions such as arrested bone metabolism. For such a case, it can be expected that the administration of the polypeptide of the present invention would cause 1α,25-dihydroxyvitamin D in serum to decrease, promote proper PTH secretion in the parathyroid glands, and provide recovery from adynamic bone disease.

For calcification of blood vessels, involvement of 1α,25-dihydroxyvitamin D as a calcification-promoting factor has been reported. The polypeptide of the present invention can be used therapeutically or prophylactically against clinical conditions associated with calcification of blood vessels, such as arteriosclerosis due to aging, diabetic angiopathy, or calcification of the cardiovascular system in dialysis patients.

Calcium absorption from the intestinal tract is known to be promoted by 1α,25-dihydroxyvitamin D in serum. The polypeptide of the present invention can be used to correct hypercalcemia by decreasing serum 1α,25-dihydroxyvitamin D levels. Examples of a cause of hypercalcemia include overproduction of PTH due to primary hyperparathyroidism, a high concentration of 1α,25-dihydroxyvitamin D along with chronic granuloma, such as sarcoidosis or tuberculosis, or accelerated bone resorption due to PTHrP produced by malignant tumors. In hypercalcemia which is mainly caused not only by excessive 1α,25-dihydroxyvitamin D, but also by excessive PTH or PTHrP, it can be expected that administration of the polypeptide of the present invention causes the serum 1α,25-dihydroxyvitamin D level to decrease, so as to improve hypercalcemia. In particular, activated macrophages in chronic granuloma, such as sarcoidosis or tuberculosis, has 1α-hydroxylase activity and excessively produces 1α,25-dihydroxyvitamin D3. It is expected that this 1α-hydroxylase activity is directly lowered by the polypeptide of the present invention.

1α,25-dihydroxyvitamin D is known to promote differentiation of osteoclasts, and administration of the polypeptide of the present invention is expected to suppress bone resorption. In vitro, 1α,25-dihydroxyvitamin D is known to be a strong osteoclast differentiation-inducing factor. Excessive bone resorption by osteoclasts causes osteopenia as represented by osteoporosis. In such diseases for which promoted bone resorption is observed, the polypeptide of the present invention is expected to restore bone turnover to the normal condition by transiently lowering serum 1α,25-dihydroxyvitamin D levels. In addition to suppressing the differentiation of osteoblasts in vitro, 1α,25-dihydroxyvitamin D has also been suggested to be a factor of suppressing bone formation in vivo in a bone transplantation experiment using vitamin D receptor-deficient mice. From such view points, it can be expected that the polypeptide of the present invention, which is capable of lowering 1α,25-dihydroxyvitamin D, is effective against metabolic bone diseases with decreased bone mass. Further, there has been a report confirming that administration of 24,25-dihydroxyvitamin D, which is one of vitamin D3 metabolites, causes increased bone mass. 24,25-dihydroxyvitamin D is a product of hydroxylation of 25-hydroxyvitamin D by 24-hydroxylase. Since the polypeptide of the present invention has an effect to enhance the expression of 24-hydroxylase gene significantly, it can be expected that administration of this peptide causes blood 24,25-dihydroxyvitamin D levels to increase, and to increase bone mass under clinical conditions in bone diseases, such as osteoporosis or skeletal dysplasia.

PTH is known to have a strong bone resorption-promoting effect. However, bone turnover can be stimulated by intermittent administration of PTH, and finally, an effect of increasing bone mass can be expressed. Physiological or biological activities of the polypeptide of the present invention that have been shown so far include: an effect of regulating 1α,25-dihydroxyvitamin D; effects of regulating serum calcium and serum phosphate levels; and effect of regulating calcification. Thus, it is conceivable that bone turnover can be regulated by allowing the polypeptide to effectively act on bone tissues. Therefore, the polypeptide can be expected to be effective against postmenopausal osteoporosis with enhanced bone turnover and senile osteoporosis with lowered bone turnover. There may be other diseases that the polypeptide of the present invention is involved in. Such a disease can be screened by an immunochemical assay as represented by ELISA combined with the use of one or more antibodies against the polypeptide of the present invention.

Accordingly, the physiological normal range of the polypeptide of the present invention can be set, and disease groups with the polypeptide levels which deviate from the range can be clarified. It can be expected that the polypeptide of the present invention is therapeutically used for diseases showing abnormally low blood levels of the polypeptide of the present invention as measured by the above method.

(2) Pharmaceutical Composition Containing the Antibody of the Present Invention

The antibody of the present invention can be used as a pharmaceutical composition for vitamin D-resistant rickets and tumor-induced osteomalacia. The neutralizing antibody of this polypeptide can be obtained as a polyclonal antibody or a monoclonal antibody by the above-mentioned method for preparing antibodies. As a method for more properly using the antibody as a medicine, a human-type antibody or a humanized antibody can be prepared. Hypophosphatemia and osteomalacia in tumor-induced osteomalacia can be treated or improved by suppressing excessive activity of the polypeptide of the present invention. It can be expected that administration of the neutralizing antibody against the polypeptide of the present invention improves tumor-induced osteomalacia symptoms. Further, since hypophosphatemia-inducing factor and calcification-suppressing factor in XLH are thought to be equivalent to the polypeptide of the present invention, the neutralizing antibody can also be a therapeutic agent against vitamin D-resistant rickets including XLH.

The antibody of the present invention can be used as a pharmaceutical composition for diseases with abnormal calcium or phosphate metabolism, or metabolic bone diseases associated with the presence of the polypeptide of the present invention in an excessive amount. As described above, in chronic renal failure or hemodialysis patients, abnormalities occur in the mechanism for maintaining the homeostasis of calcium metabolism or phosphate metabolism, and these abnormalities may be due to overproduction or accumulation of the polypeptides of the present invention. It has been shown that the polypeptide of the present invention regulates bone metabolism. Hence, it is conceivable that metabolic bone diseases which are caused by the presence of excessive amounts of the polypeptide of the present invention, may also exist. In this case, it can be expected that the clinical conditions can be treated or improved by the antibody against the polypeptide of the present invention.

Examples of diseases to which the antibody of the present invention can be applied include at least one kind of bone disease, such as osteoporosis, vitamin D-resistant rickets, renal osteodystrophy, dialysis-associated bone diseases, osteopathy with hypocalcification, Paget's disease and tumor-induced osteomalacia. Here, the bone disease may be a single disease, a complication thereof, or the bone disease complicated with any disease other than the above diseases.

(3) Administration Protocol

A pharmaceutical composition which contains the polypeptide of the present invention or the antibody thereof, as an active ingredient, may contain a pharmaceutically acceptable carriers and additives. Examples of such carriers and additives include water, pharmaceutically acceptable organic solvent, collagen, polyvinyl alcohol, polyvinylpyrrolidone, carboxy vinyl polymer, sodium alginate, water-soluble dextran, sodium carboxymethyl starch, pectin, xanthan gum, gum arabic, casein, gelatine, agar, glycerin, propylene glycol, polyethylene glycol, Vaseline, paraffin, stearyl alcohol, stearic acid, human serum albumin, mannitol, sorbitol, lactose, and surfactant which is a pharmaceutically acceptable additives. The additives to be used herein are properly selected from the above items either singly or in combination depending on the employed dosage form of the present invention.

When the polypeptide or the antibody of the present invention is used as a prophylactic or therapeutic agent for bone diseases, the subject for which the polypeptide or the antibody is used is not specifically limited.

The polypeptide of the present invention can be used as a pharmaceutical composition which is capable of regulating calcium metabolism, phosphate metabolism, calcification or vitamin D metabolism in organisms.

The antibody of the present invention can be used specifically to treat or prevent at least one kind of bone disease, such as osteoporosis, vitamin D-resistant rickets, renal osteodystrophy, dialysis-associated bone diseases, osteopathy with hypocalcification, Paget's disease, tumor-induced osteomalacia, as described above. The bone disease, for which the polypeptide or the antibody of the present invention can be used, may be a single disease, a complication thereof, or the bone disease complicated with any disease other than the above diseases.

A prophylactic agent or therapeutic agent which contains the polypeptide or the antibody of the present invention may be administered orally or parenterally in the case of the polypeptide, and parenterally in the case of the antibody.

When the polypeptide of the present invention is administered orally, the dosage form to be applied thereto may be a solid preparation, such as a tablet, granule, powder or pill, or a liquid preparation, such as a liquid drug or syrup, or the like. In particular, a granule and powder can be formulated into a unit dose form, that is, a capsule. In the case of a liquid preparation, it can be formulated into a dry product which is re-dissolved for use.

Of these dosage forms, a solid preparation for oral administration normally contains in its composition additives, which are generally pharmaceutically employed, such as a binder, excipient, lubricant, disintegrating agent or wetting agent. In addition, a liquid preparation for oral administration normally contains in its composition an additives, which is pharmaceutically generally employed, such as a stabilizer, buffer, corrigent, preservative, flavoring agent or colorant.

When the polypeptide or the antibody of the present invention is administered parenterally, it can be formulated into an injection, suppository or the like.

In the case of an injection, it is normally provided in a unit dose ampule or a vessel for multiple dose, or may be in a powdery form which is re-dissolved, when used, in an appropriate carrier, such as sterilized water containing no pyrogenic substance. These dosage forms normally contain in their compositions, additives which are pharmaceutically generally employed, such as an emulsifier or suspension. Examples of injection procedures include drip intravenous infusion, intravenous injection, intramuscular injection, intraperitoneal injection, subcutaneous injection or intradermal injection. In addition, doses differ depending on the age of the subject, route for administration and dosage frequency, and can be varied widely.

In this case, the effective dose to be administered is a combination of the effective dose of the peptide or the antibody of the present invention with an appropriate diluent, and a pharmacologically usable carrier, in the case of the polypeptide, is 0.01 to 100 µg, preferably, 0.5 to 20 µg/administration/kg of body weight. Further, in the case of the antibody, the effective dose is 0.1 µg to 2 mg, preferably, 1 to 500 µg/administration/kg of body weight.

6. Diagnostic Agent of Disease (1) The Antibody or the Polypeptide of the Present Invention The antibody of the present invention is used for detection or quantitative determination of the polypeptide of the present invention or of the metabolites existing in blood or urine, so that the relationship between the polypeptide of the present invention and clinical conditions can be elucidated, and the antibody can be applied as a diagnostic agent for associated diseases.

The term "associated disease" means a bone disease or a disease developing at least an abnormality from among: abnormal calcium metabolism, abnormal phosphate metabolism, abnormal calcification and abnormal vitamin D metabolism. Examples of such a disease include osteoporosis, vitamin D-resistant rickets, renal osteodystrophy, dialysis-associated bone diseases, osteopathy with hypocalcification, Paget's disease, renal failure, renal phosphate leak, renal tubular acidosis and Fanconi's syndrome.

Methods for quantitatively determining bound molecules using antibodies have been generalized, such as radioimmunoassay or enzyme immunoassay. Levels of the polypeptide of the present invention in blood or urine measured by these methods can be indicators for new clinical judgement. For example, when a rickets patient shows high blood levels of the polypeptide of the present invention compared to a normal subject, XLH or ADHR can be strongly suspected. Further, based on changes in blood levels of the polypeptide of the present invention, prognosis of a progress into secondary hyperparathyroidism in a chronic renal failure patient can be made.

For tumor-induced osteomalacia, generally, it is often difficult to find a tumor. However, the use of the antibody of the present invention enables to establish useful diagnostic measures. For example, when a patient with no family history of rickets or osteomalacia shows significantly higher blood levels of the polypeptide of the present invention compared to a normal individual, tumor-induced osteomalacia can be suspected.

(2) DNA of the Present Invention

In the present invention, detection of abnormal DNA of the present invention from a patient with abnormal phosphate metabolism or abnormal calcium metabolism, or a patient with a metabolic bone disease makes it possible to diagnose and prevent the disease.

A search for the nucleotide sequence of the DNA of the present invention over the Genbank nucleotide sequence database reveals that the nucleotide sequence (in the form of three fragments) matches with a sequence of human 12p13 BAC RPCI11-388F6 (Accession No. AC008012). This fragmentation indicates that the nucleotide sequence of the DNA of the present invention is provided as a splicing product from a chromosome sequence. Thus it is clear that the DNA encoding the polypeptide of the present invention contains at least a sequence ranging from the $498^{th}$ to $12966^{th}$ nucleotides of a sequence represented by SEQ ID NO: 11 or partial fragments thereof. Substitution, insertion or deletion of nucleotides within the range causes increases, decreases or disappearance of the biological and physiological activities of the polypeptide of the present invention. The polypeptide of the present invention has a strong effect on phosphate metabolism, calcium metabolism, bone metabolism, and vitamin D metabolism. Therefore, when gene polymorphism or mutation due to substitution, insertion, deletion and the like of partial nucleotides of the nucleotide sequence represented by SEQ ID NO: 11 or partial regions thereof (for example, a sequence from the $498^{th}$ to the $12966^{th}$) is shown, diagnosis and prevention of a disease containing abnormal phosphate metabolism and calcium metabolism, or a disease developing abnormal bone metabolism, or a disease developing abnormal vitamin D metabolism become possible.

Now, it has been reported that the gene responsible for ADHR is present at 12p13 as a result of linkage analysis of families having ADHR (Econs, M. J. et al., J. Clin. Invest. 100: 2653-2657, 1997). In this report, it has also been shown that the responsible gene is present within a 18 cM range between micro satellite markers D12S100 and D12S397. We confirmed that the location at which the DNA of the present invention is present on the chromosome by comparing with the reported location. The region at which the DNA encoding the polypeptide of the present invention is present was identical to the region at which the gene responsible for ADHR is present. Based on the biological activities of the polypeptide of the present invention and the location of the gene on the chromosome, it is conceivable that the polypeptide of the present invention is encoded by the responsible gene of ADHR. This can be confirmed by separating cellular components from the blood of ADHR patients, isolating chromosomal DNAs from the cellular components, and then finding mutations in the nucleotide sequence within the region represented by SEQ ID NO: 11. Hence, the gene having the above nucleotide sequence region is used as a diagnostic agent for autosomal dominant hypophosphatemic rickets, X-linked hypophosphatemic rickets, hypophosphatemic bone disease, osteoporosis and the like.

Between exon 1 and exon 2 of the DNA region encoding the polypeptide of the present invention that we have specified, STS sequence, which has been registered at NCBI Genbank under Accession No. G19259, is present. This marker is thought to be very important in studying the relationship between the DNA and hereditary characters.

The present invention will bring a big change in understanding conventional calcium metabolism, phosphate metabolism, bone metabolism and vitamin D metabolism. According to the present invention, there is provided a delayed progress to the stage of hemodialysis in chronic renal failure, or a new therapeutic method and diagnostic method for phosphate metabolism-associated and calcium metabolism-associated diseases, and metabolic bone diseases. Further, the present invention is also useful to improve or support existing therapeutic methods.

BRIEF DESCRIPTION OF DRAWINGS

FIG. 3A shows the results of predicting sites of the polypeptide having the amino acid sequence represented by SEQ ID NO: 2, which are appropriate for preparation of a peptide antibody, using a computing function of MacVector version 6.5.1.

FIG. 6 shows the results of alignment of amino acid sequence between human OST311 polypeptide and mouse OST311 polypeptide.

FIG. 9C includes photographs showing changes in mRNA levels, as detected by Northern blotting, of vitamin D-metabolizing enzymes (1αOHase, 24OHase) in the kidneys of the mice. The kidneys were collected from the mice sacrificed on days 44 to 46 after tumor transplantation.

Each value is shown in terms of mean±standard deviation.

Figure 11A:
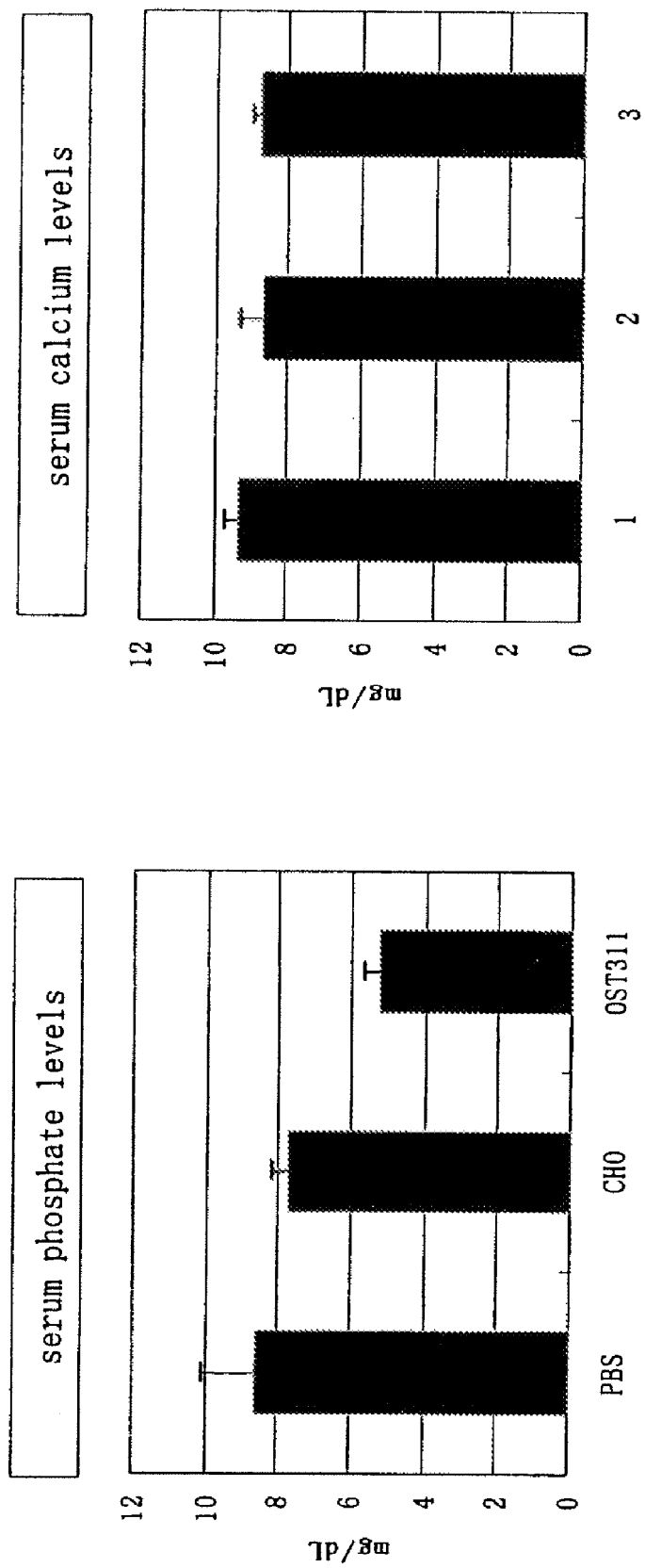
FIG. 11A includes graphs showing comparisons of serum phosphate levels and serum calcium levels, on day 2 after transplantation, among PBS, CHO ras clone-1 cells, and CHO-OST311H cells-transplanted nude mice (6-week-old, BALB/c, male).
Figure 11B:
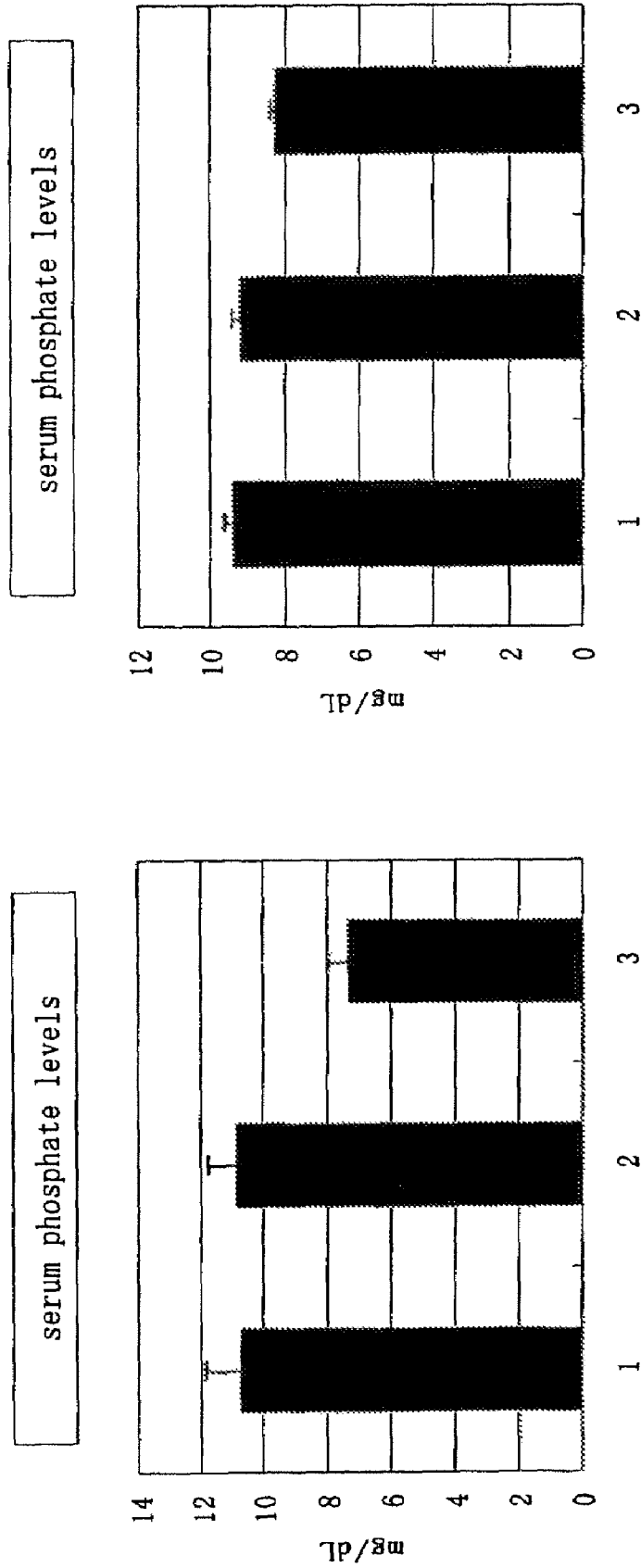

FIG. 11B includes graphs showing comparisons of serum phosphate levels and serum calcium levels, on day 6 after transplantation, among PBS, CHO ras clone-1 cells, and CHO-OST311H cells-transplanted nude mice (6-week-old, BALB/c, male).

Each value is shown in terms of mean±standard deviation.

Figure 12:
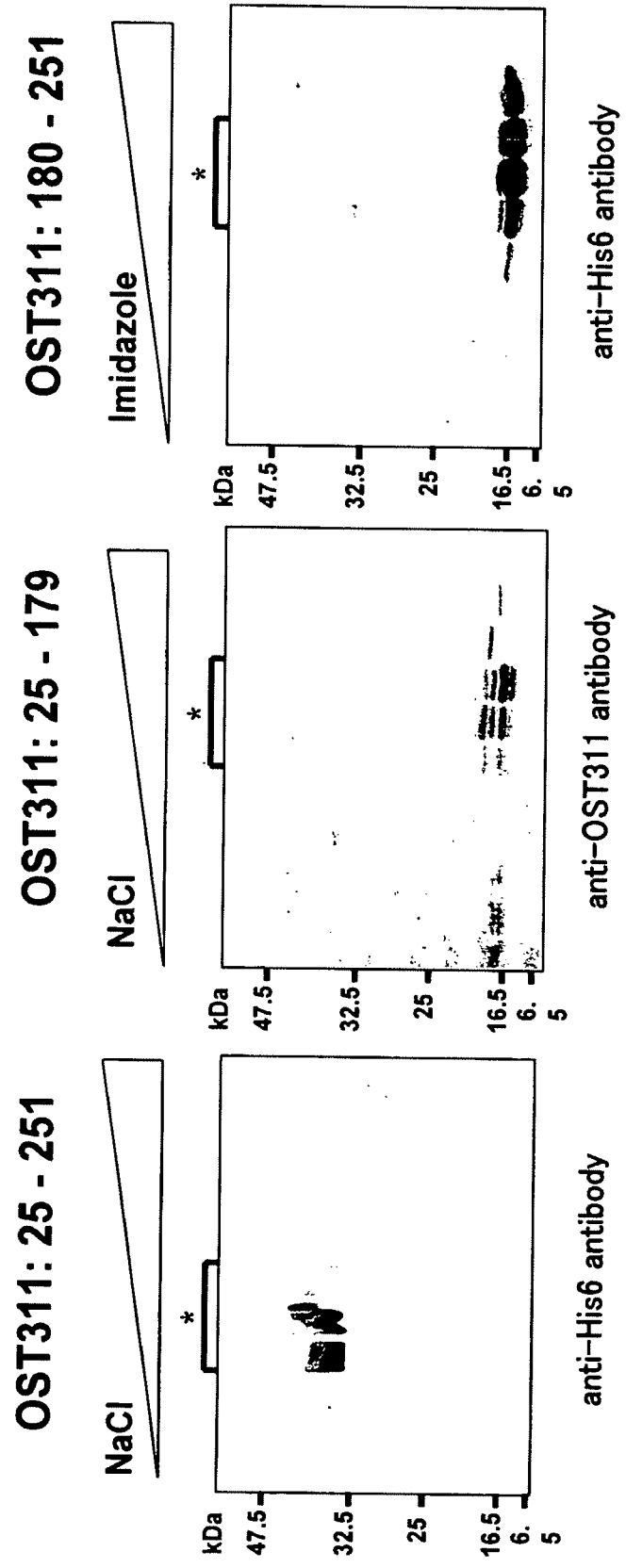

FIG. 12 includes photographs showing the results obtained by purifying the culture supernatant of CHO-OST311H cells and subjecting the elution fractions to Western blotting using anti-His6 antibody('His6' disclosed as SEQ ID NO: 88) and antiOST311 peptide antibody (311-114). The left panel shows the detection of 311:26-251, the center panel 311:25-179, and the right panel 311: 180-251. Fractions shown with "*" (placed on the upper portion of the gel photographs) were used for a single dose examination conducted on normal mice.

Figure 13:
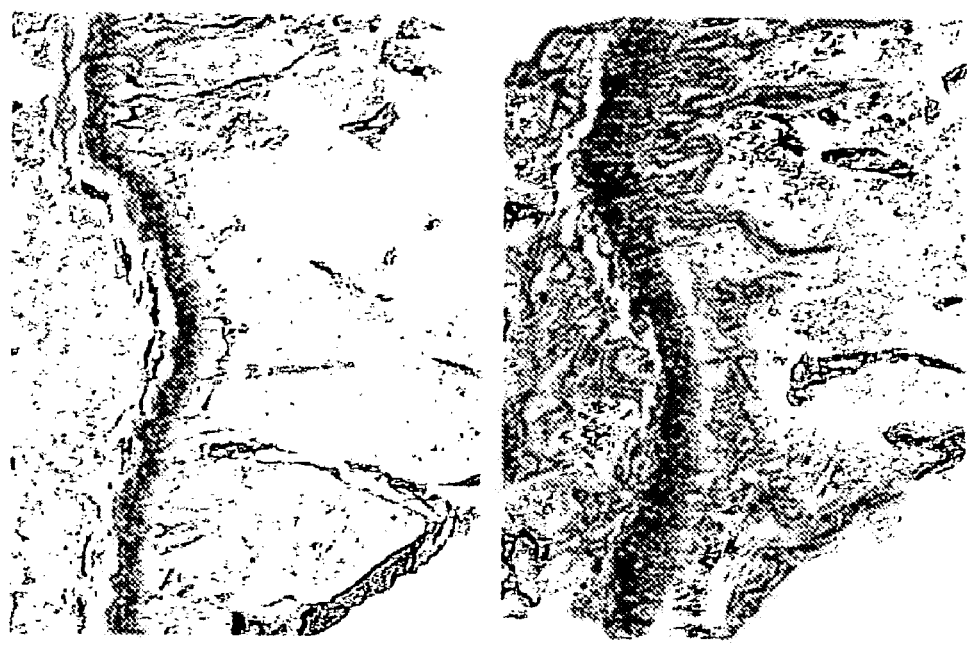

FIG. 13 includes photographs showing undemineralized slices stained with Villanueva-Goldner. The undemineralized sections were of the proximal metaphysis of tibia extracted from CHO-OST311H cells-transplanted mice and non tumor-bearing mice.

Figure 14:
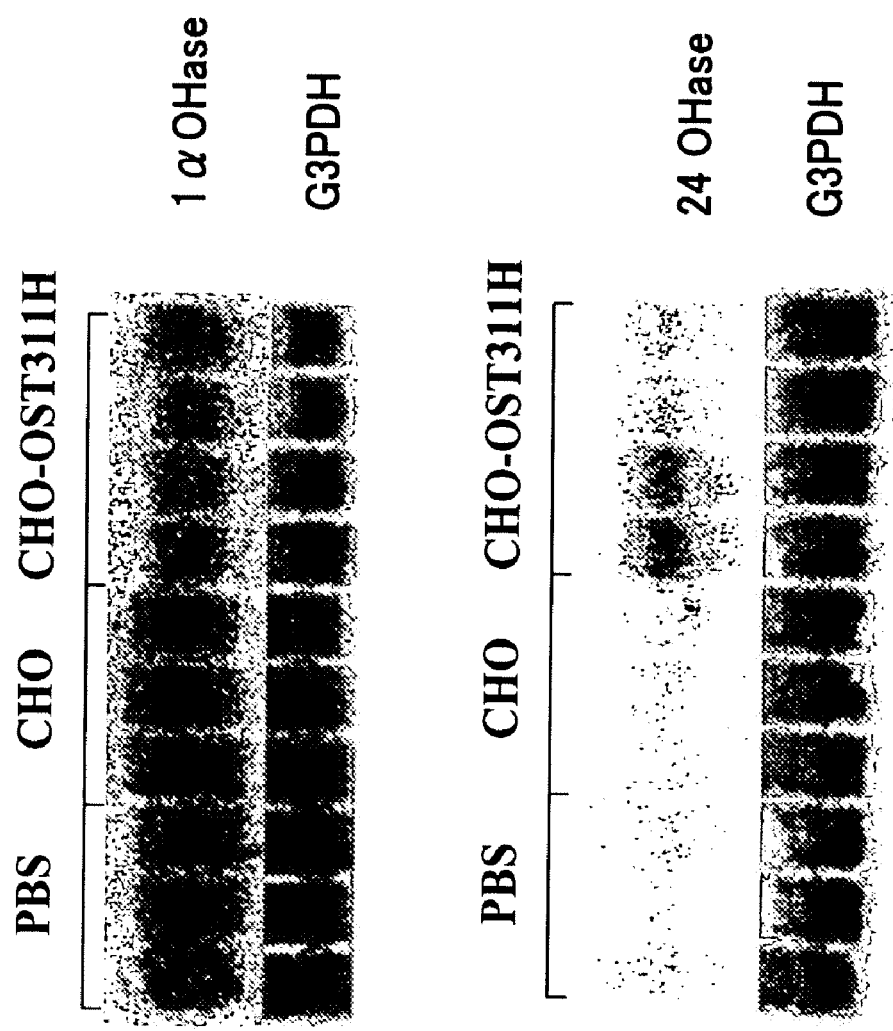

FIG. 14 includes photographs showing the results of performing Northern blotting for vitamin D-metabolizing enzyme gene products in the kidneys excised from CHO-OST311H cells-transplanted mice and control mice.

Figure 15:
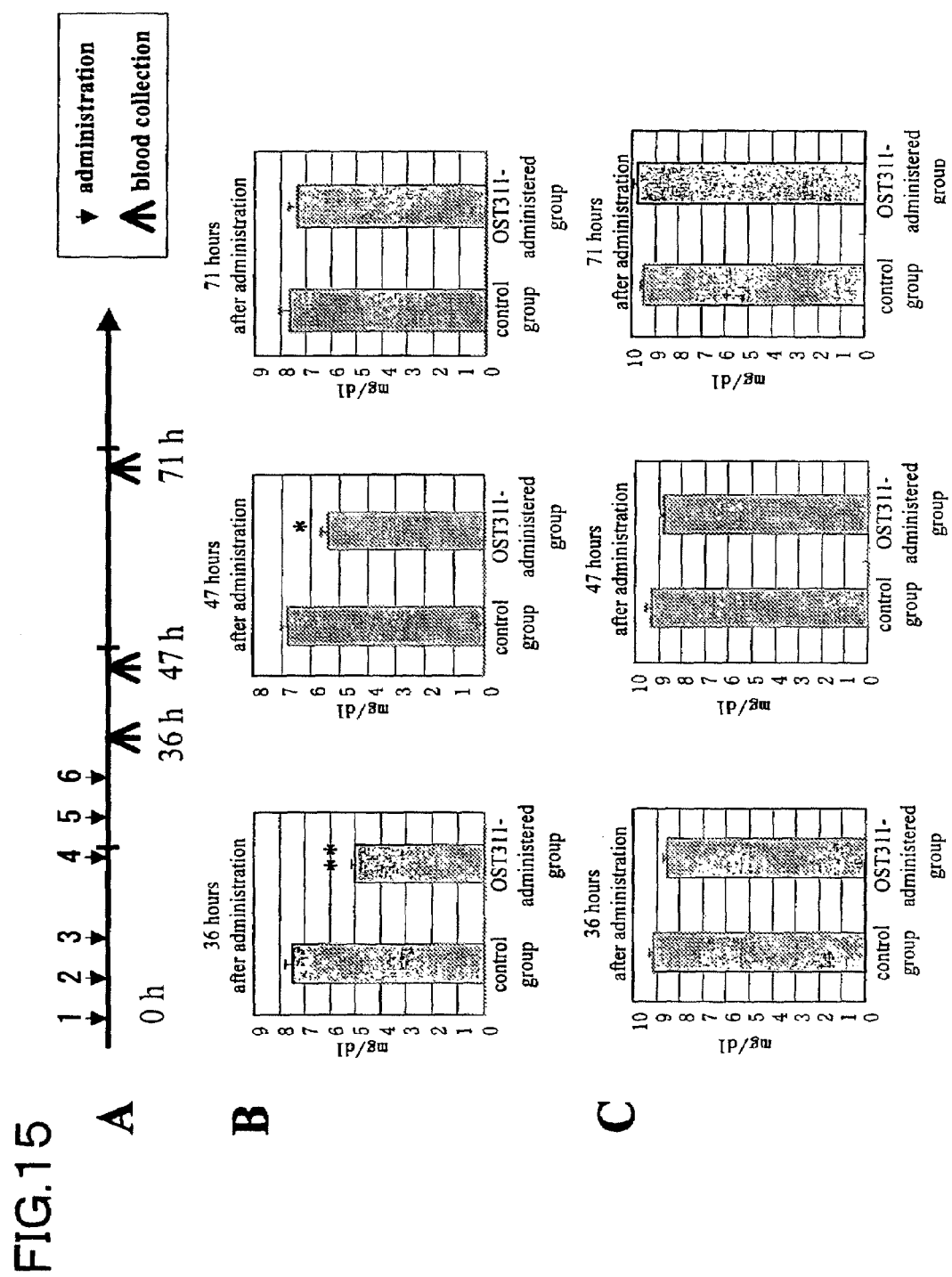

FIG. 15 A shows the time schedule of experiment 1 wherein CHO-producing recombinant OST311H full-length protein was administered to normal mice. FIG. 15 B includes graphs showing serum phosphate levels at each time point of blood collection, and FIG. 15 C includes graphs showing serum calcium levels at the same points in time.

Figure 16:
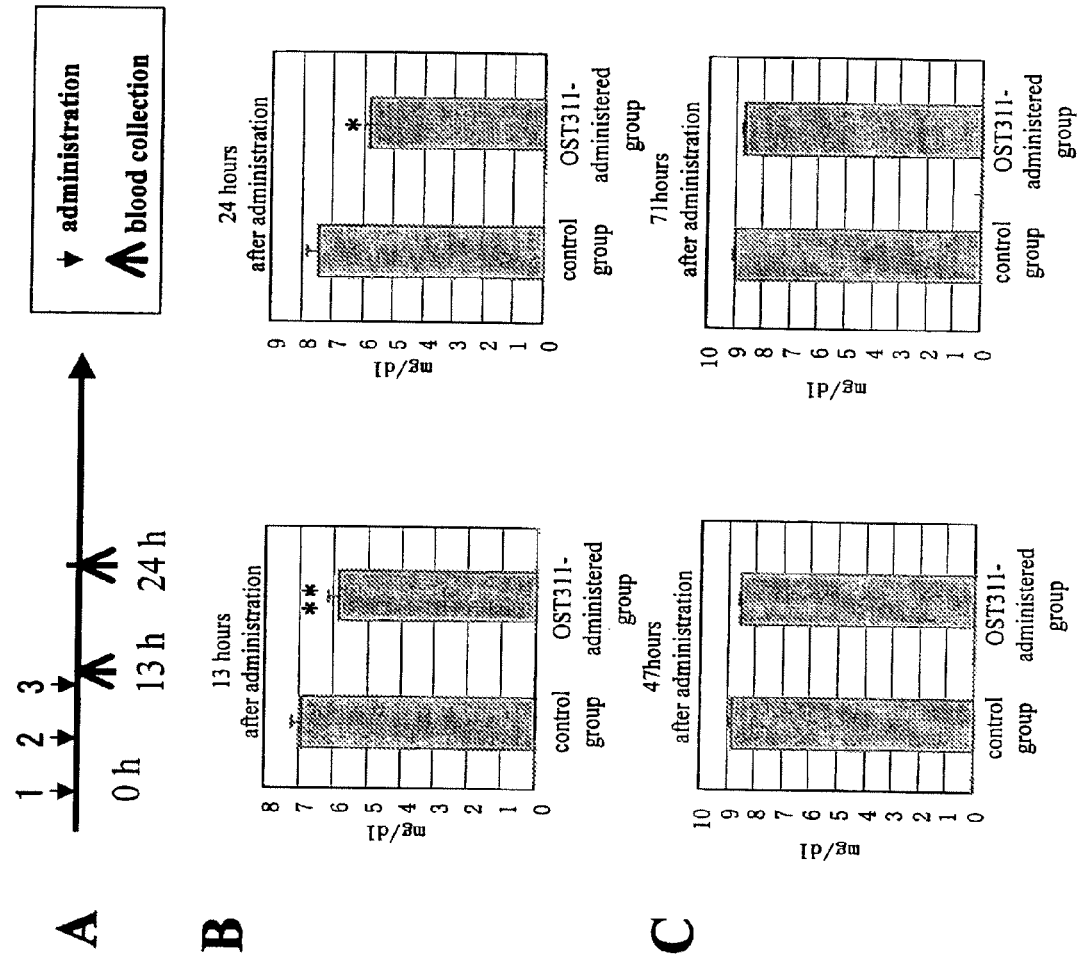

FIG. 16 A shows the time schedule of experiment 2 wherein CHO-producing recombinant OST311H full-length protein was administered to normal mice. FIG. 16 B includes graphs showing serum phosphate levels at each time point of blood collection, and FIG. 16 C includes graphs showing serum calcium levels at the same points in time.

Figure 17:
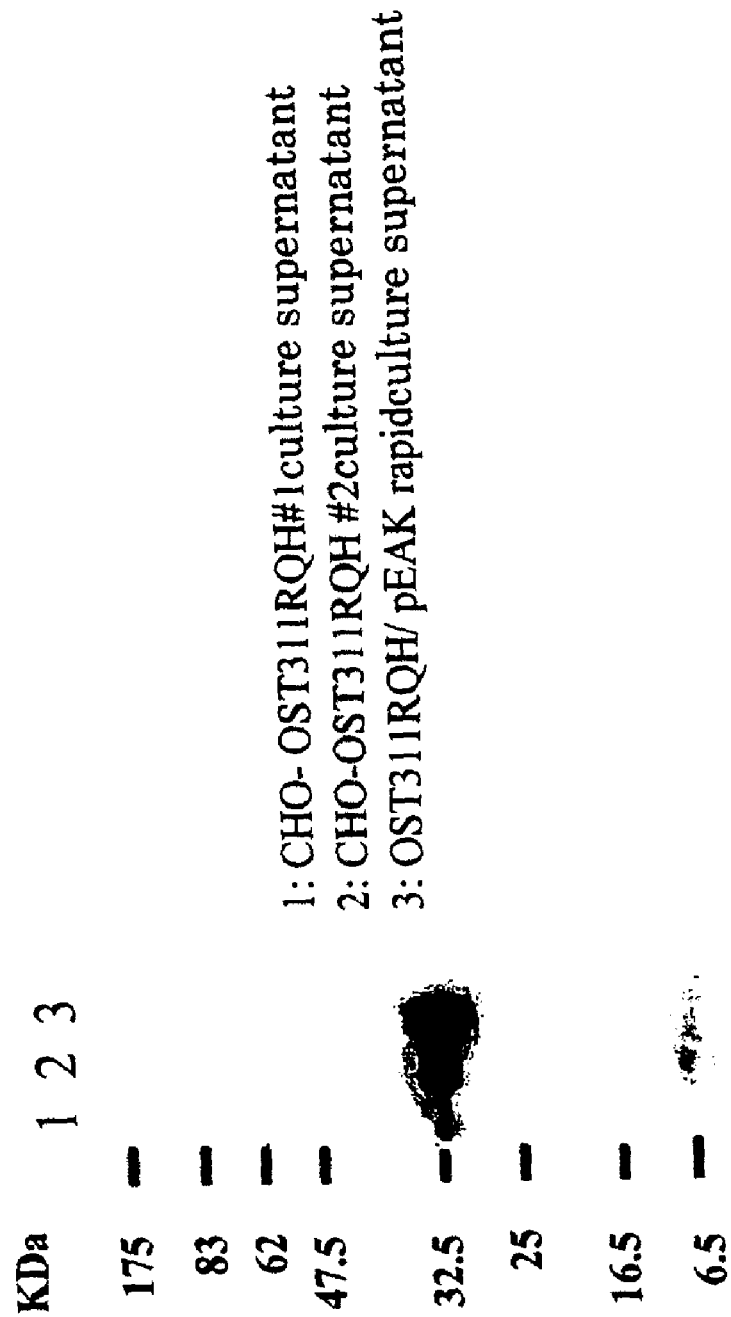

FIG. 17 is a photograph showing the recombinant protein detected in a culture supernatant when the culture supernatant of mutant recombinant OST311RQH-producing CHO-OST311RQH cells and OST311RQH/pEAK rapid cells were subjected to Western blotting.

Figure 18:
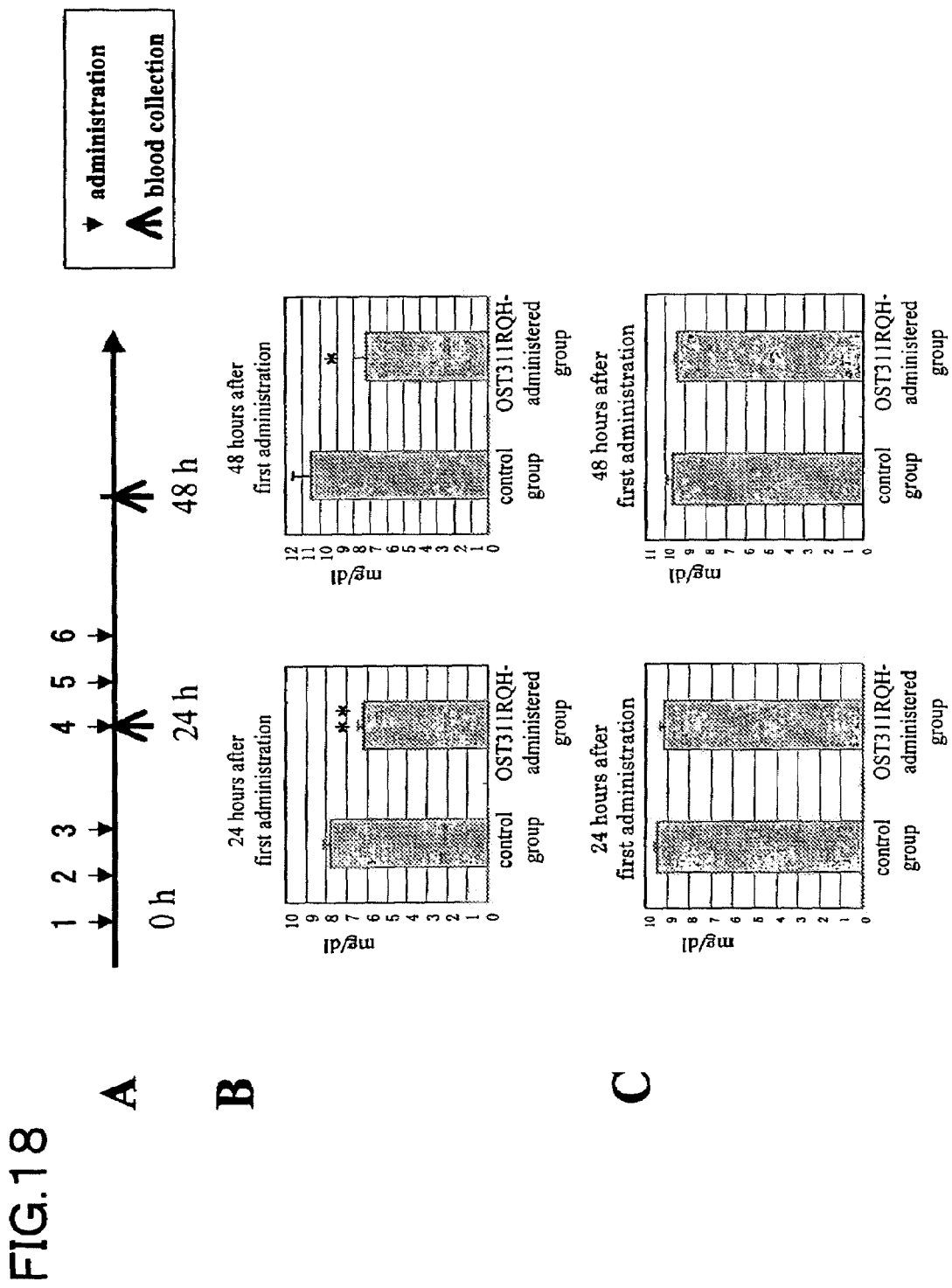

FIG. 18 A shows the time schedule of an experiment wherein mutant recombinant OST311RQH was administered to normal mice. FIG. 18 B includes graphs showing serum phosphate levels at each time point of blood collection, and FIG. 18 C includes graphs showing serum calcium levels at the same points in time.

FIG. 19 A shows serum phosphate levels on day 2 after transplantation in a CHO-OST311RQH cells-transplanted experiment. FIG. 19 B shows serum calcium levels in the same experiment.

Figure 20:

FIG. 20 includes photographs showing recombinant OST311H in serum-free culture supernatant of CHO-OST311H cells detected by Western blotting using anti-OST311 partial peptide rabbit anti-serum. 'His 6' disclosed as SEQ ID NO: 88.

Figure 21:
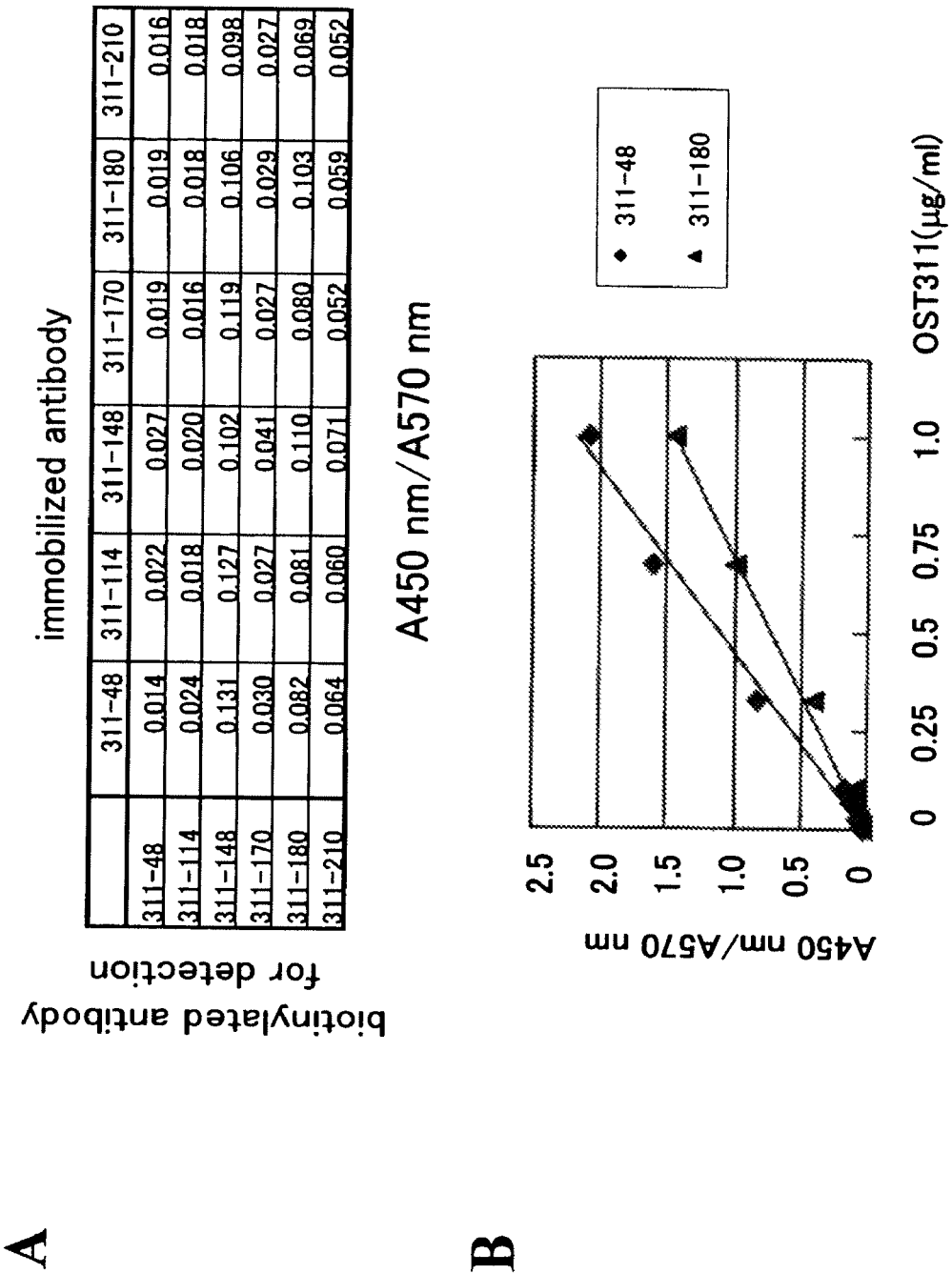

FIG. 21 A is a table showing recombinant OST311-detected levels in each combination of 6 types of anti-OST311 peptide polyclonal antibodies, when sandwich ELISA was constructed using these polyclonal antibodies.

FIG. 21 B is a graph of plotting the relations between concentrations of purified recombinant OST311H and measured values corresponding thereto that were obtained using ELISA system combined with the use of 311-48 antibody or 311-180 antibody as an immobilized antibody, and 311-148 antibody as an antibody for detection.

Figure 22:
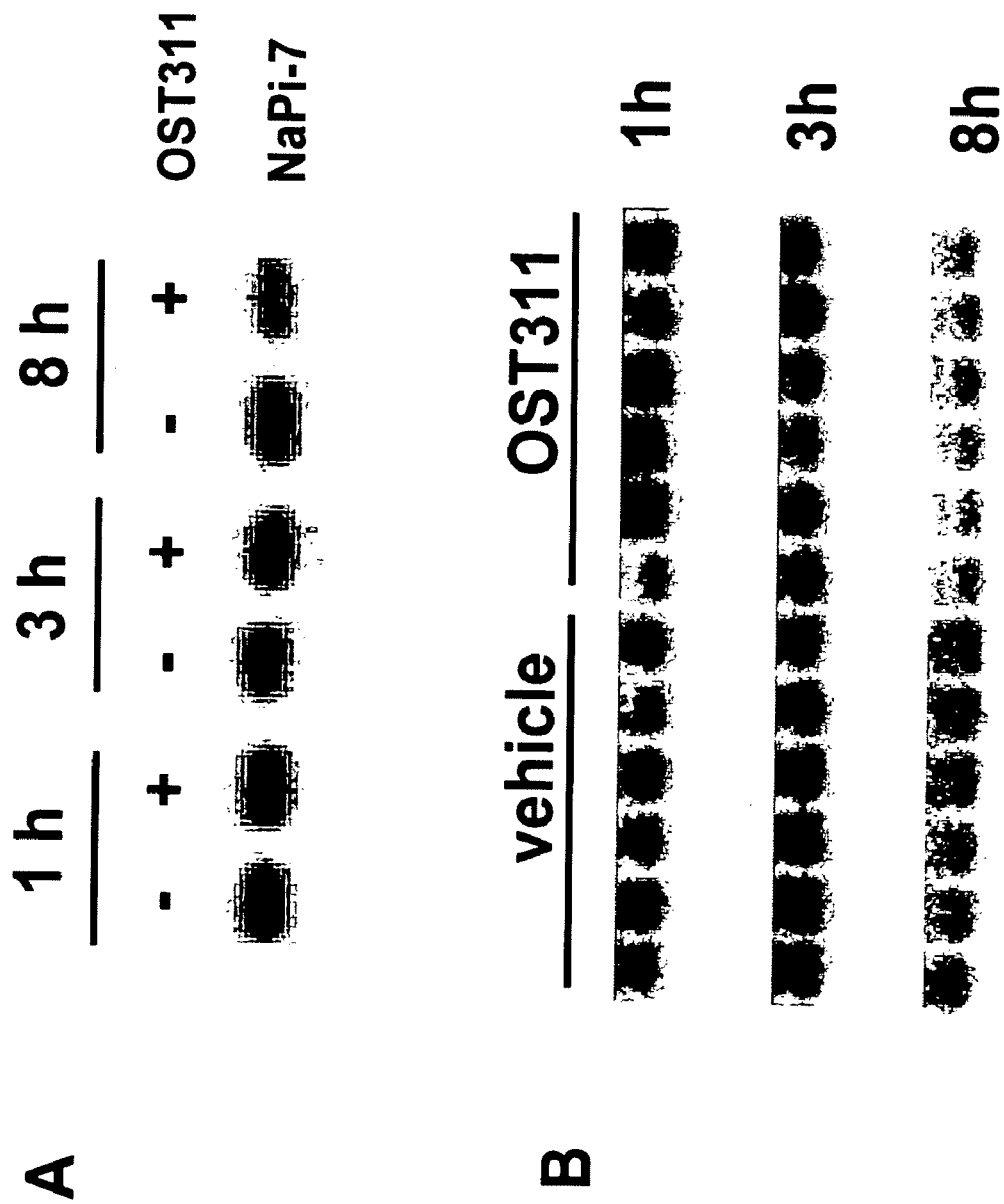

FIG. 22 A shows the expression of renal NaPi-7 analyzed by Western blotting at 1, 3 and 8 hours after administration of recombinant OST311 protein or vehicle to mice. FIG. 22 B shows the expression of NaPi-7 analyzed by Northern blotting using total RNA of kidney following the similar treatment.

Figure 23:
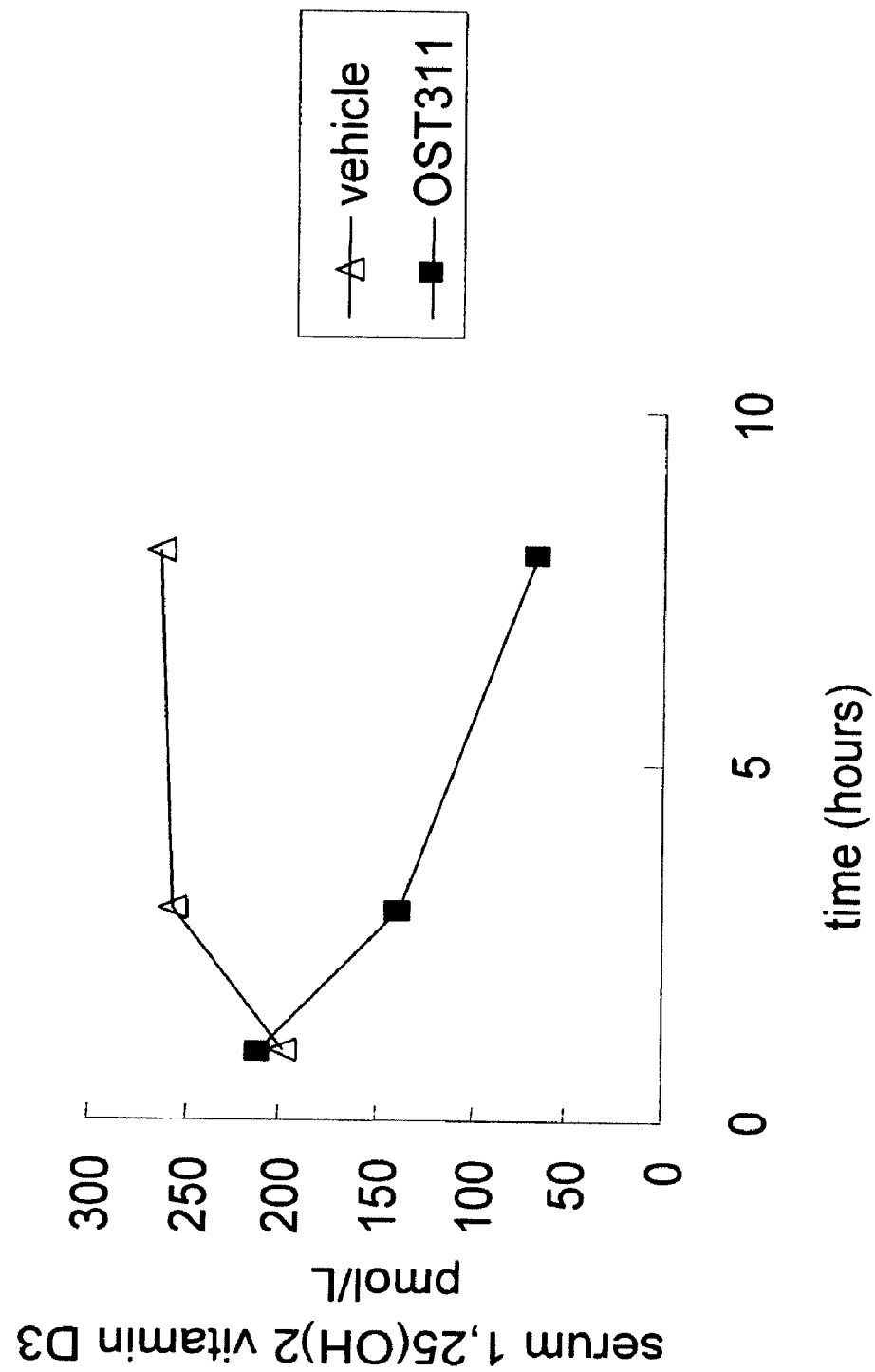

FIG. 23 shows the changes in serum 1,25-dihydroxyvitamin D3 levels at 1, 3, and 8 hours after administration of recombinant OST311 protein or a vehicle to mice.

Figure 24:
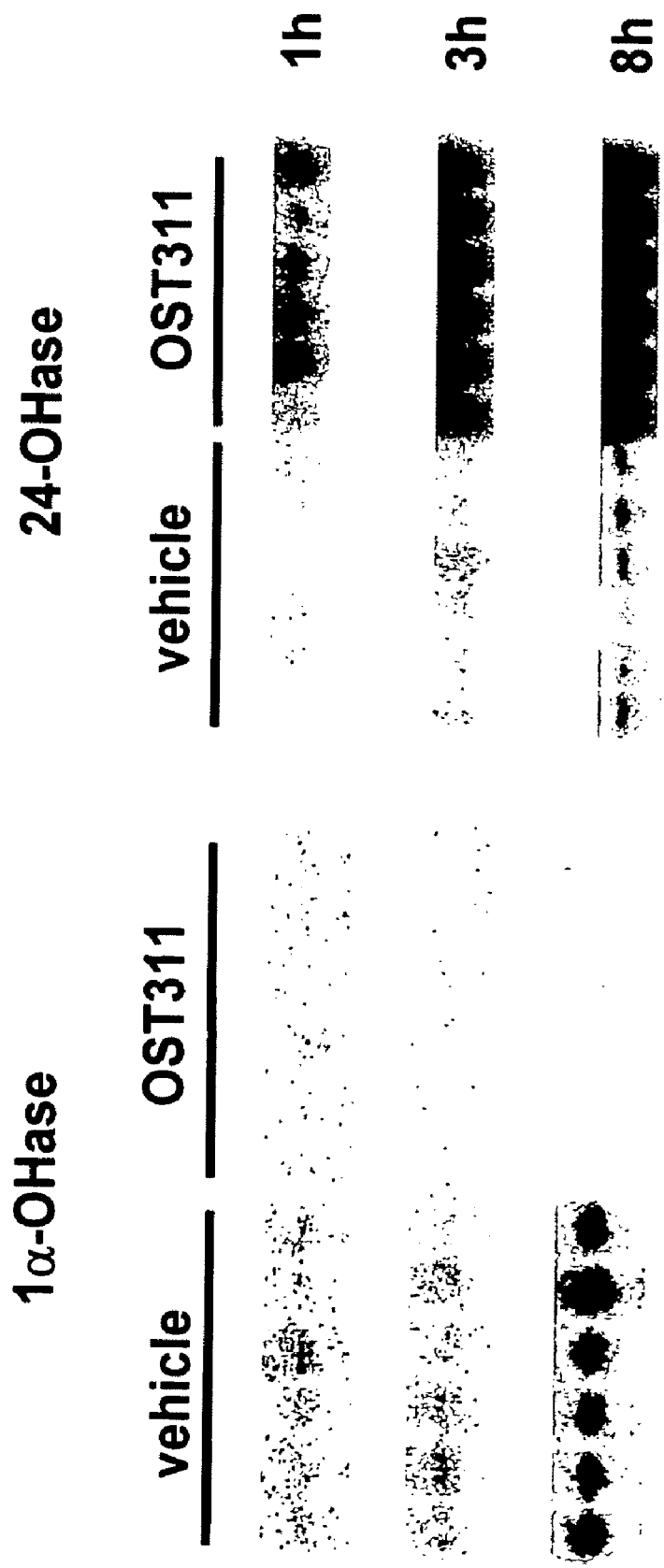

FIG. 24 shows the expression of 25-hydroxyvitamin D-1-α-hydroxylase (1αOHase) or 25-hydroxyvitamin D-24-hydroxylase (24OHase) gene analyzed by Northern blotting using total RNA of kidney at 1, 3 and 8 hours after administration of recombinant OST311 protein or a vehicle to mice.

Figure 25:
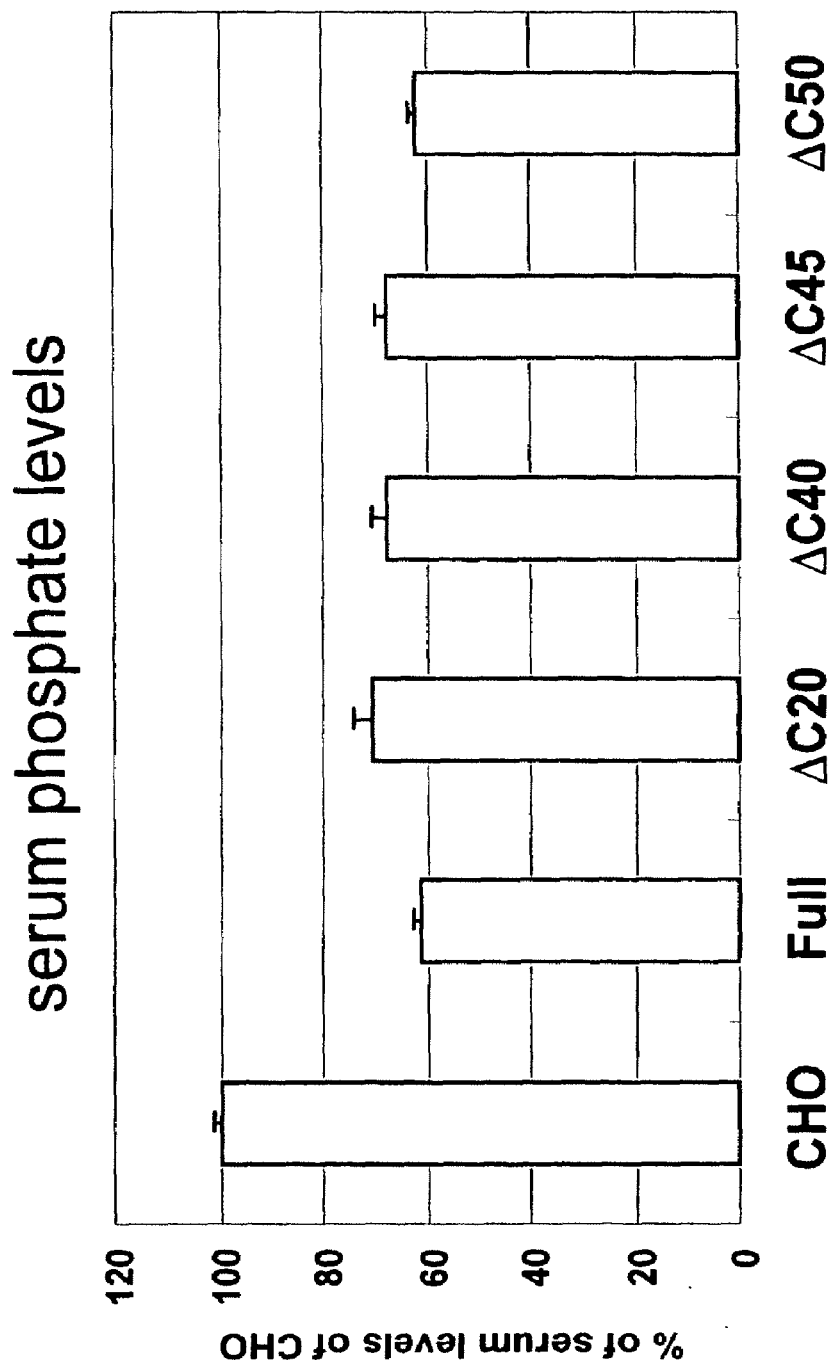

FIG. 25 shows mean serum phosphate levels in each group, when the mean blood serum phosphate level on day 3 after cell transplantation in a CHO-ras clone-1 cells-transplanted group is considered as 100%.

Figure 26:
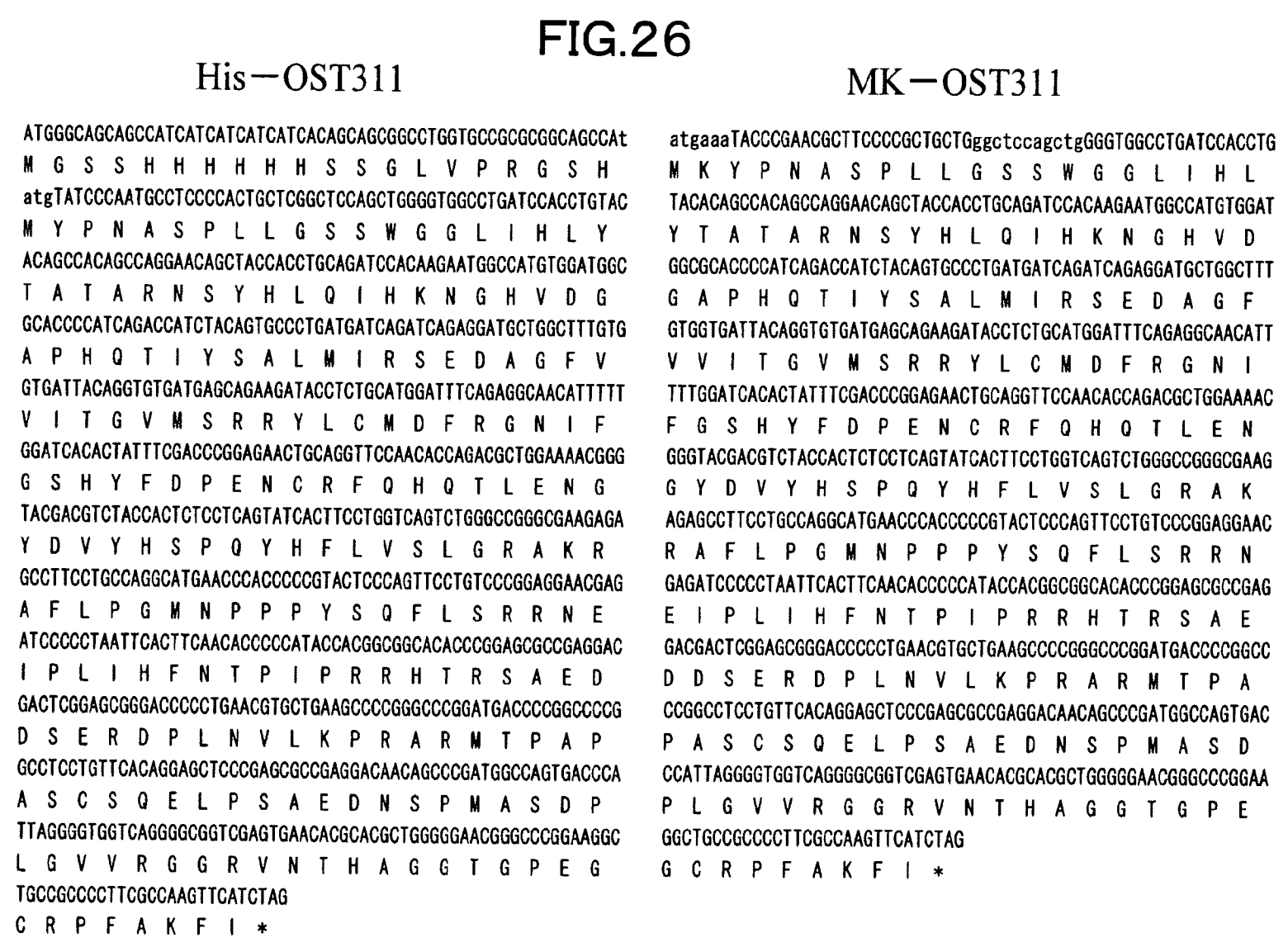

FIG. 26 shows the nucleotide sequence (SEQ ID NO: 90)and amino acid sequence (SEQ ID NO: 91)of recombinant His-OST311 encoded by plasmid OST311/pET28, and the DNA sequence (SEQ ID NO: 92)and amino acid sequence (SEQ ID NO: 93)of recombinant MK-OST311 encoded by plasmid pET22-MK-OST311.

Figure 27:
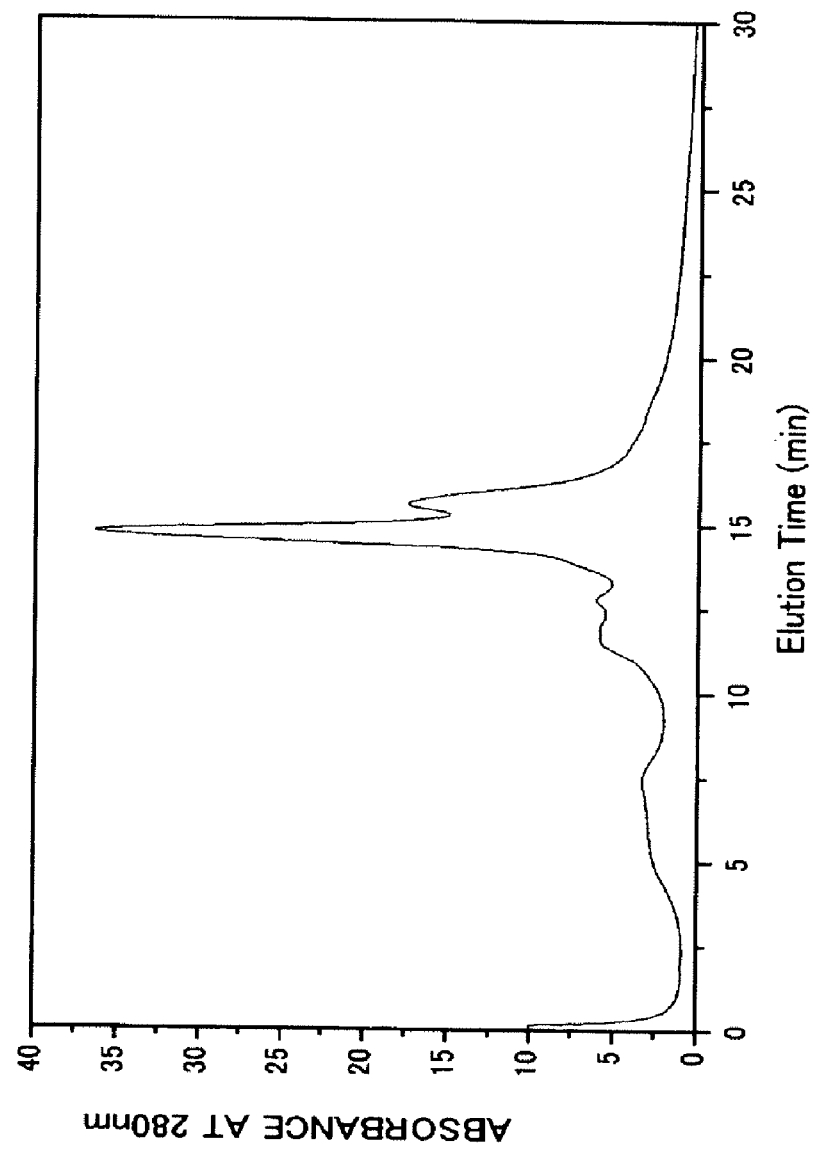

FIG. 27 shows an elution pattern when recombinant refolded His-OST311 was subjected to HPLC purification using cation-exchange column SP-5PW (TOSOH, Japan).

Figure 28:
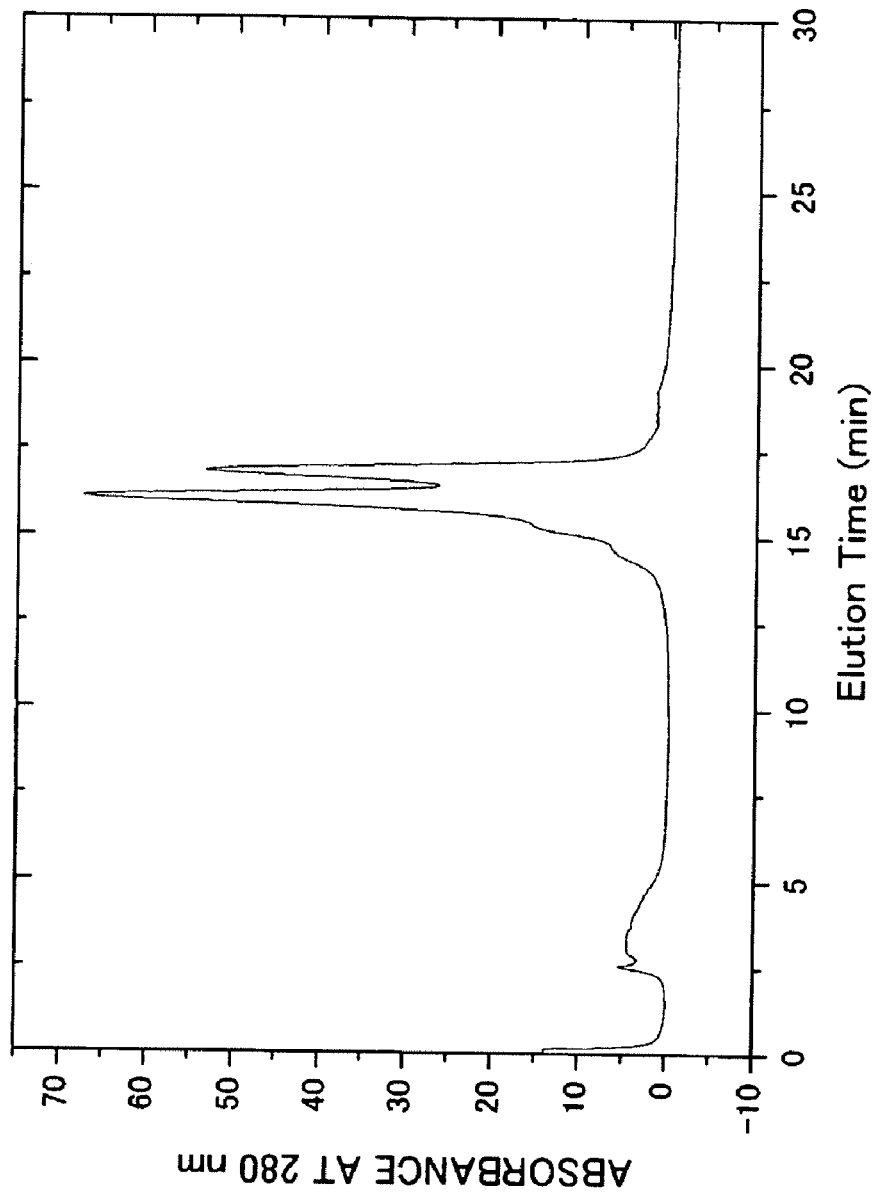

FIG. 28 shows an elution pattern when recombinant refolded MK-OST311 was subjected to HPLC purification using cation-exchange column SP-5PW (TOSOH, Japan).

Figure 29:
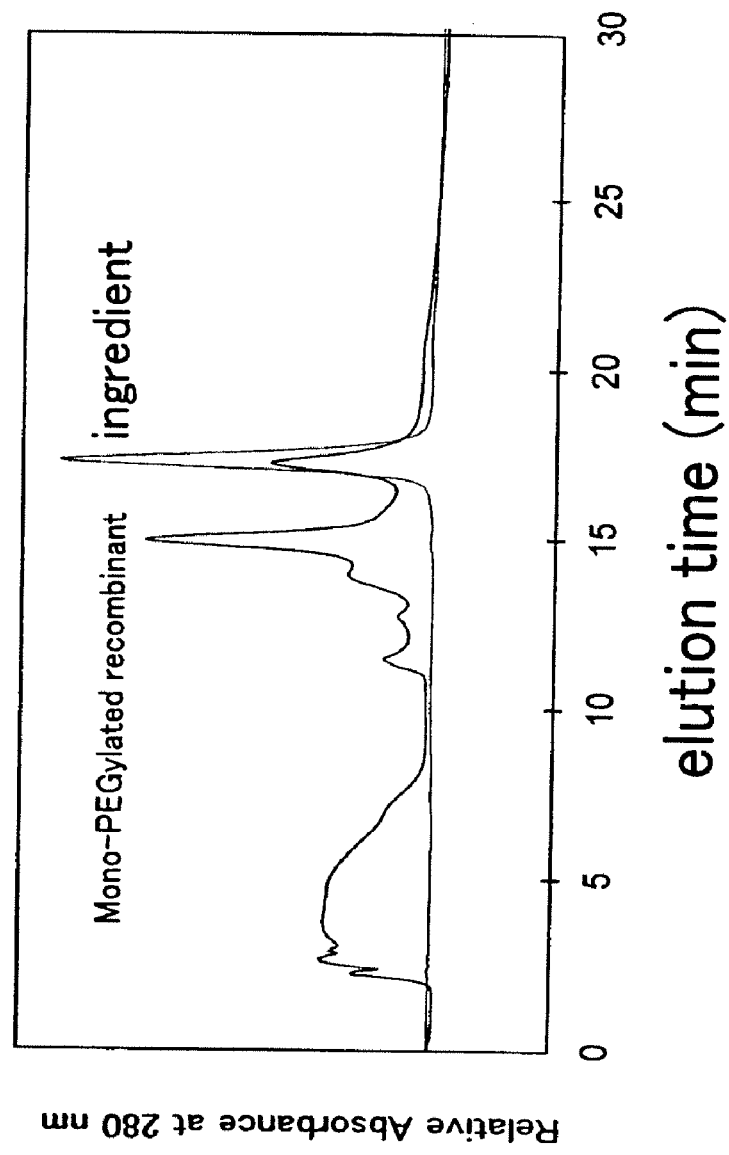

FIG. 29 shows an elution pattern when PEGylated recombinant MK-OST311 was subjected to HPLC purification using cation-exchange column SP-5PW (TOSOH, Japan).

Figure 30:
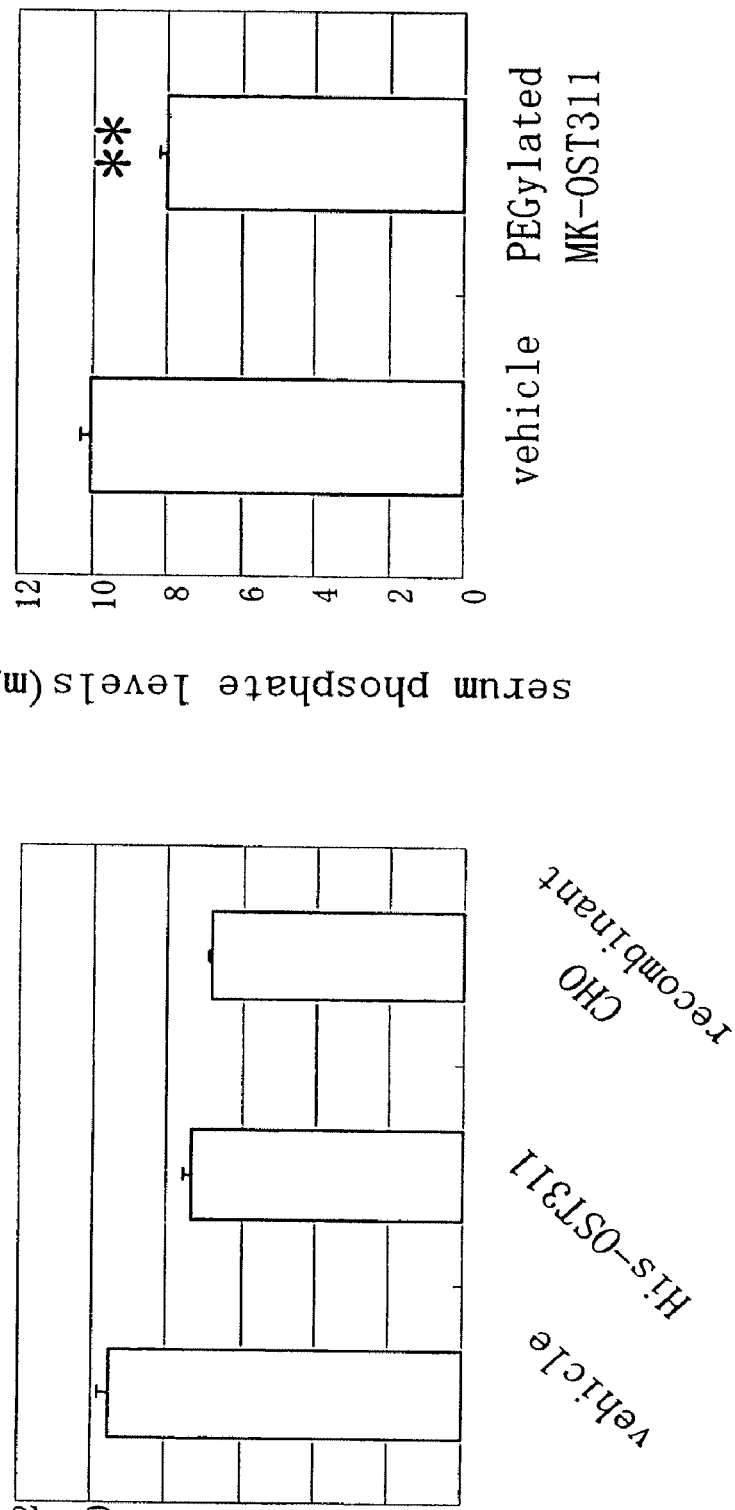

FIG. 30 includes graphs showing serum phosphate levels at 8 or 9 hours after single administration of (A) *Escherichia coli*-producing His-OST311 recombinant or (B) PEGylated MK-OST311 recombinant.

Figure 31:
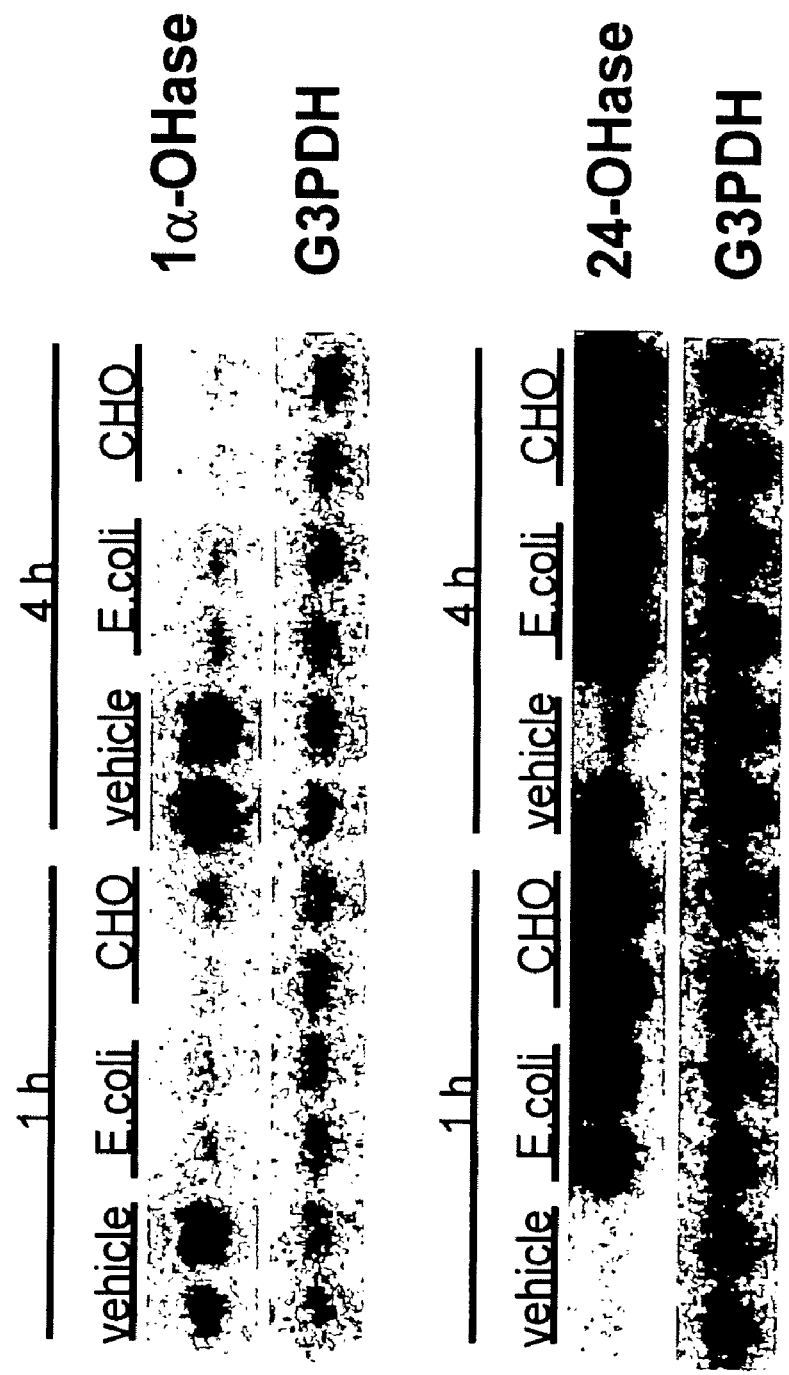

FIG. 31 shows the results of analysis by the Northern blotting method on changes in the expression of vitamin D-metabolizing enzyme gene in the kidney at 1 and 4 hours after single administration of *Escherichia coli*-producing His-OST311 recombinant.

Figure 32:
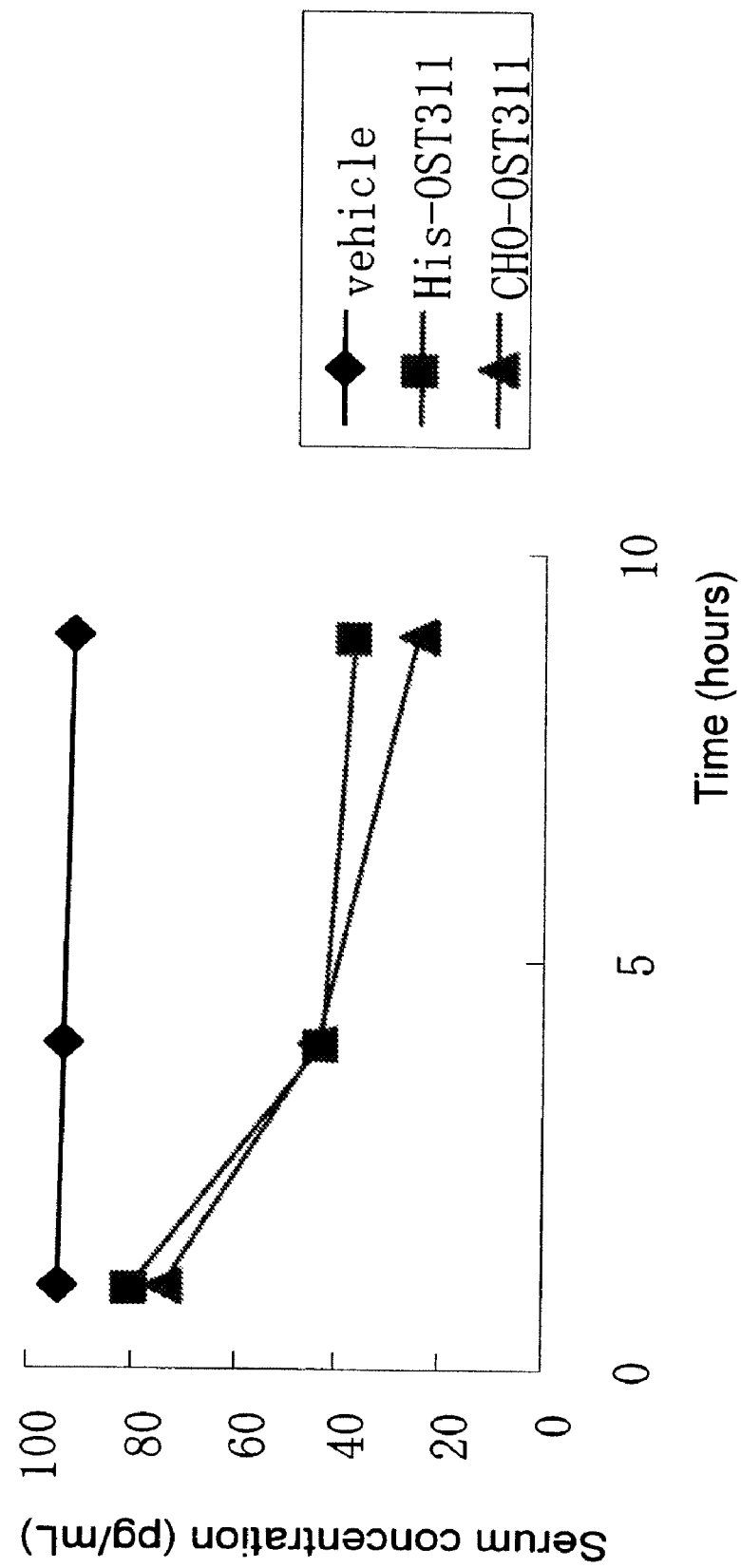

FIG. 32 shows changes in serum 1,25-dihydroxyvitamin D3 levels at 1, 4 and 9 hours after single administration of *Escherichia coli*-producing His-OST311 recombinant.

Figure 33:
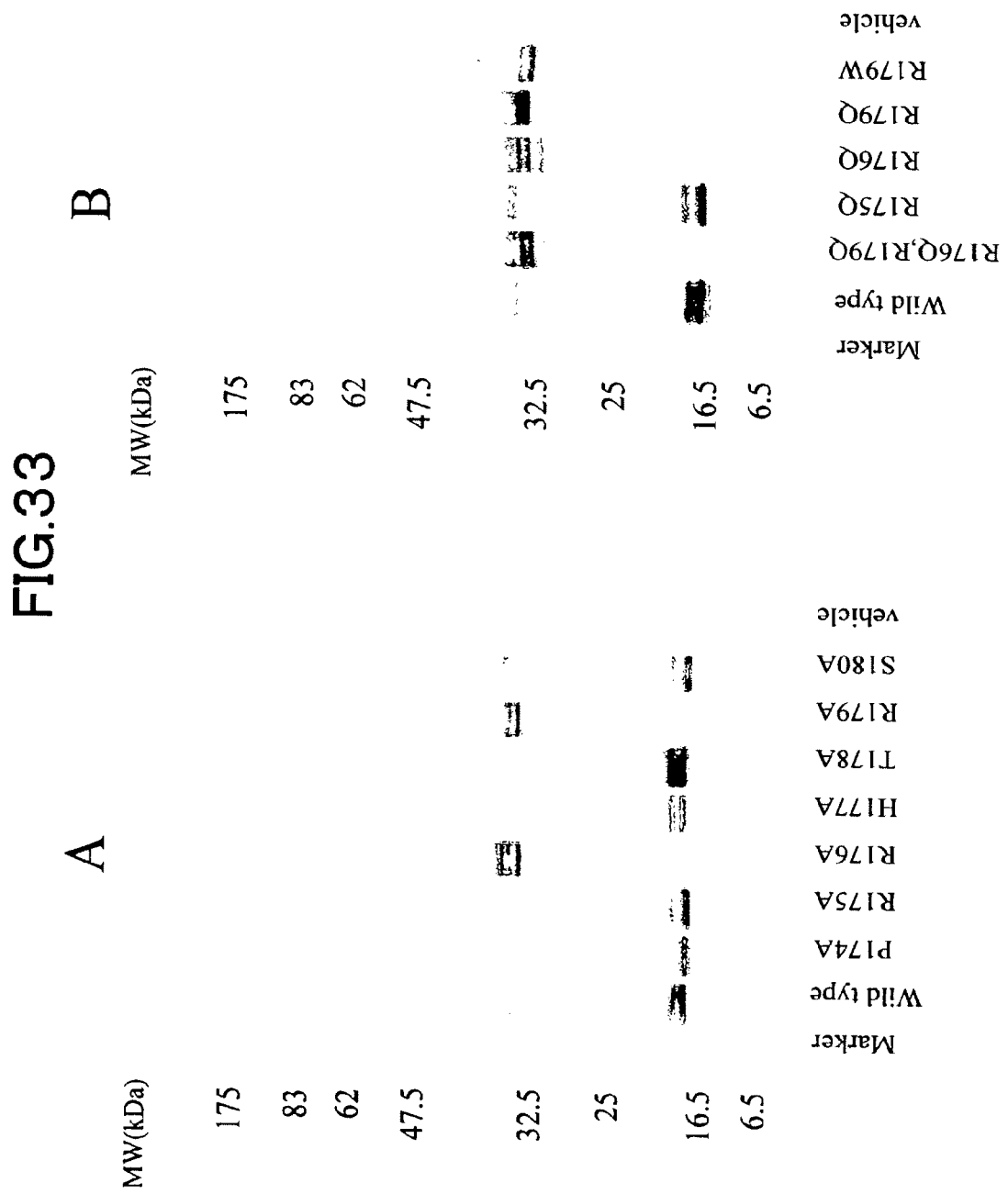

FIG. 33 shows a mutant OST311 recombinant detected by Western blotting, when mutation was introduced into amino acid Nos. 174 to 180 of OST311, and then the gene was expressed in pEAK cells so as to secrete the mutant OST311 recombinant in the cell supernatant.

BEST MODE FOR CARRYING OUT THE INVENTION

The present invention will be described more specifically by the following examples. These examples are not intended to limit the scope of the present invention.

EXAMPLE 1

Construction of Human Tumor-induced Osteomalacia-Derived Tumor cDNA Library

Tumor tissues frozen by liquid nitrogen were homogenized in 5 ml of ISOGEN (NIPPON GENE, Japan) solvent, and then approximately 0.13 mg of total RNA was prepared according to the attached manufacturer's manual. cDNA was synthesized from 1.5 µl of the total RNA using a SMART cDNA library preparation kit (CLONTECH, USA) according to the attached manufacturer's manual. Hereinafter, this cDNA is denoted as cDNA#2. EcoR I adapter was ligated to this cDNA#2, and then inserted into ?ZAPII phage vector (STRATAGENE, USA) that had been previously digested with a restriction enzyme EcoR I. Using a Gigapack III Gold phage packaging kit (STRATAGENE, USA), a tumor-induced osteomalacia tumor phage library was constructed according to the attached manufacturer's manual. The obtained library contained a total of approximately 600,000 independent clones. Further, the above phage library was allowed to infect *Escherichia coli* strain XLI-Blue MRF', and then poured onto 20 petri dishes (15 cm). The petri dishes were incubated at 37° C. for 10 hours for plaque formation. All the plaques were extracted into an SM buffer, so that tumor-induced osteomalacia tumor cDNA phage library was constructed.

EXAMPLE 2

Implementation for Positive Screening of Tumor cDNA Outline

The fact that tumor-induced osteomalacia is curable by surgically excising a tumor suggests a possibility of high and specific expression of the causative gene in tumors. In addition, it has been reported so far that tumor-induced osteomalacia tumors are often constituted of mesoblastic, in particular mesenchymal cells. Therefore, it is necessary to identify a gene group that expressed lowly in normal mesoblast-derived tissues, but expressed specifically and highly only in tumor tissues. Hence, as described below, positive screening to which a cDNA subtraction technique was applied was performed. Subtraction of tumor tissue-derived cDNA and cDNA isolated from a bone tissue as a control was performed, so as to enrich a gene group that specifically and highly expressed only in tumor tissues, but not expressed in bone tissues. Hybridization was performed for tumor cDNA phage library using the subtracted cDNA group as a probe, thereby obtaining gene fragments specifically expressed in tumors.
(1) Construction of Control Human Bone Tissue cDNA Human bone tissues frozen by liquid nitrogen were homogenized in 5 ml of ISOGEN(NIPPON GENE, Japan) solvent, and then approximately 0.011 mg of total RNA was prepared according to the attached manufacturer's manual. cDNA was synthesized from 3 µl of the total RNA using SMART cDNA library preparation kit (CLONTECH, USA) according to the attached manufacturer's manual. Hereinafter, the thus obtained cDNA is referred to as cDNA #4.
(2) Subtraction of Tumor-Induced Osteomalacia Tumor cDNA and Control Bone Tissue cDNA To enrich a gene highly expressed in cDNA#2 described in Example 1, hybridization of cDNA#2 and cDNA#4 described in Example 2(1) was performed using a PCR-Select cDNA subtraction kit (CLONTECH, USA) according to the attached manufacturer's manual, thereby subtracting gene fragments contained in cDNA#4 from cDNA#2. Then, the subtracted cDNA#2 was amplified by PCR according to the attached manufacturer's manual, so that a subtracted cDNA group (A) was obtained.

On the other hand, because of characteristics of the subtraction kit, such that its hybridization process is performed only twice, which is less than that of common techniques, it is difficult by this kit to completely subtract genes existing in many numbers in both subjects. Accordingly, when hybridization of tumor-induced osteomalacia tumor cDNA library with only subtracted cDNA group (A) as a probe, is performed, genes that cannot be subtracted completely are also obtained as positive clones. Thus, cDNA#2 was subtracted from cDNA#4 described in Example 2 (1) by the same method, and then the subtracted cDNA#4 was amplified by PCR, thereby preparing a subtracted cDNA group (B) as a control probe. Hybridization of tumor cDNA library respectively with the subtracted cDNA group (B) and the previously described subtracted cDNA group (A), and comparison of both signals make it possible to isolate gene fragments specifically contained in tumor-induced osteomalacia tumors.
(3) Differential Hybridization of Tumor-Induced Osteomalacia Tumor cDNA Library After infecting *Escherichia coli* strain XLI-Blue with the tumor-induced osteomalacia tumor cDNA phage library described in Example 1, the infected *E. coli* was inoculated again so as to form 3,000 plaques per petri dish (15 cm), and then incubated at 37° C. for 8 hours. Then, plaques on each petri dish were transferred to two Hybond N+ (Amersham Pharmacia Biotech, USA) nylon filters. The nylon filters to which plaques are transferred were subjected to DNA immobilization treatment according to the attached manufacturer's manual, and then screening was performed using the subtracted cDNA(A) described in Example 2(2) and the subtracted cDNA(B) as probes, respectively.

Probe labeling, hybridization and signal detection were performed using Alphos Direct system (Amersham Pharmacia Biotech, USA) according to the attached manufacturer's manual. The subtracted cDNA(A) and the subtracted cDNA (B) described in Example 2(2) were used as probes at 100 ng each, and then the probes were labeled with fluorescence according to protocols. The probes were respectively added to 50 ml of hybridization buffer supplied with Alphos Direct system, and at the same time, 2 sets of each of the 8 nylon filters which plaques had been transferred to were respectively hybridized and washed according to protocols. After washing, the nylon filters were subjected to luminescence reaction, exposed to ECL film (Amersham Pharmacia Biotech, USA) for 2 hours, developed with an automatic processor (FUJI FILM, Japan), and then the results were analyzed.

As a result, independent plaques placed in a portion which were strongly burnt after exposure when the subtracted cDNA (A) was used as a probe, but not burnt when the subtracted cDNA (B) was used as a probe were visually selected, scraped off from the petri dish, and then suspended in 0.5 ml SM buffer. The suspensions were allowed to stand at 4° C. for 2 hours or more, thereby extracting phages.

(4) Nucleotide Sequence Analysis of Positive Clone

Using 0.5 μl of the phage solution obtained in Example 2(3) containing positive clones as a template, T7 primer (TAATACGACTCACTATAGGG) (SEQ ID NO: 24) and T3 primer (ATTAACCCTCACTAAAGGGA) (SEQ ID NO: 25) that were internal sequences of the phage vector, and LA-taq polymerase (TAKARA SHUZO, Japan), PCR was performed for 35 cycles, each cycle (process) consisting of 96° C. for 30 seconds, 55° C. for 30 seconds, and 72° C. for 30 seconds. The PCR products were subjected to 0.8% agarose gel electrophoresis. Clones for which a clear single band was observed were sequenced by ABI377 DNA sequencer (PE Applied systems, USA) using PCR amplification fragments as templates.

When two clear bands were observed, PCR products were respectively extracted from each gel portion of the corresponding bands using QIAquick Gel Extraction kit (QIAGEN, Germany), and then sequenced by ABI377 DNA sequencer.

As a result of differential hybridization for 341,000 plaques of tumor-induced osteomalacia phage library, 456 positive plaques were identified, and the nucleotide sequences of all of these plaques were determined.

EXAMPLE 3

Narrowing Down the Candidate Genes of Human Hypophosphatemia Inducing Factor

Homology search for the sequence information of 456 positive clones obtained in Example 2 against nucleotide sequences registered at Genbank, the nucleotide sequence database provided by NCBI was performed. As a result, a group of genes listed on Table 1 was obtained as existing genes that had appeared at high frequencies. Further, as a result of database search, there are 100 clones of unknown gene fragments of which biological activities were not known. As to nucleotide sequence information of these unknown gene fragments, overlaps among clones was further extracted as frequency information. Among them, the most frequently overlapping gene, OST311 sequence consisting of 7 clones sequentially forming one contig, was obtained. The nucleotide sequence obtained at this time ranged from nucleotide Nos. 1522 to 2770 of SEQ ID NO: 1. When a search for the gene fragment of OST311 was performed over the existing database, it was not registered as cDNA or EST, and corresponded only with a genomic sequence. The relevant genomic sequence is AC008012, and it has already been reported to be located at 12p13 on the chromosome. However, a region encoding a protein (ORF) was not found within the obtained sequence, so that the sequence was predicted to correspond to a 3'-untranslated region. Hence, cloning of full-length cDNA from tumor-induced osteomalacia tumor cDNA library was performed. In addition, the ORF-predicting function of DNASIS-Mac version 3.7 was used to predict ORF.

TABLE 1

| Clone ID | Frequency | Description |
| --- | --- | --- |
| OST 131 | 236 | Dentin matrix protein-1 (DMP1) |
| OST 1 | 35 | Heat shock protein-90 (HSP90) |
| OST 2 | 13 | Osteopontin |
| OST 311 | 7 | Unknown/genomic DNA 12p13 |
| OST 1001 | 4 | CD44 antigen |
| OST 584 | 3 | Fibronectin |
| OST 666 | 3 | Translational regulatory tumor protein |
| OST 133 | 2 | Beta 2 microglobulin |
| OST 837 | 2 | Fibroblast growth factor (FGF) |
| OST 562 | 2 | Annexin H/lipocortin II |
| OST 1002 | 2 | Cytochrome c oxygenase subunit 2 |
| OST 1003 | 2 | Stathmin |
| OST 1004 | 2 | Unknown |
| OST 903 | 2 | Unknown |

EXAMPLE 4

Cloning of Full-Length OST311

Based on the OST311 sequence obtained in Example 3, the following primers were synthesized. Then, PCR was performed, using a phage solution of tumor-induced osteomalacia tumor cDNA library as a template, for 35 cycles, each cycle (process) consisting of 96° C. for 30 seconds, 55° C. for 30 seconds, and 72° C. for 30 seconds.

311-U65:   TTCTGTCTCGCTGTCTCCC   (SEQ ID NO: 12)

311-L344:  CCCCTTCCCAGTCACATTT   (SEQ ID NO: 13)

PCR products were subjected to 2% agarose gel electrophoresis, amplification of PCR products of predicted sizes was confirmed, and then the PCR products were purified using MicroSpin column S-300 HR (Amersham Pharmacia Biotech, USA). The resulting PCR products were fluorescence-labeled using Alphos Direct system (Amersham Pharmacia Biotech, USA) according to the attached manufacturer's manual. Then, plaque hybridization for 20,000 clones of tumor-induced osteomalacia tumor cDNA library was performed using these labeled products as probes.

The thus obtained 40 positive clones were amplified by PCR in the manner as described in Example 2(4) using T7 and T3. Based on the nucleotide sequence of the resulting PCR product, a primer 311-L296 (SEQ ID NO: 14, GGGGCATCTAACATAAATGC) was synthesized. Again, plaque hybridization for 20,000 clones of tumor-induced osteomalacia tumor cDNA library was performed using as probes the PCR products amplified using 311-U65 (SEQ ID NO: 12) and 311-L344 (SEQ ID NO: 13) primers. For 62 positive clones, the nucleotide sequence of a PCR product amplified using T7 and 311-L296 (SEQ ID NO: 14) primers was determined. The determined sequence was linked to the nucleotide sequences that had been determined so far. Thus, the nucleotide sequence represented by SEQ ID NO: 1 was obtained. It became clear that ORF of OST311 starts from an initiation codon located at nucleotide No. 133 of SEQ ID NO: 1. Furthermore, the following primers were synthesized to finally determine the sequence of ORF.

311-F1:
AGCCACTCAGAGCAGGGCAC   (SEQ ID NO: 15,
                       Nucleotide Nos. 112 to 131)

```
311-F2:
GGTGGCGGCCGTCTAGAACTA    (SEQ ID NO: 16,
                         Vector sequence)

311-F3:
TCAGTCTGGGCCGGGCGAAGA    (SEQ ID NO: 17,
                         Nucleotide Nos. 539 to 559)

311-L1:
CACGTTCAAGGGGTCCCGCT     (SEQ ID NO: 18,
                         Nucleotide Nos. 689 to 708)

311-L3:
TCTGAAATCCATGCAGAGGT     (SEQ ID NO: 19,
                         Nucleotide Nos. 410 to 429)

311-L5:
GGGAGGCATTGGGATAGGCTC    (SEQ ID NO: 20,
                         Nucleotide Nos. 200 to 220)

311-L6:
CTAGATGAACTTGGCGAAGGG    (SEQ ID NO: 21,
                         Nucleotide Nos. 868 to 888)
```

Using 311-F2 (SEQ ID NO: 16) and 311-L6 (SEQ ID NO: 21) primers, tumor-induced osteomalacia tumor cDNA library as a template, and Pyrobest DNA polymerase (TAKARA SHUZO, Japan), PCR was performed for 35 cycles, each cycle (process) consisting of 96° C. for 30 seconds, 55° C. for 30 seconds and 72° C. for 30 seconds.

When the PCR products were subjected to 2% agarose gel electrophoresis, a single fragment of approximately 980 nucleotide pairs was confirmed. Then, the nucleotide sequence of the amplified fragment was determined using the above primers (SEQ ID NOS. 15 to 21). The thus determined ORF region (SEQ ID NO: 1) encoding the polypeptide represented by SEQ ID NO: 2 was placed between the initiation codon ATG located at nucleotide No. 133 and the termination codon TAG located at nucleotide No. 886 of SEQ ID NO: 1.

EXAMPLE 5

Specificity of OST311 Against Tumor-induced Osteomalacia Tumor

To study the tumor specificity of OST311, PCR was performed for 35 cycles using as templates first-strand cDNAs extracted from tumor tissues and from control bone tissues, and using OST311 specific primers shown below (SEQ ID NOS: 22 and 23). Each PCR cycle is a process consisting of 96° C. for 30 seconds, 55° C. for 30 seconds and 72° C. for 30 seconds. In addition, DMSO was added into both reaction solutions to have a final concentration of 2%, and LA-taq DNA polymerase (TAKARA SHUZO, Japan) was used as an enzyme. Further, as an internal standard, PCR was performed under similar conditions using primers specific to trast, when G3PDH primers were used, PCR products with the predicted size were observed at the same level in both cases of the tumor tissues and control bone tissues. From these results, tumor tissue-specific expression of OST311 was confirmed.

EXAMPLE 6

Isolation of the CHO Cells Stably Expressing OST311

(1) Construction of OST311 Expression Vector

Using 311F1EcoRI (SEQ ID NO: 22) and 311LHisNot (SEQ ID NO: 23) primers shown in Example 5, and tumor-induced osteomalacia tumor cDNA library as a template, PCR was performed for 35 cycles, each cycle (process) consisting of 96° C. for 30 seconds, 55° C. for 30 seconds and 72° C. for 30 seconds. In addition, DMSO was added to the reaction solution to have a final concentration of 2%, and LA-taq DNA polymerase (TAKARA SHUZO, Japan) was used as an enzyme. 311F1EcoRI primer was annealed to nucleotide No. 111 of SEQ ID NO: 1 located upstream from Kozak sequence, and 311LHisNot primer was annealed to nucleotide No. 871 of SEQ ID NO: 1. A region encoding the full-length polypeptide represented by SEQ ID NO: 2 can be amplified by performing PCR using both primers. In addition, 311LHisNot primer contains a nucleotide sequence that adds six histidine residues (SEQ ID NO: 88)after the amino acid No. 251 of SEQ ID NO: 2 and also adds a termination codon after the last histidine codon. Thus, the translated recombinant protein has a His6 tag sequence (SEQ ID NO: 88) at the C-terminus, so that it is useful for recognition of a recombinant by an antibody, and purification of the recombinant using nickel resin.

After being digested with restriction enzymes EcoR I and Not I, the PCR product was ligated to plasmid vector pcDNA3.1Zeo (INVITROGEN, USA) for expression in animal cells that had been digested with EcoR I and Not I similarly. The thus obtained recombinant vector was introduced into *Escherichia coli* strain DH5α. *E. coli* was cultured in 3 ml of LB medium containing 100 mg/ml ampicillin, and then the plasmid was purified using GFX plasmid purification kit (Amersham Pharmacia Biotech, USA). The sequence of the inserted gene was determined by a standard method. Thus, it was confirmed that the sequence was identical to an equivalent portion of SEQ ID NO: 1, and a nucleotide sequence encoding the His6 tag sequence (SEQ ID NO: 88) had been added immediately before the termination codon.

(2) Isolation of the CHO Cells which Stably Express OST311

Approximately 20 pg of the plasmid, to which OST311 ORF portion prepared in Example 6 (1) had been inserted,

```
G3PDH
(FW:          ACCACAGTCCATGCCATCAC,                              (SEQ ID NO: 26)

RV:           TCCACCACCCTGTTGCTGTA.                              (SEQ ID NO: 27))

311F1EcoRI:   CCGGAATTCAGCCACTCAGAGCAGGGCACG                     (SEQ ID NO: 22)

311LHisNot:   ATAAGAATGCGGCCGCTCAATGGTGATGGTGATGATGGATGAACTTGGCGAA (SEQ ID NO: 23)
```

Figure 1:
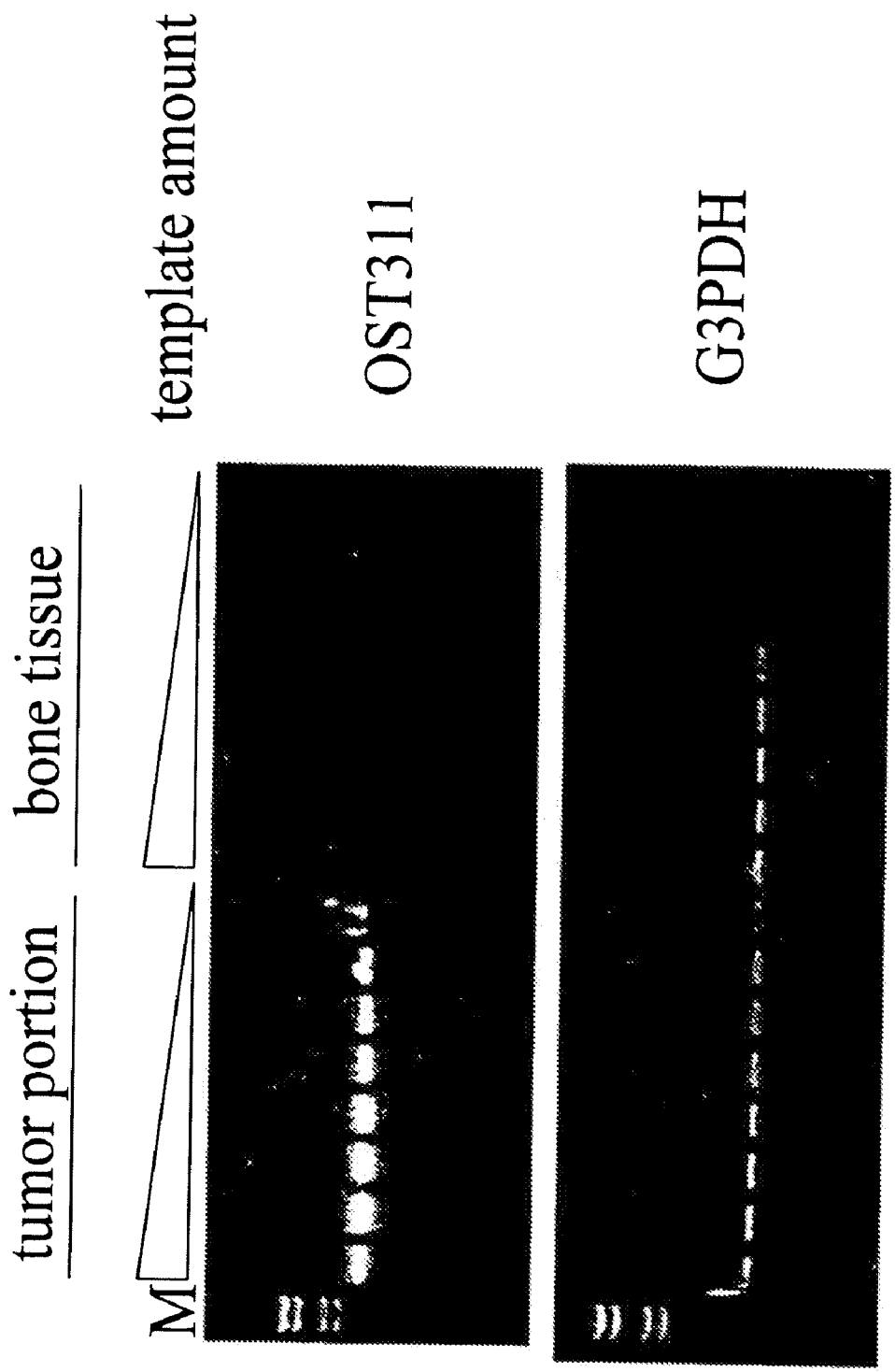
FIG. 1 includes photographs showing the amplification products analyzed using agarose electrophoresis. To study the tumor specificity of OST311, PCR was performed using, as templates, first-strand cDNA extracted from tumor tissues and first-strand cDNA extracted from control bone tissues, and using OST311 specific primers represented by SEQ ID NOS: 22 and 23, and G3PDH specific primers represented by SEQ ID NOS: 26 and 27.

As shown in FIG. 1, these PCR products were subjected to 2% agarose gel electrophoresis. When OST311 primers were used, PCR products with the predicted size were observed only when the tumor tissue was used as a template. In conwas digested with a restriction enzyme Fsp I so as to cleave a site of the ampicillin resistance gene within the vector. Then the cleaved vector was subjected to ethanol precipitation, and then dissolved in 10 μl of ultrapure water. Subsequently, the total volume of the solution was introduced into host cells by an electroporation using Gene Pulser II (Bio Rad, USA). CHO Ras clone-1 cells (Shirahata, S., Biosci. Biotech. Biochem, 59(2): 345-347, 1995) were used as host cells. CHO Ras clone-1 was cultured in a 75 cm$^2$ culture flask (CORNING, USA) containing MEMα medium supplemented with 10% FCS at 37° C. under 5% $CO_2$ and 100% humidity until the cells grew to cover approximately 90% of culturing area. Then, adherent cells were removed by trypsin treatment, so that approximately 1×10$^7$ cells were obtained. The obtained cells were resuspended in 0.8 ml of PBS, mixed with the plasmid digested with Fsp I, and then cooled on ice for 10 minutes. The cells containing the plasmid were transferred into the cuvette four millimeter in width. After electric pulse was applied at set values (0.25 kV and 975 μF), the cuvette was cooled again for 10 minutes. The gene-transferred cells were cultured in 10% FCS-containing MEMα medium for 24 hours. Then, Zeosin (INVITROGEN, USA) was added to the culture medium to have a final concentration of 0.5 mg/ml, and then further cultured for 1 week. Subsequently, for cloning cells showing drug resistance ability, the cells were re-inoculated in a 96-well plate (CORNING, USA) to 0.2 cells/well by a limited dilution method, and then cultured in the presence of zeosin with a final concentration of 0.3 mg/ml for about 3 weeks, thereby obtaining 35 clones of the drug-resistant strain.

(3) Confirmation of Production of Recombinant by CHO Cells which Stably Express OST311

For 35 clones showing drug resistance, the presence of recombinant OST311 in the conditioned medium was confirmed by the Western blotting method.

0.2 ml of collected the conditioned medium was concentrated to about 40 to 50 μl using an ultra-free MC M.W. 5,000 cut membrane system (MILLIPORE, USA). 10 μl of a sample buffer containing 1 M Tris-Cl pH6.8, 5% SDS, 50% glycerol, and 100 mM DTT was added to the concentrate, and then it was heated at 95° C. for 5 minutes. Then the protein in the conditioned medium was separated by polyacrylamide electrophoresis with a 10 to 20% gradient. Thereafter, the protein in the gel was transferred to Immobilon PVDF membrane (MILLIPORE, USA) using a semi-dry blotting system (Owl Separation Systems, USA). This PVDF membrane was incubated with anti-His (C-terminus) antibody (INVITROGEN, USA) that had been diluted 1/5000 in TTBS buffer (Sigma, USA) at room temperature for 1 hour. Then, the membrane was exposed to film for 5 minutes using ECL system (Amersham Pharmacia Biotech, USA), and developed using an automatic processor (FUJIFILM, Japan). As a result, clone #20, for which the most intense signals had been observed at approximately 32 kDa and 10 kDa, was isolated. Hereinafter, #20 cell was named CHO-OST311H, and deposited with National Institute of Advanced Industrial Science and Technology, International Patent Organism Depositary (Higashi, Tsukuba-shi, Ibaraki 1-1-1) (Accession No. FERM BP-7273).

EXAMPLE 7

Measurement of Inhibitory Activity of Phosphate Uptake by CHO-OST311H Conditioned Medium CHO-OST311H was cultured in a 225 cm$^2$ culture flask (CORNING, USA) containing MEM α medium supplemented with 10% FCS at 37° C. and under 5% $CO_2$, and 100% humidity until the cells grew to cover about 80% of the flask area. Then, the medium was replaced with 30 ml of serum-free medium CHO-S-SFM II (LIFE TECHNOLOGY, USA). 48 hours later, the conditioned medium was collected. The conditioned medium was centrifuged at 1,200 g for 5 minutes to remove suspended cells and the like, and then filtered using a Minisart-plus 0.22 μm filter (Sartorius, Germany).

Using this conditioned medium, the effect on phosphate uptake activity of a human renal proximal tubular cell line (CL-8 cells) was examined. The human renal proximal tubular cell line was cultured under 5% $CO_2$ and 100% humidity at 37° C. in DMEM medium containing 10% FCS (LIFE TECHNOLOGY). To measure phosphate uptake activity, the human renal proximal tubular cell line was first cultured in DMEM medium containing 10% FCS in a 48-well plate (CORNING, USA). When the cells grew to cover the entire bottom surface of the plate at 3 days after the start of culturing, the culture medium was replaced with 200 μl of serum-free medium CHO-S-SFM II (LIFE TECHNOLOGY, USA), followed by further culturing for 20 to 24 hours. Using the cells in this state, the following experiments for measuring phosphate uptake activity (Experiments 1 and 2) were conducted.

(1) EXPERIMENT 1

CHO-S-SFM II medium was removed, and then 200 μl of the above conditioned medium of CHO-OST311H cells prepared in CHO-S-SFM II medium was added per well. At this time as control wells, 3 wells containing media which had not been replaced with CHO-S-SFM II, and 3 wells containing media which had been supplemented respectively with 200 μl of the conditioned medium of CHO-OST190H cells prepared in a manner similar to that for CHO-OST311H were prepared. The above-described CHO-OST190H cells are recombinant cells that have been prepared by introducing OST190H, which we have cloned in a manner similar to that for CHO-OST311H cells, into CHO ras clone-1 such that OST190H can be expressed. Similar to OST311H, expressed CHO-OST190H contains a His6 tag sequence (SEQ ID NO: 88) added to the C-terminus of a polypeptide, which is same as the polypeptide named MEPE as reported by Rowe, P. S. N. et al, Genomics 67:54-68, 2000. After each sample was added, incubation was further performed in a $CO_2$-incubator for 26 hours, phosphate uptake activity of the cells in each well was measured by the following method for measuring phosphate uptake activity.

(2) EXPERIMENT 2

100 μl of cultured medium was removed from 200 μl of the culturing CHO-S-SFM II medium. Into these culture, 100 μl of the conditioned medium of CHO ras clone-1 cells was added respectively to 3 wells, and 100 μl of the conditioned medium of CHO-OST311H cells was added respectively to 3 wells. Then, incubation was performed in a $CO_2$ incubator for 24 hours. Subsequently, phosphate uptake activity of the cells in each well was measured by the following method for measuring phosphate transport.

Measurement method of phosphate uptake activity:

After the addition of the conditioned medium and incubation, the cells were washed with a buffer containing no phosphoric acid (150 mM NaCl, 1 mM $CaCl_2$, 1.8 mM $MgSO_4$, 10 mM HEPES, pH7.4), and then incubated in the same solution at room temperature for 10 minutes. The solution was removed, and then an assay solution, which had been prepared by adding radioactive $KH_2PO_4$ (NEN) to have 0.105 mM to the buffer, was added. The solution was subjected to incubation at room temperature for 10 minutes. After incubation, the cells were washed three times with a stop solution which had been ice-cooled immediately after the removal of the assay solution (150 mM choline chloride, 1 mM $CaCl_2$, 1.8 mM $MgSO_4$, 10 mM HEPES, pH7.4). This washing solution was removed, 80 μl of 0.2 N NaOH was added to the cells, and then the solution was incubated at room temperature for 10 minutes, so that the cells were lysed. To measure radioactivity in the cell lysis solution, the solution was transferred to ReadyCap (Beckman), dried at 50° C., and then placed in glass vial. Then, radioactivity was measured using a scintillation counter (Wallac1410, Pharmacia). Phosphate uptake activity in each experiment is shown in Table 2 wherein mean uptake in the control not supplemented with conditioned medium is considered as 100%. The conditioned medium of CHO-OST311H cells significantly suppressed phosphate uptake activity of the human epithelial cells of renal proximal convoluted tubules.

TABLE 2

OST311 activity against phosphate uptake by renal tubular epithelial cells

|  | Phosphate uptake activity ± SEM | t-test |
|---|---|---|
| Experiment 1 Sample |  |  |
| Not supplemented | 100 ± 1.9 | — |
| CHO-OST190H | 103.8 ± 0.9 | Not significant |
| CHO-OST311H | 87.4 ± 0.2 | p < 0.01 |
| Experiment 2 |  |  |
| Conditioned media of CHO | 100 ± 1.5 | — |
| CHO-OST311H | 87.2 ± 1.2 | p < 0.01 |

EXAMPLE 8

Partial Purification Of Recombinant Ost311 From Cho-Ost311H Conditioned medium Recombinant OST was partially purified from the conditioned medium prepared in the manner described in Example 7 by the following method. Processes 1) to 4) were performed in a chromatochamber at 4° C.

1) A disposable polypropylene column was filled with ProBond nickel resin (INVITROGEN, USA) to have a bed volume of 3 ml, and then the column was washed and equilibrated with 30 ml of buffer 1 (Table 3).

2) 120 ml of the conditioned medium prepared in the manner described in Example 7 was applied to the above nickel column by free-fall, allowing recombinant OST311 to bind.

3) 30 ml of buffer 2 shown in Table 3 was used to remove non-specifically adsorbed proteins.

4) 3 ml of buffer 3 shown in Table 3 was respectively added at four separate times, so that recombinant OST311 was eluted. 20 μl each of these four fractions was subjected directly (as original concentration) to Western blotting in the manner described in Example 6(3). Thus, detection of OST311 was attempted with anti-His antibody.

As a result, approximately 32 kDa and 10 kDa signals were intensively observed in the second fraction.

5) The above second fraction was applied to NAP25 and NAP10 columns (Amersham Pharmacia Biotech, USA), and the solvent was replaced with buffer 4 shown in Table 3.

Figure 2:
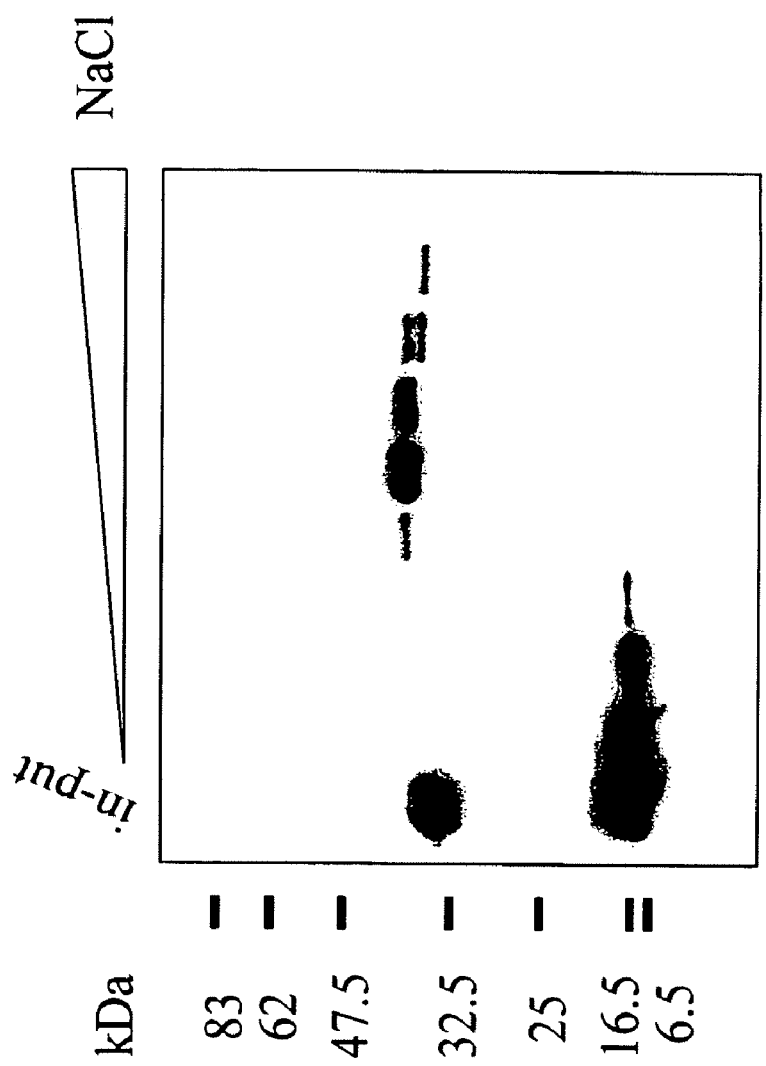
FIG. 2 is a photograph showing that recombinant OST311 was detected by performing Western blotting for elution fractions which had been prepared by subjecting recombinant OST311 to affinity purification using nickel resin, and then isolated and purified using strong cation-exchange resin SP-5PW.

6) Recombinant OST311 for which the solvent had been replaced with buffer 4 was applied to SP-5PW (strong cation-exchange resin, TOSOH, Japan) at a flow rate of 1 ml/minute using high performance liquid chromatography (Hitachi, Japan). Buffer 5 shown in Table 3 was added with a 1%/minute gradient for elution, thereby sampling 2 ml each of fractions. As shown in FIG. 2, Western blotting was performed for each elution fraction in the manner described in Example 8(5), so that detection of OST311 was attempted. Approximately 10 kDa signal was eluted with about 280 mM NaCl, and approximately 32 kDa signal was eluted with about 400 mM NaCl. The corresponding fractions were subjected to SDS-polyacrylamide gel electrophoresis, and then stained using a silver staining kit (Daiichi Chemicals, Japan). The purity of the fraction containing approximately 10 kDa and 32 kDa was 70% or more.

TABLE 3

| Buffer 1 | Buffer 2 | Buffer 3 | Buffer 4 | Buffer 5 |
|---|---|---|---|---|
| 10 mM Na/Pi pH 6.5 0.5 M NaCl | 10 mM Na/Pi pH 6.5 10 mM imidazole 0.5 M NaCl | 10 mM Na/Pi pH 6.5 0.5 M imidazole 0.5 M NaCl 5 mM CHAPS | 10 mM Na/Pi pH 6.5 5 mM CHAPS | 10 mM Na/Pi pH 6.5 1 M NaCl 5 mM CHAPS |

Na/Pi: sodium phosphate buffer

EXAMPLE 9

N-terminal Amino Acid Sequence Analysis of Partially Purified Recombinant

Approximately 10 kDa and 32 kDa of partially purified fractions recognized by anti-His antibody that had been obtained by the method described in Example 8 were subjected to SDS-polyacrylamide gel electrophoresis. Next, using a semi-dry blotting system (Owl Separation Systems, USA), protein in the gel was transferred to an Immobilon PVDF membrane (MILLIPORE, USA). The PVDF membrane was stained with CBB, approximately 10 kDa and 32 kDa bands were excised, and then the N-terminal amino acid sequences were determined using a protein sequencer Model 492 (PE Applied Systems, USA).

As a result, it became clear that the N-terminal amino acid sequence of approximately 35 kDa band was an OST311 sequence starting from residue No. 25, Tyr, of SEQ ID NO: 2. From this result, it was confirmed that a sequence ranging from residue No. 1, Met, to residue No. 24, Ala, of SEQ ID NO: 2 had been cleaved as a secretion signal sequence. On the other hand, it became clear that the N-terminal amino acid sequence of approximately 10 kDa band was an OST311 sequence starting from residue No. 180, Ser, of SEQ ID NO: 2. The presence of a motif consisting of RRXXR immediately before Ser at residue No. 180 revealed that recombinant OST311 had been cleaved by some protease derived from CHO cells.

As described above, recombinant OST311 produced by CHO-OST311 cells was shown to be present as at least 3 types of polypeptides after secretion: a polypeptide (SEQ ID NO: 4) from residue No. 25, Tyr, to No. 251, Ile, a polypeptide (SEQ ID NO: 6) from residue No. 25, Tyr, to No. 179, Arg, and a polypeptide (SEQ ID NO: 8) from residue No. 180, Ser, to No. 251, Ile of SEQ ID NO: 2.

EXAMPLE 10

Preparation of Anti-OST311 Partial Peptide Polyclonal Antibody

Figure 3B:
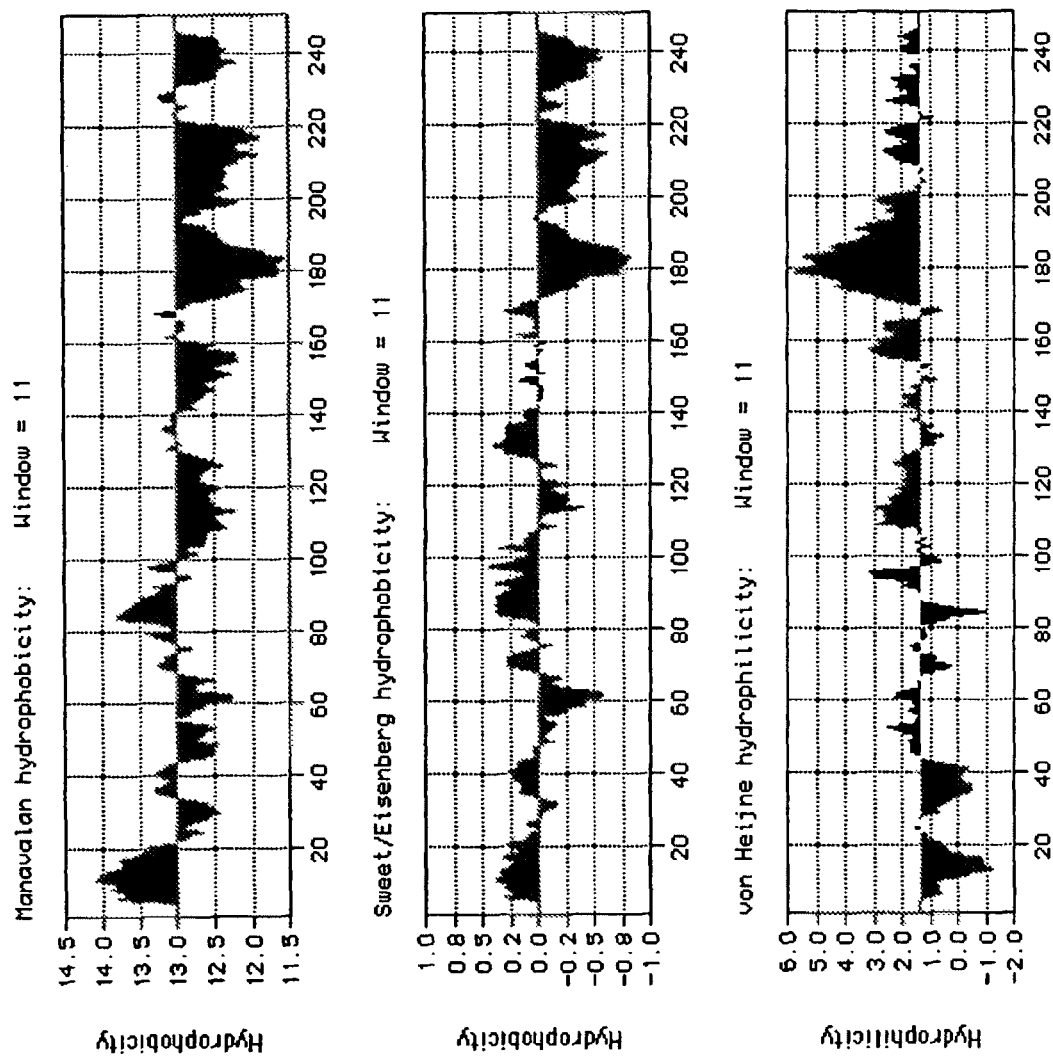
FIG. 3B shows the results of predicting the degree of hydrophobicity of the polypeptide having the amino acid sequence represented by SEQ ID NO: 2 using the computing function of MacVector version 6.5.1.

The degree of hydrophobicity of the polypeptide of SEQ ID NO: 2 was predicted using a computing function of MacVector version 6.5.1., so that sites suitable for antigen preparing peptide antibodies were predicted (FIGS. 3A and B). Here, the suitable site was predicted from the perspective that the sites have high degree of hydrophilicity, and are less subject to sugar chain modification and phosphorylation. Hence, selected and synthesized as antigens were 311-48 (SEQ ID NO: 28) prepared by artificially adding a cysteine residue at the synthetic stage to the C-terminus of a peptide consisting of 20 amino acids starting from residue No. 48, Arg, of SEQ ID NO: 2, and 311-114 (SEQ ID NO: 29) prepared by similarly adding a cysteine residue to a peptide consisting of 20 amino acids starting from residue No. 114, Arg. Specifically, cysteine residues were artificially added to the C-termini of both peptides at the synthetic stage, so that the products could be coupled with carrier proteins (bovine thyroglobulin). Coupling with carrier proteins and immunization of rabbits were consigned to IBL, Co., Ltd. (1091-1, Fujioka-shi, Gunma, Japan) (Assignment number: 1515).

```
311-48:   RNSYHLQIHKNGHVDGAPHQC   (SEQ ID NO: 28)

311-114:  RFQHQTLENGYDVYHSPQYHC   (SEQ ID NO: 29)
```

EXAMPLE 11

Experiment of Transplanting CHO-OST311H Cells into Nude Mice

To test whether OST311 is a causative factor for tumor-induced osteomalacia CHO-OST311H cells were transplanted into 6-week-old BALB/c nude mice (male) for tumor generation, thereby developing a murine tumor-induced osteomalacia model which constantly secrets recombinant OST311 from the tumors. As a control for the experiment, CHO ras clone-1 cells and CHO-OST190H described in Example 7 were used similarly for the transplantation experiment.

(1) Transplantation of CHO Cells

CHO-OST311H cells and CHO-OST190 cells were scattered by trypsin treatment from culture flasks, suspended to $1\times10^8$ cells/ml in PBS. The suspension was subcutaneously injected, 0.1 ml each, to both latera of the nude mice ($2\times10^7$ cells/mouse). In addition, as a control group, subcutaneous injection of the same number of CHO ras clone-1 cells were performed in the same manner. For about 1 month after injection, five nude mice were housed in a plastic cage and allowed access to solid food CE-2 (CLEA JAPAN, Japan) and tap water, ad libitum. 2 weeks after transplantation, tumor generation was observed for 75% of the control group and 66.7% of OST311 group.

(2) Comparison of Changes in Body Weight

Figure 4:
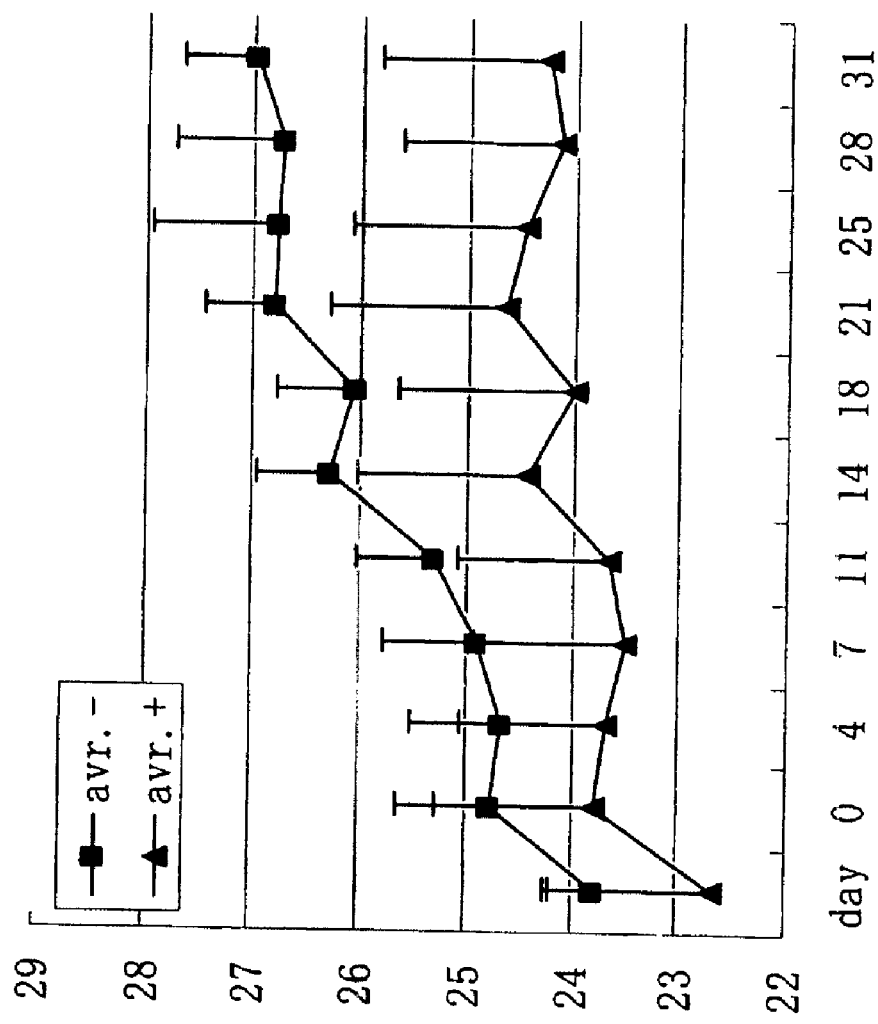
FIG. 4 shows time-course changes in average body weight for 31 days after transplantation of CHO-OST311H cells between a non tumor-bearing group (a line in the graph indicated with avr.−) and a CHO-OST311H cells-transplanted tumor-bearing group (a line in the graph indicated with avr.+).

Time-course changes in average body weight for 31 days after transplantation of CHO-OST311H cells were compared between a non tumor-bearing group (a line indicated with avr.− in the graph) and a CHO-OST311H cell tumor-bearing group (a indicated with avr.+ line in the graph). As shown in FIG. 4, the CHO-OST311H cell tumor-bearing group showed suppressed increases in body weight compared to the non tumor-bearing group, and there were clear significant differences between the two groups (24.1±1.5 g vs. 26.7±1.0 g, $p<0.001$, day 31). In contrast, similar differences were not observed in average body weight between the CHO ras clone-1 cell tumor-bearing control group and the non tumor-bearing group (27.0±1.8 g vs. 26.7±1.0 g, no significant difference, day 31).

(3) Measurement of Serum Phosphate and Calcium, and Urine Phosphate and Calcium

On days 30 to 40 after cell transplantation, nude mice were housed in metabolic cages for 24 hours. After urine was collected, blood was collected from the heart or orbital cavity of the mice under the anesthetized condition using diethylethel. The peripheral blood was subjected to preparation of serum using Microtainer (Beckton Dickinson, USA). After the volume was measured, the urine was centrifuged to collect supernatant. Serum and urine phosphate levels were measured using P-test Wako (Wako Pure Chemical Industries, Japan), and serum and urine calcium levels were measured using calcium-test Wako (Wako Pure Chemical Industries, Japan), and serum and urine creatinine levels were measured using CRE-EN KAINOS (KAINOS, Japan).

EXPERIMENT 1

On day 34 after cell transplantation, serum phosphate levels of the non tumor-bearing group, the CHO ras clone-1 cell tumor-bearing group, the CHO-OST190H cell tumor-bearing group, and the CHO-OST311H cell tumor-bearing group were measured.

EXPERIMENT 2

On days 44 to 46 after cell transplantation, serum and urine phosphate levels, calcium levels and creatinine levels of the non tumor-bearing group and the CHO-OST311H cell tumor-bearing group were measured. Renal fractional excretion of phosphate and calcium were determined by dividing phosphate or calcium clearance by creatinine clearance.

Measurement results are shown in Table 4 below.

TABLE 4

Serum and urine phosphate and calcium in cells-transplanted mice

Experiment 1

| Group | Number of mouse | Serum phosphate level ± SEM (mg/dl) | t-test |
|---|---|---|---|
| Non tumor-bearing mice | 7 | 8.17 ± 0.60 | — |
| CHO ras clone-1 | 4 | 8.50 ± 0.38 | No significant difference |
| CHO-OST190H | 4 | 9.49 ± 0.52 | No significant difference |
| CHO-OST311H | 9 | 4.39 ± 0.23 | $p < 0.001$ |

Experiment 2

| Group | Non tumor | CHO-OST311H | t-test |
|---|---|---|---|
| Number of mouse | 4 | 6 | — |
| Serum phosphate level ± SEM (mg/dl) | 8.29 ± 0.59 | 4.25 ± 0.15 | $p < 0.001$ |
| Renal fractional excretion of phosphate | 0.23 ± 0.02 | 0.44 ± 0.06 | $p < 0.05$ |
| Serum Ca level ± SEM (mg/dl) | 6.72 ± 0.27 | 4.61 ± 0.19 | $p < 0.001$ |
| Renal fractional excretion of calcium | 0.0040 ± 0.0006 | 0.0059 ± 0.0010 | No significant difference |

(4) Soft Roentgenogram of Whole Skeleton

After transplantation of the CHO-OST311H cells, individuals in which formation of tumors is recognized exhibited significant abnormalities in their physical constitutions and walking functions, compared to non tumor-bearing individuals or the control CHO ras clone-1-transplanted individuals. Hence, the tumor-bearing individuals were predicted to have skeletal abnormalities. Then, individuals in which formation of tumors is recognized were selected at random from the control CHO ras clone-1 cells-transplanted group, the CHO-OST190H cells-transplanted group and CHO-OST311H cells-transplanted group, and then X-ray pictures were taken therefor using a radiography system μFX-100 (FUJI FILM, Japan) according to the attached manufacturer's manual. X-ray pictures were taken under conditions of X-ray tube voltage of 25 kV, X-ray tube current of 0.1 mA and exposure time of 10 seconds. The individuals were exposed to a imaging plate, and then image analysis was performed using BAS2000 (FUJI FILM, Japan).

Figure 5:
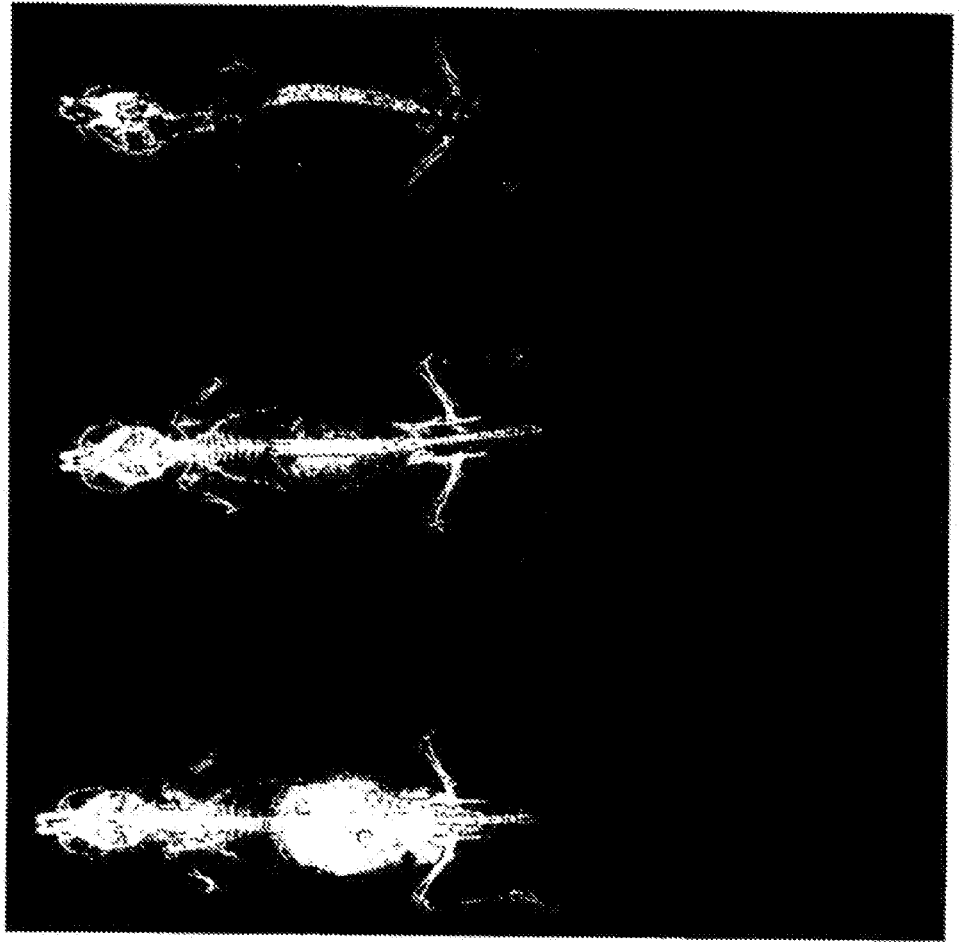
FIG. 5 includes X-ray pictures showing the whole skeletal soft roentgenogram of a control CHO ras clone-1 cells-transplanted tumor-bearing individual, a CHO-OST190H cells-transplanted tumor-bearing individual, and a CHO-OST311H cells-transplanted tumor-bearing individual.

As a result, as shown in FIG. 5, reduced brightness of soft roentgenogram of the bone was recognized in the whole skeleton of CHO-OST311H cells-transplanted individual, so that defect of mineralization was recognized. In addition, skeletal deformity, such as distortion of rib cage was also recognized.

Figure 7A:
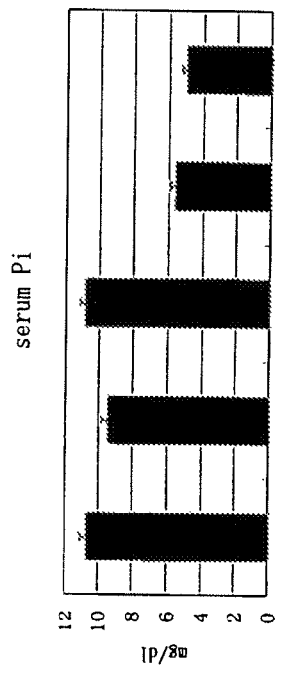
FIG. 7 shows the results of measuring serum phosphate levels, serum calcium levels and serum alkaline phosphatase activities of a non tumor-bearing group (n=6), a CHO ras clone-1 tumor-bearing group (n=10), a CHO-OST190H tumor-bearing group (n=10), and a CHO-OST311H tumor-bearing group-1 (n=6), and a CHO-OST311H tumor-bearing group-2 (n=6). Blood was collected from the heart of each individual on days 44 to 46.
Figure 7B:
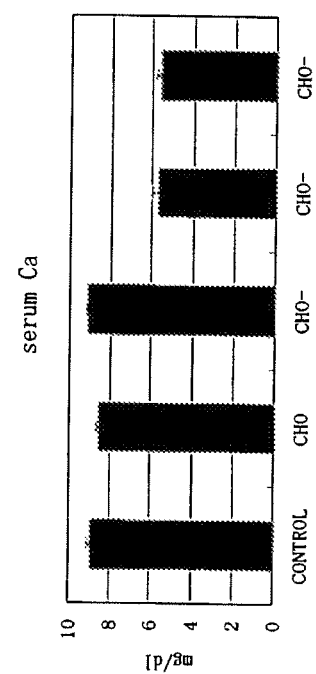
Figure 7C:
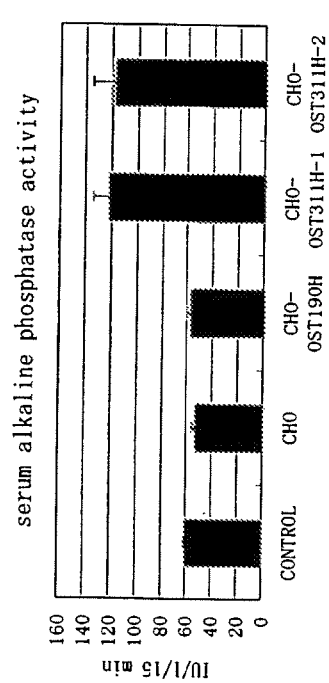

(5) Measurement of Serum Phosphate and Calcium Levels and Alkaline Phosphatase Activities The serum obtained by collecting blood from the heart on days 44 and 46 after cell transplantation was stored at −20° C. once. The serum samples were thawed together, phosphate and calcium levels contained in each serum were measured again, and alkaline phosphatase activities were also measured. Phosphate levels were measured using P-test Wako (Wako Pure Chemical Industries, Japan), calcium levels were measured using calcium-test, Wako Pure Chemical Industries, Japan), and alkaline phosphatase activities were measured using calcium alkaline phosphor B-test Wako (Wako Pure Chemical Industries, Japan). The results were classified into a non tumor-bearing group (n=6), a CHO tumor-bearing group (n=10), a CHO-OST190H cell tumor-bearing group (n=10) and a CHO-OST311H tumor group (n=6×2). The CHO-OST311H group was classified into two groups: a group sacrificed on day 44 (CHO-OST311H-1: n=6) and a group sacrificed on day 46 (CHO-OST311-2: n=6). As shown in FIG. 7, significant changes including decreased serum phosphate level (FIG. 7A), decreased serum calcium level (FIG. 7B) and increased serum alkaline phosphatase activity (FIG. 7C) were recognized in the CHO-OST311H tumor group.

(6) Expression of Sodium-Phosphate Cotransporter (NaPi-7) on Renal Proximal Tubule i) Preparation of Brush Border Membranes (Hereinafter, Referred to as BBM) of Proximal Tubular Epithelial Cell Kidneys were excised from the CHO-OST311H tumor-bearing individuals and non tumor-bearing individuals under the anesthetized condition using diethylether. Each kidney was cut in half to obtain coronal sections (Experiment 1: 6 numbers of CHO-OST311H tumor-bearing individuals and 4 numbers of non tumor-bearing individuals. Experiment 2: 6 numbers of CHO-OST311H tumor-bearing individuals, and 2 numbers of non tumor-bearing individuals). Using half of each of the respectively excised kidneys from the individuals, BBM was prepared according to the protocols as reported by Kessler et al (Biochem. Biophys. Acta. 506, pp. 136-154).

The kidney was homogenized in 3 ml of a homogenizing buffer (50 mM mannitol, 2 mM Tris/HEPES pH 7.5) using a glass-made homogenizer at 1,300 rpm for 2 minutes so that homogenous kidney extracts were obtained. After $CaCl_2$ was added to the extract to have a final concentration of 10 mM, the solution was agitated at 4° C. for 15 minutes, and then centrifuged at 4,900 g for 15 minutes at 4° C. The thus obtained supernatant was filtered using a Kimwipe, and then centrifuged at 16,200 g for 60 minutes at 4° C., thereby allowing fractions containing many BBM to precipitate. The precipitate was resuspended in 5 ml of a suspension buffer (50 mM mannitol, 2 mM Tris/HEPES, pH 7.5), and then the solution was centrifuged again at 16,200 g for 60 minutes at 4° C. This procedure was repeated twice, and then the product was resuspended in 0.1 ml of a suspension buffer. The protein concentration of the thus obtained solution was 3 to 4 mg/ml as determined by standard methods.

ii) Western Blotting of BBM Protein

As described above, BBM proteins prepared from each mouse were diluted separately with a suspension buffer to 10 μg/μl. Then, 2.5 μl of a sample buffer containing 1 M Tris-Cl pH 6.8, 5% SDS, 50% glycerol and 100 mM DTT was added to the diluted solution. After the solution was heated at 95° C. for 5 minutes, protein in BBM solution was separated by polyacrylamide electrophoresis with a 10 to 20% gradient. Subsequently, the protein in the gel was transferred to Immobilon PVDF membrane (MILLIPORE, USA) using a semi-dry blotting system (Owl Separation Systems, USA). The PVDF membrane was incubated with anti-NaPi-7 polyclonal antibody diluted 1/2000 in TTBS buffer (Sigma, USA) at room temperature for 3 hours. The antibody is a polyclonal antibody which has been obtained by immunizing a rabbit with a synthetic peptide (LALPAHHNATRL) (SEQ ID NO: 89)corresponding to the C-terminal site of mouse NaPi-7 by standard methods in KIRIN BREWERY CO., LTD., Pharmaceutical Research Laboratories, Pharmaceutical Division. After reaction with this antibody, the reaction product was further incubated with anti-rabbit IgG secondary antibody (DAKO, Denmark) bound to horseradish peroxidase (HRP), and then bands were detected using ECL system (Amersham Pharmacia Biotech, USA).

Figure 8:
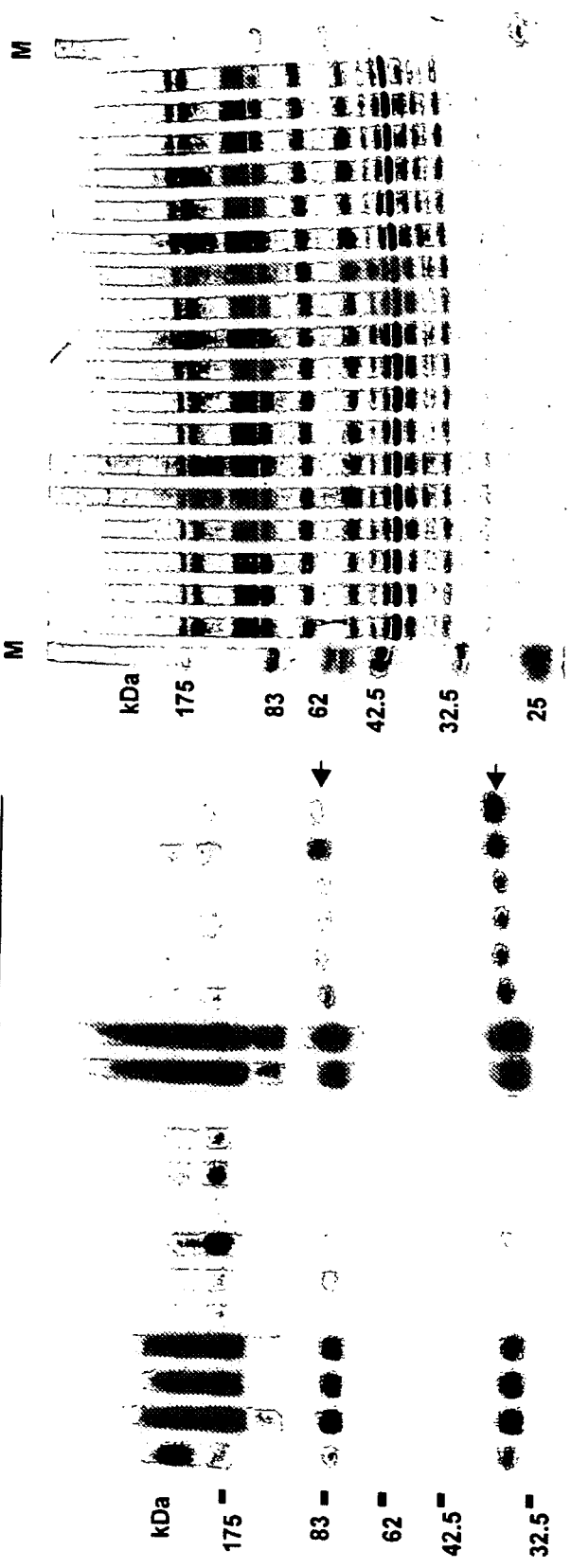
FIG. 8 includes photographs showing comparison of expression levels of sodium-phosphate cotransporter (NaPi-7) as measured by the Western blotting method. Specifically, brush border membranes of proximal tubular epithelial cells were prepared from the kidneys excised from the CHO-OST311H tumor-bearing individuals, and non tumor-bearing individuals, and then the expression levels of NaPi-7 were compared by the Western blotting method.

Under reduction conditions, approximately 80 kDa and 35 kDa of bands and 170 to 200 kDa of high molecular smears were detected with the antibody (FIG. 8). These band patterns are the same as the cases reported by Tatsumi et al in J. Biol. Chem. Vol. 273, pp 28568-28575, 1998, and these bands had been confirmed to uniformly change depending on the amount of phosphate intake from food by mice or rats. From these facts, the bands proved to the polypeptides derived from NaPi-7. As shown in FIG. 8, for all the above fragments (bands indicated with arrows), the NaPi-7 signals contained in BBM proteins that had been prepared from CHO-OST311H tumor-bearing individuals were significantly reduced compared to those prepared from non tumor-bearing individuals. These results were reproduced in individually conducted Experiment 1 and 2. On the other hand, these BBM proteins were separated by polyacrylamide electrophoresis with a 10 to 20% gradient, and then stained with CBB. BBM proteins of individuals were equally stained, suggesting that reduced signals in Western blotting are specifically observed for NaPi-7 (FIG. 8). Based on this fact, it is inferred that OST311 protein acts on renal proximal tubular cells, and downregulates the expression level of NaPi-7 at the protein level, so as to induce hypophosphatemia.

(7) Analysis of Changes in mRNAs of Phosphate Transporters and Vitamin D-Metabolizing Enzymes in the Kidney and Small Intestine i) Preparation of Total RNA Small intestines and kidneys were excised from the mice sacrificed on days 44 to 46 after cell transplantation. The kidneys were rapidly frozen in dry ice. The frozen kidneys were cryopreserved in a deep freezer at −80° C. until use. One frozen kidney was homogenized in 5 ml of ISOGEN (Nippon Gene, Japan), and then total RNA was prepared according to the attached manufacturer's manual. 15 μg of the prepared total RNA was electrophoresed by formaldehyde-containing denatured gel with 1% agarose concentration according to standard methods, and then transferred to Hybond-N+ (Amersham Pharmacia, USA) overnight by a capillary transfer method. The filter transferred with RNA was irradiated with UV using a Stratalinker (STRATAGENE, USA) for immobilization of the transferred RNA, washed with 2×SSC, air-dried, and then stored at room temperature until use. The small intestines were washed with physiological saline to remove the content, and then reversed. Next, the epithelia of the small intestine were collected by scratching with a preparation, and were then rapidly frozen with liquid nitrogen. The frozen small intestinal epithelia were cryopreserved in a deep freezer at −80° C. until use. Frozen small intestinal epithelia were homogenized in 5 ml of ISOGEN (Nippon Gene, Japan), and then total RNA was prepared according to the attached manufacturer's manual. 20 μg of the prepared total RNA was electrophoresed by formaldehyde-containing denatured gel with 1% agarose concentration according to standard methods, and then transferred to Hybond-N+ (Amersham Pharmacia, USA) overnight by a capillary transfer method. The filter transferred with RNA was irradiated with UV using a Stratalinker (STRATAGENE, USA) for immobilization of the transferred RNA, washed with 2×SSC, air-dried, and then stored at room temperature until use.

ii) Preparation of Template DNA for Probe

5 μg of the total RNA prepared from a mouse (individual mouse No. 1) was used to synthesize cDNA in 20 μL of a reaction solution (50 mM Tris (pH8.3), 75 mM KCl, 3 mM MgCl$_2$, 10 mM DTT, 25 g/mL (dT)18 (SEQ ID NO: 94), 2.5 mM dNTP, 200 units of MMLV reverse transcriptase (TOYOBO, Japan)) at 37° C. for 1 hour, and then the reaction solution was treated at 70° C. for 15 minutes to inactivate the enzyme. The synthesized cDNA was diluted 5 fold, and then used in the following reaction.

The following primers were synthesized from the sequences registered at GenBank (NCBI, USA), and then used for PCR reaction:

Synthetic primers for obtaining mouse GAPDH cDNA mGAPDHFW TGAAGGTCGGTGTGAACGGATTTGGC (SEQ ID NO: 30)

mGAPDHRV CATGTAGGCCATGAGGTCCACCAC (SEQ ID NO: 31)

Synthetic primers for obtaining mouse Npt-1 cDNA mNPt1FW GTAAAGAACCCTGTGTATTCC (SEQ ID NO: 32)

mNpt1RV CTGCCTTAAGAAATCCATAAT (SEQ ID NO: 33)

Synthetic primers for obtaining mouse NaPi-7 cDNA mNaPi7FW GAGGAATCACAGTCTCATTC (SEQ ID NO: 34)

nNaPi7RV CTTGGGGAGGTGCCCGGGAC (SEQ ID NO: 35)

Synthetic primers for obtaining mouse NaPi-2b cDNA mNaPi2bFW TCCCTCTTAGAAGACAATACA (SEQ ID NO: 36)

mNaPi2bRV GTGTTTAAAGGCAGTATTACA (SEQ ID NO: 37)

Synthetic primers for obtaining mouse vitamin D1α hydroxylase cDNA m1aOHaseFW CAGACAGAGACATCCGTGTAG (SEQ ID NO: 38)

m1aOHaseRV CCACATGGTCCAGGTTCAGTC (SEQ ID NO: 39)

Synthetic primers for obtaining mouse vitamin D 24 hydroxylase cDNA m24OhaseFW GACGGTGAGACTCGGAACGT (SEQ ID NO: 40)

m24OhaseRV TCCGGAAAATCTGGCCATAC (SEQ ID NO: 41)

A reaction solution was prepared according to the attached manufacturer's manual of TakaLa LA-Taq (TAKARA SHUZO, Japan). 1 μL of cDNA and 10 pmol of each of the primer as described above were added to 50 mL of the reaction solution. The solution was maintained at 94° C. for 1 minute, and then amplification was performed for 40 cycles, each incubation cycle consisting of 94° C. for 30 seconds, 55° C. for 30 seconds and 72° C. for 1 minute. Then the amplified bands were separated by 0.8% agarose gel electrophoresis, and then target fragments were collected using Gene Clean II (Bio101, USA). Concerning GAPDH, $^{32}$P-labeled probe was prepared using as a template the fragment obtained by the procedure and a Megaprimer Labeling kit (Amersham Pharmacia Biotech, USA), and then used for the following hybridization. Concerning other genes, the obtained PCR fragments were incorporated into pGEM-T vector (Promega, USA), and then introduced into *Escherichia coli* DH5α. T7 (SEQ ID NO: 42) and SP6 primers (SEQ ID NO: 43) were added, 10 pmol each, to a PCR reaction solution, and then transformed *Escherichia coli* was added to the same. After the solution was maintained at 94° C. for 10 minutes, amplification was performed for 40 cycles, each cycle consisting of 94° C. for 30 seconds, 55° C. for 30 seconds and 72° C. for 1 minute. The reaction solution was subjected to 0.8% agarose gel electrophoresis to separate amplified bands, and then a target fragment was extracted using Gene Clean II (Bio 101, USA).

```
T7    TAATACGACTCACTATAGGG    (SEQ ID NO: 42)
SP6   GATTTAGGTGACACTATAG     (SEQ ID NO: 43)
```

The nucleotide sequences of the amplified fragments obtained by the above procedures were determined using ABI377 DNA sequencer (PE Applied System, USA), thereby confirming that each target fragment was obtained. The thus obtained DNA fragments were $^{32}$P-labelled using a Megaprimer Labeling kit (Amersham Pharmacia, USA), and then used as probes in the following hybridization.

iii) Hybridization

Figure 9A:
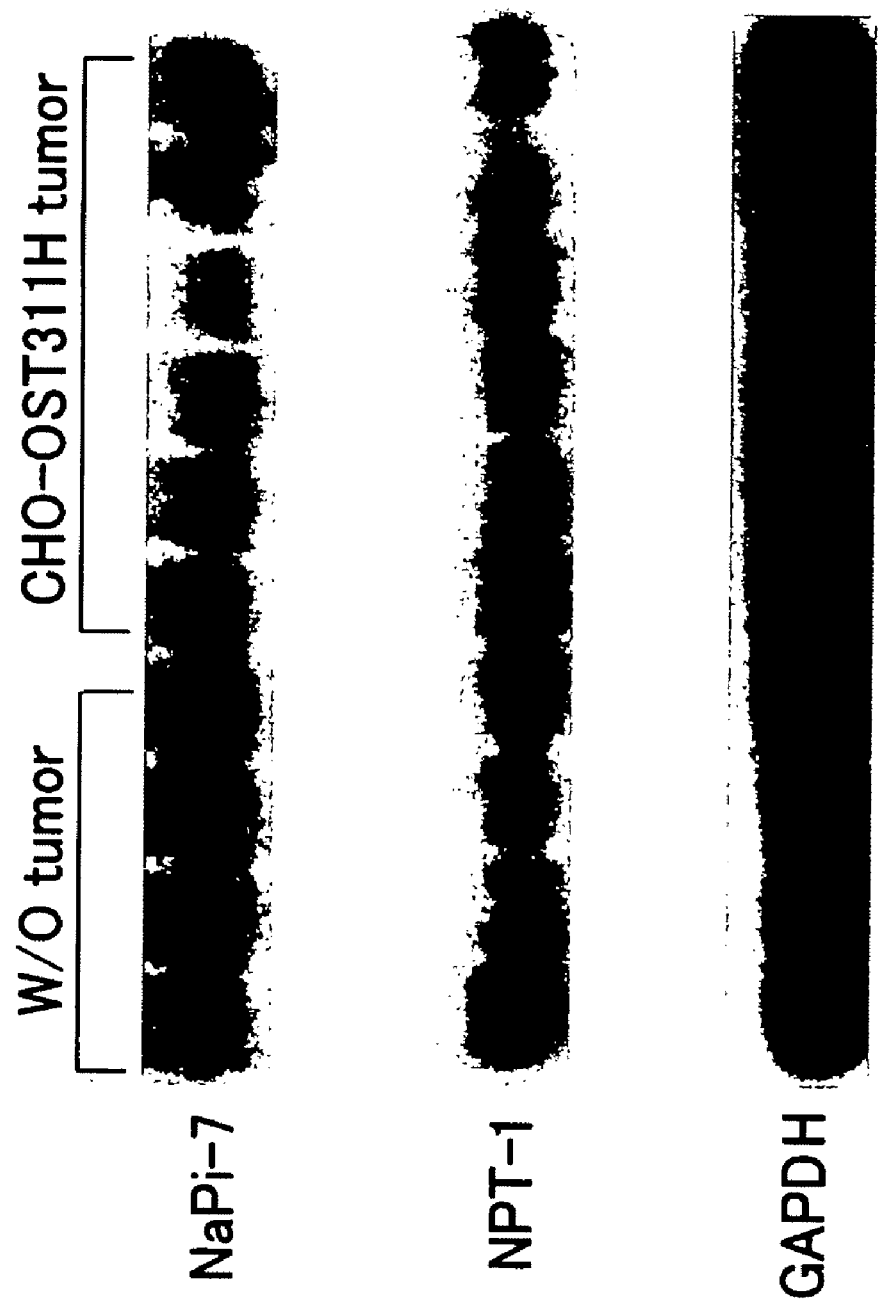
FIG. 9A includes photographs showing changes in mRNA levels, as detected by Northern blotting, of renal sodium-phosphate cotransporters (NaPi-7, NPT-1). The kidneys were collected from the mice sacrificed on days 44 to 46 after tumor transplantation.
Figure 9B:
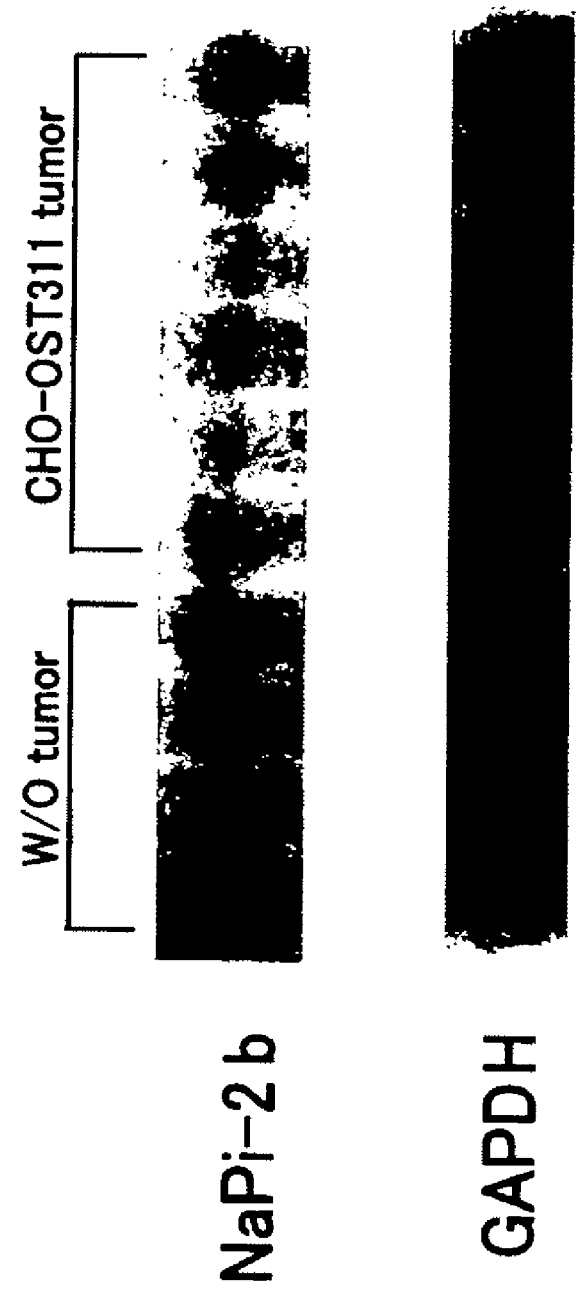
FIG. 9B includes photographs showing changes in mRNA levels, as detected by Northern blotting, of a sodium-phosphate cotransporter (NaPi-IIb) in the small intestines of the mice. The small intestines were collected from the mice sacrificed on days 44 to 46 after tumor transplantation.

Hybridization was performed according to the attached manufacturer's manual using ExpressHyb hybridization solution (CLONTECH, USA) or Perfecthyb hybridization solution (TOYOBO, Japan). After hybridization and washing, an imaging plate (FUJI FILM, Japan) was exposed for 30 minutes to overnight, and then analysis was made using BAS2000 image analyzer (FUJI FILM, Japan) (FIG. 9A to C). In addition, signal intensities of target bands were measured. After the signal intensities of each gene were corrected by the signal intensity of GAPDH, the ratio of the mean values of the non tumor-bearing group (Individual mice No. 1 to 4) to the tumor-bearing group (individual No. 5 to 10) was obtained. The following Table 5 shows the ratios. As tumors were developed in the group transplanted with CHO-OST311H, mRNA levels of NaPi-7, the type II phosphate transporter in the kidney, significantly decreased, while NPT-1, the type I phosphate transporter in the kidney, did not largely change. Further, a significant decrease was observed in mRNA of NaPi-IIb, the phosphate transporter in the small intestine. In contrast, for renal vitamin D metabolic enzyme, both mRNAs of 25-hydroxyvitamin D-1-α-hydroxylase (1αOHase) and 25-hydroxyvitamin D-24-hydroxylase (24OHase) increased.

TABLE 5

| Each mRNA ratio of the tumor-bearing group to the non tumor-bearing group (Tumor-bearing group/non tumor-bearing group) | |
|---|---|
| NPT-1 | 0.88 |
| NaPi-7 | 0.50 |
| NaPi-2b | 0.23 |
| Vitamin D1αhydroxylase | 3.90 |
| Vitamin D24 hydroxylase | 1.94 |

(8) Measurement of Serum 1,25-Dihydroxyvitamin D Levels

The sera from mice of the control group and the sera of the mice from the OST311H group were collected in equivalent amounts from each individual on days 44 and 46 after tumor transplantation. The sera collected from each group (0.5 ml of each total amount) were submitted to Mitsubishi Kagaku Bio-Clinical Laboratories, Inc, and then the 1,25-dihydroxyvitamin D levels contained in the sera were measured in a manner similar to clinical examination. As a result, serum 1,25-dihydroxyvitamin D levels of the control group and OST311 group were 28.0 pg/ml and 23.9 pg/ml, respectively. As described above, 1,25-dihydroxyvitamin D levels did not increase even when hypophosphatemia and hypocalcemia were observed. This result clearly suggests that vitamin D metabolism was affected as a result of the effect of OST311.

(9) Soft Roentgenogram of Femora

Figure 10:
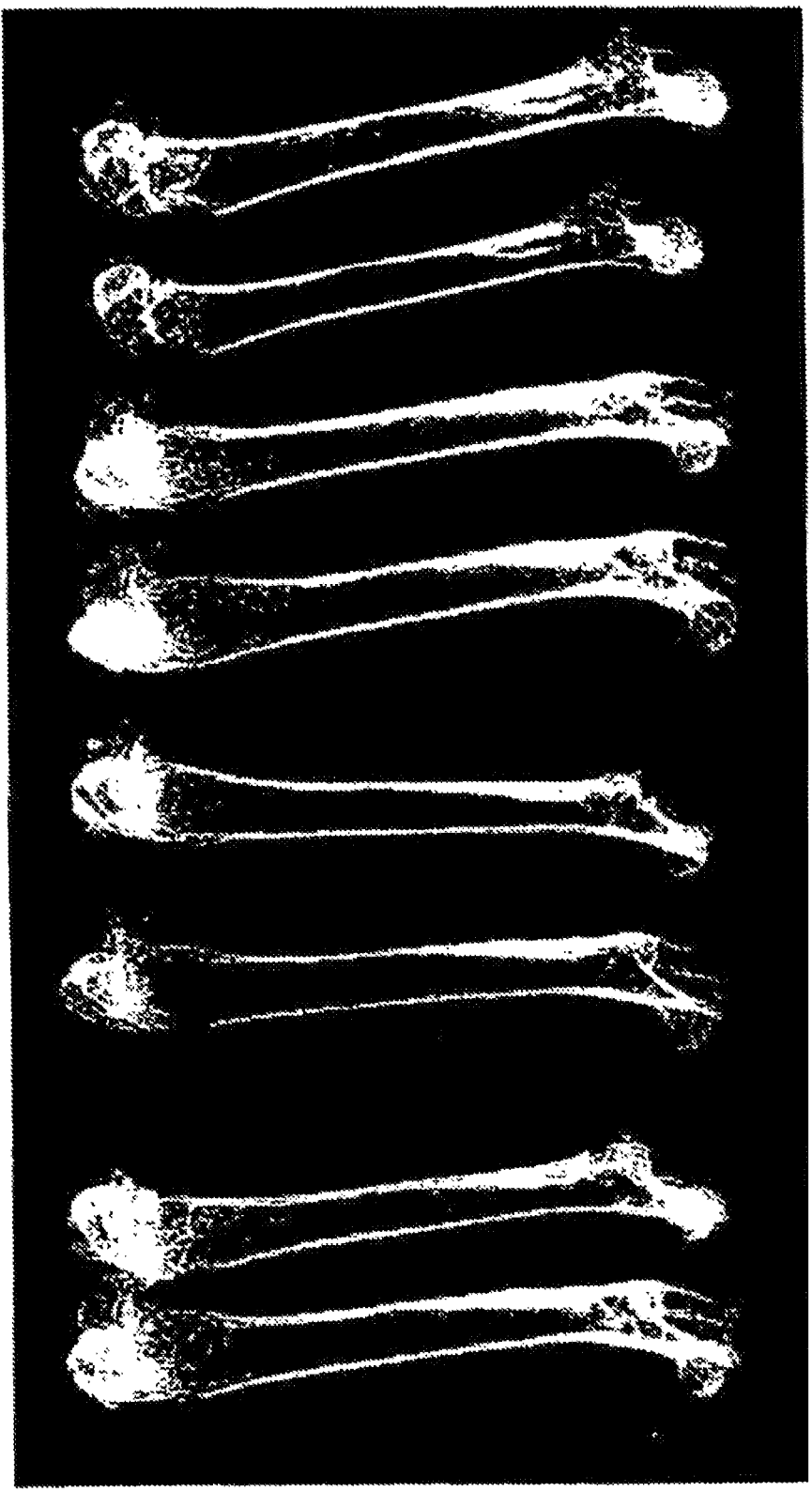
FIG. 10 shows X-ray pictures showing the femora collected from the mice that were sacrificed on days 44 to 46 after tumor transplantation.

Non tumor-bearing mice and CHO ras clone-1, CHO-OST190H or CHO-OST311H-transplanted mice were sacrificed on days 44 to 46 after transplantation, the femora were collected, and then the femora were fixed in 4% neutral formalin for 3 days. Next, the soft tissue surrounding the bone was removed. Two individuals were selected at random from each group, and then irradiated with X-ray using a radiography system μFX-100 (FUJI FILM, Japan) under the following conditions: X-ray tube voltage of 25 kV, X-ray tube current of 0.1 mA and exposure time of 5 seconds, and then exposed to an imaging plate. The results are shown in FIG. 10. Decreased bone trabecula of the cortical bone was observed in CHO-OST311H group.

EXAMPLE 12

Analysis of Nucleotide Sequence Homology and Genomic Region of OST311

Using at least a part of the amino acid sequence represented by SEQ ID No: 2 and of the nucleotide sequence represented by SEQ ID NO: 1, molecules corresponding to OST311 can be searched from various species. The mouse genome sequence database was searched using a partial nucleotide sequence of SEQ ID NO: 1, thus, a sequence having high homology with OST311 was found in the sequence of mouse chromosome 6 registered at Genbank under Accession No. AC0 15538. An amino acid sequence of a partial polypeptide of mouse OST311 obtained from the sequence is shown in SEQ ID NO: 10, and a nucleotide sequence corresponding to a partial sequence of cDNA is shown in SEQ ID NO: 9. FIG. 6 shows the results of comparing amino acid homology between human OST311 polypeptide and mouse OST311 polypeptide. As shown in Example 11, it became clear that OST311 polypeptide having the human amino acid sequence had clear biological activities in mice. These results suggest that the activity can be easily retained, even when these amino acids are substituted, deleted, or inserted within a region having low homology in the amino acid sequence as shown in FIG. 6.

The nucleotide sequence shown in SEQ ID NO: 1 and human 12p13 BAC RPCI11-388F6 (Accession No. AC008012) which had been recognized using the database to have a region that matches with a part of SEQ ID NO: 1 were compared, so that the sequence of the region encoding OST311 was determined. The nucleotide sequence neighboring OST311 gene is shown in SEQ ID NO: 11. TATAA box is present between nucleotide No. 498 to 502 of SEQ ID NO: 11. The first sequence matching with cDNA sequence (SEQ ID NO: 1) which we have determined, starts from nucleotide No. 1713 of SEQ ID NO: 11 and continues to nucleotide No. 2057. The next section matching with the nucleotide sequence represented by SEQ ID NO: 1 ranges from nucleotide No. 8732 to 8833 of SEQ ID NO: 11. This section is considered to be exon 2. The last section matching with the nucleotide sequence represented by SEQ ID NO: 1 starts from nucleotide No. 10644 and ends at nucleotide No. 12966 of SEQ ID NO: 11. The sequence ranging from nucleotide No. 498 to 12966 of SEQ ID NO: 11 can be considered to be at least a part of the gene encoding OST311. Further, it became clear that the STS sequence registered at Genbank under Accession No. G19259 is present between exon 1 and exon 2. OST311 is present in 12p13 region. According to Econs, M. J. et al., J. Clin. Invest. 100:2653-2657, 1997, it is inferred that the gene responsible for autosomal vitamin D-resistant rickets (ADHR) is present within a 18 cM region between D12S100 and D12S397, the microsatellite markers of 12p13 (particularly, within approximately a 10 cM region between D12S314 and D12S397), from a result of chain analysis. We evaluated the physical locations of the OST311 gene and the above microsatellite marker on the chromosome 12. As a result, D12S100 and D12S314 were in a 4602 to 6129 kb region, OST311 was in a 8958 to 9129 kb region, and D12S397 was in a 16280 to 16537 kb region. Based on these results and the strong phosphate metabolism-regulating activity of OST311, it was found that OST311 is the gene responsible for ADHR.

EXAMPLE 13

Short-term Experiment of Transplantation of CHO-OST311H Cells into Nude Mice

CHO-OST311H cells were transplanted subcutaneously into the dorsa of nude mice (6-week-old, BALB/c, male). On days 2 and 6 after transplantation, serum phosphate and calcium levels were measured, and the effect of recombinant OST311 within the short term was examined. CHO ras clone-1 cells were used similarly, as a control for this transplantation experiment.

(1) Transplantation of CHO Cells

In a manner similar to the method described in Example 11 (1), $2\times10^7$ CHO-OST311H cells and $2\times10^7$ CHO ras clone-1 cells were subcutaneously transplanted, each, into nude mice (n=6 each). Further, equivalent amounts of PBS were similarly subcutaneously transplanted (n=6). Each group of 6 nude mice was housed in a plastic cage and allowed to access to solid food CE-2 (CLEA JAPAN, Japan) and tap water ad libitum. At 6 days after transplantation, no significant tumor development was observed.

(2) Measurement of Serum Phosphate and Calcium Levels on Day 2 after Cell Transplantation On the next day after cell transplantation, blood was collected from the orbital cavity of the mice under the anesthetized condition using diethylethel. The peripheral blood was subjected to serum separation using Microtainer (Beckton Dickinson, USA). Serum Phosphate levels were measured using P-test Wako (Wako Pure Chemical Industries, Japan), and serum calcium levels were measured using calcium-test Wako (Wako Pure Chemical Industries, Japan). As shown in FIG. 11A, compared to the PBS-administered group and the CHO ras clone-1 cells-transplanted group, significant decreases in serum phosphate levels were observed in all cases of the CHO-OST311H cells-transplanted group. In contrast, no change was observed in serum calcium levels. These results clearly showed that OST311 caused decreases only in serum phosphate levels on day 2 after administration.

(3) Measurement of Serum Phosphate and Calcium Levels on Day 6 after Cell Transplantation On day 6 after cell transplantation, blood was collected from the hearts of the mice under the anesthetized condition using diethylethel. As described above, serum phosphate and calcium levels of each group were measured. As shown in FIG. 11B, similar to the results on day 2 after transplantation, compared to the PBS-administered group and the CHO ras clone-1 cells-transplanted group, significant decreases in serum phosphate levels were observed in all cases of the CHO-OST311H cells-transplanted group. In contrast, slight decreases were observed in serum calcium levels of among the CHO-OST311H cells-transplanted group.

EXAMPLE 14

Purification of Recombinant OST311

CHO-OST311H cells were allowed to grow in 10% FCS-containing MEMα medium within a 225 $cm^2$ culture flask (CORNING USA) at 37° C. under 5% $CO_2$ and 100% humidity. When the cells grew to cover approximately 80% of the area of the flask, the medium was replaced with 50 ml of a serum-free medium, CHO-S-SFM II (LIFE TECHNOLOGY, USA), and 48 hours later, conditioned medium was collected. Recombinant OST311 was purified by the following method using 1,000 ml in total of the conditioned medium obtained in this manner.

1000 ml of the conditioned medium was centrifuged at 16,200 g for 15 minutes at 4° C. to remove the suspended cells, and then the supernatant was subjected to SP-sepharose FF (Amersham Pharmacia, USA) packed in a glass column (30 mm in internal diameter×200 mm in length). The fraction that had passed through the column was adsorbed to Talon Superflow (metal chelate resin, CLONTECH, USA). Non-specific adsorbate was removed using a washing buffer consisting of 50 mM sodium phosphate buffer (pH 6.6) and 0.3 M NaCl, and then elution was performed using 50 mM sodium phosphate buffer (pH 6.7) and 0.2 M Imidazole. The right panel in FIG. 12 shows the elution fractions as detected by Western blotting using an anti-His6 antibody ('His6' disclosed as SEQ ID NO: 88) (INVITROGEN, USA). These fractions contained a partial polypeptide (SEQ ID NO: 8) consisting of the amino acid residue No. 180, Ser, to No. 251, Ile, described in Example 9. On the other hand, the above protein contained in the conditioned medium adsorbed to SP-sepharose FF was eluted in a 50 mM sodium phosphate buffer (pH 6.7) using a 0 to 0.7 M NaCl concentration gradient. The left panel in FIG. 12 shows the elution fractions as detected by Western blotting using an anti-His6 antibody ('His6' disclosed as SEQ ID NO: 88) (INVITROGEN, USA). These fractions eluted at approximately 0.3 M NaCl contained a partial polypeptide (SEQ ID NO: 4) consisting of the amino acid residue No. 25, Tyr, to No. 251, Ile described in Example 9. Further the center panel in FIG. 12 shows the elution fractions as detected by Western blotting using a polyclonal antibody (311-114) prepared using the OST311 partial peptide (SEQ ID NO: 29) described in Example 10. These fractions eluted at a concentration of approximately 0.4 M NaCl contained a partial peptide (SEQ ID NO: 6) which comprises amino acid residue No. 25, Tyr to No. 179, Arg, described in Example 9. Thus, the fractions containing three types of OST311 partial peptide, specifically, SEQ ID NO: 4 (hereinafter, referred to as 311: 25-251), SEQ ID NO: 6 (hereinafter, referred to as 311: 25-179) and SEQ ID NO: 8 (hereinafter, referred to as 311:180-251) were purified and separated, and then concentrated using a VIVASPIN column with a molecular weight of 10,000 (Sartorius, USA) for ultra-filtration, followed by replacement with a solvent consisting of 1 ml of 5 mM HEPES (pH 6.9) and 0.1 M NaCl.

EXAMPLE 15

Histological Analysis of Undemineralized Bone Section

When CHO-OST311H cells-transplanted mice and non tumor-bearing mice prepared in Example 11 were sacrificed, the right femora and tibiae were excised, leaving the connection at the knee joint intact. Immediately after cutting the shaft of the tibiae and the shaft of femora, the femora and tibiae were stored in previously prepared ice-cooled neutral formalin. Thus, undemineralized specimens were prepared. The method for preparing the unmineralized specimens is described below.

The bone tissues were pre-stained with Villanueva bone stain for 3 to 7 days. The tissues were dehydrated through a graded alcohol series, and then the solvent was replaced with acetone. After acetone monomer and then monomer were applied, the tissue samples were embedded in resin. Methyl methacrylate (MMA) resin was used for embedding the samples. The tissue samples were placed in an incubator at about 35° C. for complete polymerization. At this time, the tissues were kept embedded sufficiently within the resin by appropriate addition of MMA. MMA used herein for embedding samples was prepared by adding and completely dissolving 40 g of MMA polymer (Wako Pure Chemical Industries, Japan) in 100 ml of MMA monomer (Wako Pure Chemical Industries, Japan), and then adding and completely dissolving Benzoyl peroxide (Nacalai Tesque, Japan) at a rate of 1 g per solution. The specimens were prepared for tibia. To be able to observe the cancellous bone of the tibia, the frontal section was trimmed, and then 4 μm-thick frontal section samples were prepared using a microtome for hard tissues (type RM2065 super cut, Leica). Post-staining with Villanueva-Goldner was carried out. The thus obtained sections were cleared in xylene, and then sealed in using CLEAR SEAL (MARUTO, Japan) and ONE LIGHT (MARUTO, Japan).

Microscopic images of the sections are shown in FIG. 13. Increased width of the growth plate was observed in CHO-OST311H cells-transplanted tumor-bearing mice, compared to the control group. Further, significantly increased osteoid and decreased mineralized area were observed in the metaphysis. There was no evidence of ostitis fibrosa, and the bone collected from CHO-OST311 cells-transplanted tumor-bearing mouse exhibited typical features of osteomalacia.

EXAMPLE 16

Examination of Vitamin D Metabolism at an Early Stage after Transplantation with CHO-OST311H Cells To examine the effect of OST311 on vitamin D metabolism, an experiment of transplanting CHO-OST311H cells into nude mice (6-week-old, BALB/c, male) was conducted in a manner similar to the method described in Example 13. Two experimental control groups consisting of a group which was transplanted similarly with CHO ras clone-1 cells, and a group administered with PBS in an equivalent dose with the cell suspension solution were established and used for comparison. Each group consisting of 6 mice was housed in a plastic cage with free access to tap water and solid food CE2 containing 1.03% inorganic phosphate and 1.18% calcium (CLEA JAPAN, Japan). Fluctuations in serum 1,25-hydroxyvitamin D levels and changes in the expression of vitamin D-metabolizing enzyme groups on days 1, 2, 3 and 6 after transplantation were examined.

(1) Measurement of Serum 1,25-Dihydroxyvitamin D Levels

On days 1, 2, 3 and 6 after cell transplantation, blood was collected from the heart of the mice of the PBS-administered group, the CHO-ras clone-1 cells-transplanted group and the CHO-OST311H cells-transplanted group, respectively under the anesthetized condition with diethylethel, and then sera were separated using a Microtainer (Beckton Dickinson, USA). Equivalent volumes of the sera collected from each mouse were mixed together to have a total volume of 0.25 ml per group. 1,25-dihydroxyvitamin D levels contained therein were measured using 1,25(OH)2D RIA-Kit, "TFB" (TFB, Japan). As a result, as shown in Table 6, significant decreases in 1,25-dihydroxyvitamin D levels were already observed on day 1 after transplantation in the CHO-OST311H cells-transplanted group, compared to the PBS-administered group and the CHO-ras clone-1 cells-transplanted group. This decreasing effect was also observed on days 2, 3 and 6 after transplantation. These results were consistent with decreases in serum 1,25-dihydroxyvitamin D levels, which is a typical clinical finding for tumor-induced osteomalacia.

TABLE 6

Serum 1,25-dihydroxyvitamin D levels in cells-transplanted mice

| | Days after transplantation | | | |
|---|---|---|---|---|
| | 1 | 2 | 3 | 6 |
| PBS-administered group (pmol/L) n = 5 | 338 | 164.3 | 164.5 | 273.7 |
| CHO-ras clone-1 cells-transplanted group (pmol/L) n = 6 | 271.9 | 178.3 | 182.9 | 184.6 |
| CHO-OST311cells-transplanted group (pmol/L) n = 6 | 46.7 | 36.3 | 34.5 | 49.1 |

(2) Expression Analysis of Vitamin D-Metabolizing Enzyme Genes in the Kidney

To study whether the above effect of decreasing 1,25-dihydroxyvitamin D3 was due to fluctuations in 25-hydroxyvitamin D-1-α-hydroxylase (1αOHase) gene or in 25-hydroxyvitamin D-24-hydroxylase (24OHase) gene, 3 or 4 mice were selected at random from each of the PBS-administered group, the CHO-ras clone-1 cells-transplanted group and the CHO-OST311H cells-transplanted group on day 3 after transplantation. The kidneys were excised, total RNAs were prepared according to the procedures described in Example 11 (7), and then the Northern blotting was performed using the probes described in the same. FIG. 14 shows the results. mRNA expression levels of 1αOHase gene were observed to be significantly attenuated in the CHO-OST31H cells-transplanted group, compared to the PBS-administered group and the CHO-ras clone-1 cells-transplanted group. This result suggests a possibility that OST311 directly or indirectly suppresses the expression of this gene, so as to suppress biosynthesis of serum 1,25-dihydroxyvitamin D. On the other hand, mRNA expression levels of 24OHase gene were significantly enhanced in the CHO-OST311H cells-transplanted group, compared to the PBS-administered group and the CHO-ras clone-1 cells-transplanted group. This result suggests a possibility that OST311 directly or indirectly enhances the expression of this gene, so as to promote inactivation of serum 1,25-dihydroxyvitamin D.

In example 11(8), no significant difference in serum 1,25-dihydroxyvitamin D levels on days 44 and 46 after transplantation was observed, compared to the control group. Another result was different from the result in this example in that mRNA expression levels of 1αOHase tended to increase. At least one possible explanation for the difference is due to the effect of serum parathyroid hormones described in Example 17.

EXAMPLE 17

Examination of Serum Parathyroid Hormone Levels at an Early Stage after Transplantation with CHO-OST311H Cells Each mouse serum collected in equivalent volumes on days 1, 2, 3, 6 and 45 after transplantation with CHO cells described in Example 11, 13 and 16 was well mixed together to have a total volume of 0.15 ml. Then, serum parathyroid hormone levels were measured using a Rat PTH IRMA kit (Nihon Medi-Physics, Japan) according to the attached manufacturer's manual. As shown in Table 7, significantly increased levels of serum parathyroid hormone were observed in CHO-OST311-transplanted group, and the difference was significant on day 45 after transplantation.

TABLE 7

Parathyroid hormone levels in cells-transplanted mice

| | Days after transplantation | | | | |
|---|---|---|---|---|---|
| | 1 | 2 | 3 | 6 | 45 |
| PBS-administered group (pg/ml) n = 5 | 45.2 | 23.8 | 28.2 | 19.7 | [1] 41.9 |
| CHO-ras clone-1 cells-transplanted group (pg/ml) n = 6 | 15.8 | 26.6 | 15.7 | 13.8 | [2] 40.4 |
| CHO-OST311 cells-transplanted group (pg/ml) n = 6 | 13.8 | 20.6 | 44 | 57.8 | [3] 211.7 |

[1] Measured value when non tumor-bearing mice (n = 6) were used.
[2] n = 10.
[3] n = 12.

EXAMPLE 18

Experiment of Administering Cho-producing Recombinant OST311H Full-Length Protein to Normal Mice To study the effect of CHO-producing recombinant OST311H full-length protein on normal mice (BALB/c, male, 6-week-old), a polypeptide having a histidine tag added to the C-terminus of the $25^{th}$ amino acid residue, Tyr, to the $251^{st}$ Ile (SEQ ID NO: 4) was partially purified by the purification method described in Example 14 (1). This purified fraction was intraperitoneally administered to normal mice at 0.1 ml per administration. It was assumed that this purified fraction contained approximately 0.15 to 0.75 µg of recombinant OST311, based on the fluorescent intensity obtained by Western blotting. Similar to Example 14, 0.1 ml each of a solvent (5 mM HEPES buffer/0.1 M NaCl, pH=7.0) was intraperitoneally administered to the control group. The OST311-administrated group and the control group consisted respectively of five mice. Each group of 5 mice was housed in a plastic cage and allowed to access to tap water and solid food CE2 (CLEA JAPAN, Japan) containing 1.03% inorganic phosphate and 1.18% calcium ad libitum.

EXPERIMENT 1

The experimental outline is shown in FIG. 15A. Additional administration was performed at 5, 10, 23, 28 and 33 hours after the 1st intraperitoneal administration. Thus, intraperitoneal administration was performed 6 times in total. Subsequently, blood was collected from the orbital cavity using glass-made capillaries at 36, 47 and 71 hours after the 1st intraperitoneal administration, and then sera were separated using a Microtainer (Beckton Dickinson, USA).

Phosphate and calcium levels in the thus obtained sera were determined using P-test Wako or calcium-test Wako (Wako Pure Chemical Industries, Japan) according to the attached manufacturer's manual. Thus, as shown in FIG. 15B, effects of significantly decreasing serum phosphate levels were observed (t-test **p<0.001, *p<0.01) in the OST311-administered group at 36 hours after the 1st administration. In addition, this effect was further maintained at 11 hours after this time point (47 hours after the 1st administration). On the other hand, this activity disappeared at 71 hours after the 1st administration (38 hours after the final administration). Moreover, no significant change was found in serum calcium levels at any time (FIG. 15C).

EXPERIMENT 2

The experimental outline is shown in FIG. 16A. Additional administration was performed at 5 and 11 hours after the 1st intraperitoneal administration. Thus, intraperitoneal administration was performed 3 times in total. Subsequently, blood was collected from the orbital cavity using glass-made capillaries at 13 and 24 hours after the 1st intraperitoneal administration, and then sera were separated using a Microtainer (Beckton Dickinson, USA). Phosphate and calcium levels in the thus obtained sera were measured respectively using P-test Wako and calcium-test Wako according to the attached manufacturer's manual. Thus, as shown in FIG. 16B, effects of significantly decreasing serum phosphate levels were observed (t-test **p<0.05, *p<0.01) in the OST311-administered group at 13 hours after the 1st administration. Further, this effect was maintained at 11 hours following this time point. Furthermore, no significant change in serum calcium levels was observed at any time (FIG. 16C).

The results of Experiments 1 and 2 revealed that intraperitoneal administration into normal mice with the full-length fraction of CHO-producing recombinant OST311 protein induces hypophosphatemia, the effect of decreasing serum phosphate levels was already observed at 13 hours after the first administration, and the activity was maintained at least for 11 hours after the administration was stopped.

EXAMPLE 19

Introduction of Amino Acid Mutation into OST311

As described in Example 9, it was shown that a part of recombinant OST311 produced by CHO-OST311H cells is cleaved during its secreting process by a polypeptide (SEQ ID NO: 6) having a sequence from the $25^{th}$ Tyr to the $179^{th}$ Arg amino acid residues and a polypeptide (SEQ ID NO: 8) having a sequence from the $180^{th}$ Ser to the $251^{st}$ Ile amino acid residues.

This cleavage may be due to a protease which recognizes a motif consisting of RXXR sequence or RRXXR sequence located immediately before the $180^{th}$ Ser amino acid residue. When the full-length recombinant is administered into a living organism, it is considered that the recombinant has a possibility to undergo this cleavage or degradation similar to this cleavage. Hence, gene OST311RQ encoding a sequence which can substitute both the $176^{th}$ Arg and the $179^{th}$ Arg amino acid residues with Gln was prepared for introducing the mutation.

(1) Preparation of OST311/pCAGGS Plasmid

PCR was performed by LA Taq polymerase (TAKARA SHUZO, Japan) using OST311H/pcDNA3.1 plasmid as a template, and 311F1EcoRI (SEQ ID NO: 22) and 311Not (SEQ ID NO: 44) as primers. After maintaining the temperature at 94° C. for 1 minute, reaction was performed for 25 cycles, each cycle consisting of 94° C. for 30 seconds, 55° C. for 30 seconds and 72° C. for 1 minute. After reaction, the PCR products were blunt-ended using T4 DNA polymerase (Roche, Swiss), and then phenol-chloroform treatment was performed to inactivate the enzyme. DNA was precipitated using ethanol, and then the DNA ends were phosphorylated using polynucleotide kinase (Roche, Swiss). Target DNA fragments were separated by 0.8% agarose gel electrophoresis, and then collected using Gene clean II (BIO101, USA). Plasmid vector pCAGGS (Niwa H, et al., Gene. 1991 Dec. 15; 108(2): 193-9.) was digested with EcoR I, and then blunt-ended using Klenow fragments (Roche, Swiss). Subsequently, dephosphorylation of DNA ends was performed using bovine small intestine alkaline phosphatase (TAKARA SHUZO, Japan). The target DNA fragments were separated by 0.8% agarose gel electrophoresis, and then collected using Gene Clean II (BIO101, USA). The thus obtained OST311cDNA was ligated to pre-digested pCAGGS plasmid using a DNA ligation kit (version 2) (TAKARA SHUZO, Japan) according to the attached manufacturer's manual. The product was introduced into *Escherichia coli* DH5α for cloning, so that the relevant plasmid was obtained. This plasmid DNA was used for preparing OST311RQH gene.

311LNot:
ATAAGAATGCGGCCGCTCAGATGAACTTGGCGAA (SEQ ID NO: 44)

(2) Preparation of OST311RQH Gene
The following primers were synthesized.

(SEQ ID NO: 45)
OST311ME1:
ATGAATTCCACCATGTTGGGGGCCCGCCTCAGG (SEQ ID NO: 46)
OST311HNt:
ATGCGGCCGCCTAATGATGATGATGATGATGGATGAACTTGGCGAAGGG (SEQ ID NO: 47)
OST311RQF:
ATACCACGGCAGCACACCCAGAGCGCCGAG (SEQ ID NO: 48)
OST311RQR:
CTCGGCGCTCTGGGTGTGCTGCCGTGGTAT

OST311ME1 is a forward primer which is a section containing the initiation methionine of OST311, OST311HNt is a reverse primer which adds 6 histidines (SEQ ID NO: 88)to the 3' terminus of OST311, OST311RQF and OST311RQR are a forward primer and a reverse primer for introducing mutations, respectively by substituting the 527$^{th}$ and 536$^{th}$ guanines (corresponding to the 659$^{th}$ and 668$^{th}$ guanines in SEQ ID NO: 1) in the coding region of OST311 cDNA with adenines, so as to substitute the arginines at amino acid No. 176 and 179 with glutamines. 2 types of reaction solutions were prepared 20 μL each according to the attached manufacturer's manual using pfu DNA polymerase (Promega, USA). On the one hand, OST311ME1 and OST311RQR were used as primers at a final concentration of 0.2 μM, and 10 ng of OST311 expression vector described in Example 6 (1) was used as a template. After the temperature was maintained at 94° C. for 1 minute, PCR reaction was performed for 25 cycles, each cycle consisting of 94° C. for 30 seconds, 55° C. for 30 seconds and 72° C. for 1 minute. On the other hand, OST311RQF and OST311HNt were used as primers at a final concentration of 0.2 μM, and 10 ng of OST311/pCAGGS plasmid was used as a template. After the temperature was maintained at 94° C. for 1 minute, PCR reaction was performed for 35 cycles, each cycle consisting of 94° C. for 30 seconds, 55° C. for 30 seconds and 72° C. for 1 minute. The above two types of reaction products were diluted 10-fold respectively, and then 1 μL of each solution was added to 50 μL of a reaction solution prepared using LA Taq polymerase (TAKARA SHUZO, Japan) according to the attached manufacturer's manual. After the temperature was maintained at 94° C. for 1 minute, PCR reaction was performed using LA Taq polymerase (TAKARA SHUZO, Japan) and OST311 ME1 and OST311HNt as primers at a final concentration of 0.2 μM for 25 cycles, each cycle consisting of 94° C. for 30 seconds, 55° C. for 30 seconds, and 72° C. for 1 minute. After PCR reaction, the solution was maintained at 72° C. for 7 minutes. The thus obtained reaction product was subjected to phenol/chloroform treatment, deproteinization, ethanol precipitation, and then digestion with EcoR I and Not I. An approximately 800 bp DNA fragment was separated by 2% agarose gel electrophoresis, and then collected using Gene Clean II (BIO101, USA). The thus obtained DNA fragment was inserted to the EcoR I, Not I site of a vector, IRES-EGFP-pEAK8 that had been prepared by ligating an internal ribosomal entry site (IRES) and enhanced green fluorescent protein (EGFP) to a plasmid pEAK8 (EdgeBioSystems, USA), thereby obtaining OST311RQH/IRES-EGFP/pEAK8 plasmid. Plasmid DNA was prepared according to the standard methods, and then the nucleotide sequence was determined using ABI3700 fluorescence DNA sequencer (PE Applied Systems, USA), thereby confirming that the sequence encodes a polypeptide wherein relevant mutations R176Q and R179Q are introduced and the histidine tag is added to the C-terminus. The polypeptide encoded by this gene is hereinafter referred to as OST311RQH.

(3) Isolation of the CHO Cells which Stably Express OST311RQH

OST311RQH/IRES-EGFP/pEAK8 plasmid was introduced into CHO-ras clone-1 cell using Transfectam (Promega, USA) according to the attached manufacturer's manual. Drug resistant cells were selected in MEMα medium containing 5 μg/mL puromycin and 10% FCS. Then, cells with strong fluorescence intensity of GFP (Green Fluorescent Protein) were sorted using FACS vantage (Beckton Dickinson, USA), and then cloned. When the cloned cells reached confluent, the medium was replaced with serum-free DF (DMEM/F-12) medium, and then conditioned medium was collected 2 days after replacement. 50 μL of the collected conditioned medium was adsorbed to Immobilon P filter (Millipore, USA) using a 96 well convertible filter system (Lifetechoriental, USA). The prepared filter was washed with TBS and TTBS, and then subjected to blocking using Blockace (Daiichi Pharmaceutical, Japan) for 1 hour at room temperature. After blocking, the filter was allowed to react for 1 hour with HRP-labeled anti-His6 monoclonal antibody ('His6' disclosed as SEQ ID NO: 88) (Invitrogen, USA) diluted 5000 fold with Blockace. After reaction, the filter was washed with TTBS and TBS, and then signal detection was performed using ECL (Amersham Pharmacia, USA) according to the attached manufacturer's manual. Based on signal intensity, high expression clone CHO-OST311RQH was selected.

(4) Preparation of Conditioned Medium of the OST311RQH Peak Rapid Cells pEAK rapid cells (EdgeBioSystems, USA) were inoculated in 20 flasks for tissue culture (225 cm$^2$, CORNING, USA). 0.48 mg of OST311RQH/IRES-GFP/pEAK8 plasmid was transfected to the cells by a phosphate calcium method according to the attached manufacturer's manual of pEAK system (EdgeBioSystems, USA). The cells were allowed to stand for 4 hours. Next, the medium of each flask was replaced with 50 mL of serum-free MEMα medium, the cells were cultured for 2 days at 37° C., and then the conditioned medium was collected.

(5) Confirmation of Expression of Recombinant OST311RQH

The conditioned medium resulting from the transient expression of the 2 types of the above CHO-OST311RQH cell clones and pEAK rapid cells, 10 μL each, were subjected to the Western blotting in the manner as described in Example 6(3), so that the presence of recombinant OST311RQH in the culture supernatant was examined. Anti-His (C-terminus) antibody (Invitrogen, USA) was used as a detection antibody. Thus as shown in FIG. 17, a strong signal located at the same position with approximately 32 kDa band described in Example 6(3) was observed for all the culture supernatants. Moreover, for all the conditioned medium, an approximately 10 kDa signal which was present in the CHO-OST311H conditioned medium was not observed by Western blotting. It can be inferred from these results that introduction of mutations R176Q and R179Q caused inhibited or attenuated cleavage of the polypeptide that was predicted to occur at these positions, so that the ratio of the presence of the polypeptide (SEQ ID NO: 8) having a sequence from the $180^{th}$ Ser to the $251^{st}$ Ile amino acids decreased significantly.

EXAMPLE 20

Administration Experiment of Recombinant OST311RQH to Normal Mice

A purified fraction containing approximately 2.8 μg/ml recombinant OST311RQH protein was obtained from 500 ml of the culture supernatant prepared in Example 19 (5) according to the method described in Example 14 (1). The purified fraction was successively administered, 0.1 ml/administration, intraperitoneally to normal mice (BALB/c, male, 6-week-old), and then serum phosphate, calcium and 1,25-dihydroxyvitamin D levels were measured. To a control group, a vehicle (5 mM HEPES buffer/0.1 M NaCl pH=7.0) was similarly administered, 0.1 ml each, intraperitoneally. The OST311RQH-administrated group and the control group consisted respectively of 6 mice. Each group of 6 mice was housed in a plastic cage and allowed to access to tap water and solid food CE2 (CLEA JAPAN, Japan) containing 1.03% inorganic phosphate and 1.18% calcium ad libitum.

Experimental protocols are shown in FIG. 18A. Additional administration was performed at 5, 10, 24, 29 and 34 hours after the 1st administration. Thus, administration was successively performed 6 times in total. In the process of the above procedures, under the anesthetized condition with diethylethel, blood was collected from the orbital cavity using glass-made capillaries at 24 hours after the first administration (immediately before 4th administration), and blood was collected from the heart at 48 hours after the first administration.

(1) Measurement of Serum Phosphate and Calcium Levels

Serum phosphate levels of the serum collected at 24 and 48 hours after the first administration were measured by the method described in Example 14 (3). As a result, at any time of blood collection, the OST311RQH-administered group showed significant hypophosphatemia, as shown in FIG. 18B (t-test **p<0.01, *p<0.05). In contrast, no significant fluctuation was observed in serum calcium levels (FIG. 18C).

(2) Measurement of Serum 1,25-Dihydroxyvitamin D Levels

Equivalent volumes of sera collected from each mouse at 48 hours after the first administration were mixed together by each group. Then, serum 1,25-dihydroxyvitamin D levels were measured by the method described in Example 16(1). As a result, while the control group showed 244.7 pmol/L, the OST311RQH-administered group showed a significant decrease, 24.6 pmol/L.

EXAMPLE 21

CHO-OST311RQH Cell Transplantation Experiment

An experiment, wherein CHO-OST311RQH that stably expresses OST311RQH cells as established in Example 19 (3) were transplanted into nude mice (7-week-old, BALB/c-nude, male, n=8) was carried out similarly to the method described in Example 13. CHO ras clone-1 cells were similarly transplanted as a control group (n=6). Each group of the nude mice was housed in a plastic cage and allowed to access to tap water and solid food CE2 (CLEA JAPAN, Japan) 1.03% inorganic phosphate and 1.18% calcium ad libitum.

On day 2 after cell transplantation, blood was collected from the orbital cavity using glass-made capillaries, and then serum phosphate and calcium levels were measured by a method similar to the method described in Example 14(3). As shown in FIG. 19A, a significant decrease in serum phosphate levels was observed in the CHO-OST311RQH cells-transplanted group (t-test *p<0.001), while no significant change was observed in serum calcium levels (FIG. 19B)

EXAMPLE 22

Preparation of Anti-OST311 Partial Peptide Polyclonal Antibody (2)

4 types of partial OST311 peptides were prepared (SEQ ID NO: 49 to 52) in the manner described in Example 10. Rabbits were immunized with these peptides as antigens, and then Western blotting was performed according to the method described in Example 6(3) using the resulting anti-sera, so that recombinant OST311H was detected in the serum-free conditioned medium of CHO-OST311H cells. Antibody reaction was performed in a solution, which had been prepared by diluting the anti-sera for each peptide 250-fold with TTBS, at 4° C. with agitation overnight. After washing, alkaline phosphatase-labeled goat anti-rabbit antibody (DAKO, Denmark) was added to the solution for binding, and then recombinant OST311 was detected using an alkaline phosphatase coloring kit (BIO-RAD, USA) (FIG. 20).

Partial Peptides

```
311-148:   GMNPPPYSQFLSRRNEC    (SEQ ID NO: 49)

311-170:   CNTPI PRRHTR         (SEQ ID NO: 50)

311-180:   SAEDDSERDPLNVLKC     (SEQ ID NO: 51)

311-210:   LPSAEDNSPMASDC       (SEQ ID NO: 52)
```

EXAMPLE 23

Construction of ELISA System for Detecting OST311 Protein (1) Purification of Antibody from Anti-OST311 Partial Peptide Rabbit Anti-Serum Econo-Pac disposable chromatography column (BIO-RAD, USA) was filled with 3 ml slurry of protein A sepharose 4FF (Amersham pharmacia, USA), and then washed with 10 ml of 0.1 M glycine hydrochlorate buffer (pH 3.3) and 20 ml of PBS. 2 types of rabbit anti-sera described in Example 10 and 4 types of the same described in Example 22 were added 800 to 900 µl each, so that antibody fractions were adsorbed to the resin. The column was washed with 9 ml of PBS to remove contaminants, and then 1 ml each of 0.1 M glycine hydrochlorate buffer (pH 3.3) was added, thereby obtaining IgG elution fractions. Upon elution, 10 µl of a neutralization buffer (1 M Tris) was added to each fraction whenever necessary to neutralize the solutions. The absorbance at 280 nm was measured so as to determine the concentration of antibody contained in the elution fraction (absorbance coefficient calculated as: $1.34$ $(\text{mg/ml})^{-1} \cdot (\text{cm})^{-1}$). Then, some fractions were together applied to a NAP25 column, and the solvent was replaced with 50 mM sodium hydrogen carbonate solution. As a result, 5 to 15 mg of antibodies were obtained (these polyclonal antibodies are hereinafter respectively referred to as 311-48 antibody, 311-114 antibody, 311-148 antibody, 311-170 antibody, 311-180 antibody and 311-210 antibody) from each peptide anti-serum.

(2) Biotinylation of Anti-OST311 IgG

All the above 6 types of anti-OST311 peptide polyclonal antibodies were diluted to 1 mg/ml in 50 mM sodium hydrogen carbonate solution. Then, 1 mg of each type of antibodies was mixed well with Biotin-AC5-Osu solution (1.82 µg/ml) (Japan, Dojindo) dissolved in 10 µl of dimethylformamide by inversion for 2 hours at 4° C. Subsequently, the mixed solution was subjected to NAP10 column to remove unreacted Biotin-AC5-Osu and the solvent was replaced with PBS, thereby obtaining 6 types of biotinylated anti-OST311 peptide polyclonal antibodies.

(3) Detection of OST311 in the Conditioned Medium of OST311-Expressing Cells by the Sandwich ELISA Method Using Anti-OST Peptide Rabbit Polyclonal Antibody A sandwich ELISA system was constructed by combining the 6 types of anti-OST311 peptide polyclonal antibodies for immobilization and the above 6 types of biotinylated antibodies for detection. Thus, detection of OST311 protein in the conditioned medium of OST311-expressing cells was examined.

The above 6 types of anti-OST311 peptide polyclonal antibodies for immobilization obtained by Protein A purification were diluted to 10 µg/ml in 50 mM sodium hydrogen carbonate solution. 50 µl of each diluted solution was added to each well of a 96-well ELISA plate Maxisorp (Nunc, USA), and then allowed to stand for 1 hour at 37° C., thereby immobilizing IgG Next, the reaction solution was removed, and then 50 µl of Superblock blocking buffer in TBS (PIERCE, USA) was added per well to carry out blocking at room temperature for 10 minutes. After the solution was removed, OST311RQH peak rapid culture supernatant described in Example 19(5) or MEMα medium as a control was added, 50 µl per well, and then allowed to stand at room temperature for 1 hour for binding with the immobilized antibodies. After antibody reaction, the solution was washed three times with TTBS, 50 µl each of the above 6 types of biotinylated anti-OST311 antibodies (311-48, 311-114, 311-148, 311-170, 311-180 and 311-210) diluted to 10 µg/ml with TTBS containing 10% Blockace (Dainippon Pharmaceutical, Japan) was added per well, and then allowed to stand at room temperature for 30 minutes, thereby performing secondary antibody reaction. Each well was washed three times with TTBS, and then 50 µl of HRP-labeled streptavidin (DAKO, Denmark) diluted 10,000 fold with TTBS containing 10% Blockace was added per well, and then allowed to stand at room temperature for 30 minutes for binding with the biotinylated antibodies. Each well was then washed three times with TTBS, and then 50 µl of tetramethylbenzidine, the peroxidase chromogenic substrate (DAKO, Denmark) was added per well, and then allowed to develop color at room temperature for 5 minutes. Subsequently, 50 µl of 0.5 M sulfuric acid solution was added per well to stop reaction. Measurement was performed using an absorbance measurement system MTP300 (CORONA ELECTRIC, Japan) for a 96-well plate, and the absorbance at 450 nm was divided by the absorbance at 570 nm. When only MEMα was added as a control, each of values obtained by 450 nm/570 nm was 0.02 or less in every cases. In contrast, as shown in FIG. 21A, with a combination of immobilized 311-48 antibody and detection with 311-180 antibody, or a combination of immobilized 311-180 antibody and detection with 311-148 antibody, OST311RQH in the conditioned medium could be detected significantly more than the control. Moreover, with a combination of immobilized 311-48 antibody and detection with 311-148 antibody, it is inferred that not only the full-length polypeptide, but also the N-terminal partial polypeptide fragment can be detected, because the antigenic sites of both antibodies were contained in the N-terminal partial peptide (SEQ ID NO: 6) following the cleavage of OST311 protein described in Example 9. In contrast, with a combination of immobilized 311-210 antibody and detection with 311-180 antibody, it is inferred that not only the full-length, but also the C-terminal partial peptide (SEQ ID NO: 8) following cleavage described in Example 9 can be detected. Therefore, the multiple use of these combinations makes it possible to measure the absolute amount of and the ratio of the presence of OST311 full-length polypeptide and partial polypeptides in specimens, such as biological samples.

(4) Quantitative Determination of Recombinant OST311 Protein Concentration by Sandwich ELISA Method Using Anti-OST311 Peptide Rabbit Polyclonal Antibody In the above ELISA system, detection of purified recombinant OST311H consisting of a serial dilution of 1, 0.67, 0.33, 0.1, 0.067, 0.033 and 0.01 µg/ml were examined with a combination of 311-48 antibody or 311-180 antibody as an immobilized antibody and 311-148 antibody as an antibody for detection. As shown in FIG. 21B, fine linearity could thus be obtained within a range of 0.1 to 1 µg/ml (311-48: $R^2=0.990$, 311-180: $R^2=0.996$). This result revealed that recombinant OST311H at least within this concentration range can be detected.

EXAMPLE 24

Examination of Effect by Single Administration of Recombinant OST311 Protein To examine the short-term effect of CHO-producing recombinant OST311H full-length protein on normal mice (BALB/c, male, 6-week-old), purified recombinant OST311H full-length protein was administered once, 5.0 µg/0.1 ml per mouse via the caudal vein. To a control group, 0.1 ml of a vehicle (PBS) was administered per mouse via the caudal vein. At 1, 3 and 8 hours after administration, blood collection from the heart and dissection were performed, serum phosphate, calcium and vitamin D levels were measured, and then the expression amount of the sodium-phosphate cotransporter on the renal proximal tubule was analyzed. The OST311-administrated group and the control group respectively consisted of 6 mice. 6 mice per group were housed and allowed to access to tap water and solid food CE2 (CLEA JAPAN, Japan) containing 1.03% inorganic phosphate and 1.18% calcium ad libitum.

(1) Time-Course Changes in Serum Phosphate Levels

As shown in Table. 8, while no significant change was observed in serum phosphate levels at 1 and 3 hours after single administration with OST311 protein, at 8 hours after administration, a significant decrease was observed. This result clarified that the effect of OST311 requires 3 to 8 hours to lower serum phosphate levels. On the other hand, no change was observed in serum calcium levels at all time.

TABLE 8

Serum phosphate levels

| | Time | | |
|---|---|---|---|
| | 1 | 3 | 8 |
| Vehicle-administered group (mg/dL) | 9.82 ± 0.61 | 9.99 ± 0.20 | 9.55 ± 0.29 |
| OST311-administred group (mg/dL) | 9.61 ± 0.51 | 9.96 ± 0.39 | 7.82 ± 0.27 |
| t-test | p > 0.5 | p > 0.5 | p < 0.005 |

(2) Expression of Sodium-Phosphate Cotransporter on Renal Proximal Tubule

According to the method described in Example 11(6), the kidneys collected at 1, 3 and 8 hours after administration were mixed together per group, and then brush border membranes (BBM) of proximal tubule were prepared. The ratio of the presence of sodium-phosphate cotransporter (NaPi7) protein in the obtained BBM was analyzed by the Western blotting method. As shown in FIG. 22A, while the expression amounts of NaPi7 at 1 and 3 hours after administration were equivalent to that of the vehicle-administered group, NaPi7 in the OST311-administered group at 8 hours after administration was shown to be significantly decreased compared to that of the vehicle-administered group. Meanwhile, to examine if the decreased NaPi7 protein was associated with RNA transcription regulation, according to the procedure described in Example 11 (7), total RNA was prepared from the kidneys excised from each mouse and Northern blotting was performed using the probe described in the same. Thus, as shown in FIG. 22B, while mRNA levels of NaPi7 at 1 and 3 hours after administration were equivalent to that of the vehicle-administered group, NaPi7 in the OST311-administered group at 8 hours after administration was shown to be significantly decreased compared to that of the vehicle-administered group. The above results clearly showed that decreases in serum phosphate levels due to direct or indirect effect of recombinant OST311 protein correlated with downregulation of sodium-phosphate cotransporter on the renal tubule in their times of fluctuations, and suppression of NaPi-7 at the mRNA transcription level occurs at least as a factor contributing to the downregulation at the protein level.

(3) Time-course changes in serum 1,25-dihydroxy vitamin D3 levels Serum 1,25-dihydroxyvitamin D3 levels at 1, 3 and 8 hours after administration were measured by the method described in Example 16(1). As shown in FIG. 23, in the OST311-administered group, a significant decrease in serum 1,25-dihydroxyvitamin D3 level was already observed at 3 hours after administration, and a further decrease in the same was observed at 8 hours after administration.

(4) Changes in Expression of Vitamin D-Metabolizing Enzyme Genes

To elucidate whether the decreased serum 1,25-dihydroxyvitamin D3 levels were due to fluctuations in 25-hydroxyvitamin D-1-α-hydroxylase (1αOHase) or 25-hydroxyvitamin D-24-hydroxylase (24OHase) gene expressed in the kidney, total RNAs were prepared from the kidneys at 1, 3 and 8 hours after administration according to the procedure described in Example 11(7), and then Northern blotting was performed using the probe described in the same. As shown in FIG. 24, already at 1 hour after administration, decreased mRNA levels of 1αOHase gene and increased mRNA levels of 24OHase gene were observed. This tendency was shown to be more significant at 8 hours after administration. In FIG. 24, "vehicle" indicates a solvent of recombinant OST311 protein comprising 20 mM phosphate buffer (pH 6.7) and 0.3 M NaCl.

These results clearly showed that OST311 lowers serum 1,25-dihydroxyvitamin D3 levels by regulating the expression of 25-hydroxyvitamin D-1α-hydroxylase (1αOHase) or 25-hydroxyvitamin D-24-hydroxylase (24OHase) gene expressed in the kidney.

EXAMPLE 25

Examination of Activity of C-terminus-Deleted OST 311

(1) Construction of Expression System for OST311 Lacking C-Terminal Portion

The following primers were synthesized.

```
OST311R693
ATGCGGCCGCTATCGACCGCCCCTGACCACCCC    (SEQ ID NO: 53)

OST311R633
ATGCGGCCGCTACGGGAGCTCCTGTGAACAGGA    (SEQ ID NO: 54)

OST311R618
ATGCGGCCGCTCAACAGGAGGCCGGGGCCGGGGT   (SEQ ID NO: 55)

OST311R603
ATGCGGCCGCTCACGGGGTCATCCGGGCCCGGGG   (SEQ ID NO: 56)
```

OST311R693, OST311R633, OST311R618 and OST311R603 are reverse primers for deleting 20, 40, 45 and 50 amino acid residues from of the 3' terminus of OST311, respectively and introducing a termination codon and Not I recognition sequence. Each of these reverse primers and a forward primer OST311ME1 (SEQ ID NO: 45) containing the initiation methionine of OST311 and EcoR I recognition sequence described in Example 19 were combined to have a final concentration of 0.2 μM. Using these primers, Pyrobest DNA polymerase (TAKARA SHUZO, Japan) and 100 ng of OST311RQH/IRES-EGFP/pEAK8 plasmid DNA described in Example 19(2) as a template, PCR reaction was performed for 25 cycles after maintaining the temperature at 94° C. for 1 minute. Each reaction cycle consisted of 94° C. for 30 seconds, 55° C. for 30 seconds and 72° C. for 1 minute. The obtained reaction product was subjected to phenol/chloroform treatment, deproteinization and then ethanol precipitation. The reaction product was then digested with EcoR I and Not L and then subjected to 2% agarose gel electrophoresis, so that each DNA fragment was separated and collected using Gene Clean II (BIO110, USA). The obtained DNA fragment was ligated to pEAK8 vector (EdgeBioSystems, USA) that had been digested with EcoR I and Not I, thereby obtaining pPKOST311-Δ C20, -Δ C40, -Δ C45, -ΔC50 plasmids. Plasmid DNAs were prepared by standard methods, and then the nucleotide sequences were determined using ABI3700 fluorescence DNA sequencer (PE Applied Biosystems, USA), thereby confirming that base pairs had been deleted as desired from each of the 3' terminus of OST311RQH gene.

(2) Isolation of the CHO Cells Stably Expressing Recombinant pPKOST311-ΔC20, -ΔC40, -ΔC45, -ΔC50 plasmid DNAs were respectively introduced into CHO ras clone-1 cells using Transfectam (Promega, USA) according to the attached manufacturer's manual. CHO-OST311RQ-ΔC20, -ΔC40, -ΔC45 and ΔC50 cells showing drug resistance in MEMα medium containing 5 µg/ml puromycin and 10% FCS were obtained. These cells were respectively inoculated into 24-well plates, and then cultured in MEMα medium containing 5 µg/ml puromycin and 10% FCS to reach confluent. Subsequently, the medium was replaced with a serum-free DF (DMEM/F-12) medium. 3 days later, conditioned medium was collected. The obtained conditioned medium was subjected to the Western blotting method using OST311-specific polyclonal antibody 311-148 or 311-180 described in Example 22, thereby confirming the expression of each relevant protein at a position corresponding to each predicted molecular weight.

(3) Experiment of Transplanting CHO Cells Expressing C-Terminus-Deleted OST311-

CHO cells expressing the above 20, 40, 45 and 50 residues-deleted OST311 were separately transplanted subcutaneously into nude mice (6-week-old, BALB/c-nude, male, 6 mice per group) in a manner similar to the method described in Example 13. As control groups, the full-length OST311RQH-expressing CHO cells and CHO ras clone-1 cells were separately transplanted subcutaneously (n=6). Each group of mice was housed in a plastic cage and allowed to access to tap water and solid food CE2 (CLEA JAPAN, Japan) ad libitum.

On day 3 after cell transplantation, blood was collected from the heart, and then serum phosphate and calcium levels, and 1,25-dihydroxyvitamin D3 levels were measured by a method similar to that described in Example 20. As shown in FIG. 25, in all of CHO-OST311RQ-ΔC20, -ΔC40, -ΔC45 and -ΔA C50 cells-transplanted groups, significant decreases in serum phosphate levels, equivalent to that of the group transplanted with the cells expressing the full-length OST311RQH, were observed (t-test, **p<0.001). Moreover, significant decreases in serum 1,25-dihydroxyvitamin D3 levels were also observed in CHO-OST311RQ-ΔC40, -ΔC45 and -ΔC50 cells-transplanted groups (when an average serum level of CHO-ras clone-1-transplanted group was defined as 100%, full-length: 3.1%, ΔC40: 9.4%, ΔC45: 10.0% and ΔC 50: 68.1%). These results clearly showed that even when at least 50 amino acids were deleted from the C-terminus of OST311 protein, serum phosphate-decreasing activity or serum 1,25-dihydroxyvitamin D3 level-decreasing activity was maintained.

EXAMPLE 26

Examination of Activity of N-Terminus-Deleted OST311

(1) Construction of Expression System for OST311 Lacking 9 Amino Acid Residues of N-Terminus The following oligo DNAs were synthesized.

```
OST311SGFW:
                                        (SEQ ID NO: 57)
aattccaccATGTTGGGGGCCCGCCTCAGGCTCTGGGTCTGTGCTTGTGC AGCGTCTGCAGCATGAGCGTCCTgcatGC OST311SGRV:
                                        (SEQ ID NO: 58)
aattGCatgcAGGACGCTCATGCTGCAGACGCTGCACAAGGCACAGACCC AGAGCCTGAGGCGGGCCCCCAACATggtgg
```

OST311SGFW is an oligo DNA which consists of a gene sequence encoding a signal peptide portion consisting of amino acid residues from the initiation methionine of OST311 to the 24$^{th}$ Ala of SEQ ID NO: 2, and contains an EcoR I recognition sequence on its 5' terminus. OST311SGRV is a complementary strand of OST311SGFW, and contains an EcoR I recognition sequence on its 5' terminus. In addition, the recognition site of a restriction enzyme Sph I has been introduced into the 3' side of OST311SGFW and the 5' side of OST311SGRV. The 23rd Arg within the signal peptide sequence is substituted with His by introduction of the Sph I recognition site. The above oligo DNAs were annealed according to standard methods, thereby obtaining double-stranded DNA fragments containing EcoR I recognition sequences on both ends and Sph I recognition sequence at a position corresponding to the 23$^{rd}$ amino acid residue in the signal peptide, and encoding the full-length signal peptide starting from the initiation methionine of OST311 and containing one modified residue. The obtained DNA fragments were inserted into EcoR I-digested pEAK8 vectors (EdgeBioSystems, USA). Plasmid DNAs wherein both EF1 promoters and the above DNA fragments existing within the vector in forward direction were then selected, thereby obtaining plasmid pPKFGSG.

Next, the following primers were synthesized.

```
                                        (SEQ ID NO: 59)
OST311dN9:    ATATGCATGCCTCCAGCTGGGGTGGCCTGATCCAC.
```

OST311dN9 is a forward primer designed to contain a Sph I recognition site on its 5' terminus, and the 24$^{th}$ Ala residue of SEQ ID NO: 2 followed by an amino acid sequence starting from the 34$^{th}$ Ser residue of the same. Using a combination of this primer and a reverse primer OST311HNt (Example 19, SEQ ID NO: 46) which has been designed to have an Not I recognition sequence and 6 histidine residues (SEQ ID NO: 88) added to the C-terminal portion followed by a termination codon, and OST311RQH/IRES-EGFP/pEAK8 plasmid DNA described in Example 19(2) as a template, PCR amplification was performed in the manner described in Example 25(1). The obtained PCR product was digested with Sph I and Not I, and then inserted into the above-described, Sph I- and Not I-digested plasmid vector pPKFGSG according to standard methods.

The nucleotide sequence of the obtained plasmid OST311ΔN9-pPKFGSG was determined using ABI3700 fluorescence DNA sequencer (PE Applied Biosystems, USA), so that the inserted gene sequence was confirmed to contain a signal peptide from the initiation methionine to the 24$^{th}$ Ala of OST311RQH gene (wherein the 23$^{rd}$ Arg had been substituted with His), contain deletion of only a gene sequence corresponding to 9 amino acid residues from the following 25$^{th}$ Tyr to the 33$^{rd}$ Gly, and encode the whole sequence from the 34$^{th}$ Ser to the termination codon containing the histidine tag.

(2) Isolation of the CHO cells stably expressing recombinant OST311ΔN9-pPKFGSG plasmid DNA was introduced into CHO ras clone-1 cells using Transfectam (Promega, USA) according to the attached manufacturer's manual, and then CHO-OST311RQ-ΔN9 cells showing drug resistance in MEMα medium containing 5 μg/ml puromycin and 10% FSC were obtained. The conditioned medium was collected from the obtained cells in the manner described in Example 25. Western blotting was then performed using OST311 specific polyclonal antibody 311-148 described in Example 22 or a polyclonal antibody 311-237 newly obtained by immunizing a rabbit with a partial polypeptide from the 237$^{th}$ Gly to 251$^{st}$ Ile of SEQ ID NO: 2. Thus, expression of a relevant protein at the position corresponding to a predicted molecular weight was confirmed. These results revealed that OST311 signal peptide, wherein the 23$^{rd}$ Arg of SEQ ID NO: 2 had been substituted with His, functioned properly enough to secrete OST311 recombinant protein, and even when at least a portion from the 25$^{th}$ Tyr to 33$^{rd}$ Gly had been deleted, the recombinant protein could be present stably to some extent in the cultured medium after secretion.

(3) Experiment of Transplanting CHO Cells Expressing N-Terminal 9 Amino Acids-Deleted OST311

The above CHO-OST311RQ-ΔN9 cells were subcutaneously transplanted to nude mice (8-week-old, BALB/c-nude, male, 6 mice per group) in a manner similar to the methods described in Example 13. As control groups, subcutaneous transplantation of full-length OST311RQH-expressing CHO cells and of CHO ras clone-1 cells were respectively performed similarly (n=6). Each group of the nude mice was housed in a plastic cage and allowed to access to tap water and solid food CE-2 (CLEA JAPAN, Japan) ad libitum.

On day 4 after cell transplantation, blood was collected from the orbital cavity using glass-made capillaries, and then serum phosphate levels were measured in the manner described in Example 20. Thus, in CHO-OST311RQ-ΔN9 cells-transplanted group, a significant decrease in serum phosphate levels, which was equivalent to that of the full-length recombinant-expressing cells-transplanted group, was observed (CHO-ras clone-1 group: 6.85±0.12 mg/dL, CHO-OST311RQH group: 3.91±0.23 mg/dL (p<0.001, to CHO-ras clone-1 group), CHO-OST311RQ-ΔN9 group: 4.33±0.15 mg/dL (p<0.001, to CHO-ras clone-1 group).

These results revealed that even when at least 9 amino acid residues consisting of the 25$^{th}$ Tyr to 33$^{rd}$ Gly of SEQ ID NO: 2 was deleted, the biological activity of OST311 remained undamaged.

EXAMPLE 27

Examination of *Escherichia coli*-pProducing OST311 Recombinant (1) Construction of OST311 *Escherichia coli* Expression Vector OST311/pET3a The following primers were synthesized.

```
OST311N:
TGTATCCCAATGCCTCCCCACTG         (SEQ ID NO: 60)

OST311Bm:
ATGGATCCCTAGATGAACTTGGCGAAGGG   (SEQ ID NO: 61)
```

PCR was performed using as a template OST311/pCAGGS plasmid prepared in Example 19, OST311N (SEQ ID NO: 60) and OST311Bm (SEQ ID NO: 61) as primers, and pfu DNA polymerase (Promega, USA). After the temperature was maintained at 94° C. for 1 minute, reaction was performed for 35 cycles, each cycle consisting of 94° C. for 30 seconds, 55° C. for 30 seconds and 72° C. for 1 minute. After reaction, phenol/chloroform treatment was performed to inactivate the enzyme, and then DNA was collected by ethanol precipitation. The DNA was digested with BamH I, the target OST311 cDNA fragments were separated by 2% agarose gel electrophoresis, and then collected using Gene Clean II (BIO101, USA). Meanwhile, plasmid vector pET3a (Novagen, USA) was digested with Nde I, and then blunt-ended using Klenow fragments (Roche, Swiss). The vector was further digested with BamH I, the obtained plasmid DNA fragment was separated by 0.8% agarose gel electrophoresis, and then collected using Gene Clean II (BIO101, USA). The thus obtained OST311 cDNA fragment was ligated to the digested plasmid pET3a using a DNA ligation kit version 2 (TAKARA SHUZO, Japan). The product was then introduced into *Escherichia coli* DH5α for cloning, and then a plasmid was extracted. The nucleotide sequence of the plasmid was confirmed to make sure that OST311 cDNA had been inserted into pET3a as expected. The plasmid was named OST311/pET3a.

(2) Construction of OST311/pET28 Vector for Expression of OST311 in *Escherichia coli*

The following primers were synthesized.

```
OST311Nd:
ATCATATGTATCCCAATGCCTCCCCACTG   (SEQ ID NO: 62)

OST311Not:
ATGCGGCCGCCTAGATGAACTTGGCGAAGGG (SEQ ID NO: 63)
```

PCR was performed using OST311/pET3a plasmid as a template, OST311Nd (SEQ ID NO: 62) and OST311Not (SEQ ID NO: 63) as primers, and LA Taq (TAKARA SHUZO, Japan). After the temperature was maintained at 94° C. for 1 minute, reaction was performed for 35 cycles, each cycle consisting of 94° C. for 30 seconds, 55° C. for 30 seconds and 72° C. for 1 minute. After reaction, phenol/chloroform treatment was performed to inactivate the enzyme. The amplified DNA fragment was then collected by ethanol precipitation. The DNA fragment was digested with Nde I and Not I, the target OST311 cDNA fragment was separated by 2% agarose gel electrophoresis, and then collected using Gene Clean II (BIO101, USA). Meanwhile, plasmid vector pET28 (Novagen, USA) was digested with Nde I and Not I, and then dephosphorylated using bovine intestinal alkaline phosphatase (TAKARA SHUZO, Japan). The product was then separated by 0.8% agarose gel electrophoresis, and then the relevant digested plasmid was collected using Gene Clean II (BIO101, USA). The thus obtained OST311cDNA was ligated to the digested pET28 plasmid using a DNA ligation kit version 2 (TAKARA SHUZO, Japan), and then the ligated product was introduced into *Escherichia coli* DH5α for cloning, thereby extracting a plasmid. The nucleotide sequence of the plasmid was confirmed to make sure that OST311 cDNA which allowed expression of recombinant OST311 having a His-Tag sequence added to the N-terminal side had been inserted into pET28. This plasmid was named OST311/pET28. The amino acid sequence and the nucleotide sequence of the recombinant His-OST311 encoded by this vector are shown in FIG. 26.

(3) Expression of Recombinant His-OST311 in *Escherichia coli* and Preparation of the Same Plasmid OST311/pET28 was introduced into *Escherichia coli* BL21 (DE3) Codon Plus RP (STRATAGENE, USA) for transformation, and then clones were obtained. The obtained *Escherichia coli* clones were inoculated in 100 ml of LB medium containing 10 mg of kanamycin (SIGMA, USA) and cultured at 37° C. overnight. The bacterial cell suspension was inoculated in 1 L of LB medium to $A_{600}$=0.1, and then shake-cultured using a 3 L Sakaguchi flask at 37° C. Absorbance of the culture suspension was measured with time. When it reached $A_{600}$=0.6 to 1.0, isopropyl-1-thio-β-galactoside (IPTG) (Wako Pure Chemical Industries, Japan) was added to 1 mM. 4 hours later, the cells were collected by centrifugation (7700 g×15 minutes). The collected cells were suspended in 20 ml of 0.1 M Tris hydrochloride buffer (pH 7.5) containing 1 mM DTT, and then disrupted using French Press. The solution containing the disrupted cells was centrifuged (7700 g×15 minutes), and then the precipitate fraction was suspended in 15 ml of 0.1 M Tris hydrochloride buffer (pH 7.5). DNase I (Roche, Swiss) was added to the suspension to 0.1 mg/mL, and then shaken at 4° C. for 1 hour. Next, centrifugation was performed (23400 g×15 minutes), and then the precipitate fraction was collected as inclusion body. The obtained inclusion body was washed by suspending in 10 ml of 20 mM Tris hydrochloride buffer (pH 8) containing 0.75 M urea and 1% Triton-X, and then centrifuging (23,400 g×15 minutes) to collect precipitate. This washing procedure was repeated twice.

The washed inclusion body was suspended in 5 ml of a denaturing solution (50 mM phosphate buffer (pH 8) containing 1 mM DTT and 6 M guanidine hydrochloride), and then solubilized by shaking the suspension at 37° C. for 1 hour. Insoluble matters were removed as precipitate by centrifugation (23,400 g×15 minutes), and then the solution was equilibrated with 6 M guanidine hydrochloride-containing 50 mM phosphate buffer (pH 6). The solubilized sample was applied to a column filled with Ni-NTA Agarose (QIAGEN, Germany), and then washed with 6 M guanidine hydrochloride-containing 50 mM phosphate buffer (pH 6). Protein adsorbed to the column was eluted using 50 mM phosphate buffer (pH 4.5) containing 500 mM imidazole (Nacalai Tesque, Japan) and 6 M guanidine hydrochloride, thereby purifying denatured His-OST311. The concentration was obtained based on UV absorbance at 280 nm of the purified sample, and then 50 mM phosphate buffer (pH 6) containing 6 M guanidine hydrochloride was added to the sample to have a final concentration of 2 mg/ml, thereby preparing denatured His-OST311 solution. Cysteine as a reducing agent was added to the sample to have a final concentration of 1 mM, diluted 100 fold with 20 mM phosphate buffer (pH 6) containing 0.6 M guanidine hydrochloride and 0.1% Tween 20 to start refolding. Incubation was performed at 4° C. for 3 days or more.

The refolding solution was dialyzed against 0.1 M acetate buffer (pH 4.8) at 4° C. The dialyzed refolding solution was concentrated approximately 10 fold using a ultrafiltration membrane, and then purified by HPLC using cation exchange column SP-5PW (TOSOH, Japan). Protein was eluted using 10% glycerol-containing 20 mM phosphate buffer (pH 6) with a linear NaCl gradient from 0.5 M to 2 M. This elution pattern is shown in FIG. 27. SDS-PAGE analysis and mass spectrometry measurement revealed that among eluted two types of protein peaks, His-OST311 was contained in a peak eluted at a lower salt concentration. As described above, approximately 0.6 mg of the final purified product, His-OST311, could be prepared from approximately 1 L of cultured cells.

(4) Construction of pET22b-MK-OST311 Vector for Expression of MK-OST311

The following primers were synthesized.

```
                                        (SEQ ID NO: 64)
OST311MK1:
gaattcatatgaaatacccgaacgcttccccgctgctgggctccagctg (SEQ ID NO: 65)
OST311MK2:
cccaagcttgcggccgcctagatgaacttggc
```

A target sequence was amplified by PCR using the above His-OST311 expression plasmid OST311/pET28 as a template and OST311MK1 (SEQ ID NO: 64) and OST311MK2 (SEQ ID NO: 65) as primers. In the OST311 cDNA obtained by this procedure, 27 nucleotides following the initiation codon (ATG) had been converted to *Escherichia coli* type codons. The PCR product was purified using a QIAquick PCR purification Kit (QIAGEN, Germany), and then digested with restriction enzymes Nde I (TAKARA SHUZO, Japan) and Not I (TAKARA SHUZO, Japan) at 37° C. for 1 hour. The digested PCR product was separated by agarose electrophoresis, and then purified using a QIAquick PCR purification Kit (QIAGEN, Germany). The obtained DNA fragment was digested with restriction enzymes Nde I and Not I at 37° C. for 1 hour, and then ligated to plasmid vector pET22b (Novagen, USA), which had been separated and purified by agarose electrophoresis, using a DNA Ligation kit Ver 2 (TAKARA SHUZO, Japan) at 16° C. for 15 minutes. The ligated product was introduced into *Escherichia coli* JM109 (TAKARA SHUZO, Japan) for cloning, and then a plasmid was extracted by standard methods. The nucleotide sequence of the obtained plasmid was determined to make sure that the obtained OST311 cDNA had been inserted into pET22b vector as expected. This plasmid was named pET22-MK-OST311. The nucleotide sequence and amino acid sequence of recombinant MK-OST311 encoded by the vector are shown in FIG. 26.

(5) Expression of MK-OST311 in *Escherichia coli* and Preparation of the Same

Plasmid pET22-MK-OST311 was introduced into *Escherichia coli* BL21 (DE3) Codon Plus RP (STRATAGENE, USA), and then the transformed clones were obtained. The obtained *Escherichia coli* clones were inoculated in 100 ml of LB medium containing 10 mg of ampicillin and then cultured at 37° C. overnight. The bacterial cell suspension was inoculated in 1 L of LB medium to $A_{600}$=0.1, and then cultured with shaking using a 3 L Sakaguchi flask at 37° C. IPTG was added to the bacterial cell culture to induce expression of the recombinant, and then inclusion bodies were prepared in a manner similar to the above preparation method of His-OST311.

The washed inclusion bodies were suspended in 5 ml of denaturing solution (50 mM phosphate buffer (pH 8) containing 1 mM DTT and 6 M guanidine hydrochloride), and then solubilized by shaking the suspension at 37° C. for 1 hour. The solubilized product was diluted 2 fold using a denaturing solution, and then diluted 100 fold using 20 mM phosphate buffer (pH 6) containing 0.6 M guanidine hydrochloride and 0.1% Tween 20 to start refolding. Incubation was performed at 4° C. for 3 days or more. It was shown that under conditions of addition of oxidant and a pH of 7 or more, protein was precipitated so that refolding efficiency decreased significantly. The refolding solution was dialyzed against 0.1 M acetate buffer (pH 4.8) at 4° C. The dialyzed refolding solution was concentrated approximately 10 fold using an ultra-filtration membrane, and then purified by HPLC using cation exchange column SP-5PW (TOSOH, Japan). Protein was eluted using 10% glycerol-containing 20 mM phosphate buffer (pH 6) with a linear NaCl gradient from 0.5 M to 2 M. As shown in FIG. 28, there were 2 peaks of protein elution, and SDS-PAGE analysis and mass spectrometry measurement revealed that MK-OST311 was contained in a peak eluted at a lower salt concentration. Thus, approximately 0.6 mg of the final purified product, MK-OST311, could be purified from approximately 1 L of flask-cultured cells.

(6) PEGylation of MK-OST311

10 ml of MK-OST311 (0.05 mg/ml) purified with an ion exchange column was adjusted to have pH 4.8 using 10% acetic acid. 25 mg of activated PEG (Sharewater, USA) with a molecular weight of 20,000 dissolved in 10 mM acetate buffer (pH 4.8) was added to this solution with agitation in ice. 15 minutes later, 1 M sodium cyano borohydride (Nacalai Tesque, Japan) dissolved in 10 mM acetate buffer (pH 4.8) was added to the solution to have a final concentration of 15 mM, and then the solution was agitated at 4° C. for 16 hours. OST311 PEGylated by this reaction was purified by HPLC using cation exchange column SP-5PW (TOSOH, Japan). Protein was eluted using 10% glycerol-containing 20 mM phosphate buffer (pH 6) with a linear NaCl gradient from 0.5 M to 2 M. As shown in FIG. 29, PEGylated MK-OST311 was eluted as a single peak on the side of lower ion strength compared to that of MK-OST311.

(7) Examination of Activity of His-OST311 Recombinant

To examine the biological activity of the purified His-OST311 recombinant, single administration of the recombinant protein, 4.5 μg/0.1 ml each, to normal mice (5-week-old, BALB/c, male, 6 mice per group) via the caudal vein in the manner described in Example 24 was performed. 9 hours later, serum phosphate and 1,25-dihydroxyvitamin D3 levels were measured by a method similar to that described in Example 20. Single administration of the same dose of CHO-OST311H cell-derived purified recombinant was performed to a positive control group, and single administration of a vehicle comprising 20 mM phosphate buffer (pH 6.9) and 0.3 M NaCl was performed, 0.1 ml each, to a vehicle-administered group, both via the caudal vein.

As shown in FIG. 30A, in His-OST311-administered group at 9 hours after administration, a significant effect of decreasing serum phosphate levels was observed compared to the vehicle-administered group. The degree of the decrease was equivalent to that of CHO-producing recombinant protein-administered group. In addition, the serum 1,25-dihydroxyvitamin D3 levels at 9 hours after administration in His-OST311-administered group also showed a significant decrease as shown in FIG. 32.

As described in Example 24 (3) and (4), significantly decreased serum 1,25-dihydroxyvitamin D3 levels were already observed at 4 hours after single administration of CHO cell-producing OST311 protein. Before this time point, at 1 hour after administration, decreased expression of 25-hydroxyvitamin D-1-α-hydroxylase (1αOHase) and enhanced expression of 25hydroxyvitamin D-24-hydroxylase (24OHase) were observed in the kidneys. Hence, single administration of His-OST311, 4.5 μg/0.1 ml per mouse, to BALB/c mice (5-week-old, male) was performed via the caudal vein, and then the kidneys were excised 1 and 4 hours later. Changes in the expression of 1αOHase gene and 24OHase gene in the kidneys were analyzed by the Northern blotting method. Single administration of the same dose of CHO-OST311H cell-derived purified recombinant was performed to a positive control group, and single administration of a vehicle comprising 20 mM phosphate buffer (pH 7.0) and 0.3 M NaCl was performed, 0.1 ml each, to a vehicle-administered group, both via the caudal vein. As shown in FIG. 31, similar to CHO-producing recombinant, His-OST311 caused decreased expression of 1αOHase gene and enhanced expression of 24OHase gene already at 1 hour after administration. It was revealed that His-OST311 has activity regulating expression of vitamin D-metabolizing enzyme genes equivalent to that of the CHO-producing recombinant. Further, as shown in FIG. 32, changes in serum 1,25-dihydroxyvitamin D3 levels showed a moderate decrease at 4 hours after administration with recombinant, and showed a more significant decrease at 8 hours. It was revealed that this manner of changes was almost consistent with that of changes with time as observed in the experiment of administering CHO-producing recombinant described in Example 24 (3).

From the above results, it was revealed that recombinant His-OST311 produced by *Escherichia coli* has biological activities of at least serum phosphate-decreasing activity and vitamin D metabolism-regulating activity equivalent to the activities of the secreted recombinant produced by CHO-OST311H cells.

(8) Examination of Activity of PEGylated MK-OST311

The biological activity of PEGylated MK-OST311 was examined by performing single administration of PEGylated MK-OST311, 5.0 μg/0.1 ml per mouse, to normal mice (5-week-old, BALB/c, male, 8 mice per group) via the caudal vein in the manner described in Example 24, and then measuring serum phosphate levels at 9 hours after administration by a method similar to that of Example 20. Single administration of a vehicle comprising 20 mM PB (pH6.0), 10% glycerol, 1 M NaCl and 0.1% Tween 20 was performed, 0.1 ml/mouse, to a vehicle-administered group via the caudal vein. At 8 hours after administration, blood was collected from the orbital cavity using glass-made capillaries, and then inorganic phosphate levels of the obtained sera were measured. As shown in FIG. 30B, a significant effect of decreasing serum phosphate levels was observed in PEGylated MK-OST311-administered group, compared to the vehicle-administered group. The result reveled that when *Escherichia coli*-producing recombinant was PEGylated, the biological activity of it is not inhibited.

EXAMPLE 28

Introduction of Amino Acid Mutation into Cleavage Site

As described in Example 9, it was shown that OST311 was cleaved at a position between the 179th Arg and the 180th Ser amino acid residues of SEQ ID NO: 2. Meanwhile, it was confirmed as described in Example 19 that this cleavage was inhibited by simultaneous substitution of both 176th Arg and 179th Arg amino acid residues of OST311 with Gln. These facts suggest a possibility that this cleavage is due to some protease which recognizes a motif consisting of adjacent RXXR or RRXXR sequence. Moreover, when full-length recombinant consisting of the polypeptide represented by SEQ ID NO: 4 is administered in vivo, the same cleavage as described above or similar cleavage thereto may occur. Hence, the 175th to the 180th amino acid residues of SEQ ID NO: 2 were respectively substituted with Ala, Gln or Trp, and then how the substitution affected expression and secretion patterns in each mutant recombinant in CHO cells was examined.

(1) Construction of OST311 Gene with Mutations at Cleavage Site

The following primers were synthesized.

```
pyh23PA1F
AACACCCCCATAGCACGGCGGCACA        (SEQ ID NO: 66)

pyh23PA1R
TGTGCCGCCGTGCTATGGGGTGTT         (SEQ ID NO: 67)

pyh23RA1F
ACCCCCATACCAGCGCGGCACACCCG       (SEQ ID NO: 68)

pyh23RA1R
CGGGTGTGCCGCGCTGGTATGGGGGT       (SEQ ID NO: 69)

pyh23RA2F
CCCATACCACGGGCGCACACCCGGAG       (SEQ ID NO: 70)

pyh23RA2R
CTCCGGGTGTGCGCCCGTGGTATGGG       (SEQ ID NO: 71)

pyh23HA1F
ATACCACGGCGGGCCACCCGGAGCGC       (SEQ ID NO: 72)

pyh23HA1R
GCGCTCCGGGTGGCCCGCCGTGGTAT       (SEQ ID NO: 73)

pyh23TA1F
CCACGGCGGCACGCCCGGAGCGCCG        (SEQ ID NO: 74)

pyh23TA1R
CGGCGCTCCGGGCGTGCCGCCGTGG        (SEQ ID NO: 75)

pyh23RA3F
CGGCGGCACACCGCGAGCGCCGAGGA       (SEQ ID NO: 76)

pyh23RA3R
TCCTCGGCGCTCGCGGTGTGCCGCCG       (SEQ ID NO: 77)

pyh23SA1F
CGGCACACCCGGGCCGCCGAGGACGA       (SEQ ID NO: 78)

pyh23SA1R
TCGTCCTCGGCGGCCCGGGTGTGCCG       (SEQ ID NO: 79)

pyh23RKQ1F
ACCCCCATACCACAGCGGCACACCCG       (SEQ ID NO: 80)

pyh23RKQ1R
CGGGTGTGCCGCTGTGGTATGGGGGT       (SEQ ID NO: 81)

pyh23RKQ2F
CCCATACCACGGCAGCACACCCGGAG       (SEQ ID NO: 82)

pyh23RKQ2R
CTCCGGGTGTGCTGCCGTGGTATGGG       (SEQ ID NO: 83)

pyh23RKQ3F
CGGCGGCACACCCAGAGCGCCGAGGA       (SEQ ID NO: 84)

pyh23RKQ3R
TCCTCGGCGCTCTGGGTGTGCCGCCG       (SEQ ID NO: 85)

pyh23RWF
CGGCGGCACACCTGGAGCGCCGAGG        (SEQ ID NO: 86)

pyh23RWR
CCTCGGCGCTCCAGGTGTGCCGCCG        (SEQ ID NO: 87)
``` pyh23PA1F and pyh23PA1R are forward and reverse primers for introducing a mutation, in which substitution of the 652nd cytosine of OST311 cDNA (SEQ ID NO: 1) with guanine causes substitution of the 174th Pro amino acid residue of SEQ ID NO: 2 with Ala. Hereinafter, this mutation is referred to as P174A.

pyh23RA1F and pyh23RA1R are forward and reverse primers for introducing a mutation, in which substitution of the 655th cytosine and the 656th guanine of OST311 cDNA (SEQ ID NO: 1) with guanine and cytosine, respectively, causes substitution of the 175th Arg amino acid residue of SEQ ID NO: 2 with Ala. Hereinafter, this mutation is referred to as R175A.

pyh23RA2F and pyh23RA2R are forward and reverse primers for introducing a mutation, in which substitution of the 658th cytosine and the 659th guanine of OST311 cDNA (SEQ ID NO: 1) with guanine and cytosine, respectively, causes substitution of the 176th Arg amino acid residue of SEQ ID NO: 2 with Ala. Hereinafter, this mutation is referred to as R176A.

pyh23HA1F and pyh23HA1R are forward and reverse primers for introducing a mutation, in which substitution of the 661st cytosine and the 662nd adenine of OST311 cDNA (SEQ ID NO: 1) with guanine and cytosine, respectively, causes substitution of the 177th His amino acid residue of SEQ ID NO: 2 with Ala. Hereinafter, this mutation is referred to as H177A.

pyh23TA1F and pyh23TA1R are forward and reverse primers for introducing a mutation, in which substitution of the 664th adenine of OST311 cDNA (SEQ ID NO: 1) with guanine causes substitution of the 178th Thr amino acid residue of SEQ ID NO: 2 with Ala. Hereinafter, this mutation is referred to as T178A.

pyh23RA3F and pyh23RA3R are forward and reverse primers for introducing a mutation, in which substitution of the 667th cytosine and the 668th guanine of OST311 cDNA (SEQ ID NO: 1) with guanine and cytosine, respectively, causes substitution of the 179th Arg amino acid residue, of SEQ ID NO: 2 with Ala. Hereinafter, this mutation is referred to as R179A.

pyh23SA1F and pyh23SA1R are forward and reverse primers for introducing a mutation, in which substitution of the 670th adenine and the 671st guanine of OST311 cDNA (SEQ ID NO: 1) with guanine and cytosine, respectively, causes substitution of the 180th Ser amino acid residue of SEQ ID NO: 2 with Ala. Hereinafter, this mutation is referred to as S180A.

pyh23RKQ1F and pyh23RKQ1R are forward and reverse primers for introducing a mutation, in which substitution of the 656th guanine of OST311 cDNA (SEQ ID NO: 1) with adenine causes substitution of the 175th Arg amino acid residue of SEQ ID NO: 2 with Gln. Hereinafter, this mutation is referred to as R175Q.

pyh23RKQ2F and pyh23RKQ2R are forward and reverse primers for introducing a mutation, in which substitution of the 659th guanine of OST311 cDNA (SEQ ID NO: 1) with adenine causes substitution of the 176th Arg amino acid residue of SEQ ID NO: 2 with Gln. Hereinafter, this mutation is referred to as R176Q.

pyh23RKQ3F and pyh23RKQ3R are forward and reverse primers for introducing a mutation, in which substitution of the 668th guanine of OST311 cDNA (SEQ ID NO: 1) with adenine causes substitution of the 179th Arg amino acid residue of SEQ ID NO: 2 with Gln. Hereinafter, this mutation is referred to as R179Q.

pyh23RWF and pyh23RWR are forward and reverse primers for introducing a mutation, in which substitution of the 667th cytosine of OST311 cDNA (SEQ ID NO: 1) with thymine causes substitution of the 179th Arg amino acid residue of SEQ ID NO: 2 with Trp. Hereinafter, this mutation is referred to as R179W.

(1)-1 Construction of OST311P174AH Gene 2 types of reaction solutions (100 µL each) were prepared using Pyrobest DNA polymerase (TAKARA SHUZO, Japan) according to the attached manufacturer's manual. For one reaction solution, OST311ME1 (SEQ ID NO: 45) and pyh23PA1F (SEQ ID NO: 66) were used as primers at a final concentration of 0.2 µM, and for the other reaction solution, pyh23PA1R (SEQ ID NO: 67) and OST311HNt (SEQ ID NO: 46) were used as primers at a final concentration of 0.2 µM. To each reaction solution, 10 ng of OST311/pCAGGS plasmid described in Example 19(1) was added as a template, and then the solution was maintained at 94° C. for 1 minute. Then, PCR reaction was performed for 40 cycles, each cycle consisting of 94° C. for 20 seconds, 55° C. for 30 seconds and 72° C. for 1 minute. The two types of reaction solutions were diluted respectively 10 fold, and then 1 µL of each solution was added to 100 µL of a reaction solution prepared according to the document attached to Pyrobest DNA polymerase (TAKARA SHUZO, Japan). OST311ME1 (SEQ ID NO: 45) and OST311HNt (SEQ ID NO: 46) were added as primers to the solution to have a final concentration of 0.2 µM, and then the solution was maintained at 94° C. for 1 minute. Then, PCR reaction was performed for 30 cycles, each cycle consisting of 94° C. for 20 seconds, 55° C. for 30 seconds and 72° C. for 1 minute and 30 seconds. After PCR reaction, the solution was further maintained at 72° C. for 7 minutes. The thus obtained reaction products were collected using Gene Clean II (BIO101, USA) according to the attached manufacturer's manual. The products were then digested with EcoR I and Not I, and then subjected to 2% agarose gel electrophoresis to separate approximately 800 bp DNA fragments. The fragment was collected using Gene Clean II (BIO101, USA). The thus obtained DNA fragments were inserted into the EcoR I and Not I sites of pEAK8 vector (EdgeBio, USA), thereby obtaining plasmid OST311P174AH-pEAK8. Plasmid DNA was prepared according to standard methods, and the nucleotide sequence was determined using ABI3700 fluorescence DNA sequencer (PE Applied Systems, USA). Thus, it was confirmed that mutation P174H had been introduced as expected. Moreover, it was confirmed that a histidine tag had been added to the C-terminus. The polypeptide encoded by a mutant gene having mutation P174A introduced therein is referred to as OST311P174AH.

(1)-2 Preparation of OST311R175AH Gene
OST311R175AH gene was prepared using pyh23RA1F (SEQ ID NO: 68) and pyh23RA1R (SEQ ID NO: 69) primers by a method similar to that of (1)-1.

(1)-3 Preparation of OST311R176AH Gene
OST311R176AH gene was prepared using pyh23RA2F (SEQ ID NO: 70) and pyh23RA2R (SEQ ID NO: 71) primers by a method similar to that of (1)-1.

(1)-4 Preparation of OST311H177AH Gene
OST311H177AH gene was prepared using pyh23HA1F (SEQ ID NO: 72) and pyh23HA1R (SEQ ID NO: 73) primers by a method similar to that of (1)-1.

(1)-5 Preparation of OST311T178AH Gene
OST311T178AH gene was prepared using pyh23TA1F (SEQ ID NO: 74) and pyh23TA1R (SEQ ID NO: 75) primers by a method similar to that of (1)-1.

(1)-6 Preparation of OST311R179AH Gene
OST311R179AH gene was prepared using pyh23RA3F (SEQ ID NO: 76) and pyh23RA3R (SEQ ID NO: 77) primers by a method similar to that of (1)-1.

(1)-7 Preparation of OST311S180AH Gene
OST311S180AH gene was prepared using pyh23SA1F (SEQ ID NO: 78) and pyh23SA1R (SEQ ID NO: 79) primers by a method similar to that of (1)-1.

(1)-8 Preparation of OST311R175QH Gene
OST311R175QH gene was prepared using pyh23RKQ1F (SEQ ID NO: 80) and pyh23RKQ1R (SEQ ID NO: 81) primers by a method similar to that of (1)-1.

(1)-9 Preparation of OST311R176QH Gene
OST311R176QH gene was prepared using pyh23RKQ2F (SEQ ID NO: 82) and pyh23RKQ2R (SEQ ID NO: 83) primers by a method similar to that of (1)-1.

(1)-10 Preparation of OST311R179QH Gene
OST311R179QH gene was prepared using pyh23RKQ3F (SEQ ID NO: 84) and pyh23RKQ3R (SEQ ID NO: 85) primers by a method similar to that of (1)-1.

(1)-11 Preparation of OST311R179WH Gene
OST311R179WH gene was prepared using pyh23RWF (SEQ ID NO: 86) and pyh23RWR (SEQ ID NO: 87) primers by a method similar to that of (1)-1.

(2) Transient Expression of OST311 Genes with Mutation at Cleavage Site and Preparation of Conditioned Media pEAK rapid cells (EdgeBiosystems, USA) were inoculated onto a 12-well plate. The above 11 types of expression plasmids for mutant OST311 were transfected into the cells by a phosphate calcium method according to the document attached to pEAK system (EdgeBiosystems, USA). The cells were allowed to stand for 4 hours, the medium was replaced with 1.5 ml of serum-free MEMα medium, the cells were cultured at 37° C. for 2 days, and then the conditioned medium was collected.

(3) Evaluation of Expression of OST311 Genes with the Mutation at Cleavage Site

The thus obtained conditioned medium was subjected to Western blotting in the manner described in Example 6(3), and then the presence of OST311 recombinant with the mutation at cleavage site in the conditioned medium was examined. OST311-specific polyclonal antibody, 311-148 described in Example 22 was used for detection. Thus, as shown in FIG. 33, a degradation product containing the polypeptide represented by SEQ ID NO: 6 was observed at around 16 kDa, similarly to the wild type, for mutation P174A, R175A, R175Q, H177A, T178A or S180A-introduced OST311 recombinant among those substituted at the 174th to 180th amino acid residues. However, no degradation product was observed for any of the mutations R176A, R179A, R176Q, R179Q or R179W-introduced OST311 recombinant. These results suggest that in particular the 176$^{th}$ Arg and the 179$^{th}$ Arg amino acid residues play an important role in the cleavage that occurs between the 179$^{th}$ Arg and the 180$^{th}$ Ser amino acid residues. That is, cleavage is inhibited or suppressed by substitution of both residues at least with any amino acid of Ala, Gln or Trp. Hence, it is expected that production of the full-length polypeptide is promoted using this finding.

EXAMPLE 29

As shown in Example 6, a recombinant product obtained by expression of OST311 in CHO cells or COS cells is cleaved between the 179$^{th}$ arginine and 180$^{th}$ serine located immediately after RXXR motif as shown in Example 9. As clearly shown in Example 18, the hypophosphatemia-inducing activity of OST311 protein was retained in the full-length protein that had not been cleaved at this site. Further, involvement of RXXR motif in this cleavage was clear from the mutation introduction experiment shown in Examples 19 and 28. In order to produce and obtain recombinant OST311 efficiently, avoidance of this cleavage is an important problem, and introduction of the mutation into RXXR motif shown in Example 28 is one of the effective methods. Furin is known as one of proteinases which recognize RXXR motif. This enzyme is localized in the Trans-golgi region, and is thought to cleave post-translated protein by recognizing RXXR motif in the process of secretion.

(1) Involvement of Furin in Cleavage of OST311

OST311/pCAGGS plasmid was introduced into furin-deficient LoVo cells using Transfectum (Promega, USA). Then, the cells were cultured for 48 hours. When OST311 protein transiently expressed and secreted in the culture solution was analyzed by Western blotting using 311-148 antibody, no cleaved product was detected. This result suggests that furin is involved in the observed cleavage when OST311 is produced.

(2) Avoiding Cleavage of OST311

It was assumed from the above results that inhibition of furin activity was effective to improve the productivity of OST311, in which it was not cleaved between the 179$^{th}$ arginine and the 180$^{th}$ serine. Accordingly, it is conceivable that OST311 is expressed in a host, such as Lovo cells having no furin activity, or under a condition in which furin activity is suppressed by the addition of a furin inhibitor. In order to suppress furin activity of CHO-OST311H cells, α1-antitrypsin Portland (α1-PDX) was transiently expressed according to the method reported by Benjannet S et al (J Biol Chem 272: 26210-8, 1997), and then the conditioned medium was collected. The ratio of the full-length polypeptide in the recombinant products was increased, compared to that in the conditioned medium of the control CHO-OST311H cells without this gene. Accordingly, it was concluded that the production efficiency of the full-length OST311 protein can be elevated by introducing a substance suppressing furin activity extrinsically or intrinsically.

All publications, patents and patent applications cited herein are incorporated herein by reference in their entirety.

INDUSTRIAL APPLICABILITY

According to the present invention, there are provided a polypeptide regulating phosphate metabolism, calcium metabolism and/or calcification, a DNA encoding the polypeptide, and a pharmaceutical composition containing the polypeptide as an active ingredient, and an antibody recognizing the polypeptide, a pharmaceutical composition containing the antibody as an active ingredient, a diagnostic method using the antibody, and a diagnostic composition.

SEQUENCE LISTING FREE TEXT

SEQ ID NO: 12: Synthetic DNA
SEQ ID NO: 13: Synthetic DNA
SEQ ID NO: 14: Synthetic DNA
SEQ ID NO: 15: Synthetic DNA
SEQ ID NO: 16: Synthetic DNA
SEQ ID NO: 17: Synthetic DNA
SEQ ID NO: 18: Synthetic DNA
SEQ ID NO: 19: Synthetic DNA
SEQ ID NO: 20: Synthetic DNA
SEQ ID NO: 21: Synthetic DNA
SEQ ID NO: 22: Synthetic DNA
SEQ ID NO: 23: Synthetic DNA
SEQ ID NO: 24: Synthetic DNA
SEQ ID NO: 25: Synthetic DNA
SEQ ID NO: 26: Synthetic DNA
SEQ ID NO: 27: Synthetic peptide
SEQ ID NO: 28: Synthetic peptide
SEQ ID NO: 29: Synthetic DNA
SEQ ID NO: 30: Synthetic DNA
SEQ ID NO: 31: Synthetic DNA
SEQ ID NO: 32: Synthetic DNA
SEQ ID NO: 33: Synthetic DNA
SEQ ID NO: 34: Synthetic DNA
SEQ ID NO: 35: Synthetic DNA
SEQ ID NO: 36: Synthetic DNA
SEQ ID NO: 37: Synthetic DNA
SEQ ID NO: 38: Synthetic DNA
SEQ ID NO: 39: Synthetic DNA
SEQ ID NO: 40: Synthetic DNA
SEQ ID NO: 41: Synthetic DNA
SEQ ID NO: 42: Synthetic DNA
SEQ ID NO: 43: Synthetic DNA
SEQ ID NO: 44: Synthetic DNA
SEQ ID NO: 45: Synthetic DNA
SEQ ID NO: 46: Synthetic DNA
SEQ ID NO: 47: Synthetic DNA
SEQ ID NO: 48: Synthetic DNA
SEQ ID NO: 49: Synthetic peptide
SEQ ID NO: 50: Synthetic peptide
SEQ ID NO: 51: Synthetic peptide
SEQ ID NO: 52: Synthetic peptide
SEQ ID NO: 53: Synthetic DNA
SEQ ID NO: 54: Synthetic DNA
SEQ ID NO: 55: Synthetic DNA
SEQ ID NO: 56: Synthetic DNA
SEQ ID NO: 57: Synthetic DNA
SEQ ID NO: 58: Synthetic DNA
SEQ ID NO: 59: Synthetic DNA
SEQ ID NO: 60: Synthetic DNA
SEQ ID NO: 61: Synthetic DNA
SEQ ID NO: 62: Synthetic DNA
SEQ ID NO: 63: Synthetic DNA
SEQ ID NO: 64: Synthetic DNA
SEQ ID NO: 65: Synthetic DNA
SEQ ID NO: 66: Synthetic DNA
SEQ ID NO: 67: Synthetic DNA
SEQ ID NO: 68: Synthetic DNA
SEQ ID NO: 69: Synthetic DNA
SEQ ID NO: 70: Synthetic DNA
SEQ ID NO: 71: Synthetic DNA
SEQ ID NO: 72: Synthetic DNA
SEQ ID NO: 73: Synthetic DNA

| | |
|---|---|
| SEQ ID NO: 74: Synthetic DNA | SEQ ID NO: 81: Synthetic DNA |
| SEQ ID NO: 75: Synthetic DNA | SEQ ID NO: 82: Synthetic DNA |
| SEQ ID NO: 76: Synthetic DNA | SEQ ID NO: 83: Synthetic DNA |
| SEQ ID NO: 77: Synthetic DNA | SEQ ID NO: 84: Synthetic DNA |
| SEQ ID NO: 78: Synthetic DNA | SEQ ID NO: 85: Synthetic DNA |
| SEQ ID NO: 79: Synthetic DNA | SEQ ID NO: 86: Synthetic DNA |
| SEQ ID NO: 80: Synthetic DNA | SEQ ID NO: 87: Synthetic DNA |

The invention claimed is:

1. A method for treating X-linked hypophosphatemia (XLH), comprising the step of administering to a subject a pharmaceutical composition comprising:

(i) an antibody that binds to a polypeptide having the amino acid sequence of SEQ ID NO: 2 or 4; and
(ii) a pharmaceutically acceptable carrier.

* * * * *